United States Patent
Engelhardt et al.

(10) Patent No.: US 12,173,305 B2
(45) Date of Patent: Dec. 24, 2024

(54) cis AND TRANS REQUIREMENTS FOR TERMINAL RESOLUTION OF HUMAN BOCAVIRUS 1

(71) Applicants: University of Iowa Research Foundation, Iowa City, IA (US); University of Kansas, Lawrence, KS (US)

(72) Inventors: John F. Engelhardt, Iowa City, IA (US); Ziying Yan, Iowa City, IA (US); Jianming Qiu, Overland Park, KS (US)

(73) Assignees: University of Iowa Research Foundation, Iowa City, IA (US); University of Kansas, Lawrence, KS (US)

( * ) Notice: Subject to any disclaimer, the term of this patent is extended or adjusted under 35 U.S.C. 154(b) by 739 days.

(21) Appl. No.: 16/304,064

(22) PCT Filed: May 26, 2017

(86) PCT No.: PCT/US2017/034678
§ 371 (c)(1),
(2) Date: Nov. 21, 2018

(87) PCT Pub. No.: WO2017/205739
PCT Pub. Date: Nov. 30, 2017

(65) Prior Publication Data
US 2019/0203229 A1   Jul. 4, 2019

Related U.S. Application Data

(60) Provisional application No. 62/341,897, filed on May 26, 2016.

(51) Int. Cl.
| | | |
|---|---|---|
| *C12N 15/86* | (2006.01) | |
| *C12N 7/00* | (2006.01) | |
| *C12N 7/02* | (2006.01) | |

(52) U.S. Cl.
CPC .............. *C12N 15/86* (2013.01); *C12N 7/00* (2013.01); *C12N 2750/14321* (2013.01); *C12N 2750/14322* (2013.01); *C12N 2750/14343* (2013.01)

(58) Field of Classification Search
None
See application file for complete search history.

(56) References Cited

U.S. PATENT DOCUMENTS

| | | |
|---|---|---|
| 4,501,729 A | 2/1985 | Boucher et al. |
| 5,292,498 A | 3/1994 | Boucher, Jr. |
| 5,478,745 A | 12/1995 | Samulski et al. |
| 5,512,269 A | 4/1996 | Molina y Vedia et al. |
| 5,604,090 A | 2/1997 | Alexander et al. |
| 5,628,984 A | 5/1997 | Boucher, Jr. |
| 5,635,160 A | 6/1997 | Stutts, III et al. |
| 5,651,957 A | 7/1997 | Molina y Vedia et al. |
| 5,656,256 A | 8/1997 | Boucher et al. |
| 5,658,772 A | 8/1997 | Odell et al. |
| 5,683,675 A | 11/1997 | Molina y Vedia et al. |
| 5,691,176 A | 11/1997 | Lebkowski et al. |
| 5,716,931 A | 2/1998 | Molina y Vedia et al. |
| 5,725,842 A | 3/1998 | Boucher, Jr. et al. |
| 5,801,030 A | 9/1998 | McVey et al. |
| 5,831,068 A | 11/1998 | Nair et al. |
| 5,834,182 A | 11/1998 | Alexander et al. |
| 5,843,742 A | 12/1998 | Natsoulis et al. |
| 5,849,706 A | 12/1998 | Molina y Vedia et al. |
| 5,853,716 A | 12/1998 | Tattersall et al. |
| 5,855,918 A | 1/1999 | Mrsny et al. |
| 5,869,305 A | 2/1999 | Samulski et al. |
| 5,876,700 A | 3/1999 | Boucher, Jr. et al. |
| 5,902,567 A | 5/1999 | Boucher, Jr. |
| 5,916,803 A | 6/1999 | Sedlacek et al. |
| 5,935,555 A | 8/1999 | Stutts, III et al. |
| 5,990,137 A | 11/1999 | Ternansky et al. |
| 6,022,527 A | 2/2000 | Boucher, Jr. et al. |
| 6,033,688 A | 3/2000 | Mrsny et al. |
| 6,037,177 A | 3/2000 | Snyder |
| 6,083,702 A | 7/2000 | Mitchell et al. |
| 6,083,713 A | 7/2000 | Manly et al. |
| 6,110,744 A | 8/2000 | Fang et al. |
| 6,133,247 A | 10/2000 | Boucher, Jr. |
| 6,143,279 A | 11/2000 | Boucher, Jr. et al. |
| 6,153,436 A | 11/2000 | Hermonat et al. |
| 6,156,303 A | 12/2000 | Russell et al. |
| 6,200,560 B1 | 3/2001 | Couto et al. |
| 6,214,536 B1 | 4/2001 | Boucher, Jr. |
| 6,221,349 B1 | 4/2001 | Couto et al. |
| 6,235,266 B1 | 5/2001 | Stutts, III et al. |
| 6,264,975 B1 | 7/2001 | Boucher, Jr. |

(Continued)

FOREIGN PATENT DOCUMENTS

| | | |
|---|---|---|
| AU | 4091299 | 12/1999 |
| AU | 0759093 | 4/2003 |

(Continued)

OTHER PUBLICATIONS

Huang (PLoS Pathog 8(8): e1002899, p. 1-14, 2012 (Year: 2012).*
Shen et al Journal of Virology, 89, 19, 10097-10109 (Year: 2015).*
Sun et al J Virol 83:3956-3967 (Year: 2009).*
NCBI accession No. NC_029300.1, pp. 1-4 (Year: 2018).*
NCBI accession No. NC_055487, pp. 1-4 (Year: 2021).*
Paik et al J of Microbiology 12(4): e79145., 1-8 (Year: 2019).*
"U.S. Appl. No. 15/822,956, Final Office Action mailed Sep. 23, 2019", 9 pgs.

(Continued)

*Primary Examiner* — Anoop K Singh
(74) *Attorney, Agent, or Firm* — Schwegman Lundberg & Woessner, P.A.

(57) ABSTRACT

A recombinant mutant BoV genome is provided, as well as methods of using the vector, e.g., to prepare helper-free virus.

Figure 1A:
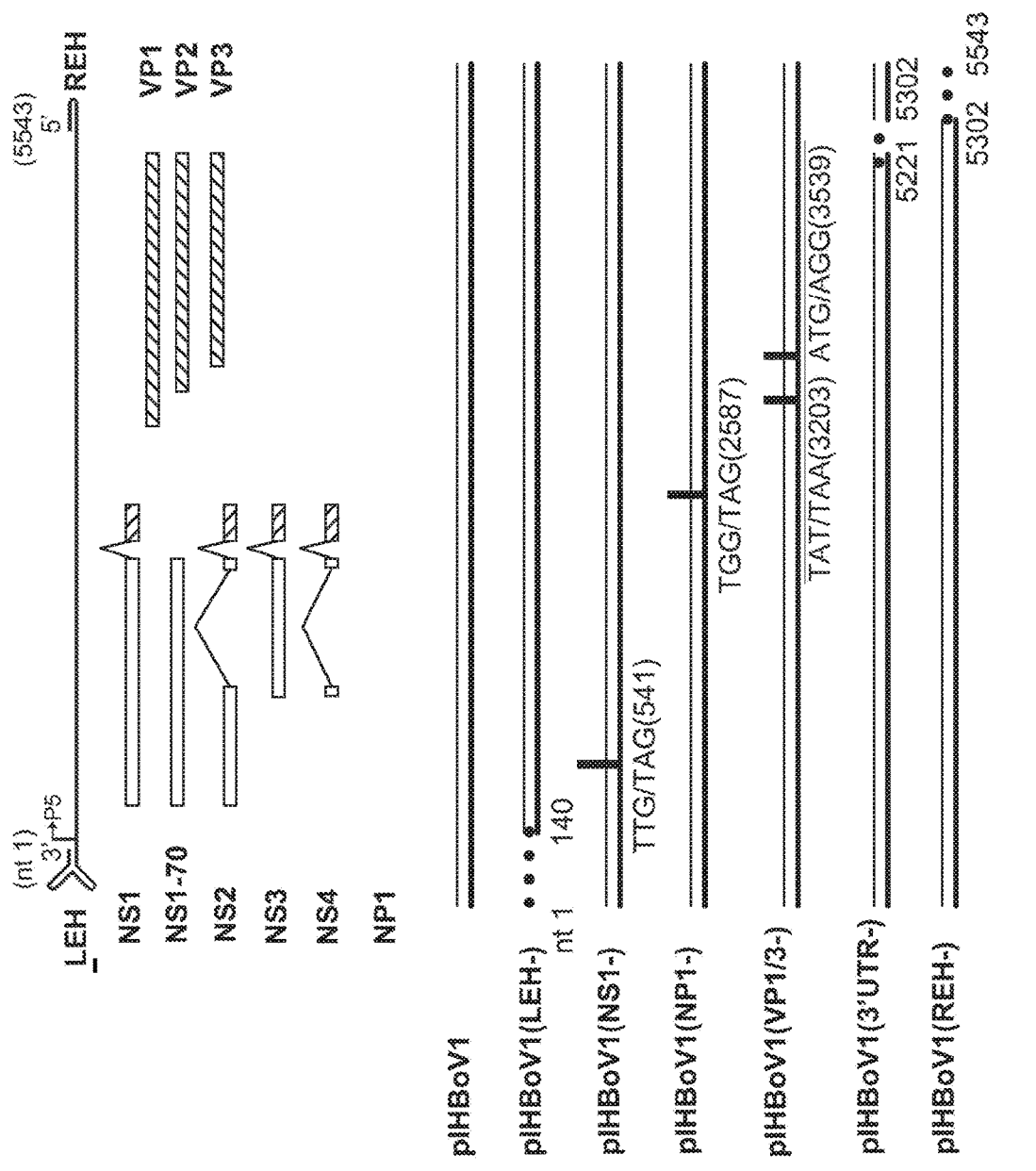

16 Claims, 31 Drawing Sheets
Specification includes a Sequence Listing.

(56) References Cited

U.S. PATENT DOCUMENTS

| | | |
|---|---|---|
| 6,270,996 B1 | 8/2001 | Wilson et al. |
| 6,287,569 B1 | 9/2001 | Kipps et al. |
| 6,290,951 B1 | 9/2001 | Mikulski et al. |
| 6,323,187 B1 | 11/2001 | Yerxa et al. |
| 6,329,181 B1 | 12/2001 | Xiao et al. |
| 6,358,524 B1 | 3/2002 | Sedlacek et al. |
| 6,416,759 B1 | 7/2002 | Firestone et al. |
| 6,420,347 B1 | 7/2002 | Jacobus et al. |
| 6,436,392 B1 | 8/2002 | Engelhardt et al. |
| 6,451,288 B1 | 9/2002 | Boucher, Jr. et al. |
| 6,468,771 B1 | 10/2002 | Einerhand et al. |
| 6,475,509 B1 | 11/2002 | Boucher, Jr. |
| 6,475,537 B1 | 11/2002 | King et al. |
| 6,485,950 B1 | 11/2002 | Kumar et al. |
| 6,491,907 B1 | 12/2002 | Rabinowitz et al. |
| 6,492,429 B1 | 12/2002 | Graus et al. |
| 6,521,225 B1 | 2/2003 | Srivastava et al. |
| 6,544,786 B1 | 4/2003 | Xiao et al. |
| 6,586,416 B2 | 7/2003 | Bubien |
| 6,596,535 B1 | 7/2003 | Carter |
| 6,602,667 B1 | 8/2003 | Walker et al. |
| 6,607,741 B2 | 8/2003 | Boucher, Jr. |
| 6,613,345 B2 | 9/2003 | Boucher, Jr. |
| 6,630,344 B1 | 10/2003 | Fang et al. |
| 6,642,051 B1 | 11/2003 | Lynch et al. |
| 6,670,365 B1 | 12/2003 | Gallemi et al. |
| 6,855,549 B1 | 2/2005 | McCray, Jr. et al. |
| 6,897,045 B2 | 5/2005 | Engelhardt et al. |
| 7,060,497 B2 | 6/2006 | Nakai et al. |
| 7,067,659 B2 | 6/2006 | Stamler et al. |
| 7,122,335 B1 | 10/2006 | Engelhardt et al. |
| 7,125,717 B2 | 10/2006 | Carter |
| 7,129,374 B2 | 10/2006 | Weissbach et al. |
| 7,241,447 B1 | 7/2007 | Engelhardt et al. |
| 7,339,046 B2 | 3/2008 | Welsh et al. |
| 7,749,491 B2 | 7/2010 | Engelhardt et al. |
| 7,803,622 B2 | 9/2010 | Engelhardt et al. |
| 8,110,350 B2 | 2/2012 | Allander et al. |
| 8,241,622 B2 | 8/2012 | Engelhardt et al. |
| 8,846,030 B2 | 9/2014 | Engelhardt et al. |
| 9,828,587 B2 | 11/2017 | Yan et al. |
| 10,793,835 B2 | 10/2020 | Yan et al. |
| 11,142,775 B2 | 10/2021 | Yan et al. |
| 11,684,679 B2 | 6/2023 | Engelhardt et al. |
| 11,702,672 B2 | 7/2023 | Yan et al. |
| 2001/0034349 A1 | 10/2001 | Boucher, Jr. |
| 2001/0041682 A1 | 11/2001 | Stutts, III et al. |
| 2001/0051611 A1 | 12/2001 | Srivastava et al. |
| 2002/0045264 A1 | 4/2002 | During et al. |
| 2002/0076754 A1 | 6/2002 | Sun et al. |
| 2002/0095135 A1 | 7/2002 | Meeker et al. |
| 2002/0099023 A1 | 7/2002 | Boucher, Jr. |
| 2002/0115619 A1 | 8/2002 | Rubenstein et al. |
| 2002/0128203 A1 | 9/2002 | Schild |
| 2002/0131956 A1 | 9/2002 | Walsh et al. |
| 2002/0132770 A1 | 9/2002 | Caplan et al. |
| 2002/0137017 A1 | 9/2002 | Aronheim |
| 2002/0156057 A1 | 10/2002 | Bubien |
| 2002/0158255 A1 | 10/2002 | Boucher, Jr. |
| 2002/0164783 A1 | 11/2002 | Feldhaus |
| 2002/0165239 A1 | 11/2002 | Boucher, Jr. |
| 2002/0197237 A1 | 12/2002 | Engelhardt et al. |
| 2003/0003583 A1 | 1/2003 | Hirsch et al. |
| 2003/0053990 A1 | 3/2003 | Rabinowitz et al. |
| 2003/0087818 A1 | 5/2003 | Jiang et al. |
| 2003/0103939 A1 | 6/2003 | Engelhardt et al. |
| 2003/0108920 A1 | 6/2003 | Zhang et al. |
| 2003/0148506 A1 | 8/2003 | Kotin |
| 2003/0166284 A1 | 9/2003 | Srivastava et al. |
| 2004/0029106 A1 | 2/2004 | Samulski et al. |
| 2004/0235947 A1 | 11/2004 | Paquin et al. |
| 2004/0248301 A1 | 12/2004 | Engelhardt et al. |
| 2005/0037497 A1 | 2/2005 | Engelhardt et al. |
| 2005/0095225 A1 | 5/2005 | Engelhardt et al. |
| 2005/0158281 A1 | 7/2005 | Chamberlain et al. |
| 2005/0181423 A1 | 8/2005 | Barak et al. |
| 2005/0239807 A1 | 10/2005 | Stamler et al. |
| 2005/0255087 A1 | 11/2005 | Engelhardt et al. |
| 2006/0093585 A1 | 5/2006 | Engelhardt et al. |
| 2007/0110724 A1 | 5/2007 | Samulski et al. |
| 2007/0265350 A1 | 11/2007 | Engelhardt et al. |
| 2008/0166758 A1 | 7/2008 | Engelhardt et al. |
| 2008/0206198 A1 | 8/2008 | Engelhardt et al. |
| 2008/0206792 A1 | 8/2008 | Engelhardt et al. |
| 2008/0213221 A1 | 9/2008 | Engelhardt et al. |
| 2008/0226600 A1 | 9/2008 | Engelhardt et al. |
| 2008/0249050 A1 | 10/2008 | Engelhardt et al. |
| 2008/0261201 A1 | 10/2008 | Engelhardt et al. |
| 2008/0292654 A1 | 11/2008 | Allander et al. |
| 2009/0017062 A1 | 1/2009 | Engelhardt et al. |
| 2009/0202490 A1 | 8/2009 | Schaffer et al. |
| 2009/0239243 A1 | 9/2009 | Engelhardt et al. |
| 2009/0241206 A1 | 9/2009 | Sun et al. |
| 2009/0265796 A1 | 10/2009 | Engelhardt et al. |
| 2009/0297557 A1 | 12/2009 | Delwart et al. |
| 2011/0014723 A1 | 1/2011 | Erdman et al. |
| 2011/0054247 A1 | 3/2011 | Sun et al. |
| 2013/0012574 A1 | 1/2013 | Monahan et al. |
| 2015/0259395 A1 | 9/2015 | Chalberg et al. |
| 2016/0068821 A1 | 3/2016 | Yan et al. |
| 2018/0127471 A1 | 5/2018 | Keravala |
| 2018/0282684 A1 | 10/2018 | Kaspar |
| 2018/0282702 A1 | 10/2018 | Yan et al. |
| 2018/0371496 A1 | 12/2018 | Li et al. |
| 2019/0083657 A1 | 3/2019 | Engelhardt et al. |
| 2019/0338312 A1 | 11/2019 | Yan et al. |
| 2021/0079421 A1 | 3/2021 | Yan et al. |
| 2021/0130413 A1 | 5/2021 | Keravala |
| 2021/0255170 A1 | 8/2021 | Engelhardt et al. |
| 2022/0154213 A1 | 5/2022 | Yan et al. |
| 2022/0195461 A1 | 6/2022 | Engelhardt et al. |
| 2022/0241436 A1 | 8/2022 | Engelhardt et al. |
| 2023/0242941 A1 | 8/2023 | Tang et al. |
| 2024/0002882 A1 | 1/2024 | Yan et al. |
| 2024/0066147 A1 | 2/2024 | Engelhardt et al. |

FOREIGN PATENT DOCUMENTS

| | | |
|---|---|---|
| AU | 0784420 | 3/2006 |
| AU | 2017229347 A1 | 11/2018 |
| AU | 2014251099 B2 | 1/2019 |
| AU | 2020289851 B2 | 11/2023 |
| CA | 2302627 | 9/2001 |
| CA | 2328447 | 4/2007 |
| CA | 3019315 A1 | 10/2016 |
| CA | 3016985 C | 7/2023 |
| CA | 2909085 C | 8/2023 |
| CN | 105142676 A | 12/2015 |
| CN | 105431170 A | 3/2016 |
| CN | 106414474 A | 2/2017 |
| CN | 106928336 A | 7/2017 |
| CN | 105431170 B | 10/2019 |
| CN | 110650733 A | 1/2020 |
| CN | 114340683 A | 4/2022 |
| CN | 114641318 A | 6/2022 |
| EA | 201892006 A1 | 4/2019 |
| EA | 202192819 A1 | 2/2022 |
| EA | 202192818 A1 | 3/2022 |
| EP | 0041682 A1 | 12/1981 |
| EP | 0132770 A1 | 2/1985 |
| EP | 0158255 A2 | 10/1985 |
| EP | 1153612 A1 | 11/2001 |
| EP | 1486567 A1 | 12/2004 |
| EP | 3426787 A1 | 1/2019 |
| EP | 2983707 B1 | 6/2019 |
| HK | 1217916 B | 9/2020 |
| IN | 10078DELNP2015 A | 4/2016 |
| JP | 2002538770 A | 11/2002 |
| JP | 2003501068 | 1/2003 |
| JP | 2003201255 | 7/2003 |
| JP | 2006521825 A | 9/2006 |
| JP | 4969002 | 4/2012 |
| JP | 2013518899 A | 5/2013 |
| JP | 2016518121 A | 6/2016 |

(56) References Cited

FOREIGN PATENT DOCUMENTS

| | | | |
|---|---|---|---|
| JP | 6516725 B2 | 4/2019 | |
| JP | 2022529457 A | 6/2022 | |
| JP | 2022529470 A | 6/2022 | |
| JP | 2023126658 A | 9/2023 | |
| VN | 92403 A | 1/2023 | |
| VN | 92404 A | 1/2023 | |
| WO | WO-9413788 A1 | 6/1994 | |
| WO | WO-9507351 A1 | 3/1995 | |
| WO | WO-9513365 A1 | 5/1995 | |
| WO | WO-9515384 A1 | 6/1995 | |
| WO | WO-9522323 A1 | 8/1995 | |
| WO | WO-9610402 A1 | 4/1996 | |
| WO | WO-9722250 A1 | 6/1997 | |
| WO | WO-9809657 A2 | 3/1998 | |
| WO | WO-9824479 A1 | 6/1998 | |
| WO | WO-9853839 A2 | 12/1998 | |
| WO | WO-9918227 A1 | 4/1999 | |
| WO | WO-9920773 A2 | 4/1999 | |
| WO | WO-9932647 A1 | 7/1999 | |
| WO | WO-9960146 A1 | 11/1999 | |
| WO | WO-9961601 A2 | 12/1999 | |
| WO | WO-0047220 A1 | 2/2000 | |
| WO | WO-0028004 A1 | 5/2000 | |
| WO | WO-0038709 A1 | 7/2000 | |
| WO | WO-0065038 A2 | 11/2000 | |
| WO | WO-0075365 A2 | 12/2000 | |
| WO | WO-0075365 A3 | 12/2000 | |
| WO | WO-0183692 A2 | 1/2001 | |
| WO | WO-0125465 A1 | 4/2001 | |
| WO | WO-01025465 A1 | 4/2001 | |
| WO | WO-0168888 A2 | 9/2001 | |
| WO | WO-0192551 A2 | 12/2001 | |
| WO | WO-0212525 A2 | 2/2002 | |
| WO | WO-0214526 A2 | 2/2002 | |
| WO | WO-0224172 A1 | 3/2002 | |
| WO | WO-0224177 A2 | 3/2002 | |
| WO | WO-02087306 A2 | 11/2002 | |
| WO | WO-03006616 A2 | 1/2003 | |
| WO | WO-03006990 A1 | 1/2003 | |
| WO | WO-03042361 A2 | 5/2003 | |
| WO | WO-03057847 A2 | 7/2003 | |
| WO | WO-03087399 A1 | 10/2003 | |
| WO | WO-03095667 A2 | 11/2003 | |
| WO | WO-03104392 A1 | 12/2003 | |
| WO | WO-2004010045 A1 | 1/2004 | |
| WO | WO-04064844 A1 | 8/2004 | |
| WO | WO-2004064844 A1 | 8/2004 | |
| WO | WO-04089423 A2 | 10/2004 | |
| WO | WO-04089423 A3 | 10/2004 | |
| WO | WO-4090145 A2 | 10/2004 | |
| WO | WO-04090145 A3 | 10/2004 | |
| WO | WO-2004090145 A2 | 10/2004 | |
| WO | WO-2004112727 A2 | 12/2004 | |
| WO | WO-2005056762 A2 | 6/2005 | |
| WO | WO-05111220 A2 | 11/2005 | |
| WO | WO-2005105806 A1 | 11/2005 | |
| WO | WO-2005111220 A3 | 11/2005 | |
| WO | WO-2005116224 A2 | 12/2005 | |
| WO | WO-2005119251 A2 | 12/2005 | |
| WO | WO-2006009975 A2 | 1/2006 | |
| WO | WO-20060009975 A1 | 1/2006 | |
| WO | WO-2006116503 A2 | 11/2006 | |
| WO | WO-2007079141 A2 | 7/2007 | |
| WO | WO-2007079141 C2 | 7/2007 | |
| WO | WO-2007127464 A2 | 11/2007 | |
| WO | WO-2007127464 A3 | 11/2007 | |
| WO | WO-2008034637 A1 | 3/2008 | |
| WO | WO-2008133904 A1 | 11/2008 | |
| WO | WO-2009028387 A1 | 3/2009 | |
| WO | WO-2011097456 A2 | 8/2011 | |
| WO | WO-2014168953 A1 * | 10/2014 | ............. A61P 11/00 |
| WO | WO-2015164758 A1 | 10/2015 | |
| WO | WO-2016118787 A1 | 7/2016 | |
| WO | WO-2017139381 A1 | 8/2017 | |
| WO | WO-2017155973 A1 | 9/2017 | |
| WO | WO-2017205739 A1 | 11/2017 | |
| WO | WO2018132747 | 7/2018 | |
| WO | WO-2018170310 A1 | 9/2018 | |
| WO | WO-2019178267 A2 | 9/2019 | |
| WO | WO-2019178267 A3 | 9/2019 | |
| WO | WO-2020214668 A1 | 10/2020 | |
| WO | WO-2020214672 A1 | 10/2020 | |
| WO | WO-2022006253 A2 | 1/2022 | |
| WO | WO-2022006253 A3 | 1/2022 | |

OTHER PUBLICATIONS

"U.S. Appl. No. 15/822,956, Non Final Office Action mailed May 8, 2019", 16 pgs.

"U.S. Appl. No. 15/822,956, Response filed Aug. 8, 2019 to Non-Final Office Action mailed May 8, 2019", 9 pgs.

"U.S. Appl. No. 16/477,762, Preliminary Amendment filed Jul. 12, 2019", 8 pgs.

"Canadian Application Serial No. 2909085, Voluntary Amendment Filed Sep. 6, 2019", 4 pgs.

"International Application Serial No. PCT/US2018/013634, International Preliminary Report on Patentability mailed Jul. 25, 2019", 12 pgs.

Ginn, S. L., et al., "Gene therapy clinical trials worldwide to 2012—an update.", J Gene Med, 15(2), (2013), 65-77.

Guido, et al., "", World Journal of Gastroenterology, (2016), 8684-8697.

Kapoor, A., et al., "Human bocaviruses are highly diverse, dispersed, recombination prone, and prevalent enteric infections", J Infect Dis. 201(11), (Jun. 2010), 1633-1643.

Ricour, C., et al., "Human Bocavirus, A Newly Discovered Parvovirus of the Respiratory Tract", International Journal of Clinical and Laboratory Medicine, vol. 63, Issue 5, Abstract only, (2008), 329-334.

Wang, Zekun, et al., "Parvovirus Expresses a Small Noncoding RNA That Plays an Essential Role in Virus Replication", Journal of Virology, vol. 91 Issue 8, (2017), 1-20.

"U.S. Appl. No. 16/477,762, Notice of Allowance mailed Jun. 10, 2021", 8 pgs.

"Canadian Application Serial No. 2,909,085, Response filed Jun. 11, 2021 to Office Action mailed Feb. 16,—", 77 pgs.

"U.S. Appl. No. 16/477,762, Notice of Allowability mailed Jun. 28, 2021", 3 pgs.

"U.S. Appl. No. 16/076,219, Response filed Sep. 7, 2021 to Non Final Office Action mailed May 7, 2021", 8 pgs.

"U.S. Appl. No. 15/822,956, Response filed Apr. 8, 2019 to Restriction Requirement mailed Feb. 7, 2019", 6 pgs.

"U.S. Appl. No. 15/822,956, Restriction Requirement mailed Feb. 7, 2019", 9 pgs.

"Israel Application Serial No. 241954, Response filed Feb. 7, 2019 to Office Action mailed Oct. 9, 2018", w/ English Translation, 14 pgs.

"Japanese Application Serial No. 2016-507610, Notification of Reasons for Refusal mailed Jan. 24, 2019", w/ English translation, 6 pgs.

"Japanese Application Serial No. 2016-507610, Response filed Mar. 6, 2019 to Notification of Reasons for Refusal mailed Jan. 24, 2019", w/o English Translation, 5 pgs.

"International Application Serial No. PCT/US2017/034678, International Search Report mailed Oct. 16, 2017", 7 pgs.

"International Application Serial No. PCT/US2017/034678, Written Opinion mailed Oct. 16, 2017", 6 pgs.

Gao, Feng, et al., "DNA-guided genome editing using the Natronobacterium gregoryi Argonaute", In Journal of Nature Biotechnology Advance Online Publication, (May 2, 2016), 1-7.

Haung, Qinfeng, et al., "Establishment of a Reverse Genetics System for Studying Human Bocavirus in Human Airway Epithella", Journal PLOS Pathogens vol. 8(8), (2012), 1-14.

Shen, Weiran, et al., "Analysis of cis and trans Requirements for DNA Replication at the Right-End Hairpin of the Human Bocavirus 1 Genome", Journal of Virology 90.17, (2016), 7761-7777.

Wei, Ran Shen, et al., "Identification and functional analysis of novel nonstructural proteins of human bocavirus 1", Journal of Virology., vol. 89, No. 19, (Oct. 1, 2015), 10097-10109.

(56) References Cited

OTHER PUBLICATIONS

Y, Sun, et al., "Molecular Characterization of Infectious Clones of the Minute Virus of Canines Reveals Unique Features of Bocaviruse", Journal of Virology vol. 83 No. 8, (Feb. 11, 2009), 3956-3967.
Zou, Wei, et al., "Nonstructural Protein NP1 of Human Bocavirus 1 Plays Critical Role in the Expression of Viral Capsid Protein", Journal of Virology May 2016 vol. 90 No. 9, (Feb. 18, 2016), 4658-4669.
"U.S. Appl. No. 16/076,219, Non Final Office Action mailed May 7, 2021", 19 pgs.
"U.S. Appl. No. 16/076,219, Response filed Apr. 6, 2021 to Restriction Requirement mailed Feb. 5, 2021", 7 pgs.
"U.S. Appl. No. 16/076,219, Restriction Requirement mailed Feb. 5, 2021", 8 pgs.
"U.S. Appl. No. 16/477,762, Non Final Office Action mailed Jan. 27, 2021", 13 pgs.
"U.S. Appl. No. 16/477,762, Response filed Apr. 27, 2021 to Non Final Office Action mailed Jan. 27, 2021", 8 pgs.
"U.S. Appl. No. 16/477,762, Response filed Oct. 7, 2020 to Restriction Requirement mailed Aug. 25, 2020", 8 pgs.
"U.S. Appl. No. 16/477,762, Restriction Requirement mailed Aug. 25, 2020", 12 pgs.
"Canadian Application Serial No. 2,909,085, Office Action mailed Feb. 16, 2021", 4 pgs.
"Canadian Application Serial No. 2,909,085, Response filed Jul. 30, 2020 to Office Action mailed Apr. 2, 2020", 29 pgs.
Allander, Tobias, et al., "Cloning of a human parvovirus by molecular screening of respiratory tract samples", PNAS, 102(36), (2005), 12891-12896.
Arnold, John, et al., "Human Bocavirus: Prevalence and Clinical Spectrum at a Children's Hospital", Clin Infect Dis. 43, (2006), 283-288.
Denby, L., et al., "Adeno-associated virus (AAV)-7 and -8 poorly transduce vascular endothelial cells and are sensitive to proteasomal degradation.", Gene Ther., 12(20), (Oct. 2005), 1534-8.
Douar, A., et al., "Intracellular trafficking of adeno-associated virus vectors: routing to the late endosomal compartment and proteasome degradation.", J Virol., 75(4), (Feb. 2001), 1824-33.
Hermonat, Paul, et al., "Use of adeno-associated virus as a mammalian DNA cloning vector: Transduction of neomycin resistance into mammalian tissue culture cells", Proc. Natl. Acad. Sci. USA, vol. 81, (Oct. 1984), 6466-6470.
Iwane, Marika, et al., "(Abstract) Population-based surveillance for hospitalizations associated with respiratory syncytial virus, influenza virus, and parainfluenza viruses among young children,", Pediatrics, 113 (6) . pp. 1758-1764, (2004), 2 pgs.
Jennings, K., et al., "Proteasome inhibition enhances AAV-mediated transgene expression in human synoviocytes in vitro and in vivo", Mol Ther., 11(4), (Apr. 2005), 600-7.
Ma, Xiaoming, et al., "Detection of Human Bocavirus in Japanese Children with Lower Respiratory Tract Infections", J Clin Microbiol, 44, (2006), 1132-1134.
Muzyczka, N., "Use of Adeno-Associated Virus as a General Transduction Vector for Mammalian Cells", In: Current Topics in Microbiology and Immunology, 158, Springer-Verlag, Berlin: R.W. Compans, et al., (Eds.), (1992), pp. 97-129.
Pratelli, Annamaria, et al., "Host range of Canine minute virus in cell culture", Journal of Veterinary Diagnostic Investigation 24(5), (Jul. 23, 2012), 981-985.
Salganik, Max, et al., "Adeno-associated Virus as a Mammalian DNA Vector", Microbiol. Spectr., 3:10.1128, (Aug. 2015), 32 pgs.
Shay, David, et al., "Bronchiolitis-Associated Hospitalizations Among US Children, 1980-1996", JAMA, vol. 282, No. 15, (1999), 1440-1446.
Sloots, Theo, et al., "Evidence of human coronavirus HKU1 and human bocavirus in Australian Children", J Clin Virol, 35, (2006), 99-102.
Wang, Jiali, et al., "Identification of a novel bocaparvovirus in a wild squirrel in Kunming, Yunnan Province, China", Archives of Virology 165, (2020), 1469-1474.

Wang, Zekun, et al., "Development of a Novel Recombinant Adeno-Associated Virus Production System Using Human Bocavirus 1 Helper Genes", Molecular Therapy: Methods & Clinical Development vol. 11, (Dec. 2018), 40-51.
Wu, Jihong, et al., "Enhanced transduction and improved photoreceptor survival of retinal degeneration by the combinatorial use of rAAV2 with a lower dose of adenovirus", Vision Research 48, (2008), 1648-1654.
Zhang, Chi, et al., "Identification and characterization of a novel rodent bocavirus from different rodent species in China", Emerging Microbes & Infections 7:48, (2018), 11 pgs.
Zinn, Eric, et al., "Adeno-associated Virus: Fit to serve", Curr Opin Virol., (Oct. 2014), 13 pgs.
"U.S. Appl. No. 15/822,956, Notice of Allowance mailed Jun. 1, 2020", 5 pgs.
"U.S. Appl. No. 15/822,956, Notice of Allowance mailed Dec. 18, 2019", 8 pgs.
"U.S. Appl. No. 15/822,956, Response Filed Nov. 22, 2019 to Final Office Action mailed Sep. 23, 2019", 8 pgs.
"Canadian Application Serial No. 2,909,085, Office Action mailed Apr. 2, 2020", 5 pgs.
"Indian Application Serial No. 10078/DELNP/2015, First Examination Report mailed Mar. 12, 2020", w/ English Translation, 8 pgs.
"Israel Application Serial No. 241954, Office Action mailed Dec. 5, 2019", w/ English Translation, 6 pgs.
"New Zealand Application Serial No. 713509, First Examiner Report mailed Nov. 14, 2019", 7 pgs.
Fakhiri, Julia, et al., "Novel Chimeric Gene Therapy Vectors Based on Adeno-Associated Virus and Four Different Mammalian Bocaviruses", Molecular Therapy: Methods & Clinical Development vol. 12, (Mar. 2019), 202-222.
Yan, Ziying, et al., "Human Bocavirus Type-1 Capsid Facilitates the Transduction of Ferret Airways by Adeno-Associated Virus Genomes", Human Gene Therapy, vol. 28, No. 8, (2017), 612-625.
"U.S. Appl. No. 14/782,876, Non Final Office Action mailed Feb. 16, 2017", 10 pgs.
"U.S. Appl. No. 14/782,876, Notice of Allowance mailed Jul. 25, 2017", 8 pgs.
"U.S. Appl. No. 14/782,876, Preliminary Amendment filed Oct. 7, 2015", 9 pgs.
"U.S. Appl. No. 14/782,876, Response filed Jan. 11, 2017 to Restriction Requirement mailed Oct. 14, 2016", 8 pgs.
"U.S. Appl. No. 14/782,876, Response filed Jun. 16, 2017 to Non Final Office Action mailed Feb. 16, 2017", 8 pgs.
"U.S. Appl. No. 14/782,876, Restriction Requirement mailed Oct. 14, 2016", 10 pgs.
"U.S. Appl. No. 15/822,956, Preliminary Amendment filed Nov. 27, 2017", 3 pgs.
"U.S. Appl. No. 15/822,956, Supplemental Preliminary Amendment filed Apr. 23, 2018", 9 pgs.
"Australian Application Serial No. 2014251099, First Examination Report mailed May 30, 2018", 4 pgs.
"Australian Application Serial No. 2014251099, Response filed Dec. 19, 2018 to Examiner's Report mailed May 30, 2018", 39 pgs.
"Chinese Application Serial No. 201480032420.6, Office Action mailed May 3, 2017", w/English Translation of Claims, 20 pgs.
"Chinese Application Serial No. 201480032420.6, Office Action mailed Jul. 13, 2018", w/English translation, 8 pgs.
"Chinese Application Serial No. 201480032420.6, Office Action mailed Dec. 14, 2017", (English Translation), 8 pgs.
"Chinese Application Serial No. 201480032420.6, Response filed Feb. 27, 2018 to Office Action mailed Dec. 14, 2017", w/ Amended Claims, 73 pgs.
"Chinese Application Serial No. 201480032420.6, Response filed Sep. 18, 2017 to Office Action mailed May 3, 2017", w/English Claims, 25 pgs.
"Chinese Application Serial No. 201480032420.6, Response filed Nov. 26, 2018 to Office Action mailed Jul. 13, 2018", w/ English Claims, 73 pgs.
"European Application Serial No. 14783418.8, Communication Pursuant to Article 94(3) EPC mailed Mar. 27, 2018", 4 pgs.
"European Application Serial No. 14783418.8, Extended European Search Report mailed Feb. 27, 2017", 15 pgs.

(56) References Cited

OTHER PUBLICATIONS

"European Application Serial No. 14783418.8, Response filed May 26, 2016", 13 pgs.
"European Application Serial No. 14783418.8, Response filed May 30, 2018 to Communication Pursuant to Article 94(3) EPC mailed Mar. 27, 2018", 271 pgs.
"European Application Serial No. 14783418.8, Response filed Sep. 22, 2017", 11 pgs.
"International Application Serial No. PCT/US2014/033343, International Preliminary Report on Patentability mailed Oct. 13, 2015", 12 pgs.
"International Application Serial No. PCT/US2014/033343, International Search Report mailed Sep. 2, 2014", 4 pgs.
"International Application Serial No. PCT/US2014/033343, Written Opinion mailed Sep. 2, 2014", 10 pgs.
"International Application Serial No. PCT/US2017/017021, International Preliminary Report on Patentability mailed Aug. 23, 2018", 12 pgs.
"International Application Serial No. PCT/US2017/017021, International Search Report mailed May 23, 2017", 8 pgs.
"International Application Serial No. PCT/US2017/017021, Written Opinion mailed May 23, 2017", 10 pgs.
"International Application Serial No. PCT/US2017/034678, International Preliminary Report on Patentability mailed Dec. 6, 2018", 9 pgs.
"International Application Serial No. PCT/US2018/013634, International Search Report mailed Jun. 18, 2018", 9 pgs.
"International Application Serial No. PCT/US2018/013634, Invitation to Pay Add'l Fees and Partial Search Report mailed Apr. 17, 2018", 14 pgs.
"International Application Serial No. PCT/US2018/013634, Written Opinion mailed Jun. 18, 2018", 12 pgs.
"Israel Application Serial No. 241954, Office Action mailed Oct. 9, 2018", W/English Translation, 10 pgs.
"Japanese Application Serial No. 2016-507610, Office Action mailed Feb. 21, 2018", with English translation of claims, 16 pgs.
"Japanese Application Serial No. 2016-507610, Response filed Aug. 21, 2018 to Office Action mailed Feb. 21, 2018", with English translation of claims, 27 pgs.
Brown, Kevin E., "The expanding range of parvoviruses which infect humans", Reviews in Medical Virology, GB, (2010), vol. 20, No. 4, (2010), 231-244.
Cheung, Andrew K., et al., "Identification and molecular cloning of a novel porcine parvovirus", Archives of Virology ; Official Journal of the Virology Division of the International Union of Microbiological Societies, Springer-Verlag, VI, vol. 155, No. 5, (2010), 801-806.
Deng, Xuefeng, et al., "In vitro modeling of human bocavirus 1 infection of polarized primary human airway epithelia", J Virol. vol. 87, No. 7, 4097-4102, (Jan. 23, 2013), 7 pgs.
Gurda, Brittney L., et al., "Human Bocavirus Capsid Structure: Insights into the Structural Repertoire of the Parvoviridae", Journal of Virology, 84(12), (Jun. 2010), 5880-5889.
Ishiawata, Akira, et al., "Phenotype correction of hemophilia A mice with adeno-associated virus vectors carrying the B domain-deleted canine factor VIII gene", Thrombosis Research, Tarrytown, NY, US, vol. 118, No. 5, (2006), (2006), 627-635.
Julia, Fakhiri, et al., "254. New Chimeric Gene Therapy Vectors Based on Four Different Mammalian Bocaviruses", Molecular Therapy, vol. 24, No. S1, (May 1, 2016), S100.
Kapoor, Amit, et al., "Bocavirus Episome in Infected Human Tissue Contains Non-Identical Termini", PLOS One, (2011), vol. 6, No. 6, e21362, (2011), 8 pgs.
Kapoor, Amit, et al., "Identification and Characterization of a New *Bocavirus* Species in Gorillas", PLOS One, (2010), vol. 5, No. 7, p. e11948, (Jul. 2010), 6 pgs.
Li, Wuping, et al., "Generation of Novel AAV Variants by Directed Evolution for Improved CFTR Delivery to Human Ciliated Airway Epithelium", Journal of Molecular Therapy vol. 17(12), (Dec. 2009), 2067-2077.

Mihaylov, Ivailo, et al., "Complementation for an essential ancillary non-structural protein function across parvovirus genera", Virology, vols. 468-470, (2014), 226-237.
Olufemi, Fasina O, et al., "NP1 protein of the Bocaparvovirus Minute Virus of Canines controls acess to the viral capsid genes via its role in RNA processing", Journal of Virology., vol. 90, No. 4, (Dec. 4, 2015), 1718-1728.
Qinfeng, Huang, et al., "Internal polyadenylation of parvoviral precursor mRNA limits progeny virus production", Virology, Elsevier, Amsterdam, NL, vol. 426, No. 2, (Jan. 26, 2012), 167-177.
Qiu, Jianming, et al., "Characterization of the transcription profile of adeno-associated virus type 5 reveals a number of unique features compared to previously characterized adeno-associated viruses", Journal of Virol., 76, No. 24, (2002), 12435-12447.
Qiu, Jianming, et al., "The Transcription Pro?le of the Bocavirus Bovine Parvovirus Is Unlike Those of Previously Characterized Parvoviruses", Journal of Virology, vol. 81, No. 21, [Online]. Retrieved from the Internet: <URL: https://jvi.asm.org/>, (2007), 12080-12085.
Ros, C, et al., "The ubiquitin-proteasome machinery is essential for nuclear translocation of incoming minute virus of mice", Virology 324, (2004), 350-360.
Sukhu, L, et al., "Characterization of the Nonstructural Proteins of the Bocavirus Minute Virus of Canines", Journal of Virology., vol. 87, No. 2, (Nov. 7, 2012), 1098-1104.
Sun, et al., "Molecular Characterization of Infectious Clones of the Minute Virus of Canines Reveals Unique Features of Bocaviruses", Journal of Virology, 83(8), (Apr. 2009), 3956-3967.
Wei, Zou, et al., "Nonstructural Protein NP1 of Human Bocavirus 1 Plays a Critical Role in the Expression of Viral Capsid Proteins", Journal of Virology., vol. 90, No. 9, (May 1, 2016), 4658-4669.
Xuefeng, Deng, et al., "DNA Damage Signaling Is Required for Replication of Human Bocavirus 1 DNA in Dividing HEK293 Cells", Journal of Virology, vol. 91 No. 1, (Jan. 1, 2017), 20 pgs.
Xuefeng, Deng, et al., "Replication of an Autonomous Human Parvovirus in Non-dividing Human Airway Epithelium Is Facilitated through the DNA Damage and Repair Pathways", PLOS Pathogens vol. 12 No. 1, (U.S. Appl. No. 01/142,016), 25 pgs.
Yan, Z, et al., "A Novel Chimeric Adenoassociated Virus 2/ Human Bocavirus 1 Parvovirus Vector Ef?ciently Transduces Human Airway Epithelia", Molecular Therapy, vol. 21 No. 12, (Dec. 2013), 2181-2194.
Yan, Z., et al., "A novel chimeric adenoassociated virus 2/human bocavirus 1 parvovirus vector efficiently transduces human airway epithelia", Mol Ther. vol. 21, No. 12, (Jul. 30, 2013), 2181-2194.
Yang, Wan-Zhu, et al., "Genome characterization of a novel porcine bocavirus", Archives of Virology ; Official Journal of the Virology Divisionof the International Union of Microbiological Societies, Springer-Verlag, VI, (2012), vol. 157, No. 11,, (Jul. 21, 2012), 2125-2132.
"U.S. Appl. No. 09/276,625, 312 Amendment filed Jan. 10, 2002", 2 pgs.
"U.S. Appl. No. 09/276,625, Non Final Office Action mailed Feb. 13, 2001", 9 pgs.
"U.S. Appl. No. 09/276,625, Notice of Allowance mailed Oct. 10, 2001", 8 pgs.
"U.S. Appl. No. 09/276,625, Preliminary Amendment filed Jul. 20, 2000", 2 pgs.
"U.S. Appl. No. 09/276,625, PTO Response to 312 Amendment mailed May 15, 2002", 2 pgs.
"U.S. Appl. No. 09/276,625, Response filed Aug. 13, 2001 to Non Final Office Action mailed Feb. 13, 2001", 10 pgs.
"U.S. Appl. No. 09/276,625, Response filed Nov. 20, 2000 to Restriction Requirement mailed Sep. 14, 2000", 5 pgs.
"U.S. Appl. No. 09/276,625, Restriction Requirement mailed Sep. 14, 2000", 5 pgs.
"U.S. Appl. No. 09/684,554, Examiner Interview Summary mailed May 17, 2005", 3 pgs.
"U.S. Appl. No. 09/684,554, Examiner Interview Summary mailed Jun. 27, 2003", 2 pgs.
"U.S. Appl. No. 09/684,554, Examiner Interview Summary mailed Sep. 7, 2004", 3 pgs.

(56) References Cited

OTHER PUBLICATIONS

"U.S. Appl. No. 09/684,554, Final Office Action mailed Apr. 19, 2004", 10 pgs.
"U.S. Appl. No. 09/684,554, Final Office Action mailed Apr. 19, 2004", 14 pgs.
"U.S. Appl. No. 09/684,554, Final Office Action mailed Nov. 15, 2005", 11 pgs.
"U.S. Appl. No. 09/684,554, Final Office Action mailed Nov. 15, 2005", 10 pgs.
"U.S. Appl. No. 09/684,554, Non-Final Office Action mailed Feb. 25, 2005", 9 pgs.
"U.S. Appl. No. 09/684,554, Non-Final Office Action mailed Mar. 11, 2003", 14 pgs.
"U.S. Appl. No. 09/684,554, Non-Final Office Action mailed Mar. 11, 2003", 10 pgs.
"U.S. Appl. No. 09/684,554, Non-Final Office Action mailed Jul. 20, 2006", 9 pgs.
"U.S. Appl. No. 09/684,554, Non-Final Office Action Mailed Jul. 20, 2006", 10 pgs.
"U.S. Appl. No. 09/684,554, Notice of Allowance mailed Mar. 2, 2007", 9 pgs.
"U.S. Appl. No. 09/684,554, Notice of Allowance mailed Mar. 2, 2007", 7 pgs.
"U.S. Appl. No. 09/684,554, Response filed Apr. 10, 2006 to Final Office Action mailed Nov. 15, 2005", 14 pgs.
"U.S. Appl. No. 09/684,554, Response filed Jun. 4, 2002 to Restriction Requirement mailed Dec. 4, 2001", 6 pgs.
"U.S. Appl. No. 09/684,554, Response filed Aug. 11, 2003 to Non Final Office Action mailed Mar. 11, 2003", 13 pgs.
"U.S. Appl. No. 09/684,554, Response filed Aug. 17, 2005 to Non Final Office Action mailed Feb. 25, 2005", 15 pgs.
"U.S. Appl. No. 09/684,554, Response filed Oct. 19, 2004 to Final Office Action mailed Apr. 19, 2004", 14 pgs.
"U.S. Appl. No. 09/684,554, Response filed Nov. 20, 2006 to Non Final Office Action mailed Jul. 20, 2006", 15 pgs.
"U.S. Appl. No. 09/684,554, Response filed Nov. 26, 2002 to Restriction Requirement mailed Aug. 26, 2002", 13 pgs.
"U.S. Appl. No. 09/684,554, Restriction Requirement mailed Aug. 26, 2002", 10 pgs.
"U.S. Appl. No. 09/684,554, Restriction Requirement mailed Dec. 4, 2001", 6 pgs.
"U.S. Appl. No. 09/689,136, Advisory Action mailed Nov. 3, 2004", 3 pgs.
"U.S. Appl. No. 09/689,136, Examiner Interview Summary mailed Apr. 18, 2005", 3 pgs.
"U.S. Appl. No. 09/689,136, Examiner Interview Summary mailed May 16, 2005", 3 pgs.
"U.S. Appl. No. 09/689,136, Examiner Interview Summary mailed Sep. 28, 2004", 3 pgs.
"U.S. Appl. No. 09/689,136, Final Office Action mailed Feb. 24, 2003", 11 pgs.
"U.S. Appl. No. 09/689,136, Final Office Action mailed Jun. 18, 2004", 8 pgs.
"U.S. Appl. No. 09/689,136, Non Final Office Action mailed Jan. 7, 2005", 10 pgs.
"U.S. Appl. No. 09/689,136, Non Final Office Action mailed Jun. 26, 2002", 13 pgs.
"U.S. Appl. No. 09/689,136, Non Final Office Action mailed Aug. 12, 2003", 8 pgs.
"U.S. Appl. No. 09/689,136, Notice of Allowance mailed Sep. 12, 2005", 10 pgs.
"U.S. Appl. No. 09/689,136, Preliminary Amendment filed Oct. 12, 2000", 2 pgs.
"U.S. Appl. No. 09/689,136, Response filed Jan. 12, 2004 to Non Final Office Action mailed Aug. 12, 2003", 12 pgs.
"U.S. Appl. No. 09/689,136, Response filed Apr. 11, 2002 to Restriction Requirement mailed Oct. 11, 2001", 12 pgs.
"U.S. Appl. No. 09/689,136, Response filed May 18, 2005 to Non Final Office Action mailed Jan. 7, 2005", 14 pgs.
"U.S. Appl. No. 09/689,136, Response filed May 30, 2003 to Final Office Action mailed Feb. 24, 2003", 13 pgs.
"U.S. Appl. No. 09/689,136, Response filed Oct. 18, 2004 to Final Office Action mailed Jun. 18, 2004", 13 pgs.
"U.S. Appl. No. 09/689,136, Response filed Nov. 26, 2002 to Non Final Office Action mailed Jun. 26, 2002", 14 pgs.
"U.S. Appl. No. 09/689,136, Restriction Requirement mailed Oct. 11, 2001", 9 pgs.
"U.S. Appl. No. 09/689,136, Supplemental Amendment filed Aug. 3, 2005", 13 pgs.
"U.S. Appl. No. 09/689,136, Supplemental Amendment filed Nov. 18, 2004", 11 pgs.
"U.S. Appl. No. 10/054,665, Non-Final Office Action mailed Jun. 16, 2004", 7 pgs.
"U.S. Appl. No. 10/054,665, Notice of Allowance mailed Nov. 8, 2004", 10 pgs.
"U.S. Appl. No. 10/054,665, Preliminary Amendment filed Jun. 25, 2002", 10 pgs.
"U.S. Appl. No. 10/054,665, Response filed Mar. 24, 2004 to Restriction Requirement mailed Feb. 24, 2004", 1 pg.
"U.S. Appl. No. 10/054,665, Response filed Sep. 16, 2004 to Non-Final Office Action mailed Jun. 16, 2004", 13 pgs.
"U.S. Appl. No. 10/054,665, Restriction Requirement mailed Feb. 24, 2004", 5 pgs.
"U.S. Appl. No. 10/194,421, Preliminary Amendment filed Jan. 14, 2003", 2 pgs.
"U.S. Appl. No. 10/194,421, Restriction Requirement mailed Mar. 21, 2005", 5 pgs.
"U.S. Appl. No. 10/815,262, Advisory Action mailed Aug. 14, 2008", 3 pgs.
"U.S. Appl. No. 10/815,262, Examiner Interview Summary mailed Feb. 6, 2007", 4 pgs.
"U.S. Appl. No. 10/815,262, Examiner Interview Summary mailed Mar. 30, 2009", 4 pgs.
"U.S. Appl. No. 10/815,262, Examiner Interview Summary mailed Nov. 18, 2009", 4 pgs.
"U.S. Appl. No. 10/815,262, Final Office Action mailed Apr. 23, 2008", 24 pgs.
"U.S. Appl. No. 10/815,262, Final Office Action mailed Aug. 6, 2009", 24 pgs.
"U.S. Appl. No. 10/815,262, Non Final Office Action mailed May 15, 2007", 25 pgs.
"U.S. Appl. No. 10/815,262, Non-Final Office Action mailed Oct. 30, 2007", 24 pgs.
"U.S. Appl. No. 10/815,262, Non-Final Office Action mailed Dec. 4, 2008", 28 pgs.
"U.S. Appl. No. 10/815,262, Notice of Allowance mailed Feb. 23, 2010", 9 pgs.
"U.S. Appl. No. 10/815,262, Response filed Jan. 31, 2008 to Non-Final Office Action mailed Oct. 30, 2007", 26 pgs.
"U.S. Appl. No. 10/815,262, Response filed Mar. 19, 2007 to Restriction Requirement mailed Sep. 18, 2006", 15 pgs.
"U.S. Appl. No. 10/815,262, Response filed May 4, 2009 to Non Final Office Action mailed Dec. 4, 2008", 22 pgs.
"U.S. Appl. No. 10/815,262, Response filed Jul. 23, 2008 to Final Office Action mailed Apr. 23, 2008", 22 pgs.
"U.S. Appl. No. 10/815,262, Response filed Aug. 14, 2007 to Non Final Office Action mailed May 15, 2007", 24 pgs.
"U.S. Appl. No. 10/815,262, Response filed Dec. 7, 2009 to Final Office Action mailed Aug. 6, 2009", 11 pgs.
"U.S. Appl. No. 10/815,262, Restriction Requirement mailed Sep. 18, 2006", 15 pgs.
"U.S. Appl. No. 10/815,262, Supplemental Amendment filed Aug. 22, 2007", 1 pg.
"U.S. Appl. No. 10/815,557, Examiner Interview Summary mailed Feb. 6, 2007", 4 pgs.
"U.S. Appl. No. 10/815,557, Final Office Action mailed Nov. 14, 2007", 29 pgs.
"U.S. Appl. No. 10/815,557, Non Final Office Action mailed May 21, 2007", 24 pgs.
"U.S. Appl. No. 10/815,557, Non-Final Office Action mailed Feb. 3, 2009", 23 pgs.

(56) References Cited

OTHER PUBLICATIONS

"U.S. Appl. No. 10/815,557, Non-Final Office Action mailed Aug. 13, 2008", 25 pgs.

"U.S. Appl. No. 10/815,557, Preliminary Amendment filed Dec. 28, 2004", 4 pgs.

"U.S. Appl. No. 10/815,557, Response filed Mar. 27, 2007 to Restriction Requirement mailed Oct. 5, 2006", 13 pgs.

"U.S. Appl. No. 10/815,557, Response filed May 14, 2008 to Final Office Action mailed Nov. 14, 2007", 18 pgs.

"U.S. Appl. No. 10/815,557, Response filed Aug. 21, 2007 to Non Final Office Action mailed May 21, 2007", 22 pgs.

"U.S. Appl. No. 10/815,557, Response filed Nov. 13, 2008 to Non-Final Office Action mailed Aug. 13, 2008", 19 pgs.

"U.S. Appl. No. 10/815,557, Restriction Requirement mailed Oct. 5, 2006", 19 pgs.

"U.S. Appl. No. 10/837,029, Examiner Interview Summary mailed Nov. 15, 2007", 3 pgs.

"U.S. Appl. No. 10/837,029, Eximaner Interview Summary mailed Jan. 9, 2012", 3 pgs.

"U.S. Appl. No. 10/837,029, Final Office Action mailed Jan. 8, 2009", 9 pgs.

"U.S. Appl. No. 10/837,029, Final Office Action mailed Mar. 9, 2012", 10 pgs.

"U.S. Appl. No. 10/837,029, Final Office Action mailed Sep. 13, 2010", 13 pgs.

"U.S. Appl. No. 10/837,029, Non Final Office Action mailed Apr. 11, 2007", 9 pgs.

"U.S. Appl. No. 10/837,029, Non Final Office Action mailed Oct. 7, 2011", 17 pgs.

"U.S. Appl. No. 10/837,029, Non-Final Office Action mailed Mar. 24, 2010", 11 pgs.

"U.S. Appl. No. 10/837,029, Non-Final Office Action mailed Jun. 2, 2008", 8 pgs.

"U.S. Appl. No. 10/837,029, Non-Final Office Action mailed Jun. 23, 2009", 11 pgs.

"U.S. Appl. No. 10/837,029, Non-Final Office Action mailed Jul. 15, 2008", 7 pgs.

"U.S. Appl. No. 10/837,029, Notice of Allowance mailed Apr. 11, 2012", 10 pgs.

"U.S. Appl. No. 10/837,029, Notice of Allowance mailed Nov. 15, 2007", 8 pgs.

"U.S. Appl. No. 10/837,029, Preliminary Amendment filed Feb. 15, 2008", 12 pgs.

"U.S. Appl. No. 10/837,029, Response filed Jan. 6, 2012 to Non Final Office Action mailed Oct. 7, 2011", 18 pgs.

"U.S. Appl. No. 10/837,029, Response filed Feb. 15, 2007 to Restriction Requirement mailed Nov. 15, 2006", 17 pgs.

"U.S. Appl. No. 10/837,029, Response filed Mar. 22, 2012 to Final Office Action mailed Mar. 9, 2012", 15 pgs.

"U.S. Appl. No. 10/837,029, Response filed Apr. 6, 2009 to Final Office Action mailed Jan. 8, 2009", 13 pgs.

"U.S. Appl. No. 10/837,029, Response filed Jun. 21, 2010 to Non-Final Office Action mailed Mar. 24, 2010", 14 pgs.

"U.S. Appl. No. 10/837,029, Response filed Aug. 17, 2007 to Non-Final Office Action mailed Apr. 11, 2007", 20 pgs.

"U.S. Appl. No. 10/837,029, Response filed Oct. 15, 2008 to Non-Final Office Action mailed Jul. 15, 2008", 13 pgs.

"U.S. Appl. No. 10/837,029, Response filed Nov. 19, 2009 to Non Final Office Action mailed Jun. 23, 2009", 14 pgs.

"U.S. Appl. No. 10/837,029, Response filed Dec. 8, 2010 to Final Office Action mailed Sep. 13, 2010", 18 pgs.

"U.S. Appl. No. 10/837,029, Restriction Requirement mailed Nov. 15, 2006", 6 pgs.

"U.S. Appl. No. 10/837,029, Supplemental Amendment filed Oct. 16, 2007 to Non-Final Office Action mailed Apr. 11, 2007", 14 pgs.

"U.S. Appl. No. 11/058,751, Advisory Action mailed Dec. 8, 2008", 3 pgs.

"U.S. Appl. No. 11/058,751, Final Office Action mailed Jan. 4, 2010", 6 pgs.

"U.S. Appl. No. 11/058,751, Final Office Action mailed Mar. 3, 2009", 7 pgs.

"U.S. Appl. No. 11/058,751, Final Office Action mailed Apr. 19, 2007", 7 pgs.

"U.S. Appl. No. 11/058,751, Non Final Office Action mailed Aug. 25, 2006", 12 pgs.

"U.S. Appl. No. 11/058,751, Non-Final Office Action mailed Jan. 28, 2008", 5 pgs.

"U.S. Appl. No. 11/058,751, Non-Final Office Action mailed Jun. 12, 2009", 6 pgs.

"U.S. Appl. No. 11/058,751, Non-Final Office Action mailed Jul. 22, 2008", 6 pgs.

"U.S. Appl. No. 11/058,751, Notice of Allowance mailed May 3, 2010", 4 pgs.

"U.S. Appl. No. 11/058,751, Response filed Jan. 25, 2007 to Non Final Office Action mailed Aug. 25, 2006", 10 pgs.

"U.S. Appl. No. 11/058,751, Response filed Apr. 5, 2010 to Final Office Action mailed Jan. 4, 2010", 6 pgs.

"U.S. Appl. No. 11/058,751, Response filed Apr. 22, 2008 to Non-Final Office Action mailed Jan. 28, 2008", 7 pgs.

"U.S. Appl. No. 11/058,751, Response filed Jun. 3, 2009 to Final Office Action mailed Mar. 3, 2009", 7 pgs.

"U.S. Appl. No. 11/058,751, Response filed Jun. 14, 2006 to Restriction Requirement mailed Dec. 14, 2005", 9 pgs.

"U.S. Appl. No. 11/058,751, Response filed Aug. 17, 2007 to Final Office Action mailed Apr. 19, 2007", 9 pgs.

"U.S. Appl. No. 11/058,751, Response filed Sep. 14, 2009 to Non Final Office Action mailed Jun. 12, 2009", 8 pgs.

"U.S. Appl. No. 11/058,751, Response filed Oct. 22, 2008 to Non Final Office Action mailed Jul. 22, 2008", 6 pgs.

"U.S. Appl. No. 11/058,751, Restriction Requirement mailed Dec. 14, 2005", 6 pgs.

"U.S. Appl. No. 11/058,751, Supplemental Amendment filed Oct. 19, 2007", 8 pgs.

"U.S. Appl. No. 11/301,601 , Response filed Feb. 21, 2014 to Non Final Office Action mailed Nov. 22, 2013", 11 pgs.

"U.S. Appl. No. 11/301,601, Advisory Action mailed Mar. 24, 2008", 6 pgs.

"U.S. Appl. No. 11/301,601, Examiner Interview Summary mailed Jan. 31, 2013", 3 pgs.

"U.S. Appl. No. 11/301,601, Examiner Interview Summary mailed Apr. 25, 2007", 4 pgs.

"U.S. Appl. No. 11/301,601, Examiner Interview Summary mailed May 28, 2010", 3 pgs.

"U.S. Appl. No. 11/301,601, Final Office Action mailed Mar. 30, 2010", 16 pgs.

"U.S. Appl. No. 11/301,601, Final Office Action mailed Apr. 3, 2009", 16 pgs.

"U.S. Appl. No. 11/301,601, Final Office Action mailed Dec. 6, 2011", 12 pgs.

"U.S. Appl. No. 11/301,601, Final Office Action mailed Dec. 13, 2007", 15 pgs.

"U.S. Appl. No. 11/301,601, Non Final Office Action mailed Mar. 28, 2013", 12 pgs.

"U.S. Appl. No. 11/301,601, Non Final Office Action mailed Jun. 27, 2011", 10 pgs.

"U.S. Appl. No. 11/301,601, Non Final Office Action mailed Nov. 22, 2013", 13 pgs.

"U.S. Appl. No. 11/301,601, Non-Final Office Action mailed Jul. 12, 2007", 29 pgs.

"U.S. Appl. No. 11/301,601, Non-Final Office Action mailed Sep. 28, 2009", 13 pgs.

"U.S. Appl. No. 11/301,601, Non-Final Office Action mailed Oct. 2, 2008", 15 pgs.

"U.S. Appl. No. 11/301,601, Notice of Allowance mailed May 22, 2014", 7 pgs.

"U.S. Appl. No. 11/301,601, Preliminary Amendment filed Dec. 13, 2005", 9 pgs.

"U.S. Appl. No. 11/301,601, Response filed Jan. 4, 2010 to Non Final Office Action mailed Sep. 28, 2009", 12 pgs.

"U.S. Appl. No. 11/301,601, Response filed Mar. 13, 2008 to Final Office Action mailed Dec. 13, 2007", 10 pgs.

(56) References Cited

OTHER PUBLICATIONS

"U.S. Appl. No. 11/301,601, Response filed Mar. 22, 2012 to Final Office Action mailed Dec. 6, 2011", 11 pgs.
"U.S. Appl. No. 11/301,601, Response filed May 2, 2007 to Restriction Requirement mailed Jan. 3, 2007", 11 pgs.
"U.S. Appl. No. 11/301,601, Response filed Jun. 27, 2013 to Non Final Office Action mailed Mar. 28, 2013", 11 pgs.
"U.S. Appl. No. 11/301,601, Response filed Jun. 30, 2010 to Final Office Action mailed Mar. 30, 2010", 11 pgs.
"U.S. Appl. No. 11/301,601, Response filed Jul. 1, 2009 to Final Office Action mailed Apr. 3, 2009", 12 pgs.
"U.S. Appl. No. 11/301,601, Response filed Sep. 27, 2011 to Non-Final Office Action mailed Jun. 27, 2011", 10 pgs.
"U.S. Appl. No. 11/301,601, Response filed Oct. 11, 2007 to Non-Final Office Action mailed Jul. 12, 2007", 14 pgs.
"U.S. Appl. No. 11/301,601, Response filed Dec. 31, 2008 to Non Final Office Action mailed Oct. 2, 2008", 12 pgs.
"U.S. Appl. No. 11/301,601, Restriction Requirement mailed Jan. 3, 2007", 5 pgs.
"U.S. Appl. No. 11/301,601, Second Preliminary Amendment filed Jan. 25, 2006", 3 pgs.
"U.S. Appl. No. 11/617,491 , Response filed Oct. 3, 2013 to Non Final Office Action mailed Jul. 3, 2013", 10 pgs.
"U.S. Appl. No. 11/617,491, Decision on Appeal Brief mailed Apr. 3, 2014", 2 pgs.
"U.S. Appl. No. 11/617,491, Examiner Interview Summary Jul. 30, 2010", 3 pgs.
"U.S. Appl. No. 11/617,491, Final Office Action mailed Mar. 2, 2009", 11 pgs.
"U.S. Appl. No. 11/617,491, Final Office Action mailed Nov. 8, 2013", 11 pgs.
"U.S. Appl. No. 11/617,491, Final Office Action mailed Nov. 26, 2010", 12 pgs.
"U.S. Appl. No. 11/617,491, Non Final Office Action mailed Jul. 3, 2013", 9 pgs.
"U.S. Appl. No. 11/617,491, Non-Final Office Action mailed May 27, 2010", 19 pgs.
"U.S. Appl. No. 11/617,491, Non-Final Office Action mailed Jun. 26, 2008", 11 pgs.
"U.S. Appl. No. 11/617,491, Non-Final Office Action mailed Oct. 2, 2009", 7 pgs.
"U.S. Appl. No. 11/617,491, Pre Appeal Brief Request for Review filed Jan. 9, 2014", 5 pgs.
"U.S. Appl. No. 11/617,491, Preliminary Amendment filed Apr. 11, 2007", 5 pgs.
"U.S. Appl. No. 11/617,491, Response filed Jan. 21, 2011 to Final Office Action mailed Nov. 26, 2010", 15 pgs.
"U.S. Appl. No. 11/617,491, Response filed Jan. 28, 2010 to Non-Final Office Action mailed Oct. 2, 2009", 9 pgs.
"U.S. Appl. No. 11/617,491, Response filed Feb. 8, 2008 to Restriction Requirement mailed Dec. 28, 2007", 10 pgs.
"U.S. Appl. No. 11/617,491, Response filed Jun. 30, 2009 to Final Office Action mailed Mar. 2, 2009", 14 pgs.
"U.S. Appl. No. 11/617,491, Response filed Aug. 26, 2010 to Non Final Office Action mailed May 27, 2010", 14 pgs.
"U.S. Appl. No. 11/617,491, Response filed Nov. 26, 2008 to Non Final Office Action mailed Jun. 26, 2008", 12 pgs.
"U.S. Appl. No. 11/617,491, Restriction Requirement mailed Dec. 28, 2007", 8 pgs.
"U.S. Appl. No. 11/796,605, Preliminary Amendment filed Sep. 11, 2007", 6 pgs.
"U.S. Appl. No. 11/796,605, Restriction Requirement mailed Jul. 7, 2009", 7 pgs.
"U.S. Appl. No. 11/821,116, Restriction Requirement mailed Jun. 26, 2009", 8 pgs.
"U.S. Appl. No. 11/890,761, Final Office Action mailed Dec. 22, 2009", 40 pgs.
"U.S. Appl. No. 11/890,761, Non Final Office Action mailed Jul. 12, 2011", 15 pgs.
"U.S. Appl. No. 11/890,761, Non-Final Office Action mailed Jul. 16, 2009", 16 pgs.
"U.S. Appl. No. 11/890,761, Preliminary Amendment filed May 19, 2008", 8 pgs.
"U.S. Appl. No. 11/890,761, Response filed Mar. 16, 2010 to Final Office Action mailed Dec. 22, 2009", 11 pgs.
"U.S. Appl. No. 11/890,761, Response filed Apr. 14, 2009 to Restriction Requirement mailed Oct. 14, 2008", 7 pgs.
"U.S. Appl. No. 11/890,761, Response filed Oct. 29, 2009 to Non Final Office Action mailed Jul. 16, 2009", 19 pgs.
"U.S. Appl. No. 11/890,761, Restriction Requirement mailed Oct. 14, 2008", 5 pgs.
"U.S. Appl. No. 11/890,762, Restriction Requirement mailed Jun. 23, 2009", 8 pgs.
"U.S. Appl. No. 11/890,767, Restriction Requirement mailed Sep. 30, 2009", 8 pgs.
"U.S. Appl. No. 11/890,775, Response filed Dec. 2, 2009 to Restriction Requirement mailed Oct. 2, 2009", 6 pgs.
"U.S. Appl. No. 11/890,775, Restriction Requirement mailed Feb. 23, 2010", 6 pgs.
"U.S. Appl. No. 11/890,775, Restriction Requirement mailed Oct. 2, 2009", 6 pgs.
"U.S. Appl. No. 11/890,776, Preliminary Amendment filed May 9, 2008", 6 pgs.
"U.S. Appl. No. 11/890,776, Restriction Requirement mailed Dec. 17, 2008", 8 pgs.
"U.S. Appl. No. 11/890,777, Preliminary Amendment filed Aug. 7, 2007", 9 pgs.
"U.S. Appl. No. 11/890,777, Restriction Requirement mailed Mar. 18, 2010", 5 pgs.
"U.S. Appl. No. 11/890,778, Preliminary Amendment filed Jan. 28, 2009", 4 pgs.
"U.S. Appl. No. 11/890,779, Preliminary Amendment filed May 9, 2008", 5 pgs.
"U.S. Appl. No. 11/890,779, Restriction Requirement mailed Feb. 18, 2010", 5 pgs.
"U.S. Appl. No. 11/890,787, Preliminary Amendment filed May 12, 2008", 6 pgs.
"U.S. Appl. No. 11/890,787, Restriction Requirement mailed Apr. 17, 2009", 5 pgs.
"U.S. Appl. No. 12/397,583, Non-Final Office Action mailed Sep. 23, 2010", 16 pgs.
"U.S. Appl. No. 12/397,583, Response filed Aug. 9, 2010 to Restriction Requirement mailed Jul. 20, 2010", 7 pgs.
"U.S. Appl. No. 12/397,583, Restriction Requirement mailed Jul. 20, 2010", 12 pgs.
"U.S. Appl. No. 12/835,102, Preliminary Amendment filed Sep. 29, 2010", 10 pgs.
"U.S. Appl. No. 12/835,102, Restriction Requirement mailed Jun. 7, 2011", 8 pgs.
"U.S. Appl. No. 16/076,219, Notice of Allowance mailed Jan. 25, 2022", 10 pgs.
"U.S. Appl. No. 16/082,767, Advisory Action mailed May 10, 2022", 3 pgs.
"U.S. Appl. No. 16/082,767, Final Office Action mailed Jan. 12, 2022", 13 pgs.
"U.S. Appl. No. 16/082,767, Non Final Office Action mailed Apr. 28, 2021", 17 pgs.
"U.S. Appl. No. 16/082,767, Response filed Jan. 6, 2021 to Restriction Requirement mailed Oct. 6, 2020", 5 pgs.
"U.S. Appl. No. 16/082,767, Response filed Apr. 12, 2022 to Final Office Action mailed Jan. 12, 2022", 6 pgs.
"U.S. Appl. No. 16/082,767, Response filed Sep. 28, 2021 to Non Final Office Action mailed Apr. 28, 2021", 9 pgs.
"U.S. Appl. No. 17/603,840, Restriction Requirement mailed Oct. 6, 2020", 8 pgs.
"U.S. Appl. No. 17/603,840, Preliminary Amendment filed Sep. 11, 2020", 7 pgs.
"U.S. Appl. No. 17/603,840, Preliminary Amendment filed Feb. 2, 2022", 6 pgs.
"U.S. Appl. No. 17/603,840, Preliminary Amendment filed Oct. 14, 2021", 7 pgs.

(56) References Cited

OTHER PUBLICATIONS

"Australia Application No. 2006332728, Examiner's Report mailed Jun. 6, 2011", 2 pgs.
"Australia Application Serial No. 2005243221 Examiner Report Dec. 10, 2009", 3 pgs.
"Australian Application No. 58694/00, Response filed Oct. 28, 2004 to Examiner's Report dated Nov. 26, 2003", 20 pgs.
"Australian Application Serial No. 2004/227358, Office Action mailed Sep. 23, 2008", 4 pgs.
"Australian Application Serial No. 2004227358, Examiner Report No. 2 mailed Aug. 27, 2009", 2 pgs.
"Australian Application Serial No. 2004227358, Response filed Jul. 10, 2009 to Examiner's First Report dated Sep. 23, 2008", 10 pgs.
"Australian Application Serial No. 2004227358, Response filed Oct. 22, 2009 to Examiner's Second Report dated Aug. 27, 2009", 16 pgs.
"Australian Application Serial No. 2004227915,, Examiner Report mailed Dec. 5, 2008", 2 pgs.
"Australian Application Serial No. 2006202785, Examiner's First Report mailed Sep. 21, 2007", 3 pgs.
"Australian Application Serial No. 2006202785, Response filed Sep. 19, 2008 to Examiner's First Report mailed Sep. 21, 2007", 29 pgs.
"Australian Application Serial No. 2006332728, Response filed Nov. 14, 2011 to Examiner Report mailed Jun. 6, 2011", 12 pgs.
"Australian Application Serial No. 2006332728, Subsequent Examiner Report mailed Nov. 24, 2011", 2 pgs.
"Australian Application Serial No. 2017229347, First Examination Report mailed Dec. 20, 2019", pgs.
"Australian Application Serial No. 2017229347, Response filed Oct. 2, 2020 to First Examination Report mailed Dec. 20, 2019", 19 pgs.
"Australian Application Serial No. 2017229347, Response filed Dec. 10, 2020 to Subsequent Examiners Report mailed Oct. 8, 2020", 16 pgs.
"Australian Application Serial No. 2017229347, Subsequent Examiners Report mailed Oct. 8, 2020", 6 pgs.
"Australian Application Serial No. 2017229347, Third Examiners Report mailed Dec. 16, 2020", pgs.
"Australian Application Serial No. 40192/99, Response filed Dec. 10, 2002 to Examiner's First Report mailed May 24, 2002", 15 pgs.
"Australian Application Serial No. 58694/00, Examiner Report No. 2 mailed Nov. 18, 2004", 3 pgs.
"Australian Application Serial No. 58694/00, Examiner's Report dated Jul. 18, 2005", 2 pgs.
"Australian Application Serial No. 58694/00, Response filed Jul. 7, 2005 to Examiner's Report dated Nov. 18, 2004", 15 pgs.
"Australian Application Serial No. 80032/00, First Examiner's Report mailed May 19, 2004", 2 pgs.
"Australian Application Serial No. 80032/00, Response filed Feb. 2, 2006 to Second Examiner's Report mailed Jan. 3, 2006", 56 pgs.
"Australian Application Serial No. 80032/00, Response filed Dec. 8, 2005 to First Examiner's Report mailed May 19, 2004", 36 pgs.
"Australian Application Serial No. 80032/00, Second Examiner's Report mailed Jan. 3, 2006", 3 pgs.
"Brazilian Application Serial No. 1120210207082, Office Action mailed Dec. 22, 2021", with machine translation, 2 pgs.
"Brazilian Application Serial No. 1120210207082, Response filed Feb. 25, 2022 to Office Action mailed Dec. 22, 2021", with machine translation, 4 pgs.
"Calbichem(r) Eicosapentaenoic Acid, EPA; 20:5 w-3; 5,8, 11, 14, 17-Eicosapentaenoic Acid", Catalog No. 324875, (Dec. 7, 1998), 2 pgs.
"Calbiochem(r) MG-132, Carbobenzoxy-L-leucyl-L-leucinal", Catalog No. 474790, (Oct. 15, 1999), 2 pgs.
"Calbiochem(r) Simvastatin, MK-733", Catalog No. 567020, (Oct. 25, 2001), 2 pgs.
"Calbiochem(r) Aminoglycoside antibiotic. Inhibits myeloperoxidase-dependent oxidant cell injury", Tobramycin, Free Base, Catalog No. 614005, (Aug. 26, 1999), 1 pg.
"Calbiochem(r) Camptothecin, Camptotheca acuminata (S)-(+)-Camptothecin; 4-Ethyl-4-hydroxy-1H-pyrano[3', 4': 6,7] indolizino [1,2-b] quinoline-3, 14 (4H, 12H) dione", Catalog No. 208925, (Oct. 2, 2000), 2 pgs.
"Calbiochem(r) Doxorubicin, Hydrochloride Adriamycin; 14-Hydroxydaunomycin, HCI", Catalog No. 324380, (Oct. 21, 1998), 2 pgs.
"Canadian Application Serial No. 2,328,447, Official Action mailed Feb. 7, 2005", 2 pgs.
"Canadian Application Serial No. 2,328,447, Response filed Aug. 8, 2005 to Official Action mailed Feb. 7, 2005", 15 pgs.
"Canadian Application Serial No. 2,376,400, Office Action mailed Apr. 7, 2008", 4 pgs.
"Canadian Application Serial No. 2,376,400, Official Action mailed Jan. 5, 2010", 3 pgs.
"Canadian Application Serial No. 2,376,400, Official Action mailed Apr. 7, 2008", 4 pgs.
"Canadian Application Serial No. 2,376,400, Response filed Oct. 7, 2008 to Official Action dated Apr. 7, 2008", 49 pgs.
"Canadian Application Serial No. 2,376,400, Response filed Oct. 7, 2008 to Office Action mailed Apr. 7, 2008", 49 pgs.
"Canadian Application Serial No. 2,386,546, Office Action mailed Jun. 30, 2009", 4 pgs.
"Canadian Application Serial No. 2,520,028, Office Action mailed Jan. 19, 2011", 3 pgs.
"Canadian Application Serial No. 2,634,670 , Response filed Sep. 30, 2013 to Office Action mailed May 17, 2013", 53 pgs.
"Canadian Application Serial No. 2,634,670, Office Action mailed Feb. 3, 2014", 3 pgs.
"Canadian Application Serial No. 2,634,670, Office Action mailed Feb. 17, 2015", 6 pgs.
"Canadian Application Serial No. 2,634,670, Office Action mailed May 17, 2013", 4 pgs.
"Canadian Application Serial No. 2,634,670, Voluntary Amendment and Submission of Sequence Listing filed Dec. 24, 2008", 19 pgs.
"Canadian Application Serial No. 2,634,670, Voluntary Amendment filed Dec. 20, 2011", 7 pgs.
"Canadian Application Serial No. 2,909,085, Office Action Mailed Feb. 17, 2022", 3 pgs.
"Canadian Application Serial No. 2386546, Response filed Oct. 14, 2008 to Office Action mailed Apr. 14, 2008", 20 pgs.
"Canadian Application Serial No. 2386546,, Office Action mailed Apr. 14, 2008", 3 pgs.
"Canadian Application Serial No. 3,016,985, Examiner's Rule 30(2) Requisition mailed Jun. 28, 2019", 3 pgs.
"Canadian Application Serial No. 3,016,985, Office Action mailed Sep. 23, 2020", 7 pgs.
"Canadian Application Serial No. 3,016,985, Office Action mailed Oct. 8, 2021", 6 pgs.
"Canadian Application Serial No. 3,016,985, Response filed Jan. 22, 2021 to Office Action mailed Sep. 23, 2020", 14 pgs.
"Canadian Application Serial No. 3,016,985, Response filed Dec. 24, 2019 to Examiner's Rule 30(2) Requisition mailed Jun. 28, 2019", 40 pgs.
"Canadian Application Serial No. 3,016,985, Response Filed Apr. 7, 2022 to Office Action mailed Oct. 8, 2021", 11 pgs.
"Canadian Application Serial No. 3,016,985, Voluntary Amendment filed Apr. 12, 2022", 12 pgs.
"Cancer Research", Contribution to Society, http://www.bikaken.or.jp/mcrf_e/contributiion, (Dec. 4, 2000), 2 pages.
"Carbiochem(r) Lovastatin, Mevinolin; MK-803", Catalolg No. 438185, (Jun. 29, 2001), 2 pgs.
"Chinese Application Serial No. 202080043595.2, Notification to Make Rectification mailed Dec. 29, 2021", with machine translation, 5 pgs.
"Chinese Application Serial No. 202080043595.2, Response filed Mar. 11, 2022", with machine translation, 4 pgs.
"DNA Vector-Based siRNA", http://www.genscript.com/rnai_intro.html, (observed Mar. 9, 2004), 3 pgs.
"Drugs for Selection of Genetic Markers Reagents for positive and negative selection of Genes involved in Nucleotide Metabolism", Calbiochem, (Mar. 2002), 6 pages.

(56) References Cited

OTHER PUBLICATIONS

"Enzyme database entry for EC No. 3.4.22", ,, [online}. Retrieved from the Internet: <http://ca.expasy.org/enzyme/3.4.22>, (Jun. 19, 2007), 2 pgs.

"Epoxomicin—a potent and selective proteasome inhibitor", Affiniti Research Products Limited, 2 pages.

"Eurasian Application Serial No. 201892006, Office Action mailed Jul. 1, 2021", w/ English Translation, 5 pgs.

"Eurasian Application Serial No. 201892006, Response filed Nov. 24, 2021 to Office Action mailed Jul. 1, 2021", w/ English claims, 10 pgs.

"European Application Serial No. 05778984.4, Office Action mailed Jul. 20, 2007", 2 pgs.

"European Application Serial No. 005778984.4, Response filed Mar. 4, 2008 to Communication mailed Jul. 20, 2007", 28 pgs.

"European Application Serial No. 00944624.6, Main Request, First Auxiliary Request and Second Auxiliary Request filed Sep. 29, 2008", 67 pgs.

"European Application Serial No. 00944624.6, Office Action Aug. 5, 2003", 3 pgs.

"European Application Serial No. 00944624.6, Office Action mailed Mar. 4, 2005", 5 pgs.

"European Application Serial No. 00944624.6, Response and Further Auxiliary Requests filed Oct. 27, 2008 to Primary Examiner's Telephonic Comments", 122 pgs.

"European Application Serial No. 00944624.6, Response filed Feb. 16, 2004 to Office Action Mailed Aug. 5, 2003", 25 pgs.

"European Application Serial No. 00944624.6, Response filed Aug. 26, 2005 to Office Action mailed Mar. 4, 2005", 31 pgs.

"European Application Serial No. 00970689.6, Communication mailed Nov. 19, 2003", 4 pgs.

"European Application Serial No. 00970689.6, Communication mailed Dec. 19, 2005", 7 pgs.

"European Application Serial No. 00970689.6, Office Action mailed Sep. 13, 2007", 5 pgs.

"European Application Serial No. 00970689.6, Office Action mailed Dec. 29, 2008", 5 pgs.

"European Application Serial No. 00970689.6, Response filed Apr. 24, 2008 to Communication mailed Sep. 13, 2007", 39 pgs.

"European Application Serial No. 00970689.6, Response filed Aug. 9, 2004 to Communication mailed Nov. 19, 2003", 10 pgs.

"European Application Serial No. 00970689.6, Response mailed Jul. 27, 2006 to Examination Report mailed Dec. 19, 2005", 51 pgs.

"European Application Serial No. 02749934.2, Communication mailed Mar. 12, 2004", 2 pgs.

"European Application Serial No. 02749934.2, Communication mailed Nov. 12, 2004", 3 pgs.

"European Application Serial No. 02749934.2, Response filed Jan. 7, 2005 to Communication mailed Nov. 12, 2004", 1 pg.

"European Application Serial No. 02749934.2, Response filed Apr. 21, 2004 to Communication mailed Mar. 12, 2004", 9 pgs.

"European Application Serial No. 04749597.3, Communication dated May 13, 2008", 5 pgs.

"European Application Serial No. 04749597.3, Office Action Nov. 20, 2006", 3 pgs.

"European Application Serial No. 04749597.3, Office Action mailed Mar. 28, 2006", 9 pgs.

"European Application Serial No. 04749597.3, Office Action", 5 pgs.

"European Application Serial No. 04749597.3, Response filed Sep. 6, 2007 to Office Action Nov. 20, 2006", 6 pgs.

"European Application Serial No. 04749597.3, Response filed Oct. 6, 2006 to Office Action mailed Mar. 28, 2006", 28 pgs.

"European Application Serial No. 04749619.5 Office Action mailed Nov. 9, 2009", 3 pgs.

"European Application Serial No. 04749619.5, Communication dated Apr. 14, 2008", 5 pgs.

"European Application Serial No. 04749619.5, Communication dated Sep. 13, 2007", 1 pg.

"European Application Serial No. 04749619.5, Communication Noting Loss of Rights dated Nov. 28, 2008", 1 pg.

"European Application Serial No. 04749619.5, Office Action mailed Mar. 11, 2009", 4 pgs.

"European Application Serial No. 04749619.5, Office Action mailed Mar. 28, 2006", 8 pgs.

"European Application Serial No. 04749619.5, Office Action mailed Nov. 20, 2006", 4 pgs.

"European Application Serial No. 04749619.5, Response filed Feb. 6, 2009 to Communication dated Nov. 28, 2008", 14 pgs.

"European Application Serial No. 04749619.5, Response filed Sep. 7, 2007 to Office Action mailed Nov. 20, 2006", 28 pgs.

"European Application Serial No. 04749619.5, Response filed Sep. 21, 2009 to Office Action mailed Mar. 11, 2009", 19 pgs.

"European Application Serial No. 04749619.5, Response filed Oct. 4, 2007 to Communication dated Sep. 13, 2007", 3 pgs.

"European Application Serial No. 04749619.5, Response filed Oct. 17, 2006 to Office Action mailed Mar. 28, 2006", 17 pgs.

"European Application Serial No. 04749619.5, Summons to Attend Oral Proceedings mailed Jun. 16, 2010", 5 pgs.

"European Application Serial No. 05778984.4, Invitation pursuant to Article 94(3) mailed Aug. 28, 2008", 5 pgs.

"European Application Serial No. 05778984.4, Response filed Feb. 26, 2009 to Communication mailed Aug. 28, 2008", 21 pgs.

"European Application Serial No. 06849005.1, Office Action mailed Apr. 21, 2010", 10 Pgs.

"European Application Serial No. 06849005.1, Office Action mailed May 15, 2009", 4 pgs.

"European Application Serial No. 06849005.1, Response filed Jan. 17, 2012 to Summons mailed Nov. 14, 2011", 13 pgs.

"European Application Serial No. 06849005.1, Response filed Aug. 1, 2011 to Office Action mailed Mar. 22, 2011", 16 pgs.

"European Application Serial No. 06849005.1, Response filed Nov. 1, 2010 to Office Action mailed Apr. 21, 2010", 17 pgs.

"European Application Serial No. 06849005.1, Response filed Nov. 24, 2009 tp Office Action mailed May 15, 2009", 16 pgs.

"European Application Serial No. 06849005.1, Summons mailed Nov. 14, 2011", 16 pgs.

"European Application Serial No. 07075464.3, Office Action mailed May 7, 2008", 6 pgs.

"European Application Serial No. 07075464.3, Office Action mailed Sep. 29, 2009", 8 pgs.

"European Application Serial No. 07075464.3, Partial European Search Report mailed Oct. 2, 2007", 13 pgs.

"European Application Serial No. 07075464.3, Response filed Feb. 26, 2009 to Communication mailed May 7, 2008", 12 pgs.

"European Application Serial No. 17712339.5, Communication Pursuant to Article 94(3) EPC mailed Aug. 20, 2019", 5 pgs.

"European Application Serial No. 17712339.5, Communication Pursuant to Article 94(3) EPC mailed Oct. 20, 2020", 4 pgs.

"European Application Serial No. 17712339.5, Response filed Feb. 24, 2021 to Communication Pursuant to Article 94(3) EPC mailed Oct. 20, 2020", 10 pgs.

"European Application Serial No. 17712339.5, Response Filed May 2, 2019 to Communication pursuant to Rules 161(2) and 162 EPC mailed Oct. 23, 2018", 14 pgs.

"European Application Serial No. 17712339.5, Response filed Dec. 23, 2019 to Communication Pursuant to Article 94(3) EPC mailed Aug. 20, 2019", 9 pgs.

"European Application Serial No. 99924404.9, Response filed Jun. 22, 2006 to Communication mailed Feb. 27, 2006", 1 pg.

"European Application Serial No. 99924404.9, Communication mailed Feb. 27, 2006", 3 pgs.

"European Application Serial No. 99924404.9, Communication Pursuant to Article 96(2) EPC mailed Feb. 27, 2006", 3 pgs.

"European Application Serial No. 99924404.9, Communication Pursuant to Article 96(2) mailed Jun. 18, 2003", 3 pgs.

"European Application Serial No. 99924404.9, EP Communication Pursuant to Article 96(2) EPC mailed Oct. 7, 2004", 3 pgs.

"European Application Serial No. 99924404.9, Response filed Apr. 8, 2004 to Communication mailed Feb. 3, 2004", 13 pgs.

"European Application Serial No. 99924404.9, Response filed Apr. 15, 2005 to Communication mailed Oct. 7, 2004", 23 pgs.

(56) References Cited

OTHER PUBLICATIONS

"European Application Serial No. EP 07075464, Partial European Search Report mailed Sep. 19, 2007", 12 pgs.
"European Application Serial No. 06849005.1, Office Action mailed Mar. 22, 2011", 11 Pgs.
"International Application Serial No. PCT/US 00/15700, International Search Report mailed Dec. 21, 2000", 9 pgs.
"International Application Serial No. PCT/US 00/15700, Written Opinion Aug. 1, 2001", 7 pgs.
"International Application Serial No. PCT/US00/15700, International Preliminary Examination Report mailed Sep. 20, 2001", 7 pgs.
"International Application Serial No. PCT/US00/27863, International Search Report mailed Mar. 19, 2001", 8 pgs.
"International Application Serial No. PCT/US00/27863, Written Opinion mailed Sep. 24, 2001", 7 pgs.
"International Application Serial No. PCT/US02/21926, International Search Report mailed Sep. 11, 2003", 8 pgs.
"International Application Serial No. PCT/US02/21926, Written Opinion mailed Jul. 14, 2004", 5 pgs.
"International Application Serial No. PCT/US2004/009950, International Preliminary Report on Patentability mailed Mar. 31, 2003", 15 pgs.
"International Application Serial No. PCT/US2004/009950, International Preliminary Report on Patentability mailed Oct. 13, 2005", 15 pgs.
"International Application Serial No. PCT/US2004/009950, International Search Report mailed Mar. 8, 2005", 8 pgs.
"International Application Serial No. PCT/US2004/009950, Written Opinion mailed Mar. 8, 2005", 15 pgs.
"International Application Serial No. PCT/US2004/010045, International Preliminary Report on Patentability mailed Oct. 13, 2005", 14 pgs.
"International Application Serial No. PCT/US2004/010045, International Search Report mailed Jan. 10, 2005", 6 pgs.
"International Application Serial No. PCT/US2005/015315, International Search Report mailed Feb. 2, 2007", 7 pgs.
"International Application Serial No. PCT/US2005/015315, International Search Report mailed Feb. 7, 2007", 7 pgs.
"International Application Serial No. PCT/US2005/015315, Invitation to Pay Additional Fees and Partial Search Reportt", 6 pgs.
"International Application Serial No. PCT/US2005/015315, Written Opinion mailed Feb. 7, 2007", 10 pgs.
"International Application Serial No. PCT/US2006/049424, International Preliminary Report on Patentability mailed Jul. 10, 2008", 17 pgs.
"International Application Serial No. PCT/US2006/049424, International Search Report mailed Nov. 26, 2007", 11 pgs.
"International Application Serial No. PCT/US2006/049424, Written Opinion mailed Nov. 26, 2007", 17 pgs.
"International Application Serial No. PCT/US2007/010434, International Search Report mailed Oct. 10, 2007", 11 pgs.
"International Application Serial No. PCT/US2007/010434, International Search Report mailed Dec. 5, 2007", 11 pgs.
"International Application Serial No. PCT/US2007/010434, Written Opinion mailed Dec. 5, 2007", 19 pgs.
"International Application Serial No. PCT/US2017/021124, International Preliminary Report on Patentability mailed Sep. 20, 2018", 7 pgs.
"International Application Serial No. PCT/US2017/021124, International Search Report mailed May 22, 2017", 6 pgs.
"International Application Serial No. PCT/US2017/021124, Written Opinion mailed May 22, 2017", 5 pgs.
"International Application Serial No. PCT/US2019/022106, International Preliminary Report on Patentability mailed Sep. 24, 2020", 10 pgs.
"International Application Serial No. PCT/US2019/022106, International Search Report mailed Sep. 12, 2019", 8 pgs.
"International Application Serial No. PCT/US2019/022106, Invitation to Pay Additional Fees mailed Jul. 17, 2019", 10 pgs.
"International Application Serial No. PCT/US2019/022106, Written Opinion mailed Sep. 12, 2019", 8 pgs.
"International Application Serial No. PCT/US2020/028264, International Preliminary Report on Patentability mailed Oct. 28, 2021", 10 pgs.
"International Application Serial No. PCT/US2020/028264, International Search Report mailed Aug. 5, 2020", 7 pgs.
"International Application Serial No. PCT/US2020/028264, Written Opinion mailed Aug. 5, 2020", 8 pgs.
"International Application Serial No. PCT/US2020/028269, International Preliminary Report on Patentability mailed Oct. 28, 2021", 9 pgs.
"International Application Serial No. PCT/US2020/028269, International Search Report mailed Aug. 7, 2020", 7 pgs.
"International Application Serial No. PCT/US2020/028269, Written Opinion mailed Aug. 7, 2020", 7 pgs.
"International Application Serial No. PCT/US2021/039860, International Search Report mailed Jan. 24, 2022", 12 pgs.
"International Application Serial No. PCT/US2021/039860, Invitation to Pay Additional Fees mailed Nov. 29, 2021", 20 pgs.
"International Application Serial No. PCT/US2021/039860, Written Opinion mailed Jan. 24, 2022", 15 pgs.
"International Application Serial No. PCT/US99/11197, International Search Report mailed Sep. 22, 1999", 9 pgs.
"International Application Serial No. PCT/US99/11197, Written Opinion mailed Mar. 13, 2000", 11 pgs.
"Israel Application Serial No. 261642, Notification of Defects in Patent Application mailed Dec. 26, 2021", w/ English Translation, 8 pgs.
"Israeli Application Serial No. 261642, Response Filed Apr. 25, 2022 to Notification of Defects in Patent Application mailed Dec. 26, 2021", W/English Claims, 7 pgs.
"Japanese Application Serial No. 2000-549752, Notice of Rejection mailed Feb. 10, 2009", (w/ English Translation), 10 pgs.
"Japanese Application Serial No. 2001-501645, Office Action mailed Jun. 8, 2010", With English Claims, 4 pgs.
"Japanese Application Serial No. 2001-501645, Office Action Response Filed Dec. 7, 2010", 8 pgs.
"Japanese Application Serial No. 2001-528616, Office Action mailed Jun. 8, 2010", 4 pgs.
"Japanese Application Serial No. 2006-509588, Office Action mailed Mar. 2, 2010", With English Translation, 14 pgs.
"Japanese Application Serial No. 2008-548723, Office Action mailed Apr. 3, 2012", (w/ English Translation), 9 pgs.
"Japanese Application Serial No. 501645/01, Preliminary Amendment filed May 31, 2007", 12 pgs.
"Japanese Application Serial No. 501645/01, Response filed Jan. 10, 2012 to Final Office Action mailed Sep. 29, 2011", 11 pgs.
"Japanese U.S. Appl. No. 50/164,501—Final Rejection filed Sep. 6, 2011", 6 pgs.
"Japanese Application Serial No. 509588/06, Final Office Action mailed Nov. 16, 2010", 1 pg.
"Japanese Application Serial No. 511645/01, Final Office Action mailed Sep. 6, 2011", 6 pgs.
"Japanese Application Serial No. JP2006-509588, Amended Claims filed Mar. 22, 2007", (w/English Translation of Claims), 28 pgs.
"LDP-341", Millennium Pharmaceuticals, http://www.biospace.com/ct/detail.cfm?ClinicalID=266404, (Jul. 18, 2001), 1 page.
"Mexican Application Serial No. MX/a/2021/012681, Office Action mailed Nov. 16, 2021", with machine translation, 9 pgs.
"Mexican Application Serial No. MX/a/2021/012681, Response filed Mar. 9, 2022", with machine translation, 129 pgs.
"Mexican Application Serial No. MX/a/2021/012681, Voluntary Amendment filed Apr. 19, 2022", with English translation of claims, 10 pgs.
"Mexican Application Serial No. MX/a/2021/012682, Voluntary Amendment filed Apr. 19, 2022", with English translation of claims, 10 pgs.
"PCT Application Serial No. PCT/US2005/015315, International Preliminary Report on Patentability, and Written Opinion, mailed Feb. 28, 2007", (Feb. 28, 2007), 11 pages.
"PCT Application Serial No. PCT/US99/11197, Written Opinion mailed Mar. 13, 2000", 11 pgs.

(56) References Cited

OTHER PUBLICATIONS

"Polymer Vectors Endosomal release and cytoplasmic delivery", Endosomal Release, http://web.bham.ac.uk/can4psd4/nonviral/endosome.html, (Jun. 3, 2001), 1.
"Product Data Sheet", Moravek Biochemicals, Inc., M-1535, Ritonavir, (Jul. 12, 2001), 1 page.
"Product Information", Sigma, Cyclosporin A, Sigma Product No. C3662, (Oct. 28, 1996), 3 pages.
"Product Information", Sigma, Bleomycin Sulfate, Sigma Prod. No. B5507, (Nov. 25, 1996), 2 pages.
"Proteasome Inhibitors", Peptides International, Inc., (Apr. 16, 2001), 1-2.
"Tannic Acid, A.C.S. reagent", Sigma, www.sigma-aldrich.com/sacatolog.nsf/productlookup/Aldrich403040?OpenDocument, (Jan. 20, 2001), 1 page.
Abe, Y, et al., "Cytotoxic mechanisms by M239V presenilin 2, a little-analyzed Alzheimer's disease-causative mutant", J. Neurosci Res. 77(4), Abstract Only, (Aug. 2004), 583-95.
Abramov, A. Y, et al., "Beta-amyloid peptides induce mitochondrial dysfunction and oxidative stress in astrocytes and death of neurons through activation of NADPH oxidase.", J Neurosci., 24(2), (Jan. 14, 2004), 565-75.
Abramov, A. Y., et al., "The role of an astrocytic NADPH oxidase in the neurotoxicity of amyloid beta peptides", Philosophical Transactions of The Royal Society B, 360, (2005), 2309-2314.
Adams, J., et al., "Proteasome inhibition: a new strategy in cancer treatment.", Invest New Drugs, 18(2), (May 2000), 109-21.
Adams, Julian, et al., "Chapter 28. Novel Inhibitors of the Proteasome and Their Theraputic Use in Inflammation", Annual Reports in Medicinal Chemistry, Academic Press, Inc., (1996), 279-288.
Adams, Julian, "Proteasome inhibition: a novel approach to cancer therapy", Trends in Molecular Medicine, 8(4), (2002), S49-S54.
Afione, S. A., et al., "In Vivo Model of Adeno-Associated Virus Vector Persistence and Rescue", Journal of Virology, 70(5), (May 1996), 3235-3241.
Aitken, M L, et al., "A Phase I Study of Aerosolized Administration of tgAAVCF to Cystic Fibrosis Subjects with Mild Lung Disease", Hum Gene Ther 12, (2001), 1907-1916.
Alavijeh, Mohammad S, et al., "Drug Metabolism and Pharmacokinetics, the Blood-Brain Barrier, and Central Nervous Systems Drug Discovery", The Journal of the American Societ for Experimental NeuroTherapeutics vol. 2, (Oct. 2005), 554-571.
Alberts, B., et al., "", In: Molecular Biology of the Cell, 3rd edition, (1994), 618-626.
Alexander, I E., et al., "Effects of Gamma Irradiation on the Transduction of Dividing and Nondividing Cells in Brain and Muscle of Rats by Adeno-Associated Virus Vectors", Human Gene Therapy, 7(7), (May 1, 1996), 841-850.
Alexander, Ian E., et al., "DNA-Damaging Agents Greatly Increase the Transduction of Nondividing Cells by Adeno-Associated Virus Vectors", Journal of Virology, 68(12), (Dec. 1994), 8282-8287.
Ali, R. R., et al., "Gene transfer into the mouse retina mediated by an adeno-associated viral vector", Human Molecular Genetics, 5 (5), (1996), 591-594.
Almond, J. B., et al., "The proteasome: a novel target for cancer chemotherapy", Leukemia, 16, (2002), 443-443.
Andre, Patrice, et al., "An inhibitor of HIV-1 protease modulates proteasome activity, antigen presentation, and T cell responses.", Proc Natl Acad Sci U S A., 95(22), (Oct. 27, 1998), 13120-13124.
Arcamone, F M, "From the Plgments of the Actinomycetes to Third Generation Antitumor Anthracyclines", Biochimie (Paris), 80(3), (Mar. 1998), 201-206.
Audige, A., et al., "Epithelial sodium channel (ENaC) subunit mRNA and protein expression in rats with puromycin aminonucleoside-induced nephrotic syndrome.", Clincial Sci., 104(4), (2003), 389-395.
Auerbach, S. D., et al., "Human Amiloride-Sensitive Epithelial Na+ Channel y Subunit Promoter: Functional Analysis and Identification of a Polypurine-Polypyrimidine Tract With the Potential for Triplex DNA Formation", Biochem. J., 347, (2000), 105-114.

Baines, D. L., et al., "Effect of LPS-Induced NF-kB Activity on the Transcriptional Response of a 5' Flanking Region of the alphaENaC Gene", Experimental Biology 2003—Translating the Genome, Abstract No. 5860 (http://www.biosis-select.org/faseb/data/FASEB005860.html, (2003), 1 pg.
Banerjee, D., et al., "The Treatment of Respiratory Pseudomonas Infection in Cystic Fibrosis: What Drug and Which Way?", Drugs, 60(5), (Abstract Only), (Nov. 2000), 1 pg.
Bank, U., "Review: Peptidases and Peptidase Inhibitors in the Pathogenesis of Diseases", Cellular Peptidases in Immune Functions and Diseases 2, (Edited by Jurgen Langner, et al., Kluwer Academic / Plenum Publishers), (2000), 349-378.
Bartlett, J S., et al., "Targeted adeno-associated virus vector transduction of nonpermissive cells mediated by a bispecific F(ab'gamma)2 antibody.", Nature Biotechnology, 17, (1999), 181-186.
Bartlett, Jeffrey S., et al., "Infectious entry pathway of adeno-associated virus and adeno-associated virus vectors", Journal of Virology, 74(6), (Mar. 2000), 2777-2785.
Bartoli, M., et al., "Mannosidase I inhibition rescues the human alpha-sarcoglycan R77C recurrent mutation.", Hum Mol Genet., 17(9), (May 1, 2008), 1214-21.
Baruchel, S., et al., "The role of oxidative stress in disease progression in individuals infected by the human immunodeficiency virus.", J Leukoc Biol., 52(1), (Jul. 1992), 111-4.
Basak, S, et al., "Infectious Entry Pathways for Canine Parvovirus", Virology, 186(2), (Feb. 1992), 368-376.
Bennett, J., et al., "Real-Time, Noninvasive In Vivo Assessment of Adeno-Associated Virus-Mediated Retinal Transduction", Investigative Ophthalmology & Visual Science, 38 (13), (Dec. 1997), 2857-2863.
Berns, K. I., et al., "Biology of Adeno-associated Virus", In: Current Topics in Microbiology and Immunology, 218, Springer-Verlag, Berlin: R.W. Compans, et al., (Eds.), (1996), 1-23.
Berns, K. I., "Parvovirus Replication", Microbiological Reviews, 54 (3), (Sep. 1990), pp. 316-329.
Beutler, K. T., et al., "Long-Term Regulation of ENAC Expression in Kidney by Angiotensin II", Hypertension, 41, (2003), 1143-1150.
Bies, J., et al., "Oncogenic activation of c-Myb by Carboxyl-Terminal truncation leads to Decreased Proteolysis by the Ubiquitin-26S proteasome pathway", Oncogene, 14(2), Abstract, (Jan. 16, 1997), 1 page.
Billington, D., et al., "Dissection of hepatic receptor-mediated endocytic pathways using self-generated gradients of iodixanol (Optiprep).", Anal. Biochem., 258(8), (1998), 251-258.
Blits, B., et al., "Adeno-associated viral vector-mediated neurotrophin gene transfer in the injured adult rat spinal cord improves hind-limb function", Neuroscience, 118(1), (2003), 271-81.
Bohenzky, R. A., et al., "Interactions Between the Termini of Adeno-Associated Virus DNA", Journal of Molecular Biology, 206, (1989), 91-100.
Bohenzky, R. A., et al., "Replication of Adeno-Associated Virus Genomes With Chimeric Termini", ICN / UCLA Symposium—Viral DNA Replication, (1987), 20 pgs.
Bohenzky, R. A., et al., "Sequence and Symmetry Requirements Wihtin the Internal Palindromic Sequences of the Adeno-Associated Virus Terminal Repeat", Virology, 166, (1988), 316-327.
Bohl, D., et al., "Control of erythropoietin delivery by doxycycline in mice after intramuscular injection of adeno-associated vector.", Blood, 92(5), (1998), 1512-1517.
Bok, D., "Gene Therapy of Retinal Dystrophies: Achievements, Challenges and Prospects", Novartis Foundation Symposium 255—Retinal Dystrophies: Functional Genomics to Gene Therapy, John Wiley & Sons, Ltd., (2004), 4-16; 177-178.
Bokkala, Shaila, et al., "Angiotensin II-induced Down-regulation of Inositol Trisphosphate Receptors in WB Rat Liver Epithelial Cells", Journal of Biological Chemistry, 272(19), (May 9, 1997), 12454-12461.
Bonacorsi, Stephane, et al., "Comparative in vitro activities of meropenem, imipenem, temocillin, piperacillin, and ceftazidime in combination with tobramycin, rifampin, or ciprofloxacin against Burkholderia cepacia isolates from patients with cystic fibrosis.", Antimicrobial Agents and Chemotherapy, 43(2), (Feb. 1999), 213-217.

(56) References Cited

OTHER PUBLICATIONS

Booth, R. E., et al., "Targeted Degradation of ENAC in Response to PKC Activation of the ERK½ Cascade", Am. J. Physiol. Renal Physiol., 284, (2003), F938-F947.
Brand, Stephen, et al., "Role of the proteasome in rat indomethacin-induced gastropathy", Gastroenterology, 116(4), (1999), 865-873.
Bravo, Laura, "Polyphenols: chemistry, dietary sources, metabolism, and nutritional significance", Nutrition Reviews, 56(11), (Nov. 1998), 317-333.
Brister, J. R., et al., "Rep-Mediated Nicking of the Adeno-Associated Virus Origin Requires Two Biochemical Activities, DNA Helicase Activity and Transesterification", Journal of Virology, 73(11), (1999), 9325-9336.
Brooijmans, N., et al., "Molecular Recognition And Docking Algorithms", Annu. Rev. Biophys. Biomol. Struct., vol. 32, (2003), 335-373.
Brotz, H., "The Lantibiotic Mersacidin Inhibits Peptidoglycan Biosynthesis and the Level of Transglycosylation", Eur. J. Biochem., 246(1), (1997), 193-199.
Bruno, T., et al., "Levels of Expression of hRPB11, a core subassembly subunit of human RNA polymerase II, affect doxorubicin sensitivity and cellular differentiation", FEBS Letters 427, (1998), 241-246.
Bubien, J. K., et al., "Expression and regulation of normal and polymorphic epithelial sodium channel by human lymphocytes", J. Biol. Chem., 276(11), (2001), 8557-8566.
Buffinton, G. D, et al., "Oxidative stress in lungs of mice infected with influenza A virus", Free Radic Res Commun., 16(2), (1992), 99-110.
Bugg, C., et al., "SRI6975 Increases Adenovirus Mediated Gene Transfer Through the Apical Surface of Polarized MDCK Cell Monolayers", Cystic Fibrosis Foundation: 2000 North American CF Conference, (Nov. 2000), 1.
Cai, J., et al., "Inhibition of influenza infection by glutathione.", Free Radic Biol Med., 34(7), (Apr. 1, 2003), 928-36.
Cameron, "Recent Advance in Transgenic Technology", Molec. Biol. vol. 7, (1997), 253-265.
Cantin, Andre M, et al., "Aerosolized Prolastin Suppresses Bacterial Proliferation in a Model of Chronic Pseudomonas aeruginosa Lung Infection", American Journal of Respiratory and Critical Care Medicine, vol. 160, (1999), 1130-1135.
Capecchi, M. R, "Altering the Genome by Homologous Recombination", Science, (244), (1989), 1288-1292.
Carter, B. J., et al., "Chapter 11—AAV DNA Replication, Integration, and Genetics", In: Handbook of Parvoviruses, vol. 1., Tijssen, P., Editor, CRC Press, Inc. (Boca Raton, FL), (1992), 169-226.
Carter, Brian J, "Adeno-Associated Virus Vectiors in Clinical Trials", Human Gene Therapy, 16(5), (2005), 541-550.
Carter, P. J., et al., "Adeno-Associated Viral Vectors as Gene Delivery Vehicles (Review)", International Journal of Molecular Medicine, 6(1), (2000), 17-27.
Cassivi, et al., "Transgene Expression After Adenovirus-Mediated Retransfection Of Rat Lungs Is Increased And Prolonged By Transplant Immunosuppression", The Journal of Thoracic and Cardiovascular Surgery, Mosby-Year Book, Inc., St. Louis, MO, US, vol. 117, No. 1, (Jan. 1, 1999), 1-7.
Chao, H., et al., "Several Log Increase in Therapeutic Transgene Delivery by Distinct Adeno-Associated Viral Serotype Vectors", Molecular Therapy, 2(6), (2000), 619-623.
Chiorini, J. A., et al., "Cloning and Characterization of Adeno-Associated Virus Type 5", Journal of Virology, 73(2), (1999), 1309-1319.
Chiorini, J. A., et al., "Determination of Adeno-Associated Virus Rep68 and Rep78 Binding Sites by Random Sequence Oligonucleotide Selection", Journal of Virology, 69(11), (1995), 7334-7338.
Chiorini, J. A., et al., "Sequence Requirements for Stable Binding and Function of Rep68 on the Adeno-Associated Virus Type 2 Inverted Terminal Repeats", Journal of Virology, 68(11), (1994), 7448-7457.

Chu, Q, et al., "Binding and uptake of Cationic Lipid: pDNA Complexes by Polarized Airway Epithelial Cells", Human Gene Therapy, 10, (1999), pp. 25-36.
Chung, King-Thom, et al., "Tannis and Human Health: A Review", Critical Reviews in Food Science and Nutrition, 38(6), (1998), 421-464.
Cifuentes, M. E., et al., "Targeting reactive oxygen species in hypertension", Current Opinion in Nephrology and Hypertension, 15, (2006), 179-186.
Clark, J., et al., "A Future for Transgenic Livestock", Nature Reviews Genetics, 4, (2003), 825-833.
Clark, K. R., et al., "Recombinant Adeno-Associated Viral Vectors Mediate Long-Term Transgene Expression in Muscle", Human Gene Therapy, 8, (Apr. 10, 1997), pp. 659-669.
Conrad, C. K., et al., "Safety of single-dose administration of an adeno-associated virus (AAV)-CFTR vector in the primate lung", Gene Therapy, 3(8), (Aug. 1996), 658-668.
Cooney, Ashley, et al., "Cystic Fibrosis Gene Therapy: Looking Back, Looking Forward", GENES, vol. 9, No. 11, (Nov. 7, 2018).
Coonrod, A, et al., "On the mechanism of DNA transfection: efficient gene transfer without viruses", Gene Therapy, 4(12), (1997), 1313-1321.
Croyle, Maria, et al., "Development of novel formulations that enhance adenoviral-mediated gene expression in the lung in vitro and in vivo.", Molecular Therapy, 4(1), (Jul. 2001), 22-28.
Desai, Shyamal, et al., "Ubiquitin-dependent Destruction of Topoisomerase I Is Stimulated by the Antitumor Drug Camptothecin", Journal of Biological Chemistry, 272(39), (Sep. 26, 1997), 24159-24164.
Dietrich, Cornelia, et al., "p53-dependent cell cycle arrest induced by N-acetyl-L-leucinyl-L-leucinyl-L-norleucinal in platelet-derived growth factor-stimulated human fibroblasts.", Proc Natl Acad Sci U S A., 93(20), (1996), 10815-10819.
Ding, W., et al., "Second-Strand Genome Conversion of Adeno-Associated Virus Type 2 (AAV-2) and AAV-5 is Not Rate Limiting Following Apical Infection of Polarized Human Airway Epithelia", Journal of Virology, 77(13), (2003), 7361-7366.
Ding, Wei, et al., "Proteasome Inhibitor LLnL (MG101) Augments AAV5 Transduction in Polarized Human Airway Epithelia", American Society of Gene Therapy, Abstracts of Scientific Presentations—Abstract No. 571, (Jun. 5, 2002), 1 page.
Dishart, Kate, et al., "Recombinant Adeno-Associated Virus-2 as a Candidate Gene Delivery Vector for Vein Grafts", American Society of Gene Therapy, Abstracts of Scientific Presentations—Abstract No. 1107, (Jun. 5, 2002), 1 page.
Djaldetti, M., et al., "SEM observations on the effect of anthracycline drugs on cultured newborn rat cardiomyocytes (Abstract Only)", Basic Res Cardiol., vol. 6, (1988), 627-7.
Doll, R. F, et al., "Comparison of promoter strengths on gene delivery into mammalian brain cells using AAV vectors", Gene Therapy, 3(5), (1996), 437-447.
Dollard, S. C, et al., "Enhanced responsiveness to nuclear factor kappa B contributes to the unique phenotype of simian immunodeficiency virus variant SIVsmmPBj14.", J Virol., 68(12), (Dec. 1994), 7800-9.
Donaldson, S. H., et al., "Regulation of the Epithelial Sodium Channel by Serine Proteases in Human Airways", The Journal of Biological Chemistry, 277(10), (2002), 8338-8345.
Dou, Q. P, et al., "Proteasome inhibitors as potential novel anticancer agents", Drug Resist Updat., 2(4), (Aug. 1999), 215-223.
Douar, Anne-Marie, et al., "Intracellular Trafficking of Adeno-Associated Virus Vectors: Routing to the Late Endosomal Compartment and Proteasome", Journal of Virology, p. 1824-1833; vol. 75, No. 4, (Feb. 2011), 1824-1833.
Droge, W., et al., "HIV-induced cysteine deficiency and T-cell dysfunction—a rationale for treatment with N-acetylcysteine", Immunol Today., 13(6), (Jun. 1992), 211-4.
Duan, D, et al., "Response to "Polarity Influences the Efficiency of Recombinant Adenoassociated Virus Infection in Differentiated Airway Epithelia"", Human Gene Therapy, 10, (1999), 1553-1557.
Duan, D., "A New Dual-Vector Approach to Enhance Recombinant Adeno-Associated Virus-Mediated Gene Expression Through Intermolecular cis Activation", Nature Medicine, 6(5), (2000), 595-598.

(56) References Cited

OTHER PUBLICATIONS

Duan, D., et al., "Chapter 15: Trans-Splicing Vectors Expand the Packaging Limits of Adeno-Associated Virus for Gene Therapy Applications", Methods in Molecular Medicine, vol. 76: Viral Vectors for Gene Therapy: Methods and Protocols, (2003), 287-307.
Duan, D., et al., "Chapter 3—Adeno-Associated Virus", In: Lung Biology in Health and Disease, vol. 169—Gene Therapy in Lung Disease, Albelda, S. M., Editor, Marcel Dekker, Inc., (2002), 51-92.
Duan, D., et al., "Chapter 3—Dual Vector Expansion of the Recombinant AAV Packaging Capacity", In: Methods in Molecular Biology, vol. 219: Cardiac Cell and Gene Transfer, Metzger, J. M., Editor, Human Press, Inc., Totowa, NJ, (2003), 29-51.
Duan, D., "Consequences of DNA-Dependent Protein Kinase Catalytic Subunit Deficiency on Recombinant Adeno-Associated Virus Genome Circularization and Heterodimerization in Muscle Tissue", Journal of Virology, 77(8), (2003), 4751-4759.
Duan, D., et al., "Endosomal processing limits gene transfer to polarized airway epithelia by adeno-associated virus", J Clin Invest., 105(11), (Jun. 2000), 1573-87.
Duan, D., et al., "Enhancement of Muscle Gene Delivery With Pseudotyped Adeno-Associated Virus Type 5 Correlates With Myoblast Differentiation", Journal of Virology, 75(16), (2001), 7662-7671.
Duan, D., et al., "Expanding AAV Packaging Capacity with Trans-splicing or Overlapping Vectors: A Quantitative Comparison", Molecular Therapy, 4(4), http://www.idealibrary.com, (2001), 383-391.
Duan, D., "Formation of Adeno-Associated Virus Circular Genomes is Differentially Regulated by Adenovirus E4 ORF6 and E2a Gene Expression", Journal of Virology, 73(1), (Jan. 1999), 161-169.
Duan, D., "Polarity Influences the Efficiency of Recombinant Adenoassociated Virus Infection in Differentiated Airway Epithelia", Human Gene Therapy, 9, (Dec. 10, 1998), 2761-2776.
Duan, D., et al., "Structural and Functional Heterogeneity of Integrated Recombinant AAV Genomes", Virus Research, 48(1), (Jan. 1997), 41-56.
Duan, Dongsheng, et al., "Circular intermediates of recombinant adeno-associated virus have defined structural characteristics responsible for long-term episomal persistence in muscle tissue", Journal of Virology, 72(11), (Nov. 1998), 8568-77.
Duan, Dongsheng, et al., "Dynamin is required for recombinant adeno-associated virus type 2 infection", Journal of Virology, 73(12), (Dec. 1999), 10371-10376.
Duan, Dongsheng, et al., "Polarity Influences the Efficiency of Recombinant Adenoassociated Virus Infection in Differentiated Airway Epithelia", Human Gene Therapy vol. 9, (Dec. 1998), 2761-2776.
Duan, Dongsheng, et al., "Structural Analysis of adeno-associated virus transduction circular intermediates", Virology, 261(1), (Aug. 15, 1999), 8-14.
Ecelbarger, C. A., et al., "Regulation of the Abudance of Renal Sodium Transporters and Channels by Vasopressin", Experimental Neurology, 171, (2001), 227-234.
Eck, Stephen L, et al., "Chapter 5: Gene-Based Therapy", Goodman & Gilman's The Pharmacological Basis of Therapeutics, 9th Edition, McGraw-Hill, New York, NY, (1996), 77-101.
Elliott, P J, et al., "Recent Advances in Understanding Proteasome Function", Current Opinion in Drug Discovery and Development, 5 (2), ISSN: 1367-6733, (1999), 484-490.
Elmarakby, A., et al., "NADPH oxidase inhibition attenuates oxidative stress but not hypertension produced by chronic ET-1", Hypertension, 45(2), (Feb. 2005), 283-7.
Engelhardt, J., et al., "Adeno-Associated Virus Vectors", U.S. Appl. No. 60/086,166, filed May 20, 1998.
Engelhardt, J., et al., "Compounds and Methods for Pharmico-Gene Therapy of Epithelial Sodium Channel Associated Disorders", U.S. Appl. No. 10/815,557, filed Mar. 31, 2004, 137 pgs.
Engelhardt, J., et al., "Compounds and Methods to Enhance Adeno-Associated Virus Transduction", U.S. Appl. No. 60/138,188, filed Jun. 8, 1999, (Jun. 8, 1999), 102 pgs.
Engelhardt, J., et al., "Compounds and Methods to Enhance rAAV TRANSDUCTION", U.S. Appl. No. 10/815,262, filed Mar. 31, 2004, 156 pgs.
Engelhardt, J. F., et al., "Direct gene transfer of human CFTR into human bronchial epithelia of xenografts with E1-deleted adenoviruses", Nature Genetics, 4(1), (1993), 27-34.
Engelhardt, J. F., "The Lung as a Metabolic Factory for Gene Therapy", The Journal of Clinical Investigation, 110(4), (2002), 429-432.
Engelhardt, John, et al., "Adeno-Associated Virus Vectors", U.S. Appl. No. 09/276,625, filed Mar. 25, 1999, (Mar. 25, 1999), 122 pgs.
Engelhardt, John, et al., "Adeno-Associated Virus Vectors", U.S. Appl. No. 10/054,665, filed Jan. 22, 2002, 138 pgs.
Engelhardt, John, et al., "Compounds and Methodsd to Enhance Adeno-Associated Virus Transduction", U.S. Appl. No. 60/201,089, filed May 2, 2000.
Engelhardt, John, et al., "Enhancement of Muscle Gene Delivery With Pseudotyped AAV-5 Correlates With Myoblast Differentiation", U.S. Appl. No. 60/305,204, filed Jul. 13, 2001.
Englehardt, John, et al., "Adeno-Associated Virus Vectors and Uses Thereof", U.S. Appl. No. 09/684,554, filed Oct. 6, 2000, 141 pgs.
Englehardt, John, "Compounds and Methods for Pharmico-Gene Therapy of Epithelial Sodium Channel Associated Disorders", U.S. Appl. No. 60/512,347, filed Oct. 16, 2003.
Englehardt, John, et al., "Compounds and Methods to Enhance rAAV TRANSDUCTION", U.S. Appl. No. 60/459,323, filed Mar. 31, 2003.
Englehardt, John, et al., "Compounds and Methods to Enhance rAAV Transduction", U.S. Appl. No. 10/194,421, filed Oct. 12, 2000, (, 138 pgs.
Englehardt, John, et al., "Pseudotyped Adeno-Associated Viruses and Uses Thereof", U.S. Appl. No. 10/194,421, filed Jul. 12, 2002.
Everett, R D., et al., "A viral activator of gene expression functions via the ubiquitin-proteasome pathway", The EMBO Journal, 17 (24), (1998), pp. 7161-7169.
Excoffon, Katherine J. D. A, et al., "Directed Evolution of Adeno-Associated Virus to an Infectious Respiratory Virus", Proceedings of the National Academy of Sciences, vol. 106, No. 10, (Mar. 10, 2009), 3865-3870.
Fallin, R. A., et al., "PMA-Induced Inhibition of Amiloride-Sensitive Sodium Absorption is Partially Mediated by ERK½ Activation", The FASEB Journal, 17(5) (Abstracts Part II), Abstract No. 585-19, (2003), A915.
Fasbender, AL, et al., "Complexes of adenovirus with polycationic polymers and cationic lipids increase the efficiency of gene transfer in vitro and in vivo", The Journal of Biological Chemistry, 272 (10), (Mar. 7, 1997), 6479-6489.
Fasbender, AL, et al., "Complexes of Adenovirus with Polycationic Polymers and Cationic Lipids Increase the Efficiency of Gene Transfer in Vitro and in Vivo", Journal of Biological Chemistry vol. 272, No. 10, (Mar. 1997), 6479-6489.
Fayadat, Laurence, et al., "Degradation of Human Thyroperoxidase in the Endoplasmic Reticulum Involves Two Different Pathways Depending on the Folding State of the Protein", Journal of Biological Chemistry, 275(21), (May 26, 2000), 15948-15954.
Fehilly, Carole B, et al., "Interspecific chimaerism between sheep and goat", Nature vol. 307, (Feb. 16, 1984.), 634-6.
Fenteany, G, et al., "Inhibition of proteasome activities and subunit-specific amino-terminal threonine modification by lactacystin", Science, 268(5211), (1995), 726-731.
Fenteany, Gabriel, et al., "Lactacystin, Proteasome Function, and Cell Fate", Journal of Biological Chemistry, 273(15), (Apr. 10, 1998), 8545-8548.
Ferrari, F K., et al., "Second-Strand Synthesis Is a Rate-Limiting Step for Efficient Transduction by Recombinant Adeno-Associated Virus Vectors", Journal of Virology, 70(5), (1996), 3227-3234.
Ferrari, Forrest, et al., "Second-Strand Synthesis Is a Rate-Limiting Step for Efficient Transduction by Recombinant Adneo-Associated Virus Vectors", Journal of Virology vol. 70, No. 5, (3227-3234), May 1996.
Figueiredo-Pereira, Maria E, et al., "The antitumor drug aclacinomycin A, which inhibits the degradation of ubiquitinated proteins, shows

(56) References Cited

OTHER PUBLICATIONS selectivity for the chymotrypsin-like activity of the bovine pituitary 20 S proteasome", Journal of Biological Chemistry, 271(28), (Jul. 12, 1996), 16455-16459.

Finn, J. D, et al., "Proteasome inhibitors decrease AAV2 capsid derived peptide epitope presentation on MHC class I following transduction", Mol Ther., 18(1), (Jan. 2010), 135-42.

Finn, Jonathan D., et al., "Proteasome Inhibitors Decrease AAV2 CAPSID-Derived Peptide Epitope Presentation on MHC Class I Following Transduction", Molecular Therapy vol. 18 No. 1, 135-142 Jan. 2010, (Jan. 1, 2010), 135-142.

Fisher, K J., et al., "Transduction with recombinant adeno-associated virus for gene therapy is limited by leading-strand synthesis", Journal of Virology, 70(1), (Jan. 1996), 520-532.

Fisher, Krishna, et al., "Recombinant adeno-associated virus for muscle directed gene therapy", Nature Medicine, 3(3), (Mar. 1997), 306-312.

Fisher, Krishna, et al., "Transduction with Recombinant Adeno-Associated Virus for Gene Therapy is Limited by Leading-Strand Synthesis", Journal of Virology vol. 70, No. 5, (1996), 520-532.

Fisher-Adams, G., et al., "Integration of Adeno-Associated Virus Vectors in CD34+ Human Hematopoietic Progenitor Cells After Transduction", Blood, 88 (2), (Jul. 15, 1996), pp. 492-504.

Flotte, TR, "(Abstract) Recombinant adeno-associated virus vectors for cystic fibrosis gene therapy", Curr Opin Mol Ther 3(5), pp. 497-502, (2001), 1 pg.

Flotte, T., et al., "A Phase I Study of an Adeno-Associated Virus-CFTR Gene Vector in Adult CF Patients With Mild Lung Disease", Human Gene Therapy, 7(9), (1996), 1145-1159.

Flotte, T. R., et al., "Adeno-Associated Virus Vector Gene Expression Occurs in Nondividing Cells in the Absence of Vector DNA Integration", American Journal of Respiratory Cell and Molecular Biology, 11, (1994), pp. 517-521.

Flotte, T. R., et al., "Chapter 40—Adeno-Associated Viral Vectors for CF Gene Therapy", In: Methods in Molecular Medicine, 70, (2002), 599-608.

Flotte, T. R., "Expression of the Cystic Fibrosis Transmembrane Conductance Regulator From a Novel Adeno-Associated Virus Promoter", The Journal of Biological Chemistry, 268(5), (1993), 3781-3790.

Furst, R., et al., "Atrial natriuretic peptide induces mitogen-activated protein kinase phosphatase-1 in human endothelial cells via Rac1 and NAD(P)H oxidase/Nox2-activation", Circ Res., 96(1), (Jan. 7, 2005), 43-53.

Gabizon, Alberto, "Long-circulating liposomes for drug delivery in cancer therapy: a review of biodistribution studies in tumor-bearing animals", Advanced Drug Delivery Reviews, (1997), 337-344.

Gabizon, Alberto, et al., "Preclinical Studies with Doxorubicin Encapsulated in Polyethyleneglycol-Coated Liposomes", Journal of Liposome Research, 3(3), (1993), 517-528.

Gadallah, M. F., et al., "Epithelial Sodium Channel-Dependent Hypertension: An Emerging Syndrome", Journal of the American Society of Nephrology, 10 (Abstracts Issue), Abstract No. A1842, (1999), 365A.

Gadallah, M. F., et al., "Preservation of Renal Function in Patients With Hypertension and Chronic Renal Impairment; RevisIted", Journal of the American Society of Nephrology, 10 (Abstracts Issue), Abstract No. A1841, (1999), 365A.

Gao, H., et al., "Critical Role for microglial NADPH Oxidase in Rotenone-induced degeneration of Dopaminergic Neurons", Journal of Neuoscience; 23(15), (Jul. 16, 2003), 6181-6187.

Gao, H. M, et al., "Critical role of microglial NADPH oxidase-derived free radicals in the in vitro MPTP model of Parkinson's disease", FASEB J., 17(13), (Oct., 2003), 1954-6.

Gao, H. M, et al., "Novel anti-inflammatory therapy for Parkinson's disease.", Trends Pharmacol Sci., 24(8), (Aug. 2003), 395-401 pgs.

Gao, Hui-Ming, et al., "Distinct Role for Microglia in Rotenone-Induced Degeneration of Dopaminergic Neurons", Journal of Neuroscience 22(3), (Feb. 1, 2002), 782-790.

Garber, Ken, "Taking Garbage In, Taking Cancer Out?", Science, vol. 295, (Jan. 25, 2002), 612-613.

Giraud, C, et al., "Recombinant Junctions Formed by Site-Specific Integration of Adeno-Associated Virus Into An Episome", Journal of Virology, 69(11), (1995), 6917-6924.

Giraud, Catherine, et al., "Recombinant junctions formed by site-specific integration of adeno-associated virus into an episome", Journal of Virology, 69 (11), (Nov. 1995), 6917-6924.

Goldberg, A L., et al., "New insights into proteasome function: from archaebacteria to drug development", Chemistry & Biology, 2(8), (1995), 503-508.

Goncalves, M. A, "Adeno-associated virus: from defective virus to effective vector", Virol J., 2, (May 6, 2005), 17 pgs.

Gormley, K., et al., "Regulation of the Epithelial Sodium Channel by Accessory Proteins", Biochem. J., 371, (2003), 1-14.

Gorvel, J. P, et al., "rab5 controls early endosome fusion in vitro.", Cell, 64(5), (Mar. 8, 1991), 915-25.

Gottlieb, T A., et al., "Actin Microfilaments Play a Critical Role in Endocytosis at the Apical but not the Basolateral Surface of Polarized Epithelial Cells", The Journal of Cell Biology, 120 (3), (1993), pp. 695-710.

Graham, J. M, et al., "Iodixanol—a new density gradient medium for the dissection of the endosomal compartment", Z Gastroenterol., 34 Suppl 3, (1996), 76-8.

Graham, J., "Purification of peroxisomes using a density barrier in a swinging-bucket rotor.", ScientificWorldJournal, 2, (May 22, 2002), 1400-3.

Graham, J., et al., "The preparation of subcellular organelles from mouse liver in self-generated gradients of iodixanol", Anal. Biochem., 220(2), (1994), 367-73.

Grimm, D., et al., "From Virus Evolution to Vector Revolution: Use of Naturally Occurring Serotypes of Adeno-Associated Virus (AAV) as Novel Vectors for Human Gene Therapy", Current Gene Therapy, 3, (2003), 281-304.

Gross, R., "Clinical problems of optimum bioavailability, in particular in cytostatic therapy (Abstract Only)", Arzneimittelforschung, vol. 26(1A), (1976), 130-5.

Gruchala, Marcin, et al., "Adeno-Associated Virus-Mediated Gene Transfer into Normal Rabbit Arteries. Assessment of the Tie and CMV Promoters and the Antiproteasome Treatment with MG-132", American Society of Gene Therapy, Abstracts of Scientific Presentations—abstract No. 1110, (Jun. 5, 2002), 1 page.

Gruenberg, J, et al., "Membrane traffic in endocytosis: insights from cell-free assays.", Annu Rev Cell Biol., 5, (1989), 453-81.

Hagstrom, J. N., et al., "Improved Muscle-Derived Expression of Human Coagulation Factor IX From a Skeletal Actin/CMV Hybrid Enhancer/Promoter", Blood, 95(8), (2000), 2536-2542.

Halbert, C. L., "Transduction by Adeno-Associated Virus Vectors in the Rabbit Airway: Efficiency, Persistence, and Readministration", Journal of Virology, 71 (8), (Aug. 1997), pp. 5932-5941.

Hamilton, Bradley A, et al., "Polarized AAVR Expression Determines Infectivity by AAV Gene Therapy Vectors", Gene Therapy, Nature Publishing Group, London, GB, vol. 26, No. 6, (Apr. 8, 2019), 240-249.

Hansen, et al., "Impaired intracellular trafficking of adeno-associated virus type 2 vectors limits efficient transduction of murine fibroblasts", Journal of Virology, (Jan. 2000), 992-996.

Hansen, J., et al., "Adeno-Associated Virus Type 2-Mediated Gene Transfer: Altered Endocytic Processing Enhances Transduction Efficiency in Murine Fibroblasts", Journal of Virology, 75(9), (2001), 4080-4090.

Hansen, J., et al., "Impaired Intracellular Trafficking of Adeno-Associated Virus Type 2 Vectors Limits Efficient Transduction of Murine Fibroblasts", Journal of Virology, 74(2), (2000), 992-996.

Harraz, et al., "SOD1 mutations disrupt redox-sensitive Rac regulation of NADPH oxidase in a familial ALS model", The Journal of Clinical Investigation, vol. 118, No. 2, (Feb. 2008), 659-670.

Hasegawa, S., et al., "Microtubule Involvement in the Intracellular Dynamics for Gene Transfection Mediated by Cationic Liposomes", Gene Therapy, 8, (2001), 1669-1673.

Hashimoto, Y, et al., "Amino- and carboxyl-terminal mutants of presenilin 1 cause neuronal cell death through distinct toxic mecha-

(56) References Cited

OTHER PUBLICATIONS nisms: Study of 27 different presenilin 1 mutants", J Neurosci Res. 75(3), Abstract Only, (Feb. 2004), 417-28.
He, Y, et al., "Minocycline inhibits microglial activation and protects nigral cells after 6-hydroxydopamine injection into mouse striatum", Brain Res. 909(1-2), Abstract Only, (Aug. 2001), 187-93.
Herzog, Roland W., et al., "Stable gene transfer and expression of human blood coagulation factor IX after intramuscular injection of recombinant adeno-associated virus", Proceedings of the National Academy of Sciences of the United States of America, 94, (May 1997), 5804-9.
Higgins, D. G., "CLUSTAL: a package for performing multiple sequence alignment on a microcomputer.", Gene, 73(1), (Dec. 15, 1988), 237-44.
Higgins, D. G., "Fast and sensitive multiple sequence alignments on a microcomputer.", Comput Appl Biosci., 5(2), (Apr. 1989), 151-153.
Hong, J., et al., "Identification of SRI6975, A Compound that Enhances Adenovirus-Mediated Gene Expression in Polarized Epithelial Cells", Cystic Fibrosis Foundation: 2000 North American CF Conference, (Nov. 2000), 1-2.
Hosseini, Hassan, et al., "Protection against experimental autoimmune encephalomyelitis by a proteasome modulator", Journal of Neuroimmunology, 188, (2001), 233-244.
Houdebine, L., "Production of Pharmaceutical Proteins From Transgenic Animals", Journal of Biotechnology, vol. 34, France, (1994), 269-287.
Hsu, A., et al., "Ritonavir. Clinical pharmacokinetics and interactions with other anti-HIV agents", Clin Pharmacokinet, 35(6), abstract, (Dec. 1998), 1 page.
Hsy, Py, et al., "Effect of Polyethylenimine on Recombinant Adeno-Associated Virus Mediated Insulin Gene Therapy", 1. J Gene Med. Oct. 2005;7(10):1311-21—School of Pharmacy, College of Medicine, National Taiwan University, 1, Jen-Ai Road, Section 1, Taipei 100 Taiwan, (Oct. 7, 2005), 1311-21.
Huang, L., et al., "Efficient lipofection with cisplatin-resistant human tumor cells", Cancer Gene Therapy, vol. 3, No. 2, (1996), 107-112.
Hummler, E., et al., "Genetic Disorders of Membrane Transport—V. The Epithelial Sodium Channel and its Implication in Human Diseases", American Journal of Physiology, Gastrointensinal and Liver Physiology, 276, (1999), G567-G571.
Hunziker, et al., "Review—Perspectives: toward a peptide-based vaccine against hepatitis C virus", Molecular Immunol, 38, (2001), 475-484.
Iqbal, Mohamed, et al., "Potent Inhibitors of Proteasome", Journal of Medicinal Chemistry, vol. 38, No. 13, (1995), 2276-2277.
Itani, O. A., et al., "Cycloheximide Increases Glucocorticoid-Stimulated alpha-ENaC mRNA in Collecting Duct Cells by p38 MAPK-dependent Pathway", Am. J. Physiol. Renal Physiol., 284, (2002), F778-F787.
Jensen, T J., et al., "Multiple Proteolytic Systems, Including the Proteasome, Contribute to CFTR Processing", Cell, 83, (1995), pp. 129-135.
Jiang, Q., et al., "Cellular Heterogenecity of CFTR Expression and Function in the Lung: Implications for Gene Therapy of Cystic Fibrosis", European Journal of Human Genetics, 6(1), (Jan. 1998), 12-31.
Jiang, Q., et al., "Cellular Heterogeneity of CFTR Expression and Function in the Lung: Implications for Gene Therapy of Cystic Fibrosis", European Journal of Human Genetics, 6, (Jan. 1998), 12-31.
Johannesson, T., et al., "[Neurodegenerative diseases, antioxidative enzymes and copper. A review of experimental research.]", Laeknabladid, 89(9), (Sep. 2003), 659-671.
Johnson, J. S., et al., "Enhancement of Adeno-Associated Virus Infection by Mobilizing Capsids into and Out of the Nucleolus", Journal of Virology, 83(6), (2009), 2632-2644.

Johnson, L. G, et al., "Efficiency of gene transfer for restoration of normal airway epithelial function in cystic fibrosis", Nature Genetics 2, (1992), 21-25.
Jorgensen, M. J., et al., "Expression of Completely y-Carboxylated Recombinant Human Prothrombin", The Journal of Biological Chemistry, 262(14), (1987), 6729-6734.
Kamynina, E., et al., "Concerted Action of ENAC, Nedd4-2, and Sgk1 in Transepithelial Na+ Transport", Am. J. Physiol. Renal Physiol., 283, (2002), F377-F387.
Kannan, R., et al., "Impairment of conjunctival glutathione secretion and ion transport by oxidative stress in an adenvirus type 5 ocular infection model of pigmented rabbits.", Free Radic Biol Med., 37(2), (Jul. 15, 2004), 229-38.
Kaplan, Johanne M., et al., "Potentiation of gene transfer to the mouse lung by complexes of adenvirus vector and polycations improves therapeutic potential", Human Gene Therapy, vol. 9, No. 10, XP000972242, (Jul. 1, 1998), 1469-1479.
Kaplitt, M. G., "Long-Term Gene Expression and Phenotypic Correction Using Adeno-Associated Virus Vectors in the Mammalian Brain", Nature Genetics, 8(2), (Oct. 1994), 148-154.
Kappell, Catherine A., et al., "Regulating gene expression in transgenic animals", Current Opinion in Biotechnology vol. 3, (1992), 548-553.
Kapturczak, M. H, et al., "Adeno-Associated Virus (AAV) as a Vehicle for Therapeutic Gene Delivery : Improvements in vector Design and Viral Production Enhance Potential to prolong Graft Survival in Pancreatic Islet Cell Transplantation for the Reversal of Type I Diabetes", Current Molecular Medicine, (2001), 245-258.
Kay, M. A., et al., "Evidence for Gene Transfer and Expression of Factor IX in Haemophilia B Patients Treated With an AAV Vector", Nature Genetics, 24, (2000), 257-261.
Kazi, A., et al., "Inhibition of the Proteasome Activity, a Novel Mechanism Associated with the Tumor Cell Apoptosis-Inducing Ability of Genistein", Biochemical Pharmacology, 66, (2003), 965-976.
Kearns, W. G., et al., "Recombinant Adeno-Associated Virus (AAV-CFTR) Vectors do not Integrate in a Site-Specific Fashion in an Immortalized Epithelial Cell Line", Gene Therapy, 3, (1996), 748-755.
Kellenberger, et al., "Epithelial Sodium Channel/Degenerin Family of Ion Channels: A Variety fo Functions for a Shared Structure", Physiological Review, 82, (2002), 735-767.
Kessler, P D, et al., "Gene delivery to skeletal muscle results in sustained expression and systemic delivery of a therapeutic protein", Proceedings of the National Academy of Sciences of the United States of America, 93(24), (Nov. 26, 1996), 14082-7.
Kessler, P., et al., "Sodium Butyrate Greatly Enhances the efficiency of Viral Transduction in Adult Ventricular Cardiomyocytes by Adeno-associated Viral Vectors", Circulation 92(8), (Oct. 15, 1995), 296.
Kim, Koanhoi, "Proteasome Inhibitors Sensitize Human Vascular Smooth Muscle Cells to Fas (CD95)—Mediated Death", Biochemical and Biophysical Research Communications, vol. 281, No. 2, (2001), 305-310.
Kim, Kyung Bo, et al., "Proteasome Inhibition by the Natural Products Epoxomicin and Dihydroeponemycin: Insights into Specificity and Potency", Bioorganic & Medicinal Chemistry Letters, (1999), 3335-3340.
Kiyomiya, K., et al., "The role of the proteasome in apoptosis induced by anthracycline anticancer agents", Int. J. Oncol., 20(6), abstract, (Jun. 2002), 1 page.
Kiyomiya, K., et al., "The role of the proteasome in apoptosis induced by anthracycline anticancer agents.", Int J Oncol., 20(6), (Jun. 2002), 1205-9.
Kiyomiya, Ken-Ichi, et al., "Mechanism of specific nuclear transport of adriamycin: the mode of nuclear translocation of adriamycin-proteasome complex", Cancer Res., 61(6), (Mar. 15, 2001), 2467-71.
Kiyomiya, Ken-Ichi, "The role of the proteasome in apoptosis induced by anthracycline anticancer agents", International Journal of Oncology, 20(6), Preliminary Report on Patentability, (Jun. 2002), 1205-9.

(56) References Cited

OTHER PUBLICATIONS

Kiyomiya, K-I, et al., "Proteasome is a Carrier to Translocate Doxorubicin From Cytoplasm into Nucleus", Life Sciences, 62(20), (1998), 1853-1860.
Kloetzel, P M., "The Proteasome system: a neglected tool for improvement of novel therapeutic strategies?", Gene Therapy, 5, (1998), pp. 1297-1298.
Kotin, R. M., et al., "Characterization of a preferred site on human chromosome 19q for integration of adeno-associated virus DNA by non-homologous recombination", The EMBO Journal, 11 (13), (1992), pp. 5071-5078.
Kumar, Gita, "Side-stepping the side effects", BioCentury, The Bernstein Report on BioBusiness, (Dec. 17, 2001), 7.
Lambeth, J. D., "Nox enzymes and the biology of reactive oxygen", Nature Reviews, Immunology,4(3), (2004), 181-189.
Lebkowski, J., "Adeno-Associated Virus: a Vector System for Efficient Introduction and Integration of DNA into a Variety of Mammalian Cell Types", Molecular and Cellular Biology, 8(10), (Oct. 1988), 3988-3996.
Lechardeur, D., et al., "Intracellular Barriers to Non-Viral Gene Transfer", Curr. Gene Therapy, 2, (2002), 183-194.
Lee, D. H, et al., "Proteasome inhibitors: valuable new tools for cell biologists", Trends Cell Biol., 8(10), (Oct. 1998), 397-403.
Lee, Do Hee, et al., "Selective Inhibitors of the Proteasome-dependent and Vacuolar Pathways of Protein Degradation in *Saccharomyces cerevisiae*", Journal of Biological Chemistry, (Nov. 1, 1996), 27280-27284.
Lee, Do Hee, et al., "The Proteasome Inhibitors and Their Uses", Proteasomes: The World of Regulatory Proteolysis, (2000), 154-175.
Lee, K., et al., "Shuttle PCR-based cloning of the infectious adeno-associated virus type 5 genome", Journal of Virological Methods, 111(2), (Aug. 2003), 75-84.
Lee, Sang Goo, et al., "Enhancement of adenoviral transduction with polycationic liposomes in vivo", Cancer Gene Therapy, vol. 7, No. 10, (2000), 1329-1335.
Lefebvre, R. B., et al., "Conformation Takes Precedence Over Sequence in Adeno-Associated Virus DNA Replication", Molecular and Cellular Biology, 4(7), (1984), 1416-1419.
Li, et al., "Cloned ferrets produced by somatic cell nuclear transfer", Dev. Biol vol. 293, Iss. 2, (2006), 439-448.
Li, et al., "Progress toward generating a ferret model of cystic fibrosis by somatic cell nuclear transfer", Reprod. Biol. And Endocrinology vol. 1, (2003), 1-8.
Li, M., et al., "Macrophage colony stimulatory factor and interferon-gama trigger distinct mechanisms for augmentation of beta-amyloid-induced microglia-mediated neurotoxicity", J. Neurochem 91(3), Abstract Only, (Nov. 2004), 1 pg.
Q., et al., "Nox2 and Rac1 regulate H2O2-dependent recruitment of TRAF6 to endosomal interleukin-1 receptor complexes", Mol Cell Biol., 26(1), (Jan. 2005), 140-54.
Liang, E., et al., "Oligonucleotide delivery: a cellular prospective", Pharmazie, vol. 54,No. 8, XP000965598, (Aug. 1999), 559-566.
H. C, et al., "Prediction of tyrosine sulfation sites in animal virus", Biochemical And Biophysical Research Communications,312(4), (Dec. 26, 2003), 1154-1158.
Lin, S, et al., "Delivery of a Novel AAV, AV.T165-CFTR, to Human Bronchial Epithelial Cells from Patients with Cystic Fibrosis Augments Functional Recovery of Chloride Conductance", Pediatric Pulmonology; 33rd Annual North American Cystic Fibrosis Conference Oct. 31, 2019 to Nov. 2, 2019 Nashville, TN, John Wiley & Sons, Inc, US, vol. 54, No. Supplement 2, (Oct. 1, 2019), p. 218.
Linden, R. M., et al., "Site-specific integration by adeno-associated virus", PNAS, 93, (Oct. 1994), pp. 11288-11294.
Linden, R. M., et al., "The Recombinant Signals for Adeno-Associated Virus Site-Specific Integration", Proc. Natl. Acad. Sci. USA, 93, (Jul. 1996), 7966-7972.
Loguercio, C., et al., "Oxidative stress in viral and alcoholic hepatitis.", Free Radic Biol Med., 34(1), (Jan. 1, 2003), 1-10.
Lu, Wei, et al., "HIV protease inhibitors restore impaired T-cell proliferative response in vivo and in vitro: a viral-suppression-independent mechanism", Blood, vol. 96, No. 1, (Jul. 1, 2000), 250-258.
Lu, X., et al., "Synthesis and biological evaluations of novel apocynin analogues", Eur J Med Chem., 46(7), (Jul., 2011), 2691-8.
Lull, M. E, et al., "Chronic apocynin treatment attenuates beta amyloid plaque size and microglial number in hAPP(751)(SL) mice", PLoS One, 6(5), (2011), e20153.
Luo, Hongyu, et al., "A Proteasome Inhibitor Effectively Prevents Mouse Heart Allograft Rejection", Transplantation, vol. 72, No. 2, (Jul. 27, 2001), 196-202.
Ma, Y., et al., "p53-Independent Down-Regulation of Mdm2 in Human Cancer Cells Treated with Adriamycin", Molecular Cell Biology Research Communications, 3(2), (Feb. 2000), 122-128.
Macías-Pérez, Martha Edith, et al., "Ethers and Esters Derived ROM Apocynin Avoid the Interaction Between p47phox AND p22phox Subunits of NADPH Oxidase: Evaluation in Vitro and in Silico", (Biosci. Rep., 33: e00055 (2013)), (2013), 605-616.
Mah, C, et al., "Adeno-Associated Virus Type 2-Mediated Gene Transfer: Role of Epidermal Growth Factor Receptor Protein Tyrosine Kinase in Transgene Expression", Journal of Virology, 72 (12), (1998), pp. 9835-9843.
Mah, C., et al., "Improved Method of Recombinant AAV2 Delivery for Systemic Targeted Gene Therapy", Molecular Therapy, 6(1), (2001), 106-112.
Maitra, R., et al., "Increased Functional Cell Surface Expression of CFTR and deltaF508-CFTR by the Anthracycline doxorubicin", Am. J. Physiol. Cell Physiol., 280, (May 2001), C1031-C1037.
Malik, B., et al., "ENaC Degradation in A6 Cells by the Ubiquitin-Proteosome Proteolytic Pathway", The Journal of Biological Chemistry, 276(16), (Apr. 20, 2001), 12903-12910.
Marshall, E., "Gene Therapy's Growing Plans", Science 269(5227), (1995), 1050-1055.
Mastroianni, Claudio M, et al., "Ex Vivo and In Vitro Effect of Human Immunodeficiency Virus Protease Inhibitors on Neutrophil Apoptosis", Journal of Infectious Diseases (182), (Nov. 2000), 1536-1539.
Matalon, S., et al., "Lung Edema Clearance: 20 Years of Progress—Invited Review: Biophysical Properties of Sodium Channels in Lung Alveolar Epithelial Cells", J. Appl. Physiol., 93, (2002), 1852-1859.
Mattsson, Karin, et al., "Proteins associated with the promyelocytic leukemia gene product (PML)-containing nuclear body move to the nucleolus upon inhibition of proteaseome-dependent protein degradation", Proc. National Academy of Science, vol. 98, No. 3, (Jan. 30, 2001), 1012-1017.
McAuliffe, O., et al., "Lantibiotics: Structure, Biosynthesis and Mode of Action", FEMS Microbiology Reviews, 25(3), (2001), 285-308.
McCarty, D. M., et al., "Identification of Linear DNA Sequences That Specifically Bind the Adeno-Associated Virus Rep Protein", Journal of Virology, 68(8), (1994), 4988-4997.
McCarty, D. M., et al., "Interaction of the Adeno-Associated Virus Rep Protein With a Sequence Within the A Palindrome of the Viral Terminal Repeat", Journal of Virology, 68(9), (1994), 4998-5006.
McFadden, G., "Even viruses can learn to cope with stress.", Science, 279(5347), (Jan. 2, 1998), 40-1.
McLaughlin, Susan K., et al., "Adeno-associated virus general transduction vectors: analysis of proviral structures", Journal of Virology, 62 (6), (Jun. 1988), pp. 1963-1973.
Meng, Lihao, et al., "Eponemycin Exerts Its Antitumor Effect through the Inhibition of Proteasome Function", Cancer Research, vol. 59, (Jun. 15, 1999), 2798-2801.
Meng, Lihao, et al., "Epoxomicin, a potent and selective proteasome inhibitor, exhibits in vivo antiinflammatory activity", Proc Natl Acad Sci U S A, 96(18), (Aug. 31, 1999), 10403-8.
Meyer, Stephanie, et al., "Cyclosporine A is an uncompetitive inhibitor of proteasome activity and prevents NF-kB activation", Federation of European Biochemical Societies, (1997), 354-358.
Mihm, S., et al., "Inhibition of HIV-1 replication and NF-kappa B activity by cysteine and cysteine derivatives.", AIDS, 5(5), (May 1991), 497-503.

(56) References Cited

OTHER PUBLICATIONS

Mikulski, S. M, et al., "Enhanced in vitro cytotoxicity and cytostasis of the combination of onconase with a proteasome inhibitor", Int J Oncol., 13(4), (Oct. 1998), 633-44.
Mingozzi, Federico, et al., "Pharmacological Modulation of Humoral Immunity in a Nonhuman Primate Model of AAV Gene Transfer for Hemophilia B", Molecular Therapy, vol. 20, No. 7, (May 8, 2012), 1410-1416.
Mirshahi, M., et al., "Paradoxical Effects of Mineralocorticoids on the lon Gated Sodium Channel in Embryologically Diverse Cells", Biochemical and Biophysical Research Communications, 270, (2000), 811-815.
Mitsiades, Constantine, et al., "TRAIL/Apo2L ligand selectively induces apoptosis and overcomes drug resistance in multiple myeloma: theraputic applications", Blood, vol. 98, No. 3, (Aug. 1, 2001), 795-804.
Monahan, P E, et al., "Proteasome inhibitors enhance gene delivery by AAV virus vectors expressing large genomes in hemophilia mouse and dog models: a strategy for broad clinical application", Mol Ther 18, (2010), 1907-1916.
Mondejar-Lopez, Pedro, et al., "Cystic Fibrosis Treatment: Targeting the Basic Defect", Expert Opinion on Orphan Drugs, vol. 5, No. 2, (Feb. 26, 2017), 181-192.
Mosnaim, Aron, et al., "Degradation Kinetics of Leucine5-Enkephalin by Plasma Samples from Healthy Controls and Various Patient Populations: In Vitro Drug Effects", American Journal of Therapeutics, vol. 7, (2000), 185-194.
Mullins, et al., "Perspectives Series: Molecular Medicine in Genetically Engineered Animals", J. Clin. Invest. vol. 97, (1996), 1557-1560.
Mullins, et al., "Transgenesis in *nonmurine* species", Hypertension vol. 22, (1993), 630-633.
Muramatsu, S., et al., "Nucleotide Sequencing and Generation of an Infectious Clone of Adeno-Associated Virus-3", Virology, 221(1), (1996), 208-217.
Murray, R. Z, et al., "Proteasome inhibitors as anti-cancer agents", Anticancer Drugs, 11(6), (Jul. 2000), 407-17.
Musatov, S. A., et al., "Induction of Circular Episomes During Rescue and Replication of Adeno-Associated Virus in Experimental Models of Virus Latency", Virology, 275, (2000), 411-432.
Nakai, H., et al., "Helper-Independent and AAV-ITR-Independent Chromosomal Integration of Double-Stranded Linear DNA Vectors in Mice", Molecular Therapy, 7(1), (2003), 101-111.
Nakai, H., et al., "Increasing the Size of rAAV-Mediated Expression Cassettes in vivo by Intermolecular Joining of Two Complementary Vectors", Nature Biotechnology, 18, (2000), 527-532.
Nakai, H., et al., "Recruitment of Single-Stranded Recombinant Adeno-Associated Virus Vector Genomes and Intermolecular Recombination Are Responsible for Stable Transduction of Liver In Vivo", Journal of Virology, 74(20), (2000), 9451-9463.
Nakamura, H., et al., "Redox imbalance and its control in HIV infection", Antioxid Redox Signal., 4(3), (Jun. 2002), 455-64.
Nakayama, M., et al., "Hypomethylation Status of CpG Sites at the Promoter Region and Overexpression of the Human MDR1 Gene in Acute Myeloid Leukemias", Blood, 92(11), (1998), 4296-4307.
Nam, Sangkil, et al., "Tannic Acid Potently Inhibits Tumor Cell Proteasome Activity, Increases p27 and Bax Expression, and Induces G1 Arrest and Apoptosis", Cancer Epidemiology, Biomarkers & Prevention, vol. 10, (Oct. 2001), 1083-1088.
Nathwani, Amit C., et al., "Enhancing Transduction of the Liver by Adeno-Associated Viral Vectors", Gene Ther. Jan. 2009; 16(1): 60-69. doi:10.1038/gt.2008.137, (Jul. 1, 2009), 60-69.
Nepka, Ch., et al., "Tannins, xenobiotic metabolism and cancer chemo-prevention in experimental animals", European Journal of Drug Metabolism and Pharmacokinetics, vol. 24, No. 2, (1999), 183-189.
Nepka, Charitini, et al., "Chemopreventive activity of very low dose dietary tannic acid administration in hepatoma bearing C3H male mice", Cancer Letters, vol. 141, (1999), 57-62.

Neves, D. D. C., et al., "Differentiation-dependent sensitivity to cell death induced in the developing retina by inhibitors of the ubiquitin-proteasome proteolytic pathway", European Journal of Neuroscience, vol. 13, (2001), 1938-1944.
Newman, G. W, et al., "Opposing regulatory effects of thioredoxin and eosinophil cytotoxicity-enhancing factor on the development of human immunodeficiency virus 1.", J Exp Med., 180(1), (Jul. 1, 1994), 359-63.
Nicolaus, B. J, "Symbiotic Approach to Drug Design", Decision Making in Drug Research, (Jan. 1, 1983), 173-186.
Nielsen, J., et al., "Spironolactone-Mediated Downregulation of the Epithelial Sodium Channel (eNaC) in Rat Kidney", FASEB Journal, 15(1) (Abstracts Part I), Abstract No. 393.11, (2001), A432.
Niikura, T, et al., "Characterization of V642I-AbetaPP-induced cytoxicity in primary neurons", J. Neruosci Res. 77(1), Abstract Only, (Jul. 2004), 54-62.
Oberdorf, J., et al., "Redundancy of Mammalian Proteasome & Subunit Function during Endoplasmic Reticulum Associated Degradation", Biochemistry; 40(44), (2001), 13397-13405.
Obin, M, et al., "Neurite outgrowth in PC12 cells. Distinguishing the roles of ubiquitylation and ubiquitin-dependent proteolysis", Journal of Biological Chemistry, 274 (17), (Apr. 23, 1999), 11789-11795.
Oda, T., et al., "Oxygen radicals in influenza-induced pathogenesis and treatment with pyran polymer-conjugated SOD.", Science, 244(4907), (May 26, 1989), 974-6.
Ogiso, Y., et al., "Proteasome inhibition circumvents solid tumor resistance to topoisomerase II-directed drugs", Cancer Res., 60(9), (May 1, 2000), 2429-34.
Orkin, S. H., et al., "Report and recommendation of the Panel to Assess the NIH Investment in Research on Gene Therapy", [online]. [retrieved Jul. 6, 2007]. Retrieved from the Internet, (Dec. 7, 1995), 39 pgs.
Palombella, Vito, et al., "Role of the proteasome and NF-kB in streptococcal cell wall-induced polyarthritis", Proc. National Academy of Science USA, vol. 95, (Dec. 1998), 15671-15676.
Paolini, Rossella, et al., "Ubiquitination and degradation of Syk and ZAP-70 protein tyrosine kinases in human NK cells upon CD16 engagement", PNAS, vol. 98, No. 17, (Aug. 14, 2001), 9611-9616.
Pardridge, William M, "Blood-Brain Barrier Drug Targeting: The Future of Brain Drug Development", Molecular Interventions 3(2), (Mar. 2003), 90-105.
Parker, J. S., et al., "Cellular Uptake and Infection by Canine Parvovirus Involves Rapid Dynamin-Regulated Clathrin-Mediated Endocytosis, Followed by Slower Intracellular Trafficking", Journal of Virology, 74(4), (2000), 1919-1930.
Patel, et al., "identification of Yeast DNA Topoisomerase II Mutants Resistant to the Antitumor Drug Doxorubcin: Implications for the Mechanisms of Doxorubicin Action and Cytotoxicity", Pharmacol. 52(4), (1997), 658-666.
Petrov, Victor, et al., "Effect of Protease Inhibitors on Angiotensin-Converting Enzyme Activity in Human T-Lymphocytes", American Journal of Hypertension, vol. 13, No. 5, (May 2000), 535-539.
Phelps, C. J, et al., "Production of alpha 1,3-galactosyltransferase-deficient pigs", Science, 299(5605), (Jan. 17, 2003), 411-4.
Piccinini, M., et al., "The human 26S proteasome is a target of antiretroviral agents", AIDS, 16(5), abstract, (Mar. 29, 2002), 1 page.
Pickles, R J., et al., "Limited Entry of Adenovirus Vectors into Well-Differentiated Airway Epithelium Is Responsible for Inefficient Gene Transfer", Journal of Virology, 72 (7), (1998), pp. 6014-6023.
Plonne, D., et al., "Separation of the intracellular secretory compartment of rat liver and isolated rat hepatocytes in a single step using self-generating gradients of iodixanol.", Anal Biochem., 276(1), (Dec. 1, 1999), 88-96.
Ponnazhagan, S., et al., "Lack of Site-Specific Integration of the Recombinant Adeno-Associated Virus 2 Genomes in Human Cells", Human Gene Therapy, 8, (Feb. 10, 1997), pp. 275-284.
Princiotta, Michael F, et al., "Cells adapted to the proteasome inhibitor 4-hydroxy-5-iodo-3-nitrophenylacetyl-Leu-Leu-leucinal-vinyl sulfone require enzymatically active proteasomes for continued survival", PNAS, vol. 98, No. 2, (Jan. 16, 2001), 513-518.

(56) References Cited

OTHER PUBLICATIONS

Prydz, K, et al., "Effects of Brefeldin A on Endocytosis, and Transport to the Golgi Complex in Polarized MDCK Cells", The Journal of Cell Biology, 119 (2), (1992), pp. 259-272.
Puttaraju, M., et al., "Spliceosome-mediated RNA trans-splicing as a tool for gene therapy", Nature Biotechnology, 17 (3), (Mar. 1999), pp. 246-252.
Qing, K., et al., "Adeno-Associated Virus Type 2-Mediated Gene Transfer: Correlation of Tyrosine Phosphorylation of the Cellular Single-Stranded D Sequence-Binding Protein with Transgene Expression in Human Cells In Vitro and Murine Tissues In Vivo", Journal of Virology, 72 (2), (Feb. 1998), pp. 1593-1599.
Qing, K., et al., "Human Fibroblast Growth Factor Receptor 1 is a Co-Receptor for Infection by Adeno-Associated Virus 2", Nature Medicine, 5(1), (Jan. 1999), 71-77.
Qing, K., "Role of Tyrosine Phosphorylation of a Cellular Protein in Adeno-Associated Virus 2-Mediated Transgene Expression", Proc. Natl. Acad. Sci. USA, 94, (Sep. 1997), 10879-10884.
Rabinowitz, Joseph, et al., "Cross-Packaging of a Single Adeno-Associated Virus (AAV) Type 2 Vector Genome into Multiple AAV Serotypes Enables Transduction with Broad Specificity", Journal of Virology, (Jan. 2002), 791-801.
Ramage, A. D., et al., "Improved EBV-Based Shuttle Vector System: Dicistronic mRNA Couples the Synthesis of the Epstein-Barr Nuclear Antigen-1 Protein to Neomycin Resistance", Gene, 197(102), (1997), 83-89.
Rao, Sharmila, et al., "Lovastatin-mediated G1 arrest is through inhibition of the proteasome, independent of hydroxymethyl glutaryl-CoA reductase", Proc. National Academy of Science USA, vol. 96, (Jul. 1999), 7797-7802.
Reich, S. J., et al., "Efficient Trans-Splicing in the Retina Expands the Utility of Adeno-Associated Virus as a Vector for Gene Therapy", Human Gene Therapy, 14, (2003), 37-44.
Rendahl, K. G., et al., "Regulation of Gene Expression in vivo Following Transduction by Two Separate rAAv Vectors", Nature Biotechnology, 16, (1998), 757-761.
Richards, R. Gregg, et al., "E2-Induced Degradation of Uterine Insulin Receptor Substrate-2: Requirement for an IGF-I-Stimulated, Proteasome-Dependent Pathway", Endocrinology, 142(9), (Sep. 2001), 3842-3849.
Rivett, A. J, et al., "Proteasome inhibitors: from in vitro uses to clinical trials", Journal of Peptide Science, 6(9), (Sep. 2000), 478-488.
Rock, K L., et al., "Inhibitors of the Proteasome Block the Degradation of Most Cell Proteins and the Generation of Peptides Presented on MHC Class I Molecules", Cell, 78, (1994), pp. 761-771.
Ross, G., et al., "Gene Therapy in the United States: A Five-Year Status Report", Human Gene Therapy, 7, (1996), 1781-1790.
Rotin, D., "Regulation of the Epithelial Sodium Channel (ENaC) by Accessory Proteins", Current Opinion in Nephrology and Hypertension, 9, (2000), 529-534.
Rotin, D., et al., "Trafficking and Cell Surface Stability of ENaC", Am. J. Physiol. Renal Physiol., 281, (2001), F391-F399.
Rubanyi, Gabor M., "The Future of Human Gene Therapy", Molecular Aspects of Medicine, 22, (2001), 113-142.
Russell, D W., et al., "DNA synthesis and topoisomerase inhibitors increase transduction by adeno-associated virus vectors", PNAS, 92, (1995), pp. 5719-5723.
Russell, S. J, "Replicating Vectors for Gene Therapy of Cancer: Risks, Limitations and Prospects", European J Cancer, vol. 30A (8), (1994), 1165-1171.
Ryan, J. H., et al., "Sequence Requirements for Binding of Rep68 to the Adeno-Associated Virus Terminal Repeats", Journal of Virology, 70(3), (1996), 1542-1553.
Saha, D., et al., "The antiangiogenic agent SU5416 down-regulates phorbol ester-mediated induction of cyclooxygenase 2 expression by inhibiting nicotinamide adenine dinucleotide phosphate oxidase activity", Cancer Res., 63(20), (Oct. 15, 2003), 6920-7.
Sakai, H., et al., "Cloning and functional expression of a novel degenerin-like Na+ channel gene in mammals", J. Physiol 519, (1999), 323-333.
Samulski, R. J., et al., "A Recombinant Plasmid from Which an Infectious Adeno-Associated Virus Genome Can Be Excised In Vitro and Its Use To Study Viral Replication", Journal of Virology, 61(10), (Oct. 1987), 3096-3101.
Samulski, R. J., "Adeno-Associated Virus: Integration at a Specific Chromosomal Locus", Current Opinion in Genetics & Development, 3(1), (1993), 74-80.
Samulski, R. J., et al., "Helper-Free Stocks of Recombinant Adeno-Associated Viruses: Normal Integration Does Not Require Viral Gene Expression", Journal of Virology, 63 (9), (Sep. 1989), pp. 3822-3828.
Sanlioglu, et al., "Novel Approaches to Augment Adeno-Associated Virus TYPE-2 Endocytosis and Transduction", Virus Research and Transduction, 104(1), (Aug. 2004), 51-59.
Sanlioglu, S, et al., "Cellular redox state alters recombinant adeno-associated virus transduction through tyrosine phosphatase pathways", Gene Therapy vol. 6, No. 8, (Aug. 1999), pp. 1427-1437.
Sanlioglu, S., et al., "Endocytosis and Nuclear Traffickling of Adeno-Associated Virus Type 2 Are Controlled by Rac1 and Phosphatidylinositol-3 Kinase Activation", Journal of Virology, 74(19), (Oct. 2000), 9184-9196.
Sanlioglu, S., et al., "Lipopoolysaccharide Induces Rac1-Dependent Reactive Oxygen Species Formation and Coordinates Tumor Necrosis Factor-alpha Secretion Through IKK Regulation of NF-kB", The Journal of Biological Chemistry, 276(32), (2001), 30188-30198.
Sanlioglu, S., "Loss of ATM Function Enhances Recombinant Adeno-Associated Virus Transduction and Integration Through Pathways Similar to UV Irradiation", Virology, 268, (2000), 68-78.
Sanlioglu, S., et al., "Rate Limiting Steps of AAV Transduction and Implications for Human Gene Therapy", Current Gene Therapy, 1, (2001), 137-147.
Sanlioglu, S., et al., "Two Independent Molecular Pathways for Recombinant Adeno-Associated Virus Genome Conversion Occur After UV-C and E4orf6 Augmentation of Transduction", Human Gene Therapy, 10(4), (1999), 591-602.
Sasaki, T., et al., "Inhibitory Effect of di- and Tripeptidyl Aldehydes on Calpains and Cathepsins", Journal of Enzyme Inhibition, 3(3), (1990), 195-201.
Schaefer, et al., "Molecular cloning, functional expression and chromosomal localization of an amiloride-sensitive Na+ channel from human small intestine", FEBS Letters 471, (2000), 205-210.
Schlabach, Michael R, et al., "Synthetic design of strong promoters", Proceedings of the National Academy Of Sciences, vol. 107, No. 6, (Feb. 9, 2010), 2538-2543.
Schnepp, B. C., et al., "Genetic Fate of Recombinant Adeno-Associated Virus Vector Genomes in Muscle", Journal of Virology, 77(6), (2003), 3495-3504.
Schreck, R., et al., "Antioxidants selectively suppress activation of NF-kappa B by human T-cell leukemia virus type I Tax protein", J Virol., 66(11), (Nov. 1992), 6288-93.
Schwartz, Donald, et al., "The neutral cysteine protease bleomycin hydrolase is essential for epidermal integrity and bleomycin resistance", Proc. National Academy of Science USA, vol. 96, (Apr. 1999), 4680-4685.
Schwartz, O, et al., "Antiviral Activity of the Proteasome on Incoming Human Immunodeficiency Virus Type 1", Journal of Virology, 72 (5), (1998), pp. 3845-3850.
Schwarz, K., "Oxidative stress during viral infection: a review.", Free Radic Biol Med., 21(5), (1996), 641-9.
Schwarz, Katrin, et al., "The Selective Proteasome Inhibitors Lactacystin and Epoxomicin can be used to either Up- or Down-Regulate Antigen Presentation at Nontoxic Doses", Journal of Immunology, (2000), 6147-6157.
Schwarzbach, M., et al., "Sensitization of Sarcoma cells to doxorubicin treatment by concomitant wild-type adeno-associated virus type 2(AAV-2) infection", Oncology,20, (2002), 1211-1218.
Sen, S, et al., "Characterisation of gene transfer to vascular cell lines using adenoassociated virus (AAV Serotype-2)", Endocrine Abstracts, 4 DP31; Dept. of medicine, National Univ. of Ireland, Galway,

(56) References Cited

OTHER PUBLICATIONS

Ireland; 2The Ohio State Univ. School of Medicine and Molecular Virology, Columbus, Ohio, USA, (2002), 1 pg.
Serwer, et al., "Systemic and Local Drug Delivery for Treating Diseases of the Central Nervous System in Rodent Models", Jove, vol. 42, (2010), 1-6.
Shah, S. A., et al., "26S Proteasome Inhibition Induces Apoptosis and Limits Growth of Human Pancreatic Cancer", Journal of Cellular Biochemistry, vol. 82, (2001), 110-122.
Sharma, A, et al., "Pig cells that lack the gene for alpha1-3 galactosyltransferase express low levels of the gal antigen", Transplantation, 75(4), (Feb. 27, 2003), 430-6.
Shisler, J. L, et al., "Ultraviolet-induced cell death blocked by a selenoprotein from a human dermatotropic poxvirus", Science,279(5347), (Jan. 2, 1998), 102-5.
Smith, Andrew, et al., "The Role of the Epidermal Growth Factor Receptor in Recombinant Adeno-Associated Virus Type-2 Mediated Transgene Expression in Lung Epithelial Cells", Molecular Therapy, 5(5), abstract, (May 2002), S186.
Smith, H., et al., "Effect of a cancer cachectic factor on protein synthesis/degradation in murine C2C12 myoblasts: modulation by eicosapentaenoic acid", Cancer Res., 59(21), abstract, (Nov. 1999), 1 page.
Snyder, P. M., et al., "Serum and Glucocorticoid-Regulated Kinase Modulates Nedd4-2-Mediated Inhibition of the Epithelial NA+ Channel", The Journal of Biological Chemistry, 277(1), (2002), 5-8.
Snyder, R. O., et al., "Features of the Adeno-Associated Virus Origin Involved in Substrate Recognition by the Viral Rep Protein", Journal of Virology, 67(10), (1993), 6096-6104.
Snyder, R. O., et al., "Persistent and therapeutic concentrations of human factor IX in mice after hepatic gene transfer of recombinant AAV vectors", Nature Genetics, 16, (Jul. 1997), pp. 270-276.
Son, K, et al., "Factors influencing the drug sensitization of human tumor cells for in situ lipofection", Gene Therapy (3), (1996), 630-634.
Son, Kyonghee, et al., "Exposure of human ovarian carcinoma to cisplatin transiently sensitizes the tumor cells for liposome-mediated gene transfer", Proc. National Academy of Science USA, vol. 91, (Dec. 1994), 12669-12672.
Son, Kyonghee, et al., "Nitric oxide-mediated tumor cell killing of cisplatin-based interferon-y gene therapy in murine ovarian carcinoma", Cancer Gene Therapy, vol. 7, No. 10, (2000), 1324-1328.
Sonntag, Florian, et al., "Adeno-associated Virus Type 2 Capsids with Externalized VP1/VP2 Trafficking Domains Are Generated Prior to Passage through the Cytoplasm and Are Maintained until Uncoating Occurs", Journal of Virology, vol. 80, No. 22, (Nov. 2006), 11040-11054.
Spindler, B., et al., "Characterization of Early Aldosterone-induced RNAs identified in A6 Kidney Epithelia", Pfluegers Archiv, vol. 434, Springer Verlag, Berlin, DE XP001025924 ISSN: 0031-6768, (1997), 323-331.
Srivastava, C. H., et al., "Construction of a Recombinant Human Parvovirus B19: Adeno-Associated Virus 2 (AAV) DNA Inverted Terminal Repeats are Functional in an AAV-B19 Hybrid Virus", Proc. Natl. Acad. Sci USA, 86(20), (1989), 8078-8082.
Staub, O., "Chapter 5 Regulation of ENAC by Interacting Proteins and by Ubiquitination", Current Topics in Membranes, 47—Amiloride-Sensitive Sodium Channels—Physiology and Functional Diversity, Edited by Dale J. Benos, Academic Press, Publisher, (1999), 65-87.
Staub, O., "Regulation of Stability and Functional of the Epithelial Na+ Channel (ENaC) by Ubiquitination", The EMBO Journal, 16(21), (1997), 6325-6336.
Stockand, J. D., et al., "Targeted Degradation of the Epithelial Na Channel (ENaC) in Response to PKC Activation of the MAPK ½ Cascade", The FASEB Journal, 17(5), Abstracts (Part II), (Abstract No. 585.7), (2003), A913.
Stokes, J. B., "Regulation of rENac mRNA by Dietary NaCI and Steroids: Organ, Tissue, and Steroid Heterogeneity", American Journal of Physiology, Cell Physiology, 274, (1998), C1699-C1707.
Stutts, M. J, et al., "Cystic fibrosis transmembrane conductance regulator inverts protein kinase A-mediated regulation of epithelial sodium channel single channel kinetics.", J. Biol. Chem., 272(22), (1997), 14037-14040.
Summerford, C., et al., "alphaVbeta5 integrin: a co-receptor for adeno-associated virus type 2 infection", Nature Medicine, 5 (1), (Jan. 1999), 78-82.
Summerford, C., et al., "Membrane-Associated Heparan Sulfate Proteoglycan Is a Receptor for Adeno-Associated Virus Type 2 Virions", Journal of Virology, 72 (2), (Feb. 1998), pp. 1438-1445.
Sun, A. Y, et al., "Botanical phenolics and brain health", Neuromolecular Med., 10(4), (2008), 259-74.
Swinney, David C, et al., "Targeting protein ubiquitination for drug discovery. What is in the drug discovery toolbox?", DDT, vol. 6, No. 5, (Mar. 2001), 244-250.
Tajima, Kimihisa, et al., "The proteasome inhibitor MG132 promotes accumulation of the steroidogenic acute regulatory protein (StAR) and steriodogenesis", Federation of European Biochemical Societies, 490, (Jan. 24, 2001), 59-64.
Tang, Y, "435: Immunosuppressants improve the transduction of AAV2.5T after repeat dosing of ferret lungs", Pediatric Pulmonology; 34th Annual North American Cystic Fibrosis Conference; 20201007 TO Oct. 23, 2020; Phoenix, AZ, USA, John Wiley & Sons, Inc, US, vol. 55, No. Suppl 2, (Oct. 1, 2020), p. 208.
Tang, Y, et al., "Study of the Neutralizing Antibody after rAAV. TL65 Transduction in Ferret Airway", Pediatric Pulmonology; 33rd Annual North American Cystic Fibrosis Conference, Nashville, TN, John Wiley & Sons, Inc, US, vol. 54, No. Supplement 2, (Oct. 1, 2019), p. 325.
Tenenbaum, et al., "Cellular contaminants of adeno-associated virus vector stocks can enhance transduction", Gene Therapy, 6, (1999), 1045-1053.
Tenenbaum, et al., "Evaluation of Risks Related to the Use of Adeno-Associated Virus-Based Vectors", Current Gene Therapy, 3, (2003), 545-565.
Teodori, L., et al., "Reduction of 1-beta-D-arabinofuranosylcytosine and adriamycin cytotoxicity following cell cycle arrest by anguidine", Cancer Res., 41(4), abstract, (Apr. 1981), 1 page.
Teoh, M. L, et al., "Tumorigenic poxviruses up-regulate intracellular superoxide to inhibit apoptosis and promote cell proliferation", J Virol., 79(9), (May 2005), 5799-811.
Teramoto, S., "Factors influencing adeno-associated virus-mediated gene transfer to human cystic fibrosis airway epithelial cells: comparison with adenovirus vectors", Journal of Virology, 72(11), (Nov. 1998), 8904-8912.
Teramoto, S., et al., "Factors influencing adeno-associated virus-mediated gene transfer to human cystic fibrosis airway epithelial cells: comparison with adenovirus vectors.", J Virol., 72(11), (Nov. 1998), 8904-12.
Thakur, et al., "Strategies for ocular siRNA delivery: Potential and limitations of non-viral nanocarriers", Journal of Biological Engineering, 6, (2012), 1-7.
Thomas, C. P., et al., "Genomic Organization of the 5' End of Human B-ENaC and Preliminary Characterization of its Promoter", Am. J. Physiol. Renal Physiol. 282, (2002), F898-F909.
Thrasher, A J, et al., "Generation of recombinant adeno-associated virus (rAAV) from an adenoviral vector and functional reconstitution of the NADPH-oxidase", Gene Therapy, Macmillan Press Ltd., Basinstoke, GB, Vo. 2, 1995, pp. 481-485, XP000651495, (1995), 5.
Touyz, R. M, et al., "Expression of a functionally active gp91phox-containing neutrophil-type NAD(P)H oxidase in smooth muscle cells from human resistance arteries: regulation by angiotensin II", Circ Res., 90(11), (Jun. 14, 2002), 1205-13.
Trischler, M., et al., "Biochemical analysis of distinct Rab5- and Rab11-positive endosomes along the transferrin pathway.", J Cell Sci., 112 ( Pt 24), (Dec. 1999), 4773-4783.
Tweedale, Tony, "[Dioxin-I] Inhibits Estrogen-Induced Breast Cancer Cell Proliferation", Reuters Health, http//lists.essential.org/pipermail/dioxin-I/Week-of-Mon-2000103/000096.html, (Dec. 1999), 1 page.
Unzu, Carmen, et al., "Transient and intensive pharmacological immunosuppression fails to improve AAV-based liver gene transfer

(56) References Cited

OTHER PUBLICATIONS in nonhuman primates", Journal of Translational Medicine, Biomed Central, vol. 10, No. 1, (Jun. 15, 2012).
Van Den Worm, E., et al., "Apocynin: A Lead-Compound for New Respiratory Burst Inhibitors", van den Worm thesis, Chapter 3, entitled Apocynin: a lead compound for new respiratory burst inhibitors? (2001)), (2001), 49-58.
Van Den Worm, E., et al., "Effects of Methoxylation of Apocynin and Analogs on the Inhibition of Reactive Oxygen Species Production by Stimulated Human Neutrophils", Eur J Pharmacol. Dec. 21, 2001;433(2-3):225-30 (Abstract), (Dec. 21, 2001), 1 pg.
Van Den Worm, E., et al., "Effects of methoxylation of apocynin and analogs on the inhibition of reactive oxygen species production by stimulated human neutrophils", Euro. Jour. of pharm.;433(2-3), (Dec. 21, 2001), 225-230 Pgs.
Van Kerkhof, Peter, et al., "Proteasome Inhibitors Block a Late Step in Lysosomal Transport of Selected Membrane but not Soluble Proteins", Molecular Biology of the Cell, vol. 12, (Aug. 2001), 2556-2566.
Verma, I. M., et al., "Gene Therapy—Promises, Problems and Prospects", Nature, 389, (1997), 239-242.
Vihinen-Ranta, M, et al., "Intracellular Route of Canine Parvovirus Entry", Journal of Virology, 72 (1), (1998), pp. 802-806.
Villani, P., et al., "Antiretrovirals: Simultaneous determination of five protease inhibitors and three nonnucleoside transcriptase inhibitors in human plasma by a rapid high-performance liquid chromatography-mass spectrometry assay", The Drug Monit., 23(4), abstract, (Aug. 2001), 1 page.
Voinea, et al., "Designing of Intelligent liposomes for efficient delivery of drugs", J. cell. Mol. Med. 6(4), (2002), 465-474.
Wagner, J. A., et al., "A Phase I/II Study of tgAAV-CF for the Treatment of Chronic Sinusitis in Patients With Cystic Fibrosis", Human Gene Therapy, 9(6), (1998), 889-909.
Wagner, J. A., et al., "Safety and Biological Efficacy of an Adeno-Associated Virus Vector-Cystic Fibrosis Transmembrane Regulator (AAV-CFTR) in the Cystic Fibrosis Maxillary Sinus", The Laryngoscope, 109(2, Part 1), (1999), 266-274.
Wall, R. J., "Transgenic Livestock: Progress and Prospects for the Future", Theriogenology, 45, (1996), 57-68.
Walsh, C. E., "Phenotypic Correction of Fanconi Anemia in Human Hematopoietic Cells with a Recombinant Adeno-associated Virus Vector", The Journal of Clinical Investigation, 94(4), (Oct. 1994), 1440-1448.
Walters, W., et al., "Basolateral localization of fiber receptors limits adenovirus infection from the apical surface of airway epithelia", The Journal of Biological Chemistry, 274(15), (Apr. 9, 1999), 10219-10226.
Walters, R W., et al., "Incorporation of Adeno-Associated Virus in a Calcium Phosphate Coprecipitate Improves Gene Transfer to Airway Epithelia In Vitro and In Vivo", Journal of Virology, 74 (1), (2000), 535-540.
Wang, Kaiyu, et al., "Improvement of Pharmacokinetics Behavior of Apocynin by Nitrone Derivatization: Comparative Pharmacokinetics of Nitrone-Apocynin and its Parent Apocynin in Rats", (PLoS One, 8:e70189 (2013)), (2013), 6 pgs.
Weitzman, M. D., et al., "Adeno-Associated Virus (AAV) Rep Proteins Mediate Complex Formation Between AAV DNA and its Integration Site in Human DNA", Proc. Nat. Acad. Sci. USA, 91(13), (1994), 5808-5812.
Westfall, T. D., et al., "The Ecto-ATPase Inhibitor ARL 67156 Enhances Parasympathetic Neurotransmission in the Guinea-Pig Urinary Bladder", European Journal of Pharmacology, 329, (1997), 169-173.
Whitehouse, Alison, et al., "Downregulation of Ubiquitin-Dependent Proteolysis by Eicosapentaenoic Acid in Acute Starvation", Biochemical and Biophysical Research Communications, vol. 285, No. 3, (2001), 598-602.
Wickham, T J., et al., "Adenovirus targeted to heparan-containing receptors increases its gene delivery efficiency to multiple cell types", Nature Biotechnology, 14, (1996), pp. 1570-1573.
Wickham, T J., et al., "Targeted Adenovirus Gene Transfer to Endothelial and Smooth Muscle Cells by Using Bispecific Antibodies", Journal of Virology, 70 (10), (1996), pp. 6831-6838.
Woessner, Richard, et al., "Comparison of Three Approaches to Doxorubicin Therapy: Free Doxorubicin, Liposomal Doxorubicin, and B-Glucuronidase-Activated Prodrug (HMR 1826)", Anticancer Research, (2000), 2289-2296.
Wojcik, "Inhibition of the proteasome as a therapeutic approach", Drug Discovery Today, 4(4), (Apr. 1999), pp. 188-189.
Wojcik, Cezary, et al., "Lovastatin and simvastatin are modulators of the proteasome", Int J Biochem Cell Biol., 32(9), (Sep. 2000), 957-65.
Working, Peter, et al., "Pharmacological-Toxicological Expert Report (Stealth Liposomal Doxorubicin HCI)", Human & Experimental Toxicology, (1996), 752-785.
Wu, C. W, et al., "Gene Therapy for Detached Retina by Adeno-Associated virus vecto Expressing Glial Line-Derived Neurotrophic Factor", Investigative Ophthalmology and visual science, 43(11), (Nov. 2002), 3480-3488.
Wu, D., et al., "NADPH—oxidase in a transgenic mouse model of familial amyotrophic lateral sclerosis", Society for Neuroscience Abstract Viewer and Iteinerary Planner, 2003, Abstract No. 528-13, URL-http://sf, XP008085727 & 33rd Annual Meeting of the Society of Neuroscience, New Orleans, LA, USA, (Nov. 8-12, 2003), 1 pg.
Wu, D., et al., "NADPH—Oxidase in a transgenic mouse model of familial amyotrophic lateral sclerosis (ABSTRACT)", Program No. 528.12. Abstract Viewer/Itinerary Planner, (2003), 1 pg.
Wu, D., et al., "The inflammatory NADPH oxidase enzyme modulates motor neuron degeneration in amyotrophic lateral sclerosis mice", Proc Natl Acad Sci U S A., 103(32), (Aug. 8, 2006), 12132-7.
Wu, Du Chu, et al., "Blockade of Microglial Activation Is Neuroprotective in the 1-Methyl-4-Phenyl-1,2,3,6-Tetrahydropyridine Mouse Model of Parkison Disease", Journal of Neuroscience, (Mar. 1, 2002), 1763-1771.
Wu, J., "On the role of proteasomes in cell biology and proteasome inhibition as a novel frontier in the development of immunosuppressants. ", Am J Transplant., 2(10), (Nov. 2002), 904-12.
Wu, P., et al., "Adeno-Associated Virus Vector-Mediated Transgene Integration into Neurons and Other Nondividing Cell Targets", Journal of Virology, 72 (7), (Jul. 1998), pp. 5919-5926.
Xia, W., et al., "Presenilin 1 regulates the processing of beta-amyloid precursor protein C-terminal fragments and the generation of amyloid beta-protein in endoplasmic reticulum and Golgi", Biochemistry, 37(47), (Nov. 24, 1998), 16465-71.
Xiao, et al., "Efficient Long-Term Gene Transfer Into Muscle Tissue of Immunocomponent Mice by Adeno-Associated Virus Vector", Journal of Virology, 70(11), (Nov. 1, 1996), 8098-8108.
Xiao, W, et al., "Adeno-Associated Virus as a Vector for Liver-Directed Gene Therapy", Journal of Virology, 72 (12), (1998), pp. 10222-10226.
Xiao, X, et al., "A Novel 165-Base-Pair Terminal Repeat Sequence Is the Sole cis Requirement for the Adeno-Associated Virus Life Cycle", J Virol, vol. 71, (1997), 941-948.
Xiao, X., et al., "A Novel 165-Base-Pair Terminal Repeat Sequence Is the Sole cis Requirement for the Adeno-Associated Virus Life Cycle", Journal of Virology, 71(2), (Feb. 1997), 941-948.
Yalkinoglu, A. O, et al., "Inhibition of N-methyl-N'-nitro-N-nitrosoguanidine-induced methotrexate and adriamycin resistancce in CHO cells by adeno-associated virus type 2", Cancer,45(6), (1990), 1195-1203.
Yamagishi, S., et al., "Nifedipine inhibits tumor necrosis factor-alpha-induced monocyte Chemoattractant protein-1 overexpression by blocking NADPH oxidase-mediated reactive oxygen species generation", Drugs Exp Clin Res., 29(4), (2003), 147-52.
Yan, Z, "Trans-splicing vectors expand the utility of adeno-associated virus for gene therapy", Proc Natl Acad Sci U S A, 97(12), (Jun. 6, 2000), 6716-6721.
Yan, Z., et al., "A New Class of Hybrid Adeno-Associated Viral Vectors With Non-Homologous ITRs Improves Directional Recombination and Dual-Vector Reconstitution of Large Transgenes", Molecular Therapy, 9(Suppl. 1), (2004), S5-S6.
Yan, Z., et al., "Distinct classes of proteasome-modulating agents cooperatively augment recombinant adeno-associated virus type 2

(56) References Cited

OTHER PUBLICATIONS and type 5-mediated transduction from the apical surfaces of human airway epithelia", J Virol., 78(6), (Mar. 2004), 2863-74.
Yan, Z., et al., "Inverted terminal repeat sequences are important for intermolecular recombination and circularization of adeno-associated virus genomes", Journal of Virology, 79(1), (Jan. 2005), 364-379.
Yan, Z., "Recombinant AAV-Mediated Gene Delivery Using Dual Vector Heterodimerizatiion", In: Methods in Enzmology, vol. 346: Gene Therapy Methods, Phillips, M. I., Editor, Academic Press, San Diego, CA, (2002), 334-357.
Yan, Z., et al., "Trans-splicing vectors expand the utility of adeno-associated virus for gene therapy", Proceedings of the National Academy of Sciences, 97(12), (Jun. 6, 2000), 6716-6721.
Yan, Z., et al., "Trans-splicing vectors expand the utility of adeno-associated virus for gene therapy.", Proc Natl Acad Sci U S A., 97(12), (Jun. 6, 2000), 6716-21.
Yan, Z., et al., "Ubiquitination of Both Adeno-Associated Virus Type 2 and 5 Capsid Proteins Affects the Transduction Efficiency of Recombinant Vectors", Journal of Virology, 76(5), (2002), 2043-2053.
Yan, Ziying, et al., "A Common Theme for Ubiquitination-Dependent Transduction of rAAV Type 2 and 5", American Society of Gene Therapy, Abstracts of Scientific Presentations—Abstract No. 569, (Jun. 5, 2002), 1 page.
Yan, Ziying, et al., "Optimization of Recombinant Adeno-Associated Virus-Mediated Expression for Large Transgenes, Using a Synthetic Promoter and Tandem Array Enhancers", Human Gene Therapy, vol. 26, No. 6, (Jun. 1, 2015), 334-346.
Yang, J., et al., "Concatamerization of Adeno-Associated Virus Circular Genomes Occurs Through Intermolecular Recombination", Journal of Virology, 73(11), (Nov. 1999), 9468-9477.
Yu, J., et al., "The Role of the Methoxyphenol Apocynin, a Vascular NADPH Oxidase Inhibitor, as a Chemopreventative Agent in the Potential Treatment of Cardiovascular Diseases", (Curr. Vasc. Pharmacol., 6:204 (2008), (2008), 14 pgs.
Zabner, J, et al., "Adenovirus-mediated gene transfer to ciliated airway epithelia requires prolonged incubation time", Journal of Virology, 70(10), (Oct. 1996), 6994-7003.
Zabner, J, et al., "Adenovirus-mediated generation of CAMP-stimulated CI-transport in cystic fibrosis airway epithelia in vitro: effect of promoter and administration method.", Gene Therapy, 3(5), (1996), 458-465.
Zeitlin, Pamela L, "Novel pharmacologic therapies for cystic fibrosis", Perspective Series on cystic fibrosis 103(4), (Feb. 1999), 447-452.
Zentner, M. D., "The Amiloride-Sensitive Epithelial Sodium Channel a-Subunit is Transcriptionally Down-Regulated in Rat Parotid Cells by the Extracellular Signal-Regulated Protein Kinase Pathway", The Journal of Biological Chemistry, 273(46), (1998), 30770-30776.
Zentner, M. D, et al., "The Amiloride-sensitive epithelial Sodium Channel Alpha subunit is Transcriptionally down regulated in rat parotid cells by the extracellular signal-regulatedprotine Kinase pathway.", The Journal of the Biological Chemistry, vol. 273(46), (1998), 30770-30776.
Zhang, F, et al., "Proteasome Function is Regulated by Cyclic AMP-dependent Protein Kinase through Phosphorylation of Rpt6", The journal of Biological Chemistry;282(31), (Aug. 3, 2007), 22460-22471.
Zhang, L. N., "Dual Therapeutic Utility of Proteasome Modulating Agents for Pharmaco-Gene Therapy of the Cystic Fibrosis Airway", Molecular Therapy, 10(6), (2004), 990-1002.
Zhou, Liqiao, et al., "Improvement of Transduction Efficiency from Split AAV Vectors", American Society of Gene Therapy, Abstracts of Scientific Presentations—Abstract, (Jun. 5, 2002), 1 page.
"U.S. Appl. No. 16/076,219, Notice of Allowability mailed Sep. 19, 2022", 6 pgs.
"U.S. Appl. No. 16/076,219, Notice of Allowance mailed Aug. 2, 2022", 6 pgs.
"U.S. Appl. No. 16/082,767, Decision on Pre-Appeal Brief Request for Review mailed Aug. 17, 2022", 2 pgs.
"U.S. Appl. No. 16/082,767, Notice of Allowance mailed Aug. 22, 2022", 8 pgs.
"U.S. Appl. No. 16/082,767, Pre-Appeal Brief Request filed Jul. 12, 2022", 5 pgs.
"Australian Application Serial No. 2020289851, First Examination Report mailed Aug. 8, 2022", 4 pgs.
"Canadian Application Serial No. 2,909,085, Response Filed Aug. 26, 2022 to Office Action Mailed Feb. 17, 2022", 12 pages.
"Canadian Application Serial No. 3,174,963, Voluntary Amendment Filed Sep. 29, 2022", 10 pgs.
"Chilean Application Serial No. 202102701, Acceptance to Continue Prosecution mailed Oct. 19, 2022", with machine translation, 2 pgs.
"Chinese Application Serial No. 202080043579.3, Voluntary Amendment Filed Jul. 28, 2022", w/English Claims, 23 pgs.
"Chinese Application Serial No. 202080043595.2, Voluntary Amendment filed Oct. 8, 2022", with English claims, 13 pgs.
"Eurasian Application Serial No. 201892006, Office Action mailed Apr. 29, 2022", w/ English translation, 7 pgs.
"Eurasian Application Serial No. 201892006, Response Filed Aug. 29, 2022 to Office Action mailed Apr. 29, 2022", w/ English Claims, 9 pgs.
"European Application Serial No. 17712339.5, Communication Pursuant to Article 94(3) EPC mailed May 12, 2022", 4 pgs.
"European Application Serial No. 17712339.5, Response Filed Sep. 15, 2022 to Communication Pursuant to Article 94(3) EPC mailed 05-12-2", 10 pgs.
"European Application Serial No. 20727413.5, Response Filed Jun. 20, 2022 to Communication Pursuant to Rules 161(1) and 162 EPC mailed Dec. 9, 2021", 10 pgs.
"European Application Serial No. 20728248.4, Response Filed Jun. 20, 2022 to Communication Pursuant to Rules 161(1) and 162 EPC mailed Jan. 26, 2022", 9 pgs.
"Japanese Application Serial No. 2021-561893, Notification of Reasons for Refusal mailed Nov. 1, 2022", w/ English Translation, 10 pgs.
"Mexican Application Serial No. MX/a/2018/010842, Office Action mailed May 13, 2022", with machine translation, 9 pgs.
"Mexican Application Serial No. MX/a/2018/010842, Response Filed Sep. 19, 2022 to Office Action mailed May 13, 2022", w/ English Claims, 18 pgs.
"Singapore Application Serial No. 11202111334S, Voluntary Amendment filed Apr. 27, 2022", 10 pgs.
"Singaporean Application Serial No. 11202111353Q, Response Filed May 11, 2022 to Request for Examination Notice mailed Apr. 4, 2022", w/ English Claims, 18 pgs.
"Vietnamese Application Serial No. 1-2021-07262, Office Action mailed Sep. 13, 2022", w/English translation, 2 pgs.
"Vietnamese Application Serial No. 1-2021-07262, Response Filed Nov. 7, 2022 to Office Action mailed Sep. 13, 2022", w/ English Claims, 11 pgs.
"Vietnamese Application Serial No. 1-2021-07263, Office Action mailed Sep. 13, 2022", w/English translation, 2 pgs.
"Vietnamese Application Serial No. 1-2021-07263, Response Filed Nov. 7, 2022 to Office Action mailed Sep. 13, 2022", w/ English Claims, 8 pgs.
"U.S. Appl. No. 16/076,219, Final Office Action mailed Oct. 7, 2021", 9 pgs.
"U.S. Appl. No. 16/076,219, Response filed Dec. 7, 2021 to Final Office Action mailed Oct. 7, 2021", 6 pgs.
"South African Application Serial No. 2015/07946, Voluntary Amendment filed Jul. 24, 2020", 21 pgs.
"U.S. Appl. No. 16/076,219, Notice of Allowability mailed Feb. 28, 2023", 3 pgs.
"U.S. Appl. No. 16/076,219, Notice of Allowance mailed Feb. 9, 2023", 6 pgs.
"U.S. Appl. No. 16/082,767, Notice of Allowance mailed Jan. 26, 2023", 7 pgs.
"Canadian Application Serial No. 3,137,015, Examiners Rule 86(2) Requisition mailed Jan. 13, 2023", 5 pgs.

(56) References Cited

OTHER PUBLICATIONS

"Canadian Application Serial No. 3,137,078, Examiners Rule 86(2) Requisition mailed Jan. 16, 2023", 5 pgs.
"International Application Serial No. PCT/US2021/039860, International Preliminary Report on Patentability mailed Jan. 12, 2023", 17 pgs.
"Japanese Application Serial No. 2021-561893, Response Filed Feb. 1, 2023 to Notification of Reasons for Refusal mailed Nov. 1, 2022", W/ English Claims, 11 pgs.
"Mexican Application Serial No. MX/a/2018/010842, Office Action mailed Jan. 3, 2023", with machine translation, 12 pgs.
"U.S. Appl. No. 16/980,268, Restriction Requirement mailed Sep. 20, 2023", 10 pgs.
"U.S. Appl. No. 18/313,661, Preliminary Amendment filed Sep. 25, 2023", 8 pgs.
"Canadian Application Serial No. 3,174,963, Examiners Rule 86(2) Report mailed Sep. 13, 2023", 3 pgs.
"International Application Serial No. PCT/US2004/010045, Written Opinion mailed Jan. 10, 2005", 15 pgs.
"Japanese Application Serial No. 2023-119196, Voluntary Amendment Filed Aug. 18, 2023", with machine translation, 22 pgs.
"Singapore Application Serial No. 11202111334S, Search Report and Written Opinion mailed Sep. 14, 2023", 12 pgs.
"Singaporean Application Serial No. 11202111353Q, Written Opinion mailed Sep. 14, 2023", 12 pgs.
Halbert, C. L., et al., "Successful Readministration of Adeno-Associated Virus Vectors to the Mouse Lung Requires Transient Immunosuppression during the Initial Exposure", Journal of virology, vol. 72, No. 12, (Dec. 1, 1998), 9795-9805.
Lynch, C M, et al., "Small synthetic promoter elements increase expression of the full length CFTR cDNA in AAV vectors", Cystic Fibrosis Conference, Pediatric Pulmonology Supplement, 19, p. 230, (1999), 19 pgs.
"Canadian Application Serial No. 3,174,963, Response filed Jan. 11, 2024 to Examiners Rule 86(2) Report mailed Sep. 13, 2023", 6 pgs.
"Eurasian Application Serial No. 202192819, Office Action mailed Oct. 18, 2023", w/ English Translation, 6 pgs.
"Israeli Application Serial No. 261642, Response filed Nov. 15, 2023 to Notification of Defects in Patent Application mailed Mar. 15, 2023", w/ English claims, 11 pgs.
"Japanese Application Serial No. 2023-119196, Voluntary Amendment Filed Oct. 16, 2023", w/English Claims, 10 pgs.
"Canadian Application Serial No. 3,137,015, Response filed Apr. 22, 2024 to Examiners Rule 86(2) Requisition mailed Dec. 20, 20 23", w/ current English claims, 21 pgs.
"Canadian Application Serial No. 3,198,936, Examiners Rule 86(2) Report mailed Apr. 17, 2024", 7 pgs.
"Chinese Application Serial No. 202080043579.3, Office Action mailed Mar. 18, 2024", w/English Translation, 21 pgs.
"Chinese Application Serial No. 202080043595.2, Office Action mailed Mar. 18, 2024", with current pending claims, 16 pgs.
"Eurasian Application Serial No. 202192818, Response filed Apr. 19, 2024 to Office Action mailed Jun. 26, 2023", with English claims, 16 pgs.
"European Application Serial No. 17712339.5, Communication Pursuant to Article 94(3) EPC mailed Feb. 19, 2024", 4 pgs.
"Japanese Application Serial No. 2021-561742, Notification of Reasons for Rejection mailed Apr. 16, 2024", W/English Translation, 10 pgs.
"UniProtKB/TrEMBL, Accesion No. P13569, entry version 243", [Online] Retrieved from the internet: <https://rest.uniprot.org/unisave/P13569?format=txt&versions=2>, (Dec. 5, 2018), 35 pgs.
Ri Ordan, J R, "Human cystic fibrosis mRNA, encoding a presumed transmembrane conductance regulator (CFTR)", Genebank database, M28668.1, (Apr. 27, 1993), 3 pgs.
Yan, Ziying, et al., "Optimizing rAAV Vector for CFTR Expression Using Synthetic Promoter and Enhancers", Molecular Therapy, vol. 22, No. 1, Retrieved from the Internet: <URL: https://www.cell.com/molecular-therapy-family/molecular-therapy/pdf/S1525-0016(16)35307-2.pdf>, (May 1, 2014), p. S113.
"U.S. Appl. No. 16/980,268, Non Final Office Action mailed May 2, 2024", 16 pgs.
"U.S. Appl. No. 17/470,560, Notice of Allowability mailed Apr. 24, 2024", 2 pgs.
"U.S. Appl. No. 17/470,560, PTO Response to Rule 312 Communication mailed Apr. 5, 2024", 2 pgs.
"U.S. Appl. No. 17/603,831, Restriction Requirement mailed May 10, 2024", 12 pgs.
Lynch, et al., "Wnt Signaling Regulates Airway Epithelial Stem Cells In Adult Murine Submucosal Glands", Stem Cells, 34(11), (2016), 2758-2771.
"U.S. Appl. No. 16/082,767, Supplemental Notice of Allowability mailed May 17, 2023", 2 pgs.
"U.S. Appl. No. 17/470,560, Non Final Office Action mailed Jul. 25, 2023", 13 pgs.
"U.S. Appl. No. 17/470,560, Response filed Jun. 23, 2023 to Restriction Requirement mailed Apr. 25, 2023", 6 pgs.
"U.S. Appl. No. 17/470,560, Restriction Requirement mailed Apr. 25, 2023", 9 pgs.
"Australian Application Serial No. 2020289851, Response Filed Jul. 17, 2023 to First Examination Report mailed Aug. 8, 2022", 13 pgs.
"Brazilian Application Serial No. 1120210207066, Voluntary Amendment Filed Apr. 14, 2023", W/English Claims, 15 pgs.
"Brazilian Application Serial No. 1120210207082, Voluntary Amendment Filed Apr. 13, 2023", W/ English Claims, 15 pgs.
"Canadian Application Serial No. 3, 137,015, Response Filed May 15, 2023 to Examiners Rule 86(2) Requisition mailed Jan. 13, 2023", 20 pgs.
"Canadian Application Serial No. 3,137,078, Response Filed May 16, 2023 to Examiners Rule 86(2) Requisition mailed Jan. 16, 2023", 18 pgs.
"Eurasian Application Serial No. 202192818, Office Action mailed Jun. 26, 2023", w/ English Translation, 7 pgs.
"Israel Application Serial No. 261642, Notification of Defects in Patent Application mailed Mar. 15, 2023", w/ English Translation, 7 pgs.
"Japanese Application Serial No. 2021-561724, Voluntary Amendment Filed Apr. 10, 2023", W/English Claims, 10 pgs.
"Japanese Application Serial No. 2021-561893, Examiners Decision of Final Refusal mailed Mar. 22, 2023", w/ English Translation, 9 pgs.
Excoffon, Katherine, et al., "Directed evolution of adeno-associated virus to an infectious respiratory virus", PNAS, vol. 106, No. 10, (2009), 3865-3870.
"U.S. Appl. No. 17/470,560, Notice of Allowance mailed Jan. 2, 2024", 2 pgs.

* cited by examiner

ΔREH21 (HBoV1 OriR)

CGCGAAACTCTATATCTTTTAATGTGTTGTTGTTGTACATGCGCCA
GCGCTTTGAGATATAGAAAATTACACAACAACAACATGTACGCGGT
|                                              |
5357                                         5402

PLA (anti-BrdU and anti-NP1)

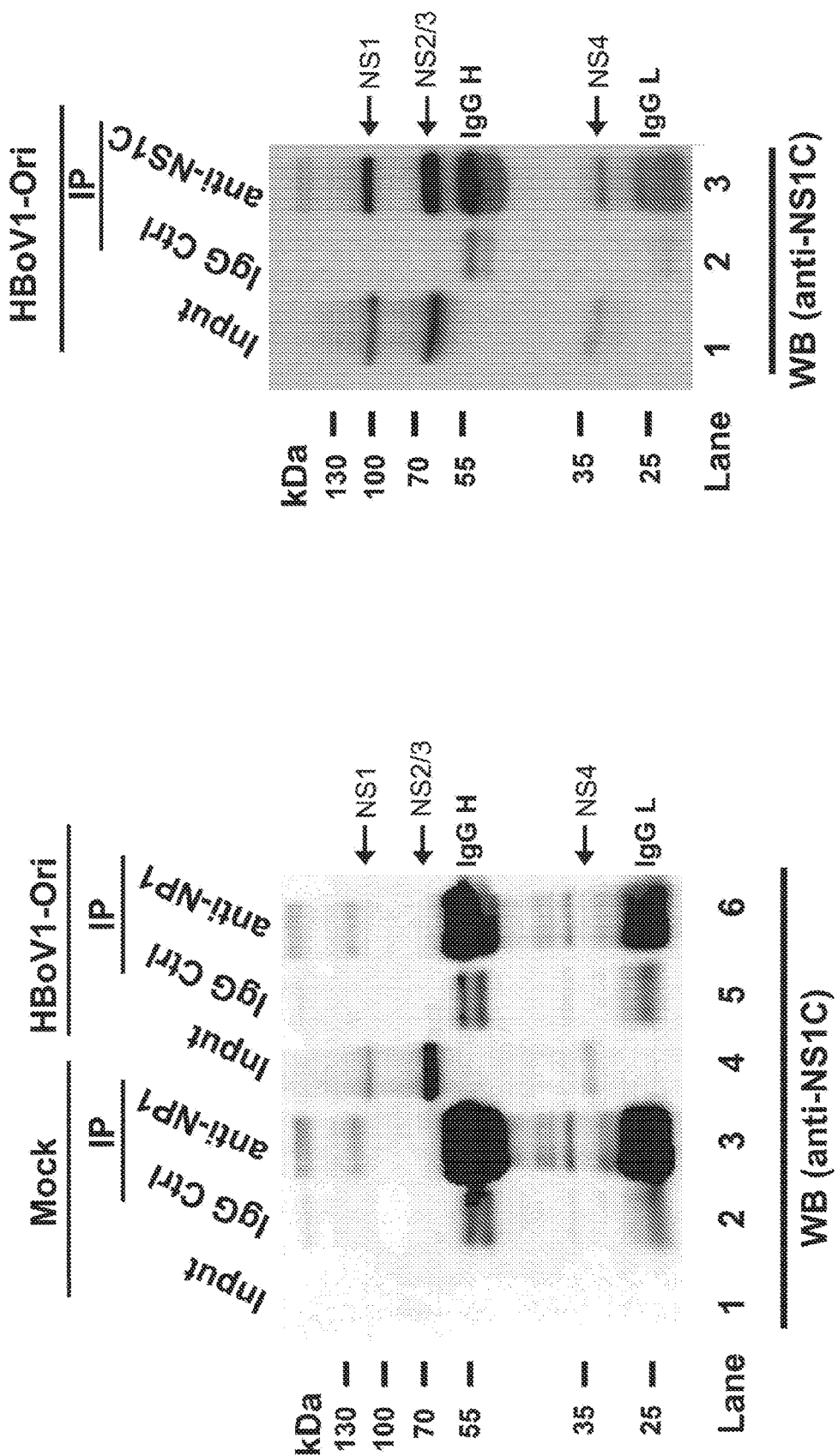

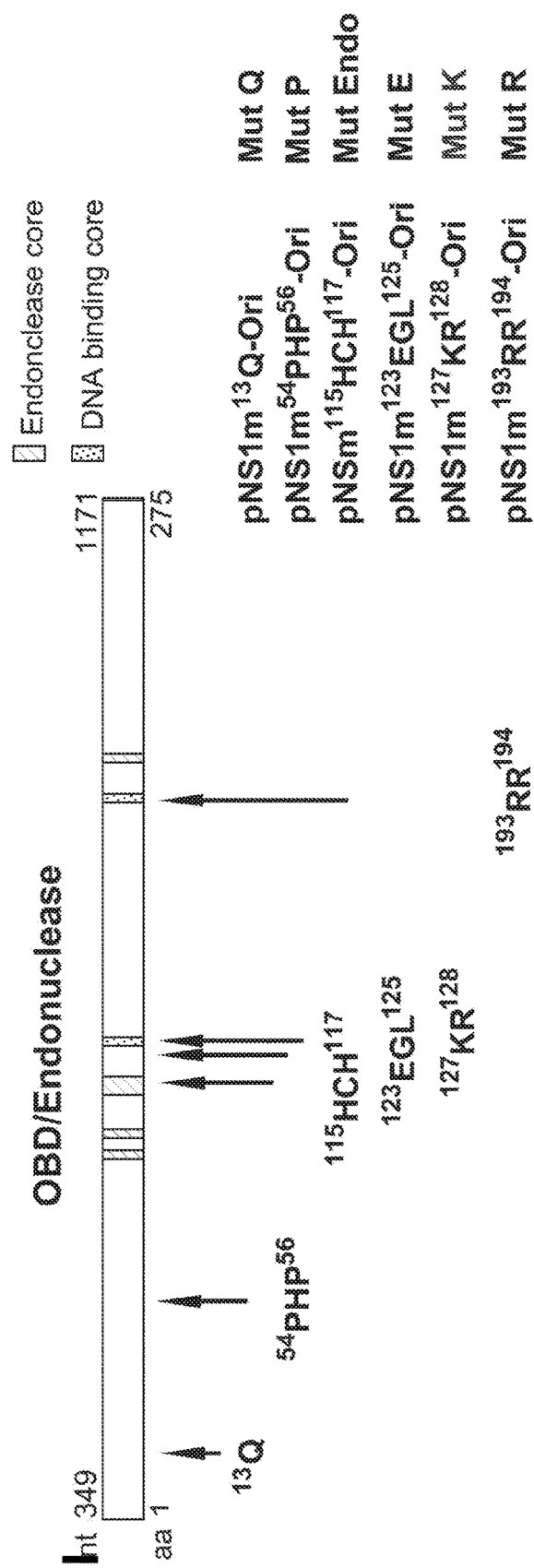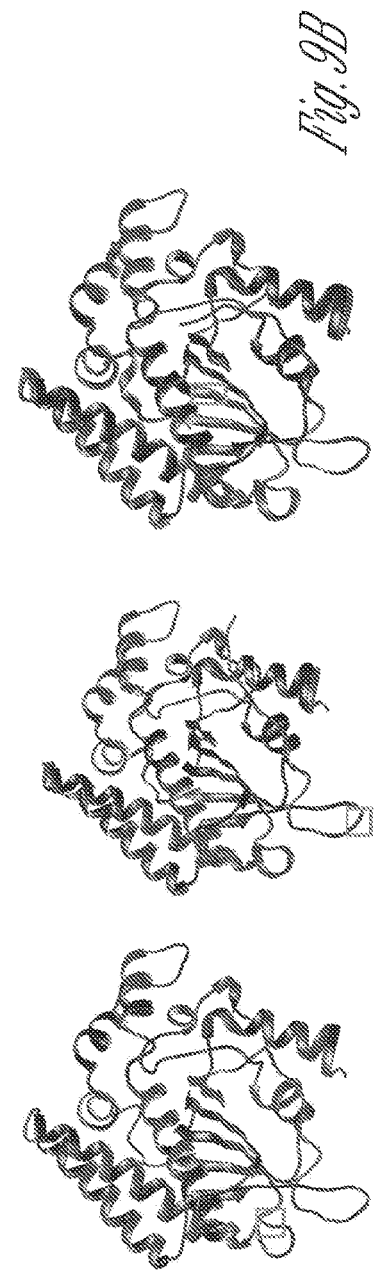
Fig. 9A
Fig. 9B

```
   1 gtggttgtac agacgccatc ttggaatcca atatgtctgc cggctcagtc atgcctgcgc
  61 tgcgcgcagc gcgctgccgc cgcgcatgat ctaatcgccg gcagacatat tggattccaa
 121 gatggcgtct gtacaaccac gtcacatata aaataataaa tattcacaag gaggagtggt
 181 tatatgatgt aatccataac cactcccagg aaatgacgta tgatagccaa tcagaattga
 241 gtattaaacc tatataagct gctgcacttc ctgattcaat cagactgcat ccggtctccg
 301 gcgagtgaac atctctggaa aaagctccac gcttgtgtg agtctactat ggctttcaat
 361 cctcctgtga ttagagcttt ttctcaacct gctttacct atgtcttcaa atttccatat
 421 ccacaatgga aagaaaaaga atggctgctt catgcacttt tagctcatgg aactgaacaa
 481 tctatgatac aattagaaa ctgcctcct catccggatg aagacataat ccgtgatgac
 541 ttgcttattt ctttagaaga tcgccattgt ggggctgttc tctgcaaggc tgtttacatg
 601 gcaacaacta ctctcatgtc acacaaacaa aggaatatgt ttcctcgttg tgacatcata
 661 gttcagtctg agctaggaga gaaaaactta cactgccata ttatagttgg gggagaagga
 721 ctaagcaaga ggaatgctaa atcatcctgt gctcagttct atgtttaat actagctgaa
 781 ataattcaac gctgcaaatc tcttctggct acacgtcctt ttgaacctga agaggtgac
 841 atatttcaca ctttaaaaaa ggctgagcga gaggcatggg ggagaccttc atggaggttac tggcggcaac
 901 atgcaaatcc ttcaatatag agatcgcaga ggagaccttc atgcaacaaac agtggatcct
 961 cttcgcttct tcaaaaacta cctttacct aaaaaatagat gtatttcatc ttacagcaaa
1021 cctgatgtt gtactctcc tgacaactgg ttcattttag ctgaaaaaac ttactctcac
```

Fig. 13A

```
1081 actcttatta acgggctgcc gctccagaaa cattacagaa aaaactacca cgcaaccta
1141 gataacgaag tcattccagg gcctcaaaca atggcctatg gaggactgg tccgtgggaa
1201 catcttcctg aggtaggaga tcagcgccta gctgcgtctt ctgttagcac tacttataaa
1261 cctaacaaaa aagaaaaaact tatgctaaac ttgctagaca aatgtaaaga gctaaatcta
1321 ttagtttatg aagacttagt agctaattgt cctgaactac tccttatgct tgaaggtcaa
1381 ccaggagggg cacgccttat agaacaagtc ttgggcatgc accatattaa tgttgttct
1441 aactttacag ctctcacata tctttttcat ctacatctgc ttacttcgct tgactcagac
1501 aataaagctt tacagctttt gttgattcaa ggctataatc ctctagccgt tggtcacgcc
1561 ctatgctgtg tcctgaacaa acaattcggg aaacaaaaca ctgttgctt ttacgggcct
1621 gcctcaacag gtaaaacaaa tatggccaag gcaatcgtcc aaggattag acttatggg
1681 tgtgttaatc attgaacaa aggatttgta ttaatgact gcagacaacg cctagttgtt
1741 tggtgggagg agtgcttaat gcaccaggat tgggtggaac ctgcaaagtg tatcttgggc
1801 gggacagaat gcagaattga cgtcaagcat agagacagtg tactttaac tcaaaacct
1861 gtaattatat ccactaacca cgatatctac gcggttgttg gtgccattcc tgtttctcat
1921 gttcacgcgg ctccattaaa agaaagagtg attcagctaa attttatgaa acaacttcct
1981 caaacatttg gagaaatcac tgctactgag attgcagctc ttcacagtg gtgtttcaat
2041 gagtacgact gtactgac aggattaaa caaaaaatga attagataa aatccaaaac
2101 tcattcctc tgggtgcct ttgtcctact cattcacagg acttacact tcacgaaaac
2161 ggatactgca ctgattgcgg tggttacctt cctcatagtg ctgacaattc tatgtacact
```

*Fig. 13B*

```
2221 gatcgcgcaa gcgaaaactag cacaggagac atcacaccaa gtaagtaaat acgcatgcgc
2281 aagtaattct tttacttca cttcgctatt tttaccaatt tttactttta ggtgacttgg
2341 gggattcgga cggagaagac accaagcctg agacatcgca agtggactat tgtccaccca
2401 agaaacgtcg tctaactgct ccagcaagtc ctccaaactc acctgcgagc tctgtaagta
2461 ctattacttt cttttaacact tggcacgcac agccacgtga cgaagatgag ctcaggaat
2521 atgaaagaca agcatcgctc ctacaaaaga aaagggagtc cagaaagag ggagaggaag
2641 gagagaggct cgggctcata tcatcaggaa cacccaatca gccacctatc gtcttgcact
2701 gcttcgaaga cctcagacca agtgatgaag acgaggggaga gtacatcggg gaaaaaagac
2761 aatagaacaa atccatacac tgtattcagt caacacagag cttccaatcc tgaagctcca
2821 gggtggtgtg ggttctactg gcactctact cgcattgcta gagatggtac taattcaatc
2881 tttaatgaaa tgaaacaaca gttcaacacag ctacaaattg ataataaaat aggatgggat
2941 aacactagag aactattgtt taatcaaaag aaaacactag atcaaaaaata cagaaatatg
3001 ttctgcact ttagaaataa ctctgattgt gaaagatgta attactggga tgatgtgtac
3061 cgtagacact tagctaaatgt ttcctcacag acagaagcag acgagataac tgacgaggaa
3121 atgctttctg ctgctgaaag catggaagca gatgcctcca attaaagagac agcctagagg
3181 gtgggggctg cctggataca gatatcttgg gccatttaat ccacttgata acggtgaacc
3241 tgtaaataaac gctgatcgcg ctgctcaatt acatgatcac gcctactctg aactaataaa
3301 gagtggtaaa aatccataac tgtatttcaa taaagctgat gaaaaattca ttgatgatct
3361 aaaagacgat tggtcaattg gtggaattat tgataccagt ttttttaaaa taaagcgcgc
```

*Fig. 13C*

```
3421 cgtggctcct gctctgggga ataaagagag agcccaaaaa agacactttt acttgctaa
3481 ctcaaataaa ggtgcaaaaa aaacaaaaaa aagtgaacct aaaccaggaa cctcaaaaat
3541 gtctgacact gacattcaag accaacaacc tgatactgta gacgcaccac agaacacctc
3601 aggggagga acaggaagta ttggaggagg aaaaggatct ggtgtgggga tttccactgg
3661 agggtggtc ggaggttctc actttcaga caaatatgtg gttactaaaa acacaagaca
3721 atttataacc acaattcaga atggtcacct ctacaaaaca gaggccattg aaacaacaaa
3781 ccaaagtgga aaatcacagc gctgcgtcac aactccatg acatactta actttaatca
3841 atacagctgt cacttctcac cacaggattg gcagcgcctt acaaatgaat ataagcgctt
3901 cagaactaaa gcaatgcaag taaagattta caacttgcaa ataaaacaaa tactttcaaa
3961 tggtgctgac acaacataca acaatgacct cacagctggc gttcacatct tttgtgatgg
4021 agagcatgct tacccaaatg catctcatcc atgggatgag gacgtcatgc ctgatcttcc
4081 atacaagacc tggaaactttt tcaatatgg atatattcct attgaaaatg aactcgcaga
4141 tcttgatgga aatgcagctg gaggcaatgc tacagaaaaa gcacttctgt atcagatgcc
4201 ttttttcta cttgaaaaca gtgaccacca agtacttaga actggtgaga gcactgaatt
4261 tactttaac tttgactgtg aatggttaa caatgaaaga gcatacactc ctcctggact
4321 aatgtttaat ccaaaagttc caacaagaag agttcagtac ataagacaaa acggaagcac
4381 agcagccagc acaggcagaa ttcagccata ctcaaaacca acaagctgga tgacaggacc
4441 tgcctgctc agtgcacaga gagtaggacc acagtcatca gacactgctc cattcatggt
4501 ttgcactaac ccagaaggaa cacacataaa cacaggtgct gcaggattttg gatctggctt
```

*Fig. 13D*

```
4561 tgatcctcca agcggatgtc tggcaccaac taaactagaa tacaaaactc agtggtacca
4621 gacaccagaa ggaacaggaa ataatggaaa cataattgca aaccatcac tctcaatgct
4681 tagagaccaa ctcctataca aaggaaacca gaccacatac aatctagtgg gggacatatg
4741 gatgttttcca aatcaagtct gggacagatt tcctatcacc agagaaaatc caatctggtg
4801 caaaaaacca agagctgaca aacacacaat catggatcca tttgatggat caattgcaat
4861 ggatcatcct ccaggcacta tttttataaa aatggcaaaa attccagttc caactgcctc
4921 aaatgcagac tcatacctaa acatatactg tactggacaa gtcagctgtg agattgtatg
4981 ggaagtaaaa agatacgcaa caaagaactg gcgtccagaa agaagacata ctgcactcgg
5041 gatgtcactg ggagagaaaa gcaactacac gcctacatac cacgtggatc caacaggagc
5101 atacatccag cccacgtcat atgatcaatg tatgccagta aaaacaaaca tcaataaagt
5161 gttgtaaatct tataagcctc tttttgctt ctgcttacaa gtcctcctc aatgacaag
5221 cggaaagtga agggtgactg tagtcctgag ctcatggggt caagaccaca gcccgatggt
5281 agtgtgtta ccgtctcgaa cctagccgac agcccttgta cattgtgggg ggagctgttt
5341 tgtttgctta tgcaatcgcg aaactctata tctttttaatg tgttgttgtt gtacatgcgc
5401 catcttagtt ttatatcagc tggcgcctta gttatataac atgcatgtta tataactaag
5461 gcgccagctg atataaaact aagatgggcg atgtacaaca acaacacatt aaaagatata
5521 gagtttcgcg attgcataag caa
```

*Fig. 13E* cis AND TRANS REQUIREMENTS FOR TERMINAL RESOLUTION OF HUMAN BOCAVIRUS 1

Cross-Reference to Related Applications

This application is a U.S. National Stage Filing under 35 U.S.C. 371 from International Application No. PCT/US2017/034678, filed on May 26, 2017, and published as WO 2017/205739 on Nov. 30, 2017, which application claims the benefit of the filing date of U.S. application Ser. No. 62/341,897, filed on May 26, 2016, the disclosures of which are incorporated by reference herein.

STATEMENT OF GOVERNMENT RIGHTS the invention was made with the Government Support under grant 1R 21AI112803-01 by the National Institutes of Health. The Government has certain rights in the invention.

BACKGROUND

Human bocavirus 1 (HBoV1) is a recently identified respiratory virus associated with acute respiratory tract infections in young children (Allander et al., 2007; Gendrel et al., 2007; Kahn, 2008; Schildgen et al., 2008; Garcia-Garcia, 2010; Don et al., 2010; Jartti et al., 2011; Brodizinski and Rhady, 2009; Martin et al., 2015), HBoV1 belongs to the *Bocaparvovirus* genus within the *Parvoviridae* (Allander et al., 2005; Cotmore et al., 2014) family. Other species in the *Bocaparvovirus* genus include minute virus of canines (MVC), bovine parvovirus 1 (BPV1), porcine bocavirus, and gorilla bocavirus (Cotmore et al., 2014; Sun et al., 2009; Qin et al., 2007; Cheng et al., 2010; Kapoor et al., 2010).

A unique feature of bocaparvoviruses, differed from other parvoviruses, is that they express the small nuclear phosphoprotein NP1 from an open-reading frame (ORF) located in the middle of the genome (Sun et al., 2009; Qin et al., 2007; Chen et al., 2010). NP1 is a non-structural protein and is indispensable for viral DNA replication (Sun et al., 2009; Huang et al., 2012). The role of the NP1 proteins of HBoV1 and BPV1 in viral DNA replication is conserved to that of MVC, and they are exchangeable in supporting MVC DNA replication (Sun et al., 2009), While the mechanism defining how NP1 facilitates bocaparvovirus DNA replication remains largely unknown, it has been revealed that NP1 plays an important role in processing viral precursor mRNA (pre-mRNA) to matured viral mRNA polyadenylated at the distal polyadenylation site, and therefore is important for capsid protein expression (Zan et al., 2016; Fasina et al., 2015; Sukhu et al., 2013). In addition, HBoV1 holds unique features in the genus *Bocaparvovirus*: it naturally replicates in non-dividing/polarized human airway epithelial cells, and the replication is dependent on the cellular DNA damage and repair machinery (Deng et al., 2016). Upon transfection, the duplex replicative form genome (RF DNA) of HBoV1 replicates in human embryonic kidney (HEK) 293 cells and produces infectious progeny virions (Huang et al., 2012). Aside from the NP1, HBoV1 expresses one large non-structural protein, NS1, and three other small nonstructural proteins, NS2, NS3, and NS4 (Shen et al., 2015). They share a C-terminus of 184 amino acids (aa). NS2 is indispensable for viral replication during infection of polarized human airway epithelial cells (Shen et al., 2015), whereas NS2-4 proteins are dispensable for viral DNA replication in HEK293 cells.

Parvovirus replication generates monomer duplex and concatemeric duplex DNA (mRF and dRF DNA, respectively) replicative intermediates via a unidirectional strand-displacement mechanism, from which the ends of progeny genomes are excised by viral replication initiator protein Rep78/68 or NS1 (Cotmore et al., 2005; Berns, 1990; Ward, 2006). For homotelomeric parvoviruses (e.g., adeno-associated virus [AAV]), in which the two genomic termini are inverted in sequence and identical in structure, the replication process is symmetrical. The tip of the T structure formed on the termini is critical for Rep78/68 binding to the replication origin (Ryan et al., 1996). For heterotelomeric autonomous parvoviruses (e.g., MVM and HBoV1), in which the two genomic termini are dissimilar, the left-end hairpin (LEH) structure that has the junction resolution site is critical to produce the ssDNA genome for progeny virion production, and the right-end hairpin (REH) structure contains the terminal resolution site (TRS) that is required to replicate viral RF DNA (Cotmore et al., 2015). In MVM, the cruciform structure at REH is required for RF DNA replication (Cotmore et al., 2000).

At either hairpin end of both homotelomeric and heterotelomeric viruses, there is a replication origin sequence that contains Rep78/68 or NS1 binding elements (RBEs/NSBEs) and TRS which is recognized and nicked by Rep78/68 or NS1 (Ryan et al., 1996; Cotmore et al., 1994, 2000, 2015). The binding and nicking properties characterized by in vivo or in vitro studies suggest that RBE or NSBE is several tetra-nucleotide repeats, which are directly recognized by the origin binding domain (OBD) of the Rep78/68 or NS1. The TRS is normally 7-17-nt (nucleotide) ahead of the RBE or NSBE at the 5' end. The genome structure of HBoV1 is unique among these heterotelomeric, parvoviruses. The LEH forms a rabbit-ear structure of 140-nt with mismatched nucleotides ("bubbles") inside, and the REH consists of a perfect palindromic sequence of 200-nt in length (Huang et al., 2012). Of note, the REH of two other bocaparvoviruses, MVC and BPV1, are able to form a cruciform structure (Sun et al., 2009).

SUMMARY

Because of the unique REH structure of the HBoV1 genome, the minimal requirements for terminal resolution of HBoV1 both in cis and in trans were defined using the duplex HBoV1 genome in HEK293 cells. A 46-nt minimal replication origin at the REH of HBoV1 (OriR) was identified, which contains a TRS and an unconventional NSBE. In addition, properties of nonstructural proteins NS1 and NP1 during viral DNA terminal resolution at the OriR were identified. In particular, by using the duplex replicative form of the HBoV1 genome in human embryonic kidney (HEK) 293 cells, the HBoV1 minimal replication origin (OriR) was identified at the right-end hairpin. Mutagenesis analyses confirmed the putative NS1 binding and nicking sites within the OriR. Of note, unlike the large non-structural protein (Rep78/68 or NS1) of other parvoviruses, HBoV1 NS1 did not specifically bind OriR in vitro, indicating that other viral components or cellular proteins are required for the NS1 binding to the OriR. In vivo studies demonstrated that residues responsible for NS1 binding and nicking are within the origin-binding domain. Further analysis identified that the small non-structural protein NP1 is required for terminal resolution of HBoV1 DNA at OriR. The NP1 and other viral non-structural proteins (NS1-4) colocalized within the viral DNA replication centers in both OriR-transfected cells and virus-infected cells, highlighting a direct involvement of the NP1 in the terminal resolution of viral DNA. Overall, the present study revealed characteristics of HBoV1 terminal resolution at OriR.

The disclosure provides, in one embodiment, a vector having a recombinant BoV genome useful to provide a helper-virus free ("helper-free") preparation which genome comprises a LEH, a 3' UTR (e.g., encompassing nucleotides 5221 to 5291 of SEQ ID NO:1), and a REH, wherein the REH includes a 46 nucleotide sequence comprising an OriR, e.g., an OriR having a TRS and NS1 nicking and binding site, and wherein the genome includes a mutation in one or more of NS2, NS3, NS4, VP1, VP2 or VP3, and or any combination thereof, and optionally a mutation in one or more of NS1 or NP1, so that NS2 protein, NS3 protein, NS4 protein, VP1 protein, VP2 protein or VP3 protein, or any combination thereof, and optionally also NS1 protein and/or NP1 protein, is/are not expressed from the vector. A mutation includes a deletion of one or more nucleotides, an insertion of one or more nucleotides, or a substitution of one or more nucleotides, e.g., a substitution that creates a stop codon, or creates or eliminates a splice site, or any combination thereof. In one embodiment, the genome comprises an expression cassette encoding a heterologous gene product. In one embodiment, the gene product encodes a therapeutic protein. In one embodiment, the gene product is a viral, bacterial, tumor, parasite, or fungal antigen. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, a neutralizing antibody or an antigen binding fragment thereof, SARS virus protein, DNA endonuclease for gene editing, e.g., CRISPR associated protein 9 (Cas9), zinc finger nuclease. Transcription activator-like effector nucleases (TALEN), Argonaute, or a cytokine, e.g., IFN-alpha, IFN-gamma, TNF, IL-1, IL-17, or IL-6. In one embodiment, the BoV genome comprises a human genomic DNA segment as template for gene correction through homologous recombination between the viral genome and genomic DNA (see FIG. 12). For example, the insert includes homology arms, e.g., >100 bp, >500 bp or >1 kb, on each side of the target alterations, e.g., an insert in rBoV of about 5.8 kb of genome homology (about 2.6 kb on either site of the targeted base pairs), where the arms individually have at least 95%, 96%, 97%, 98%, 99%, or 100% sequence identity to the genome target sequences. In one embodiment, 1 to 3 bp alterations may be targeted (e.g., in a gene like CFTR). Targets in CFTR include but are not limited to the deltaF508 CFTR mutation (a deletion of 3 bp) and the G551D CFTR mutation (a 1 bp mutation). In one embodiment, an insertion (or a sequence that includes a deletion) may be 2 kb leaving 1.6 kb homology arms. Vectors for gene correction do not necessarily include a heterologous promoter or poly A. In one embodiment, the human genomic DNA segment is the exons/intron sequence at the 189 kb cystic fibrosis transmembrane conductance regulator locus. In one embodiment, OriR includes nucleotides 5357 to 5402 or 5430 of SEQ ID NO:1. In one embodiment, the OriR includes $(TGT)_a$-$(TGT)_b$-$(TGT)_c$-$(TGT)_d$, where at least two of a, b, c or d is present. In one embodiment, the nicking site includes CTATATCT.

A recombinant BoV e.g., rHBoV1, helper free preparation, e.g., vector generation in the absence of wild-type (WT) virus contamination, is also provided. The identification of minimal oriR allows for replication of BoV, e.g., rHBoV1, genomes without generating WT virus. Moreover, having a predominantly negative strand genome may allow for higher level of specificity as certain viral proteins could be included without viral replication to boost the immune response, e.g., the helper free virus is an attenuated BoV. In addition, having a predominantly negative strand genome may allow for higher efficiency for gene editing and/or gene correction in rBoV, as the accumulation of single strand genomes could elicit DNA damage signaling and recruit cellular DNA repair and homologous recombination factors, which facilitate the gene targeting correction. Further, the mutant genomes may enhance titers of recombinant virus and functionality of the recombinant genomes, and have applications in gene editing (homologous recombination of viral genomes with the genomic DNA) since the virus only packages one strand of the genome. By removing BoV coding regions, but not at the expense of sequences for replication and/or packaging, thereby providing a mutant BoV genome, the mutant BoV genome may be modified by adding open reading frames for certain HBoV1 proteins or other microbial proteins to enhance immune response against microbial infection. Moreover, the mutant genomes may be useful in packaging systems for chimeric AAV/HBoV1 vector. Further, a mutated REH (such as inactivated the nick site) may be incorporated into a BoV helper vector, for instance, a HBoV1 helper vector. The helper might generate replicative duplex HBoV1 genomes in transfected cells, but they are defective and would not be nicked for ss genome to produce HBoV1 replication competent virus (RCV) contamination, and such replicative forms of an HBoV1 helper might be more efficient in HBoV1 VP gene expression.

A method is provided to express a heterologous gene product in mammalian cells which employs a helper-free virus preparation having a mutant BoV genome; and infecting the cells with the virus in an amount effective to express the heterologous gene product. In one embodiment, the gene product is a therapeutic gene product, a catalytic RNA, a microRNA, RNA pre-transplicing molecule (PTM-RNA), a neutralizing antibody or an antigen binding fragment thereof, a prophylactic gene product, a polypeptide or a peptide. In one embodiment, the mammalian cell is a mammalian nasal epithelial cell, tracheobronchial cell or a lung cell. In one embodiment, the REH corresponds to nucleotides 5357 to 5430, e.g., 5357 to 5402, of SEQ ID NO:1. In one embodiment, the 3'UTR corresponds to nucleotides 5221 to 5302, e.g., 5221 to 5291, of SEQ ID NO:1.

In one embodiment, a method is provided to inhibit or treat a condition associated with aberrant expression of an endogenous gene product is provided. The method contacting a mammal at risk of or having the condition, with an effective amount of a helper-free virus composition having a mutant BoV genome, wherein the mutant genome comprises a transgene encoding at least a portion of a functional gene product, the expression of which in the mammal inhibits or treats at least one symptom of the condition. In one embodiment, the trangene encodes cystic fibrosis transmembrane conductance regulator, β-globin, γ-globin, alpha-antitrypsin, tyrosine hydroxylase, glucocerebrosidase, aryl sulfatase A, factor VIII, dystrophin or erythropoietin. In one embodiment, an agent, e.g., a proteasome inhibitor, a chemotherapeutic, a lipid lowering agent, a mucolytic agent, an antibiotic or a food additive, is further administered. In one embodiment, the agent and the virus are administered to the lung, nasal epithelium, gastrointestinal tract, or blood. In one embodiment, the virus is orally or parenterally administered.

Also provided is a method to correct endogenous gene defects in mammalian cells. The method includes administering to a mammal a rBoV, e.g., rBoV, having a segment of human genomic DNA, which serves as a template for DNA repair through homologous recombination. In one embodiment, the rBoV, e.g., rHBoV1, also expresses RNA-guided DNA endonuclease, e.g., CRISPR associated protein 9 (Cas9) and guide RNA, or an engineered endonuclease, such as a zinc finger nuclease or TALEN, to introduce double strand DNA breaks (DSB) or single strand nick(s) at a desired site in the chromosome for gene correction and/or gene editing. In one embodiment, the DNA correction template and the endonuclease components may be delivered in a single rBoV vector or separately delivered using two rBoV vectors, a rBoV and chimeric rAAV/BoV vector or a rBoV vector and another non-parvovirus vector including a non-viral vector. In the case of the chimeric vector, in one embodiment, the rAAV/BoV vector may be used to express the endonuclease and gRNA, while the rBoV vector may serve as the single stranded DNA template for homologous recombination. In one embodiment, the gene to be corrected is a defective human cystic fibrosis transmembrane conductance regulator gene. In one embodiment, an agent that enhances viral transduction or expression and the virus are administered to the lung, nasal epithelium, gastrointestinal tract, or blood. In one embodiment, the virus is orally or parenterally administered, for example, to the lung, nasal epithelium or blood. In one embodiment, the virus is administered to the lung, nasal epithelium or blood.

Further provided is a method to immunize a mammal. The method includes administering to a mammal a rBoV, e.g., rHBoV, having a mutant genome and encoding a prophylactic gene product in an amount effective to prevent or inhibit microbial infection or replication. In one embodiment, the gene product is an antigen of a virus or bacteria. In one embodiment, the mammalian cells or mammal are/is contacted with the virus before the cell is contacted with an agent, such as a proteosome inhibitor. In one embodiment, the cells or mammal are/is contacted with the virus and an agent, e.g., a proteasome inhibitor, concurrently. In one embodiment, the agent and the virus are administered to the lung, nasal epithelium, gastrointestinal tract, or blood. In one embodiment, the virus is orally or parenterally administered, for example, to the lung, nasal epithelium or blood. In one embodiment, the virus is administered to the lung, nasal epithelium or blood.

In one embodiment, a method to immunize a mammal is provided. The method includes administering to a mammal an isolated rBoV comprising bocavirus capsid proteins and a mutant rBoV genome, which genome also encodes a prophylactic gene product, in an amount effective to prevent or inhibit microbial infection or replication. In one embodiment, the capsid proteins are human bocavirus proteins. In one embodiment, the capsid proteins are non-human bocavirus protein. In one embodiment, the virus is administered to the lung, nasal epithelium or blood. In one embodiment, the rBoV is a human rBoV. In one embodiment, the rBoV is a non-human rBoV. In one embodiment, the rBoV is a swine, feline or canine BoV. In one embodiment, the BoV is a human rBoV. In one embodiment, the BoV is a non-human, mammalian rBoV. In one embodiment, the mutation is a deletion or a stop codon. In one embodiment, the deletion is in VP1, VP2 or VP3, or any combination. In one embodiment, OriR includes nucleotides 5357 to 5402 or 5430 of SEQ ID NO:1. In one embodiment, the OriR includes $(TGT)_a$-$(TGT)_b$-$(TGT)_c$-$(TGT)_d$, where at least two of a, b, c or d is present. In one embodiment, the nicking site includes CTATATCT.

Also provided are methods to prepare helper-free rBoV. In one embodiment, the proviral cis plasmid contains all the minimal BoV cis-elements for replication and packaging, that is, the minimal sequence at left side (5' terminus), including the LEH and the minimal sequence at the right side (including the right REH, as well as nucleotides 5,22 to 5,291 at the 3' UTR. The helper plasmid provides all viral necessary proteins in trans, e.g., via a plasmid based expression system, which does not have any cis elements, so that no homologous recombination occurs between the cis and trans plasmids to generate the wild-type genome.

Other systems (not plasmid-based) for helper-free BoV, e.g., helper-free HBoV1, vector includes but is not limited to an inducible cell line, which is integrated with an defective BoV genome, such as a defective HBoV1 genome (cis-element minus), to express viral proteins for packaging and replication under an inducible promoter. In addition, bocavirus proteins for replication and packaging may be provided using one or more exogenous vectors encoding one or more, but not all, of the bocavirus proteins for replication and packaging, which is/are introduced to cells having stably integrated vectors that express one or more, but not all of the proteins, for replication and packaging, where the exogenous vectors and the stably integrated vectors together provide for all of the bocavirus proteins for replication and packaging.

In one embodiment, a method of preparing a helper virus-free preparation is provided. The method includes providing a mutant bocavirus genome genome comprising a LEH, a 3' UTR and a REH, wherein the REH includes a 46 nucleotide sequence comprising OriR having a TRS and a NS1 nicking or binding site, wherein the mutant genome includes a mutation in one or more of NS2, NS3, NS4, VP1, VP2 or VP3, and or any combination thereof, and optionally a mutation in NS1 or NP1 or both, so that NS2 protein, NS3 protein, NS4 protein, VP1 protein, VP2 protein or VP3 protein, or any combination thereof, and optionally NS1 protein and/or NP1 protein, is/are not expressed when the mutant genome is introduced to cells. Also provided in trans are one or more of NP1, NS1, VP1, VP2 and VP3, e.g., using one or more vectors or one or more expression cassettes for NP1, NS1, VP1, VP2 and VP3. The mutant bocavirus genome and the one or more vectors or one or more expression cassettes are introduced to cells, or the mutant BoV genome is introduced to cells that express BoV proteins in trans, and helper free virus is isolated from the cells. In one embodiment, the mutant genome comprises an expression cassette encoding a heterologous gene product. In one embodiment, the gene product encodes a therapeutic protein. In one embodiment, the gene product is a viral, bacterial, tumor, parasite, or fungal antigen. In one embodiment, the gene product is cystic fibrosis transmembrane conductance regulator, β-globin, γ-globin, tyrosine hydroxylase, glucocerebrosidase, aryl sulfatase A, factor VIII, dystrophin, alpha 1-antitrypsin, surfactant protein SP-D, SP-A or SP-C, erythropoietin, HBoV protein, influenza virus protein, RSV protein, a neutralizing antibody or an antigen binding fragment thereof, SARS virus protein, or a cytokine, e.g., IFN-alpha, IFN-gamma, TNF, IL-1, IL-17, or IL-6. In one embodiment, the bocavirus is a human bocavirus. In one embodiment, what is provided are one or more vectors that express bocavirus VP1, VP2, VP3, NP1 and NS1, but optionally do not express one or more of bocavirus NS2, NS3 or NS4, and a mutant BoV genome comprising a LEH, a 3' UTR and a REH, wherein the REH includes a 46 nucleotide sequence comprising OriR having a TRS and NS1 nicking or binding sites, wherein the mutant genome includes a mutation in one or more of NS2, NS3, NS4, VP1, VP2 or VP3, and optionally a mutation in NS1 or NP1 or both, so that NS2 protein, NS3 protein, NS4 protein, VP1 protein, VP2 protein or VP3 protein, and optionally NS1 protein and/or NP1 protein, is/are not expressed. The one or more vectors and the mutant genome are expressed in the cells and helper free virus is collected.

BRIEF DESCRIPTION OF THE FIGURES

FIGS. 1A-C. Identification of the cis-acting sequences and trans-acting proteins required for HBoV1 replication. (A) Diagram of HBoV1 genome and mutants. HBoV1 genome is shown as a negative sense ssDNA. Sequentially from left to right, the functional elements are left-end hairpin (LEH, 3' end), P5 promoter, NS-coding region, NP1-coding region, VP-coding region, 3' untranslated region (3' UTR), and the right-end hairpin (REH, 5' end). The wild-type infectious clone is shown as duplex form DNA (dsDNA). Non-coding sequences LEH, 3' UTR, and REH were deleted as described below. The ORF of NS, NP1, or VP was terminated as described below. Dotted lines indicate sequence deletion; vertical bars indicate nucleotide mutations. (B&C) Southern blot analysis. The wild-type infectious clone (pIHBoV1) or the indicated mutants were transfected into HEK293 cells. At 2 days post transfection, low molecular weight (Hirt) DNA was extracted and applied for Southern blotting after Dpn I digestion. One hundred twenty ng of pIHBoV1 digested with Dpn I at the same condition as Hirt DNA samples was used as Dpn I digestion control (Dpn I-Dig. Ctrl). RF, replicative form DNA intermediate; dRF, double RF DNA intermediate; ssDNA, single-stranded DNA. Asterisks indicate replicated DNA from the entire HBoV1 DNA-contained plasmid. M: a size marker.

FIGS. 2A-F. Identification of the minimal replication origin (OriR) at the REH. (A) Diagram of REH deletion mutants. All REH deletion mutants were constructed based on the LEH-deleted and VP1/3-knockout plasmid pIHBoV1 (LEH-VP1/3-). Group I mutants had deletions at the 3' end from nt 5,543 to 5,383. Group II mutants shared the 3' end deletion to nt 5,430 and were further deleted at the 5' end from nt 5,354 nt to 5,384. Group III mutants shared the 5' end deletion to nt 5,357 except for ΔREH18, which had a 5' end at nt 5,360. The deletion at the 3' end started from nt 5,410 nt to 5,390. (B-D) Southern blot analyses. HEK293 cells were transfected with linearized mutant HBoV1 DNAs, and Hirt DNA samples were extracted at two days post transfection. DpnI digested Hirt DNA samples were applied for Southern blotting. (E) Quantification. Three experiments were repeated for panel D, and the RF DNA was quantified in each lane. The level of RF DNA from the wild-type HBoV1 was set up as 100% (Lane 1) after normalization with the main Dpn I-digested bands. N.S., not significant; -*, $P<0.05$; **, $P<0.01$. (F) Minimal replication origin (OriR). The sequence of the identified OriR is shown in duplex DNA.

FIGS. 3A-B. HBoV1 OriR replicated independent of upstream 3' UTR. (A) Diagram of λ DNA insertion mutants. Based on pHBoV1-Ori, 200 bp, 400 bp, or 1000 bp of λ DNA was inserted between 3' UTR and REH. (B) Southern blot analysis. HEK293 cells were transfected with linearized mutants. At two days post transfection, Hirt DNA samples were extracted and digested with Dpn I before they were applied for Southern blotting. pIHBoV1(NS1-) was used as a negative control. Sixty ng of pIHBoV1 was digested as Dpn I digestion control.

FIG. 4. Both NS1 and NP1 are required for replication of the Ori. HEK293 cells were transfected with HBoV1-Ori or its mutants pHBoV1(NS1-)-Ori and pHBoV1(NP1-)-Ori. Hirt DNA samples were extracted at two days post transfection and were digested with Dpn I for Southern blotting. Sixty ng of pIHBoV1 digested by DpnI was used as a digestion control.

FIGS. 5A-G. NS and NP1 co-localized with the BrdU-chased viral DNA replication centers. (A-C) Localization of NS, NP1, and BrdU-incorporated HBoV1 DNA in transfected cells. HEK 293 cells were transfected with pBB (vector backbone), pIHBoV1, or pHBoV1-Ori. At two days post transfection, the cells were incorporated with BrdU before being harvested and then applied for immunofluorescence staining. Anti-NS1C with anti-BrdU (A), anti-NP1 with anti-BrdU (B), and anti-NS1C with anti-NP1 were co-stained. (D-F) Localization of NS1, NP1, and BrdU incorporated HBoV1 DNA during infection. HAE-ALI cultures were infected by HBoV1 at an MOI of 10. At 7 days post infection, cells were incorporated with BrdU and applied for immunofluorescence analysis. NS, NP1, or BrdU were co-stained in different combinations. (G) Interaction of NP1 with BrdU-chased viral DNA. Transfected cells, as indicated, were pulse chased with BrdU, and were analyzed by PLA with anti-NP1 and anti-BrdU antibody. DAPI was used to stain the nucleus. Confocal images were taken at 100× under a Nikon confocal microscope.

FIGS. 6A-B. NS and NP1 did not interact directly. HEK 293 cells were transfected with pHBoV1-Ori or mock transfected. At two days post-transfection, cells were washed, lysed and pre-cleared with normal rat serum as described below. Pre-cleared lysates were immunoprecipitated with either rat IgG and rat anti-NP1 rat serum, respectively (A), or rat IgG and rat anti-NS1C serum, respectively (B). Immunoprecipitated proteins were analyzed by Western blotting using an anti-NS1C antibody. Four μl of the pre-cleared lysates were loaded as input controls.

FIGS. 7A-C. Characterization of the putative NS1 binding element in vivo. (A) Diagram of NSBE mutants. The wild-type OriR and mutated sequences of the putative NSBE are shown. The putative NSBE include $(TGT)_4$, and the mutants were constructed based various mutations of the "TGT" repeats. (B) Southern blot analysis. HEK293 cells were transfected with linearized wild-type Ori and NSBE mutants as indicated. Hirt DNA samples were extracted and applied for Southern blotting after Dpn I digestion. (C) Quantification. After normalization with Dpn I-digested bands, the RF DNA bands on blots were quantified. Related levels to the RF DNA from pHBoV1-Ori (lane 9) are shown with averages and standard deviations from three independent experiments.

FIGS. 8A-B. Identification of the terminal resolution site (TRS) within OriR in vivo. (A) Diagram of the TRS mutants. The dynamic TRS identified by rapid amplification of the 3' end of nicked DNA are indicated by arrows. The sequenced results of poly-adenosine starting sites derived from transfection of the HBoV1 full-length genome (IHBoV1) and HBoV1-Ori are shown with stipled and solid arrowheads, respectively. Mutations at seven of these polyA starting sites, as shown, were performed. (B) Southern blot analysis. Linearized HBoV1 DNAs were transfected into HEK293 cells. At two days post-transfection, Hirt DNA samples were extracted, Dpn I digested, and analyzed by Southern blotting. Sixty ng of pHBoV1-Ori was digested by Dpn I as a control.

Figure 9C:
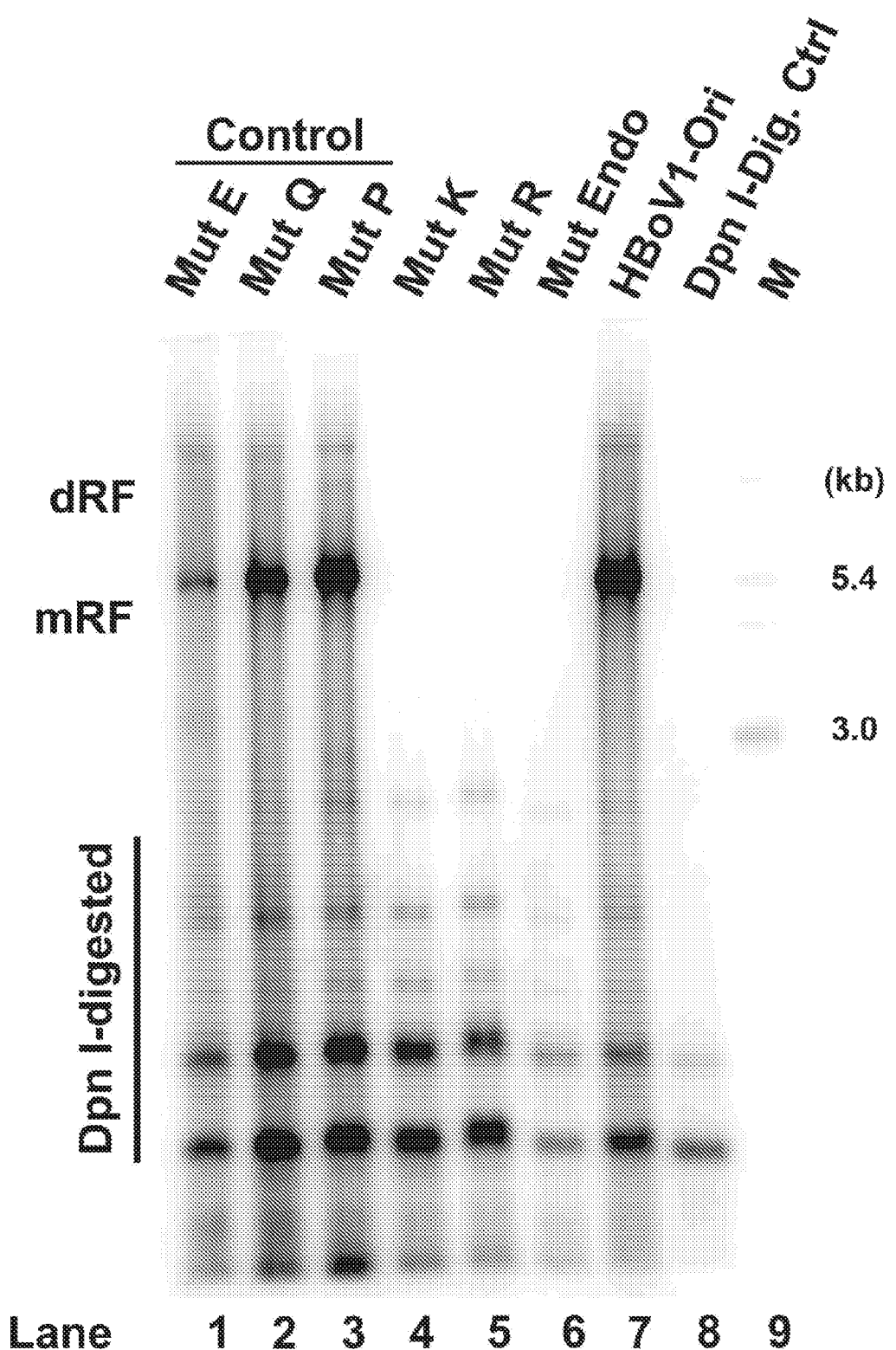

FIGS. 9A-C. Characterization of the Ori binding domain (OBD) of the NS1 in vivo. (A) Diagram of NS1 mutants. The NS1 OBD is diagrammed to scale with putative Ori binding site and endonuclease activity shown. Based on pHBoV1-Ori, OBD mutants that have NS1 amino acid mutations at the indicated positions are shown. (B) Superimposition of three NS1 OBD mutants with the wild-type NS1 OBD structure. The NS1 OBD structures of Mut K, Mut R, and Mut Endo mutants were predicted by the web server 'I-TASSER' based on the wild-type structure (Zhang, 2008). The predicted structures of the mutants were individually superimposed with wild-type NS1 OBD structure using the web server 'Superpose 1.0' (Maiti et al., 2004). The mutated amino acids in the putative DNA binding loop K and loop R and the endonuclease activity core are labeled with boxes. (C) Southern blot analysis. Linearized HBoV1 DNAs, as indicated, were transfected into HEK293 cells. At two days post-transfection, Hirt DNA samples were extracted, digested with Dpn I, and analyzed for DNA replication using Southern blotting. Dpn I digestion control was 60 ng of pHBoV1-Ori plasmid digested with Dpn I.

FIGS. 10A-D. HBoV1 NS1 alone did not specifically bind the OriR in an in vitro setting. (A) NS1 protein purification. Five µl (15 pmol) of purified HBoV1 NS1 (lane 1) and B19V NS1 (lane 2) were analyzed on SDS-PAGE, and stained with Coomassie brilliant blue. Lane 3, 2 µg of bovine serum albumin (BSA); lane 4, a protein ladder. (B) B19V NS1 specifically binds B19V Ori in vitro. γ-ATP labeled B19V Ori (lanes 1-7) or Ori-mut (lanes 8 and 9) was incubated with (lanes 2-6 and 9) or without B19V NS1 (lanes 1 and 8) in the binding buffer with 2 µg/ml Poly[d(I-C)]. Cold Ori probe at ratios of 20 times (lane 3) and 200 times (lane 4) or cold Ori-mut probe at levels of 20 times (lane 5) and 200 times (lane 6) was added for competition. Free and shifted probes are indicated. GST protein was added as a negative control (lane 7). (C) HBoV1 NS1 did not bind HBoV1 OriR in vitro. γ-ATP labeled HBoV1 OriR was incubated with (lane 2-8) or without (lane1) HBoV1 NS1 in the binding buffer with 2 µg/ml Poly[d(I-C)]. Cold OriR and OriR-mut probes at 10 times (lanes 3 and 6), 100 times (lanes 4 and 7), and 1,000 times (lanes 5 and 8) were included for competition. Free and shifted probes are indicated. (D) Non-specific HBoV1 NS1 binding to OriR. γ-ATP labeled HBoV1 Ori was incubated with (lanes 2-8) or without (lane1) HBoV1 NS1 in the absence of Poly[d(I-C)]. Cold OriR/OriR-mut probe at 50 times (lanes 3 and 6), 10 times (lanes 4 and 7), 4 times (lanes 5 and 8) was included for competition. Free and shifted probes are indicated.

FIGS. 11A-D. HBoV1 NS1 alone or with NP1 did not specifically bind OriR in a pull-down assay. (A&B) Detection of B19V NS1 and B19V Ori binding. (A) Nuclear extract (NE) prepared from OptiB19VNS1-transfected HEK 293 cells were used to incubate with Biotin-labeled B19V Ori (Bio-Ori; lanes 3-5) and B19V Ori-mut (lane 6), followed with streptavidin-conjugated beads. Additionally, some reactions were additionally incubated with B19V Ori-mut at 30 times (lane 4) and B19V Ori at 30 times (lane 5). NS1 bands pulled down by the Bio-Ori are indicated. (B) The NS1 bands pulled down by Bio-Ori were quantified. Relative levels to the NS1 in lane 4 are shown with averages and standard deviations from three independent experiments. (C&D) Detection of HBoV1 NS1 and HBoV1 OriR binding. (C) NE prepared from OptiHBoV1NS1-transfected HEK 293 cells were used to incubate with HBoV1 OriR (lane 2), and HBoV1 OriR-mut (lane 3), followed with streptavidin-conjugated beads. NS1 detected in the input is indicated. (D) NE prepared from OptiHBoV1NS1- and OptiHBoV1NP1-transfected HEK293 cells were used to incubate with HBoV1 OriR or OriR-mut, followed with streptavidin-conjugated beads. NS1 and NP1 detected in the input are indicated.

Figure 12:
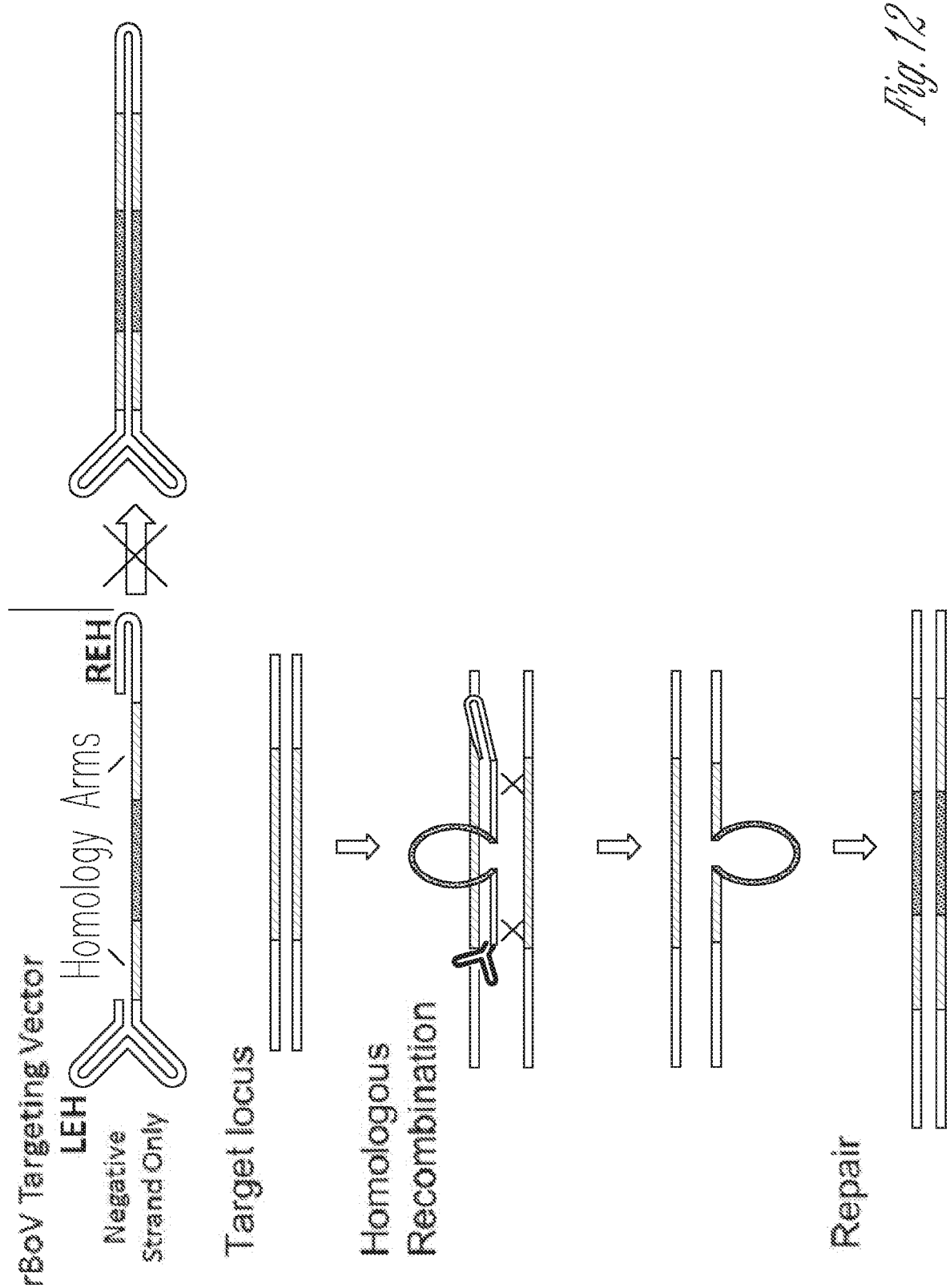

FIG. 12. Schematic of an exemplary use of a rBoV vector for homologous recombination.

FIG. 13A-E. Exemplary BoV nucleotide sequence (SEQ ID NO:1).

DETAILED DESCRIPTION

Definitions

An "origin of replication" ("ori") is a DNA sequence, e.g., in a bocavirus, that when present in a cell may be capable of maintaining linked sequences, and/or is a site at or near where DNA synthesis initiates. As described hereinbelow an ori for bocavirus includes TRS and NS1 nicking and binding sequences (NSBEs).

A "BoV vector" as used herein refers to a BoV vector which may comprise a polynucleotide sequence not of BoV origin (i.e., a polynucleotide heterologous to AAV), typically a sequence of interest for the genetic transformation of a cell. Vector constructs, the heterologous polynucleotide is flanked by LEH and 3'UTR-REH, or a minimal OriR. The term BoV vector encompasses both BoV vector particles and BoV vector plasmids.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest for gene therapy. Vectors include, for example, viral vectors (such as adenoviruses, parvoviruses include bocavirus and adeno-associated viruses (AAV), lentiviruses, herpesvirus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Large varieties of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene includes at least a portion of an open reading frame of a gene which is partly or entirely heterologous (Le., foreign) to the transgenic organism, or may represent an open reading frame or a portion thereof of a gene homologous to an endogenous gene of the organism, which portion optionally encodes a polypeptide with substantially the same activity as the corresponding full length polypeptide, e.g., wild-type polypeptide, or at least one activity of the corresponding full length polypeptide.

By "transgenic cell" is meant a cell containing a transgene. For example, a stem cell transformed with a vector containing an expression cassette can be used to produce a population of cells having altered phenotypic characteristics. A "recombinant cell" is one which has been genetically modified, e.g., by insertion, deletion or replacement of sequences in a nonrecombinant cell by genetic engineering.

The term "wild-type" or "native" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector and preferably via a replication-defective viral vector.

The term "heterologous" as it relates to nucleic acid sequences such as gene sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAVITR promoters, as well as heterologous promoters.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture.

The term "recombinant DNA molecule" as used herein refers to a DNA molecule that is comprised of segments of DNA joined together by means of molecular biological techniques.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

The term "prophylactically effective amount" is meant to refer to the amount necessary to, in the case of infectious agents, prevent an individual from developing an infection, and in the case of diseases, prevent an individual from developing a disease.

The term "therapeutically effective amount" is meant to refer to the amount necessary to, in the case of infectious agents, reduce the level of infection in an infected individual in order to reduce symptoms or eliminate the infection, and in the case of diseases, to reduce symptoms or cure the individual.

"Inducing an immune response against an immunogen" is meant to refer to induction of an immune response in a naïve individual and induction of an immune response in an individual previously exposed to an immunogen wherein the immune response against the immunogen is enhanced.

"Gene expression" or "expression" refers to the process of gene transcription, translation, and post-translational modification.

A "detectable marker gene" is a gene that allows cells carrying the gene to be specifically detected (e.g., distinguished from cells which do not carry the marker gene). A large variety of such marker genes are known in the art.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art, some of which are described below.

A "chimeric virus" or "chimeric viral particle" refers to a viral particle composed of at least one capsid protein and an encapsidated polynucleotide which is from a different virus.

An "infectious" virus or viral particle is one that comprises a polynucleotide component which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" or "TRS," as used herein, refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a TRS or promoter that is removed from its native coding sequence and operably linked to a different coding sequence is a heterologous TRS or promoter.

"Packaging" as used herein refers to a series of subcellular events that results in the assembly and encapsidation of a viral vector. Thus, when a suitable vector is introduced into a packaging cell line under appropriate conditions, it can be assembled into a viral particle. Functions associated with packaging of viral vectors are described herein and in the art.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, e.g., mammalian cells, such human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene," "prophylactic gene," "target polynucleotide," "transgene," "gene of interest" and the like generally refer to a gene or genes to be transferred using a vector. Typically, in the context of the present invention, such genes are located within the rBoV vector (which vector is flanked by LEH, 3'UTR and REH and thus can be replicated and encapsidated into rBoV particles). Target polynucleotides can be used in this invention to generate rBoV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as E1A tumor suppressor genes or p53 tumor suppressor genes for the treatment of various cancers. To effect expression of the transgene in a recipient host cell, it is operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The rBoV vector may also contain a selectable marker.

A "gene" refers to a polynucleotide containing at least one open reading frame that in one embodiment is capable of encoding a particular protein after being transcribed and translated.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. The genetic element may be introduced into a chromosome or mini-chromosome in the cell; but any alteration that changes the phenotype and/or genotype of the cell and its progeny is included in this term.

"Homologous recombination" is a type of genetic recombination in which nucleotides are exchanged between two similar or identical nucleotide sequences of DNA.

"Gene targeting" is a genetic technique that uses homologous recombination to change an endogenous gene, e.g., delete the gene, remove exons, add a gene or alter the splice donor and receptor sequence, add a gene, or change one or more bases in the DNA. See exemplary disorders and associated mutations below:

| Disorder | Mutation | Chromosome |
|---|---|---|
| 22q11.2 deletion syndrome | D | 22q |
| Angelman syndrome | DCP | 15 |
| Canavan disease | | 17p |
| Charcot-Marie-Tooth disease | | |
| Color blindness | P | X |
| Cri du chat | D | 5 |
| Cystic fibrosis | P | 7q |
| Down syndrome | C | 21 |
| Duchenne muscular dystrophy | D | Xp |
| Haemochromatosis | P | 6 |
| Haemophilia | P | X |
| Klinefelter syndrome | C | X |
| Neurofibromatosis | | 17q/22q/? |
| Phenylketonuria | P | 12q |
| Polycystic kidney disease | P | 16 (PKD1) or 4 (PKD2) |
| Prader-Willi syndrome | DC | 15 |
| Sickle-cell disease | P | 11p |
| Spinal muscular atrophy | DP | 5q |
| Tay-Sachs disease | P | 15 |
| Turner syndrome | C | X |

P—Point mutation, or any insertion/deletion entirely inside one gene;
D—Deletion of a gene or genes;
C—Whole chromosome extra, missing, or both (chromosome abnormality);
T—Trinucleotide repeat disorders: gene is extended in length "Gene editing" is a type of genetic engineering in which DNA is inserted, deleted or replaced in the genome of an organism using a recombinant nuclease, e.g., a heterologous nuclease.

"Gene correction template" is the exogenous template that is used to introduce DNA into, delete DNA from or otherwise replace or alter DNA in the genome of an organism.

A cell is said to be "stably" altered, transduced or transformed with a genetic sequence if the sequence is available to perform its function during extended culture of the cell in vitro. In some examples, such a cell is "inheritably" altered in that a genetic alteration is introduced which is also inheritable by progeny of the altered cell.

The terms "polypeptide" and "protein" are used interchangeably herein to refer to polymers of amino acids of any length. The terms also encompass an amino acid polymer that has been modified; for example, disulfide bond formation, glycosylation, acetylation, phosphonylation, lipidation, or conjugation with a labeling component. Polypeptides such as "CFTR" and the like, when discussed in the context of gene therapy and compositions therefor, refer to the respective intact polypeptide, or any fragment or genetically engineered derivative thereof, that retains the desired biochemical function of the intact protein. Similarly, references to CFTR, and other such genes for use in gene therapy (typically referred to as "transgenes" to be delivered to a recipient cell), include polynucleotides encoding the intact polypeptide or any fragment or genetically engineered derivative possessing the desired biochemical function.

A preparation of virus is said to be "substantially free" of helper virus if the ratio of infectious virus particles to infectious helper virus particles is at least about $10^2:1$; e.g., at least about $10^4:1$, including at least about $10^6:1$ or at least about $10^8:1$. Preparations may also be free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the capsid proteins VP1, VP2 and VP3).

"Efficiency" when used in describing viral production, replication or packaging refers to useful properties of the method: in particular, the growth rate and the number of virus particles produced per cell. "High efficiency" production indicates production of at least 100 viral particles per cell; e.g., at least about 10,000 or at least about 100,000 particles per cell, over the course of the culture period specified.

An "individual" or "subject" treated in accordance with this invention refers to vertebrates, particularly members of a mammalian species, and includes but is not limited to domestic animals, sports animals, and primates, including humans.

"Treatment" of an individual or a cell is any type of intervention in an attempt to alter the natural course of the individual or cell at the time the treatment is initiated, e.g., eliciting a prophylactic, curative or other beneficial effect in the individual. For example, treatment of an individual may be undertaken to decrease or limit the pathology caused by any pathological condition, including (but not limited to) an inherited or induced genetic deficiency, infection by a viral, bacterial, or parasitic organism, a neoplastic or aplastic condition, or an immune system dysfunction such as autoimmunity or immunosuppression. Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent.

The practice of the present invention will employ, unless otherwise indicated, conventional techniques of molecular biology, virology, microbiology, recombinant DNA, and immunology, which are within the skill of the art. Such techniques are explained fully in the literature. See, e.g., Sambrook et al., 1989; Gait, 1984; Freshney, 1987; the series *Methods in Enzymology* (Academic Press, Inc.); Miller et al., 1987; Weir et al., 1996; Ausubel et al., 1998; Coligan et al., 1991; Coligan et al., 1995; and Scopes 1994.

rBoV Vectors

Besides prophylactic or therapeutic gene products, recombinant BoV vectors and/or viruses can also comprise polynucleotides that do not encode proteins, including, e.g., polynucleotides encoding for antisense mRNA (the complement of mRNA) which can be used to block the translation of normal mRNA by forming a duplex with it, and polynucleotides that encode ribozymes (RNA catalysts). In addition selected pairs of rBoV vectors having portions of open reading frames flanked by appropriately placed splice acceptor sites and/or splice donor sites, or having transcription regulatory sequences such as a heterologous enhancer, a heterologous promoter, or a heterologous enhancer and a promoter, may be employed.

A BoV vector of the invention may comprise a polynucleotide that is heterologous to BoV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or in place of the BoV genomic coding region, but is generally flanked on either side by LEH, 3'UTR and REH.

A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. One sub-class of inducible promoters are those that are induced by the helper virus that is used to complement the replication and packaging of the rHBoV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters.

Removal of one or more BoV genes is in any case desirable, to reduce the likelihood of generating replication-competent virus ("RCV"). Accordingly, sequences encoding structural and/or non-structural, or both, may be removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are in one embodiment not flanked by BoV LEH, 3'UTR and/or REH and in one embodiment do not share any substantial homology with the BoV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCV.

The BoV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the BoV vector and complementary packaging gene(s), if any, are provided in the form of bacterial plasmids, BoV particles, or any combination thereof. In other embodiments, either the BoV vector sequence, the packaging gene(s), or both, are provided in the form of genetically altered (e.g., inheritably altered) eukaryotic cells. The development of host cells inheritably altered to express the BoV vector sequence, BoV packaging genes, or both, provides an established source of the material that is expressed at a reliable level.

A variety of different genetically altered cells can thus be used in the context of this invention. By way of illustration, a mammalian host cell may be used with at least one intact copy of a stably integrated BoV vector. A BoV packaging plasmid can be used to supply replication functions. Alternatively, a stable mammalian cell line can be used to supply replication functions. The BoV VP genes, providing the encapsidation proteins, can be provided together with a BoV NS1 and/or NP1 gene or separately. Other combinations are possible and included within the scope of this invention.

Uses of rBoV

The rBoV can be used for administration to an individual for purposes of gene therapy or vaccination. Suitable diseases for therapy include but are not limited to those induced by viral, bacterial, or parasitic infections, various malignancies and hyperproliferative conditions, autoimmune conditions, and congenital deficiencies.

Gene therapy can be conducted to enhance the level of expression of a particular protein either within or secreted by the cell. Gene therapy can also be conducted to edit genomic DNA through homologous recombination with the viral genome (e.g., correct a gene defect encoded in the endogenous gene loci). Vectors of this invention may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic or prophylactic polynucleotide comprising a sequence capable, for example, of forming a stable hybrid with either the target gene or RNA transcript (antisense therapy), capable of acting as a ribozyme to cleave the relevant mRNA or capable of acting as a decoy for a product of the target gene. Vectors of this invention may also be used to deliver gene-editing components and a single stranded DNA template to genetically correct gene defects through homologous recombination. For example, negative single strand rBoV genomes without positive strands may facilitate homologous combination, e.g., in conjunction with a DNA endonuclease that cleaves at the target site of homology in the genome that is contained within the rBoV genome. In this case, the rBoV genome may encode, for example, CRISPR/Cas9 and a guide RNA (gRNA) and the site of genomic homology targeted for gene editing. Conversion of a subset of the rBoV genomes allows for expression of the Cas9/gRNA while other rBoV genomes may remain single stranded. An advantage of rBoV over rAAV is that the rAAV vector system contains equal percentages of positive and negative strand genomes while the rBoV vector system contains only the negative strand, which can anneal after infection and reduce the efficiency of HR. In antoher example, a rBoV genome may be employed along with a guide DNA (gDNA) for use with the NgAgo-gDNA gene editing system (see, Gao et al., *Nature Biotech.*, 2016, doi:10.1038/nbt.3546, the disclosure of which is incorporated by reference herein). In this system, a region of the rBoV genome contains an expression cassette for the Argonaute (NgAgo), and the gDNA (5' phosphorylated single strand guide DNA) is introduced using different delivery methods including non-viral delivery system. Conversion of a subset of rBoV genome allows for expression of the NgAgo while other rBoV genomes will remain single stranded and serves as gene correction template.

The introduction of the rHBoV vectors by the methods of the present invention may involve use of any number of delivery techniques (both surgical and non-surgical) which are available and well known in the art. Such delivery techniques, for example, include vascular catheterization, cannulization, injection, inhalation, endotracheal, subcutaneous, inunction, topical, oral, percutaneous, intra-arterial, intravenous, and/or intraperitoneal administrations. Vectors can also be introduced by way of bioprostheses, including, by way of illustration, vascular grafts (PTFE and dacron), heart valves, intravascular stents, intravascular paving as well as other non-vascular prostheses. General techniques regarding delivery, frequency, composition and dosage ranges of vector solutions are within the skill of the art.

In particular, for delivery of a vector of the invention to a tissue, any physical or biological method that will introduce the vector to a host animal can be employed. Vector means both a bare recombinant vector and vector DNA packaged into viral coat proteins, as is well known for administration. Simply dissolving a chimeric or rHBoV vector in phosphate buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the chimeric or rHBoV vector as a free acid (DNA contains acidic phosphate groups) or a pharmacologically acceptable salt can be prepared in water suitably mixed with a surfactant such as hydroxypropylcellulose. A dispersion of viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the chimeric or rHBoV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the methods of preparation include but are not limited to vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade dimethylsulfoxide (DMSO).

Of interest is the correction of the genetic defect of cystic fibrosis, by supplying a properly functioning cystic fibrosis transmembrane conductance regulator (CFTR) to the airway epithelium. Thus, the use of chimeric or rHBoV vectors encoding native CFTR protein, and mutants and fragments thereof, is envisioned.

Compositions of this invention may be used in vivo as well as ex vivo, in vivo gene therapy comprises administering the vectors of this invention directly to a subject. Pharmaceutical compositions can be supplied as liquid solutions or suspensions, as emulsions, or as solid forms suitable for dissolution or suspension in liquid prior to use. For administration into the respiratory tract, one mode of administration is by aerosol, using a composition that provides either a solid or liquid aerosol when used with an appropriate aerosolubilizer device. Another mode of administration into the respiratory tract is using a flexible fiberoptic bronchoscope to instill the vectors. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, at least about 80%, at least about 95%, or at least about 99% of the cells of the desired tissue type. As a guide, the number of vector particles present in a single dose given by bronchoscopy will generally be at least about $1\times10^{12}$, e.g., about $1\times10^{13}$, $1\times10^{14}$, $1\times10^{15}$ or $1\times10^{16}$ particles, including both DNAse-resistant and DNAse-susceptible particles. In terms of DNAse-resistant particles, the dose will generally be between $1\times10^{12}$ and $1\times10^{16}$ particles, more generally between about $1\times10^{12}$ and $1\times10^{15}$ particles. The treatment can be repeated as often as every two or three weeks, as required, although treatment once in 180 days may be sufficient.

To confirm the presence of the desired DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence of a polypeptide expressed from a gene present in the vector, e.g., by immunological means (immunoprecipitations, immunoaffinity columns, ELISAs and Western blots) or by any other assay useful to identify the presence and/or expression of a particular nucleic acid molecule falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

Thus, the effectiveness of the genetic alteration can be monitored by several criteria, including analysis of physiological fluid samples, e.g., urine, plasma, serum, blood, cerebrospinal fluid or nasal or lung washes. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic or prophylactic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic or prophylactic regimen is ultimately the responsibility of the prescribing physician.

The foregoing description provides, inter alia, methods for generating high titer preparations of recombinant chimeric viruses or rHBoV that are substantially free of helper virus (e.g., adenovirus) and cellular proteins. It is understood that variations may be applied to these methods by those of skill in this art without departing from the spirit of this invention.

The invention will be described the following non-limiting example.

EXAMPLE

Parvoviruses are single-stranded DNA viruses that use the palindromic structures at the ends of the viral genome for their replication. The mechanism of parvovirus replication has been studied mostly in *Dependoparvovirus* adeno-associated virus 2 (AAV2) and *Protoparvovirus* minute virus of mice (MVM).

Human bocavirus 1 (HBoV1), a *Bocaparvovirus*, HBoV1 was first identified in 2005. HBoV1 causes acute respiratory tract infections in young children. HBoV1 infects and replicates autonomously only in well-differentiated human airway epithelial cells. However, the duplex HBoV1 genome replicates in HEK293 cells, and produces progeny virions that are infectious in well-differentiated airway epithelial cells.

As described below, both cis-acting elements and trans-acting proteins that are required for HBoV1 DNA terminal resolution in HEK293 cells were identified. The minimal replication origin was localized to a 46-nt sequence in the right-end hairpin, which contains both NS1 nicking and binding sites. The identification of these elements of HBoV1 DNA replication acting both in cis and in trans allows for antiviral strategies targeting terminal resolution, and for design of next generation recombinant HBoV1 vectors, a tool for gene therapy of lung diseases.

Materials and Methods

Cell Culture

HEK293 cells (CRL-1573, ATCC) were cultured in Dulbecco's Modified Eagle Medium (DMEM) with 10% fetal calf serum (FCS). Cells were incubated at 37° C. with 5% $CO_2$. HEK 293F cells (Life Technologies/Thermo Fisher Scientific Inc, Carlsbad, CA) were cultured in suspension in Freestyle™ 293 medium (Life Technologies) at 37° C. with 8% $CO_2$.

Primary human airway epithelium cultured at an air-liquid interface (HAE-ALI) was generated and cultured as previously described (Huang et al., 2012; Deng et al., 2016). HAE-ALI cultures that had a transepithelial electrical resistance (TEER) of >1000 $\Omega\cdot cm^2$were selected to use in this study.

Plasmid DNA Construction (i) pIHBoV1-based constructs: The parent HBoV1 infectious clone (pIHBoV1) has been described previously (Huang et al., 2012). The LEH-deleted plasmid pIHBoV1 (LEH-) was constructed by deleting the HBoV1 genome sequence of nt 1-140 in pIHBoV1. pIHBoV1(NS1-) and pIHBoV1(NP1-), which have the NS1 and NP1 ORFs, respectively, early terminated, and pIHBoV1(VP1/3-) that has both the capsid proteins VP1 and VP3 ORFs early terminated, were previously described (Huang et al., 2012). pIHBoV1(REH-), the REH-deleted plasmid, was constructed by deleting the HBoV1 sequence of nt 5,303-5,543 in pIHBoV1. pIHBoV1(LEH-VP1/3-) was constructed by deleting LEH and early terminating VP1 and VP3 ORFs. Based on the pIHBoV1(LEH-VP1/3-), an Xba I was inserted at nt 5,344 to construct REH-truncated mutants pΔREH1-24, which are diagrammed in FIG. 2. pHBoV1(3'UTR-), the 3' untranslated region (3' UTR)-deleted plasmid, was constructed by deleting the HBoV1 sequence of nt 5,221-5,291 in pIHBoV1. pIHBoV1(VP-) was constructed by deleting the HBoV1 sequence of nt 3,380-5,119 in pIHBoV1.

Figure 7A:
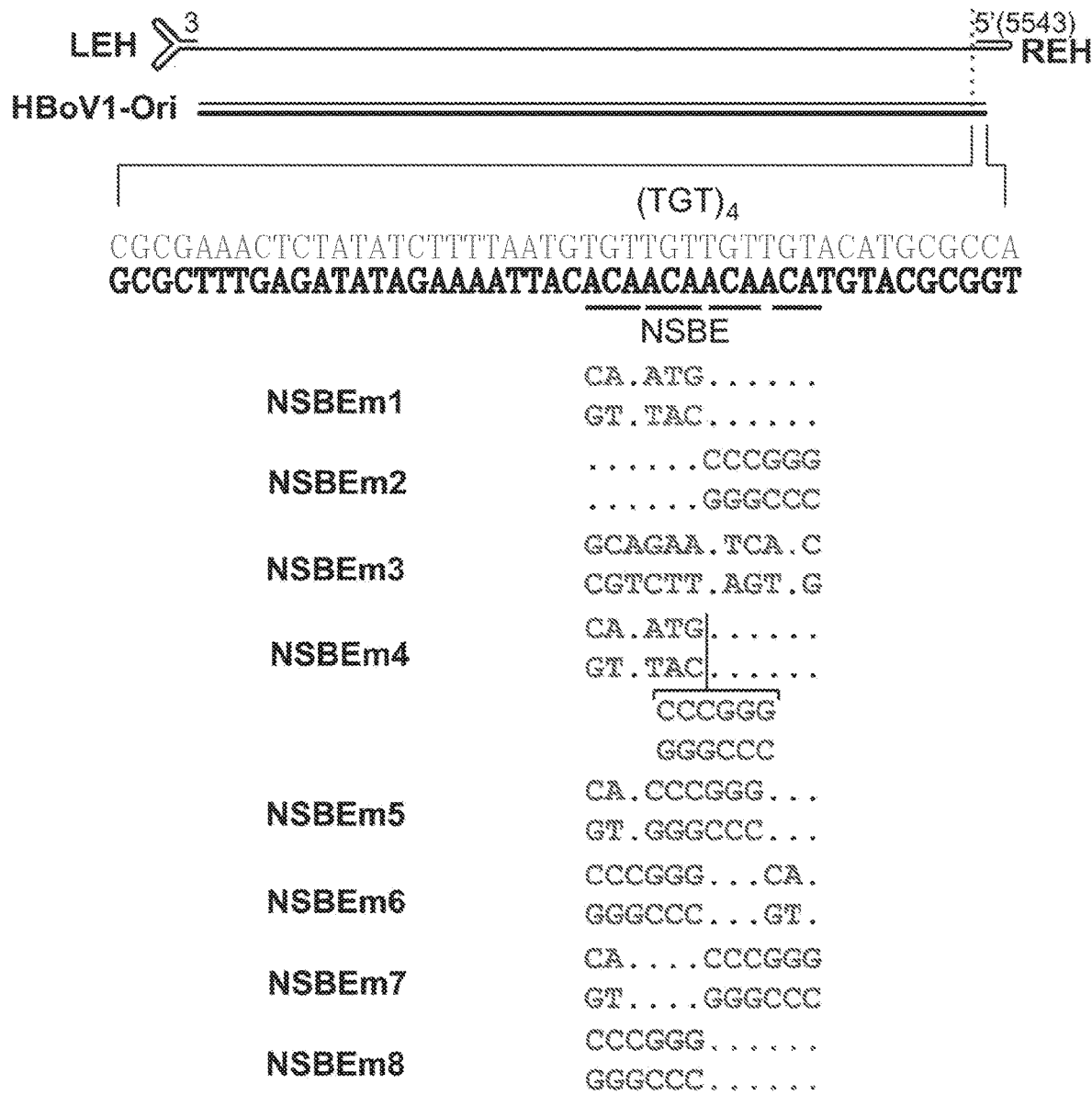
Figure 7C:
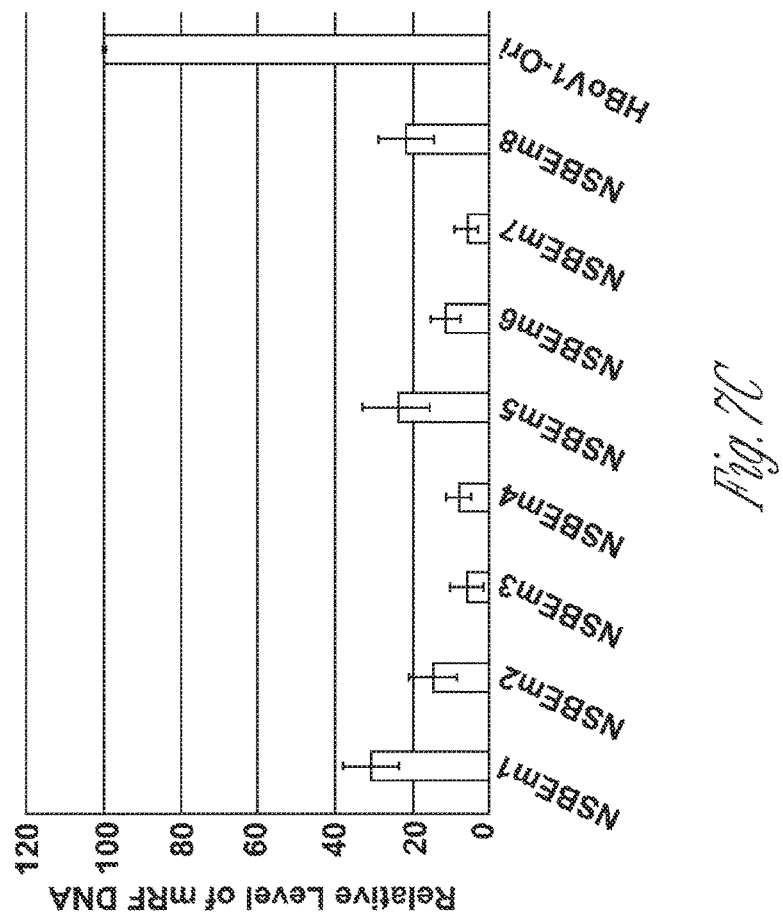

(ii) pHBoV1-Ori and pHBoV1-Ori-based constructs: pΔREH21 was renamed pHBoV1-Ori that has the minimal replication origin at the REH (OriR) of nt 5,357-5,402.

pHBoV1λ200Ori, pHBoV1λ400Ori, and pHBoV1λ1000Ori were constructed by inserting Lambda (λ) DNA sequences of 200 bp (nt 10,030-10,230), 400 bp (nt 10,030-10,430), and 1,000 bp (nt 10,030-11,030), respectively, in front of the Ori in pHBoV1Ori.

pHBoV1(NS1-)-Ori and pHBoV1(NP1-)-Ori were constructed by early terminating the NS1 and NP1 ORFs, respectively, in pHBoV1-Ori using strategies described previously in Huang et al. (2012).

pNS1m$^{13}$Q-Ori (Mut Q), pNS1m$^{54}$PHP$^{56}$-Ori (Mut P), pNS1m$^{123}$EGL$^{125}$-Ori (Mut E), pNS1m$^{115}$HCH$^{117}$-Ori (Mut Endo), pNS1m$^{127}$KR$^{128}$-Ori (Mut K), and pNS1m$^{193}$RR$^{194}$-Ori (Mut R) were constructed by mutating the amino acids as indicated by the positions to alanine(s) in the context of pHBoV1-Ori. They are diagrammed in FIG. 9.

pNSBEm1-8 and pTRSm1-7 plasmids were constructed by introducing various mutations in the putative NSBEs and TRS of the OriR, respectively, in pHBoV1-Ori. These plasmids are diagrammed in FIG. 7A and FIG. 8A, respectively, with mutations shown.

(iii) HBoV1 NS1 and B19V NS1-expressing plasmids: HBoV1 and B19V NS1 coding sequences were optimized for mammalian cell expression at Integrated DNA Technologies, Inc. (IDT, Coralville, IA), tagged with a Flag tag at the C-terminus, and were cloned in pCI expression vector (Promega, Madison, WI.), resulting in pOptHBoV1NS1 and pOptB19VNS1.

All nucleotide numbers of HBoV1 and Lambda (λ) DNA are referred to as Genbank accession no. JQ923422 and NC_001416, respectively, unless otherwise specified.

In Vivo DNA Replication Analysis

HEK293 cells were seeded in 6 well plates or 60 mm dishes one day before transfection. At a confluence of 70%, cells were transfected with LipoD293 reagent (SignaGen, Gaithersburg, MD) or Lipofactamine and Plus reagent (Life Technologies) following the manufacturers' instructions.

Low-molecular weight DNA (Hirt DNA) was extracted and digested with Dpn I, followed by Southern blotting. These steps were performed exactly as described in Guan et al. (2009). After hybridization, the membrane was exposed to a phosphor screen. The screen was then scanned on a phosphor imager (GE Typhoon FLA 9000, Fuji). The developed image was processed and analyzed using ImageQuant TL8,1 software (GE Healthcare, Marlborough, MA).

BrdU Incorporation, Immunofluorescence (IF) Assay, and Proximity Ligation Assay (PLA)

For virus-infected differentiated airway epithelial cells, we treated the infected HAE-ALI treated with 5 mM EDTA for 5 minutes and then trypsinized the infected cells off the insert. We resuspended about $1 \times 10^5$ cells in 1 ml of the ALI medium with BrdU (Sigma, St Louis, MO) at 30 μM for 20 minutes. For transfected HEK293 cells, at two days post-transfection, the cells were incubated with BrdU for 30 minutes, followed a previously published method (Luo et al., 2013). Then, the labeled cells were cytospun onto slides for IF analysis.

IF analysis was performed following a method described in Luo et al. (2013) and Luo et al. (2011), with antibodies against proteins or BrdU as indicated in FIG. 5. Confocal images were taken with an Eclipse C1 Plus confocal microscope (Nikon) controlled by Nikon EZ-C1 software. DAPI (4',6-diamidino-2-phenylindole) was used to stain the nucleus.

The Duolink PLA Kit (Sigma) was used to perform PLA according to the manufacturer's instructions as previously described in Deng et al. (2016).

Antibody Production and Antibodies Used

HBoV1 anti-NS1C antibody was produced as previously described (Chen et al., 2010), which reacts with all four NS proteins (NS1-4) (Shen et al., 2015). All animal procedures were approved by the Institutional Animal Care and Use Committee of the University of Kansas Medical Center. Rabbit anti-HBoV1 NP1 antibody (Mihaylov et al., 2014) was a kind gift from Dr. Peter Tattersall at Yale University. Rabbit anti-BrdU (cat no.: 600-401-C29, Rockland, Limerick, PA), mouse anti-Flag monoclonal antibody (Sigma, St. Louis, MO), and secondary antibodies for immunofluorescence assay (Jackson ImmunoResearch Inc., West Grove, PA) were purchased.

Rapid Amplification of the 3' End of the Nicked DNA

DNA tailing reaction was performed using terminal transferase (NEB, Ipswich, MA). Basically, the reaction was composed of 5.0 μL of 2.5 mM $CoCl_2$, 1 μL of 10-50 times diluted Hirt DNA (from about 500 cells), 0.5 μL of 10 mM dATP, 0.5 μL of Terminal Transferase (20 units/μL), and deionized $H_2O$ in a final volume of 50 μL. The reaction was incubated at 37° C. for 30 minutes. Two μL of the product was used as template for PCR amplification using forward primer (5'-CTG TCT AGA ATG ATC AAT GTA TGC CAG-3' (SEQ ID NO:2), nt 5,121 to nt 5,138) and reverse primer (5'- is CAC GGA TCC TTT TTT TTT TTT TTT T-3' (SEQ ID NO:3)). Amplified fragments were cloned into pcDNA3 (Life Technologies) through Xba I and BamH I sites. Twenty positive clones were sequenced.

Protein Expression and Purification

One 500 mL suspension culture of 293F cells ($10^6$ cells/mL) was transfected with pOpti-HBoVNS1 or pOptiB19VNS1, using TransIT-PRO® following the manufacturer's instructions. At 3 days post-transfection, cells were lysed in L buffer (50 mM Tris pH 7.4, 150 mM NaCl, 1 mM EDTA, 1% Triton-X100, 1 mM dithiothreitol (DTT), 5 mM ATP, and 5 mM $MgCl_2$) supplemented with protease inhibitors (Cat. No: S8820, Sigma). Crude lysate was sonicated for 3 minutes at a frequency of 15 seconds/25 seconds on/off, pulse 70% by the VCX130 sonicator (Sonics & Materials Inc., Newtown, Conn.). The lysate was then centrifuged at 10,000 rpm for 15 minutes and filtrated through a 0.2 μm filter. The filtered lysate was incubated with 1 mL of PBS (phosphate buffered saline, pH7.4)-prewashed anti-Flag G1 affinity resin (Genscript, Piscataway, NJ) at 4° C. for at least 1 hour. Then, the beads were washed with washing buffer (50 mM Tris, pH7.4, 500 mM NaCl, 0.05% Triton-X100, and protease inhibitors) 5 times of resin volume, and were eluted with 3× Flag peptide (APExBIO, Houston, TX) at a concentration of 200 μg/mL.

Finally, the eluted protein was dialyzed against PBS twice and against binding buffer (B buffer: 20 mM Tris-HCl, pH 8.0, 125 mM NaCl, 10% glycerol, 1% NP-40, 5 mM DTT, and protease inhibitors) once, and was concentrated 10 times using polyethylene glycol 6000 (PEG). The concentrated protein was quantified, aliquoted, and stored at −80° C.

Gel Shift Assay

Gel shift assay was performed essentially following a method in Christensen et al. (1995). Duplex DNA probe was generated by annealing complementary oligos, at a concentration of 45 µM, in an annealing buffer (10 mM Tris, pH 7.5, 50 mM NaCl, 1 mM EDTA) after boiling for 5 minutes. The dsDNA probe was desalted using a G-50 column (GE Healthcare). Duplex DNA probes are HBoV1 OriR (FIG. 2F), HBoV1 OriR-mut (5'-CGC GAA ACT CTA TAT CTT TTA ATG GCA GAA TTC AGC ACA TGC GCC A-3' (SEQ ID NO:4)), B19V Ori (5'-GCC GCC GGT CGC CGC CGG TAG GCG GGA CTT CCG GTA CA-3' (SEQ ID NO:5)) (Tewary et al., 2014), and B19V Ori-mut (5'-AGC TAT TGG TCG CTA TTG GTA GGC GGG ACT-3' (SEQ ID NO:6) (Tewary et al., 2014).

One µL of the duplex DNA probe was labeled with γ-p32-ATP using T4 polynucleotide (NEB) following the manufacturer's instructions. The binding reaction consisted of 8 µL of 2.5×B buffer, 2 µL of diluted duplex DNA probe (at 1:10,000), with/without 2 µL of purified protein (300 ng/µl), 2 µL of unlabeled (cold) probe at a concentration (ratio) specified in FIG. 10, and dH$_2$O to a total volume of 20 µL. The reactions were incubated on ice for 20 minutes, loaded directly into a pre-run 5% non-denaturing polyacrylamide gel, and electrophoresed for 45 minutes at 100 volts. Finally, the acrylamide gel was dried by vacuum at 70° C. and exposed to a phosphor screen.

Nuclear Extract (NE) Preparation

Nuclear extraction was performed following a method described in Dignam et al. (1983). HEK293 cells of one dish of 100 mm were transfected with pOptiHBoV1NS1 or pOptiB19VNS1. At 2 days post-transfection, cells were collected, washed with ice-cold PBS, and pelleted. The cell pellet was lysed in 5× L buffer (10 mM HEPES, pH7.5, 10 mM KCl, 0.1 mM EDTA, 1 mM DTT, 0.5% NP-40, and protease inhibitors). The lysate was vortexed and centrifuged at 500 g for 5 minutes at 4° C. The pelleted nuclei were washed 3 times with 1 ml W buffer (10 mM HEPES, pH 7.5, 10 mM KCl, 0.1 mM EDTA, 1 mM DTT, and protease inhibitors). Nuclei were resuspended in 0.25 mL of NE buffer (20 mM HEPES, pH 7.5, 420 mM NaCl, 1 mM EDTA, 1 mM DTT, 25% glycerol (v/v), and protease inhibitors), and were incubated on ice for 30 minutes. Finally, nuclear extract was obtained as the supernatant by centrifuging the lysed nuclei at 12,000 g for 10 minutes at 4° C., and was adjusted the NaCl concentration to 100 mM using B1 buffer (=buffer NE without NaCl).

Pull-down Assay

Biotin-labeled probe was generated by annealing two complementary oligos, in which one oligo was biotinylated, at a concentration of 5 µM. Annealed dsDNA probe was desalted using a G-50 column. Streptavidin-conjugated beads (Gold Biotechnology, St. Louis, MO) were prewashed following the manufacturer's instructions. Binding reaction consisted of 200 µL of 2.5×B buffer, 100 µL of nuclear extract (about 5 µg/ml), 1 µL of biotinylated probe, with/without unlabeled probe, and dH$_2$O in a total volume of 0.5 ml. The reactions were rotated at 4° C. overnight, and were pelleted by centrifugation at 1,000 g for 3 minutes. The pellet was then washed 3 times with cold PBS before adding loading buffer. The samples were boiled for 5 minutes and analyzed by SDS-polyacrylamide gel electrophoresis, followed by Western blotting.

Immunoprecipitation (IP) Assay

HEK293 cells cultured in one 60 mm dish were mock-transfected or transfected with plasmids. At 2 days post-transfection, the cells were washed and lysed with 300 µL radioimmunoprecipitation assay (RIPA) buffer (50 mM Tris-HCl, pH 8.0, 150 mM NaCl, 1% NP-40, 0.5% sodium deoxycholate, 0.1% SDS, and protease inhibitors) with constant agitation for 30 minutes at 4° C. The cell lysates were centrifuged at 14,000 g for 3 minutes at 4° C., and the supernatant was collected. The rest supernatant (about 220 µL) was pre-incubated with 40 µL normal rat serum, 30 µL of prewashed protein A/G bead (ThermoFisher), and 2 µL of benzonase (ThermoFisher) for 3 hours at 4° C. with rotation. After preclearing, the supernatant was equally divided for incubation with either 2 µL of normal rat IgG (0.4 mg/mL; Santa Cruz, Dallas, TX) or 20 µL of rat antisera, 30 µL of protein A/G beads, and 300 µL of RIPA buffer at 4° C. overnight. Finally, the protein A/G beads were pelleted down and washed 3 times with ice cold PBS before mixing with loading dye for Western blotting.

Results

Figure 1B:
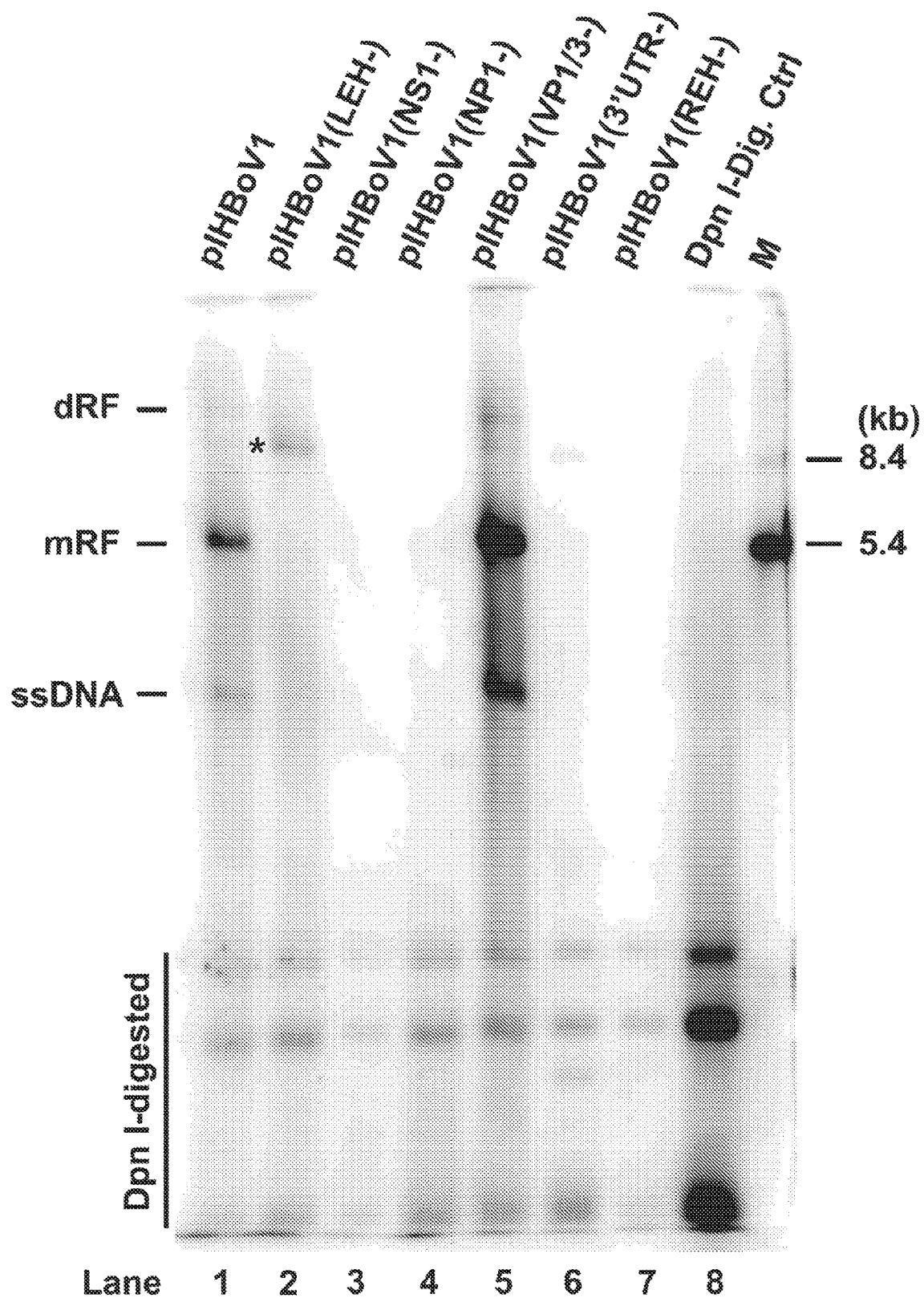
Figure 1C:
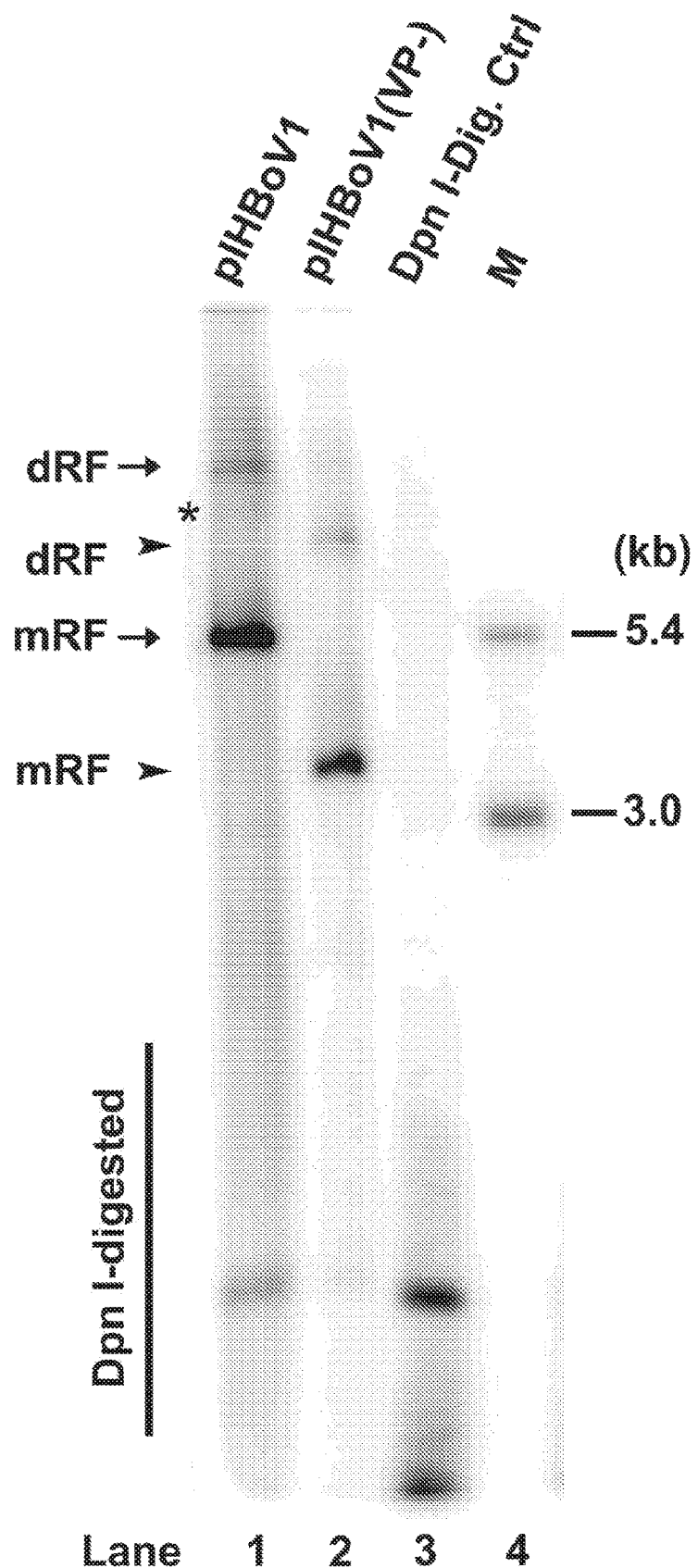

Identification of Viral Elements Required in cis or in Trans for HBoV1 Replication To understand the DNA replication mechanism of HBoV1, viral DNA signals and viral proteins that are required for viral DNA replication were delineated. As diagrammed in FIG. 1A, the HBoV1 genome contains four noncoding sequences (LEH, P5 promoter region, 3' UTR, REH) and three ORFs that encode NS1-4, NP1, and VP1-3 proteins, respectively (Zou et al., 2016; Shen et al., 2015). To dissect the minimal requirements for viral DNA replication, sequential deletions of the noncoding regions and early termination of the ORFs were carried out in the context of pIHBoV1. Southern blotting results showed a representative pattern of HBoV1 DNA replication including the Dpn I-digestion resistant bands: viral single-strand DNA (ssDNA, genome size), viral RF DNA and double RF (dRF) DNA, and plasmid-replicated DNA (FIG. 1B, lane 1). The results suggested that, without the LEH sequence, pIHBoV1 (LEH-) still replicated but failed to excise the HBoV1 RF DNA out of the plasmid (FIG. 1B, lane 2). VP1/3-knockout plasmid pIHBoV1(VP1/3-) replicated better than the parent pIHBoV1 (FIG. 1B, lanes 5 vs 1). However, pIHBoV1 (NS1-), pIHBoV1(3'UTR-), and pIHBoV1(REH-) did not replicate (FIG. 1B, lanes 3, 6 and 7, respectively), and pIHBoV1(NP1-) replicated very poorly (FIG. 1B, lane 4), suggesting that the sequence at the 3' end, including REH and 3' UTR, and expression of NS1 and NP1 proteins were apparently important to HBoV1 DNA replication, pIHBoV1 (VP-), in which the VP encoding ORFs were largely deleted, replicated as well as the pIHBoV1 (FIG. 1C, lane 2).

Taken together, these results suggest that REH and 3' UTR are largely responsible for HBoV1 DNA replication as cis-acting elements, while NS1 and NP1 serve trans-acting functions (Shen et al., 2015). In the following experiments, both LEH deletion and the VP1/3 knockout HBoV1 plasmid, pIHBoV1(LEH-VP-) were used, for further characterization of HBoV1 DNA replication at REH.

Identification of the HBoV1 Minimal Replication Origin (OriR) at REH

Figure 2A:
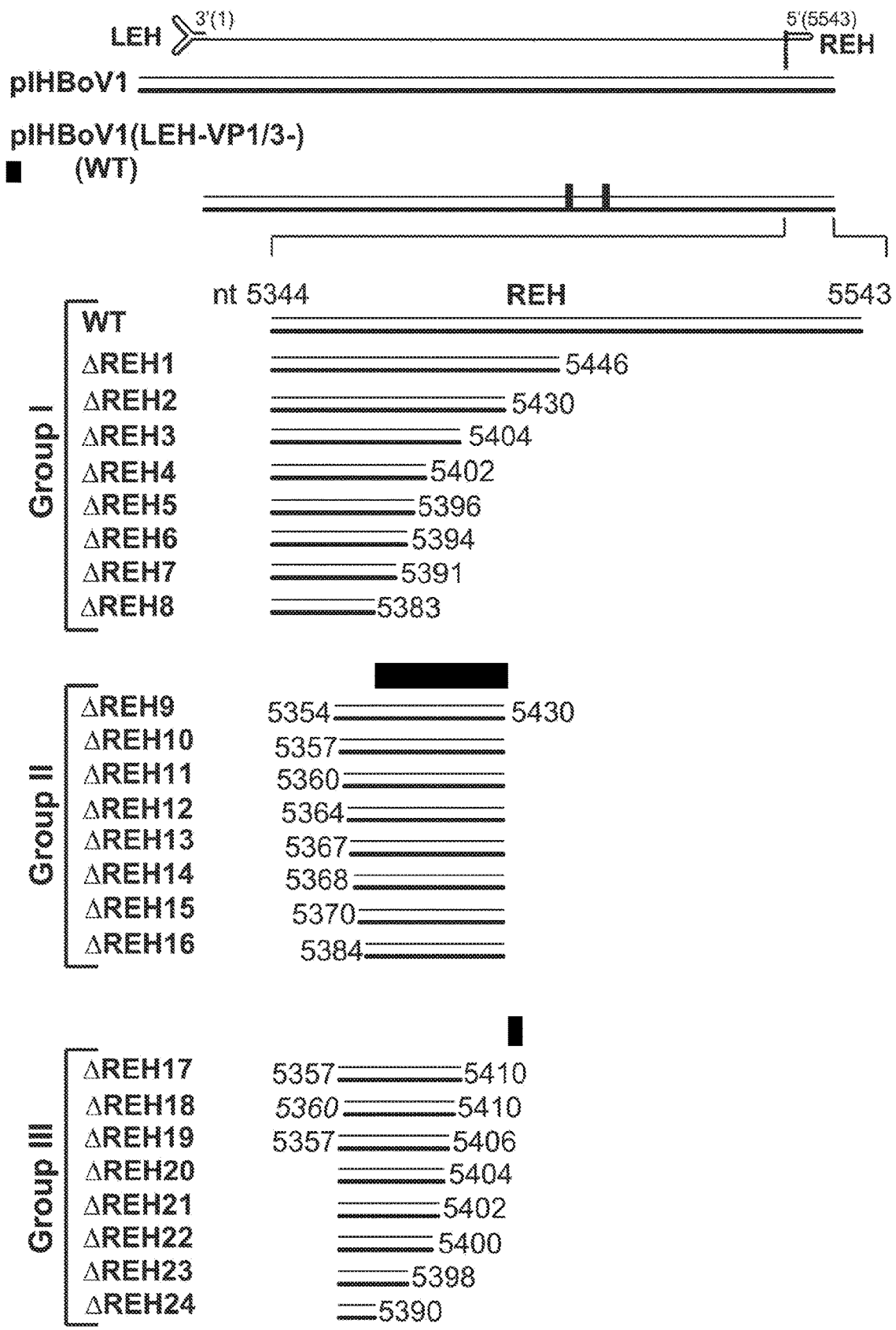
Figure 2B:
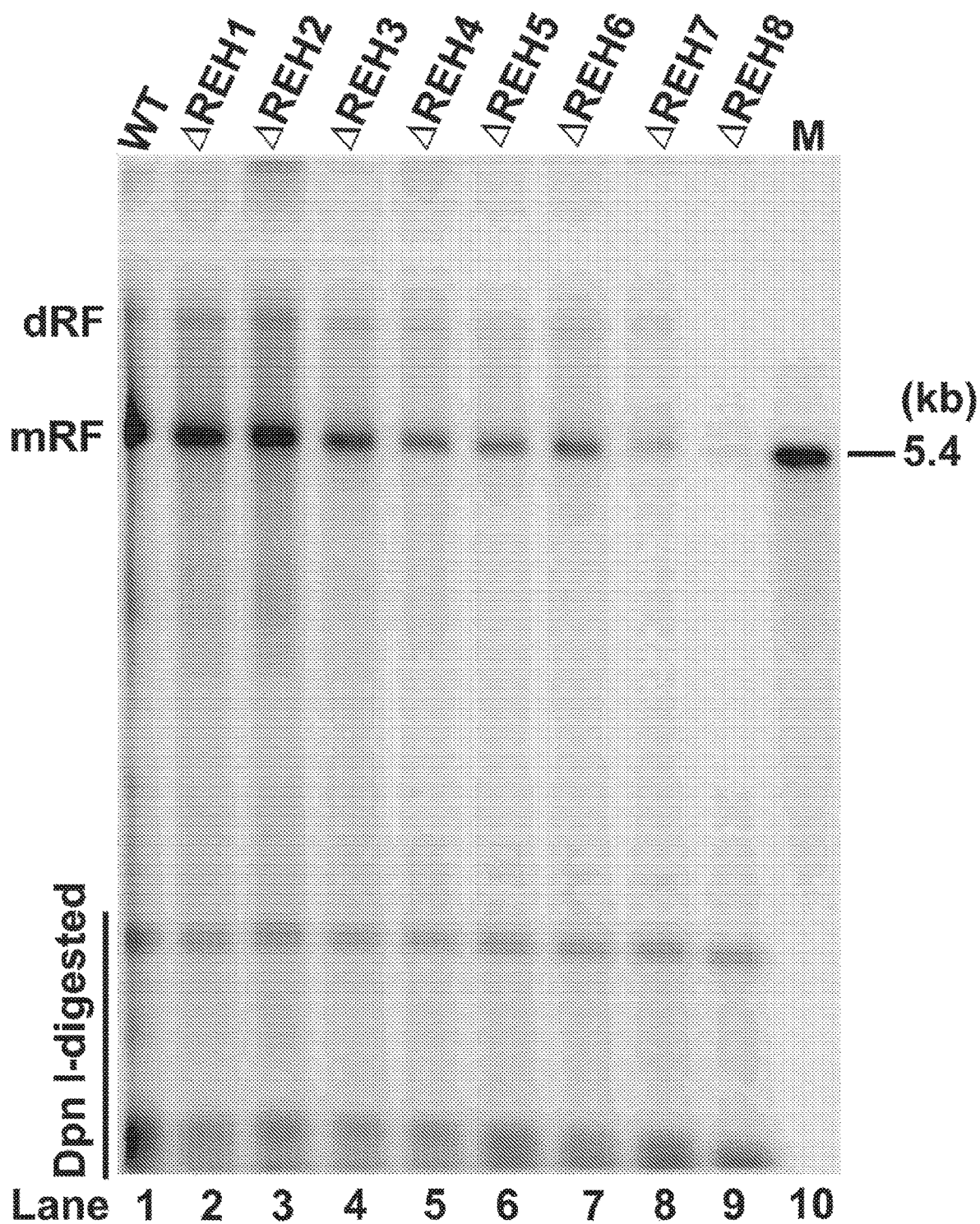
Figure 2C:
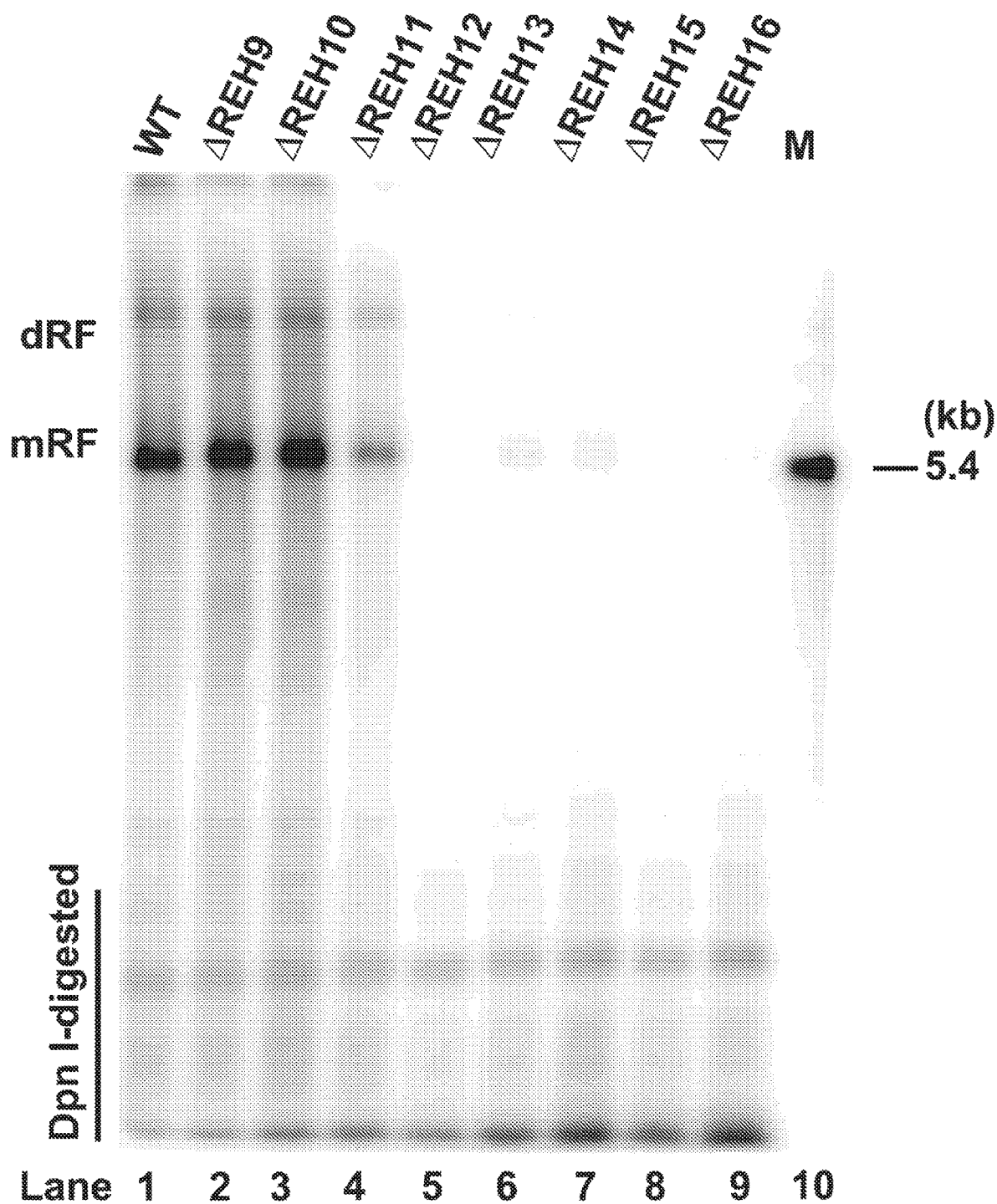

For DNA replication of either dependoparvovirus or autonomous parvovirus, RBEs or NSBEs and a TRS are requisite at the end palindromic hairpinned sequence (Ryan et al., 1996; Cotmore et al, 2000; Cotmore et al., 1994;

Cotmore et al., 2005). These two cis-signals are necessary for Rep78/68 or NS1 to recognize the replication origin and perform strand-specific nicking, and to initiate DNA replication. To identify the minimal replication-requisite sequence on REH, a serial of truncation mutants of the REH on the base of pIHBoV1(LEH-VP1/3-) were constructed (FIG. 2A). Linearized HBoV1 DNA was used for in vivo DNA replication analysis, in order to avoid circular plasmid DNA replication as that seen from pIHBoV1(LEH-) (FIG. 1B, lane 2). The first group of truncations contained a progressive deletion from the 3' end of the REH (FIG. 2A, Group I). The results showed that the level of viral DNA replication progressively decreased as 3' end nucleotides of the REH were removed (FIG. 2B). As there was a clear decrease of viral DNA replication resulting from ΔREH2 to ΔREH3 HBoV1 DNA (FIG. 2B, lanes 3 vs 4), the right end was fixed at nt 5,430 of the ΔREH2 HBoV1 DNA, and progressive truncations from the 5' end (nt 5,344) were prepared (FIG. 2A, Group II). Results of viral DNA replication analysis showed a large decrease in RF DNA from ΔREH10 to ΔREH11 (FIG. 2C, lanes 3 vs 4). Thus, the 5' end of the OriR was determined to be at nt 5,357, the 5' end of ΔREH10.

Figure 2D:
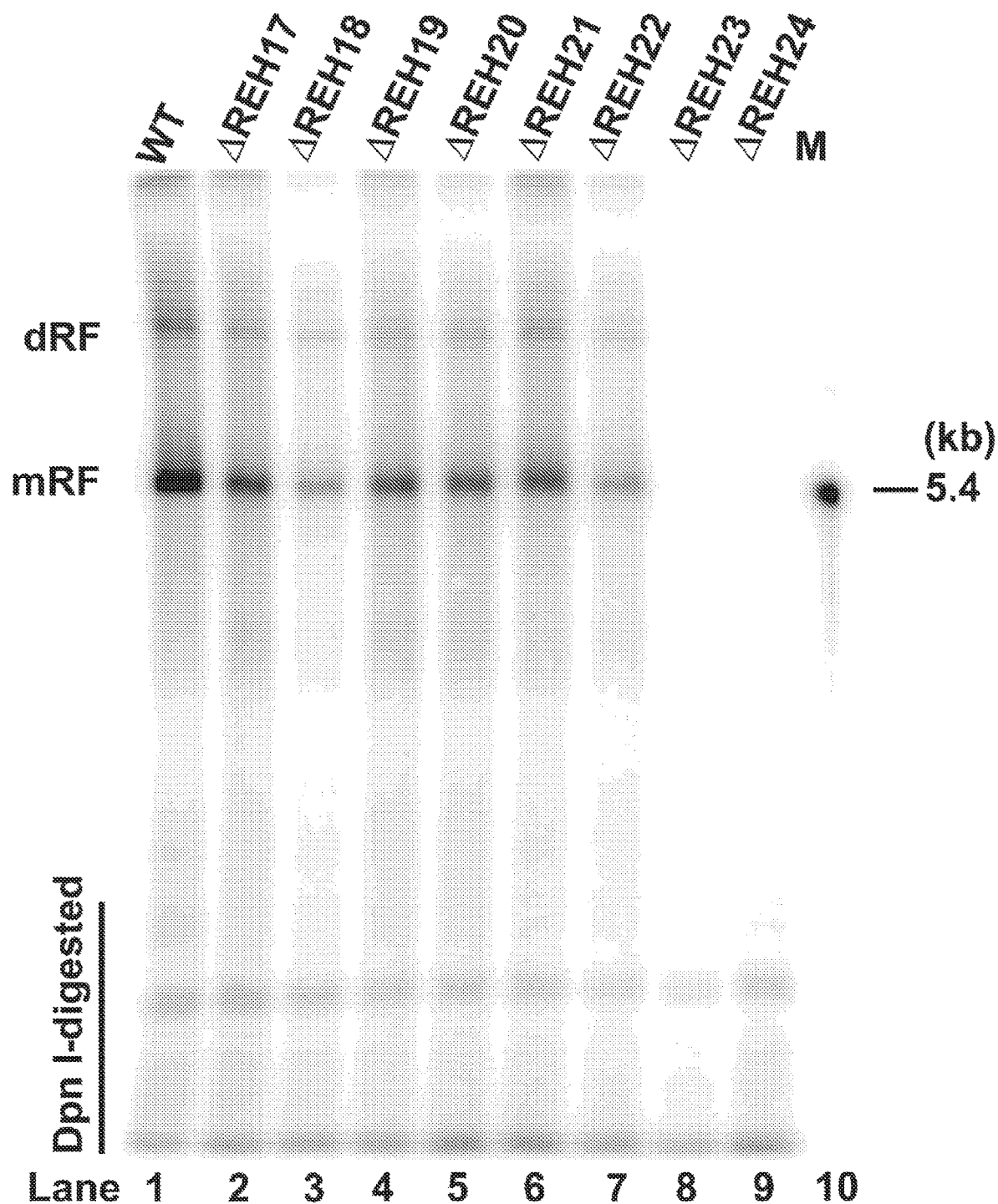
Figures 2E, 2F:
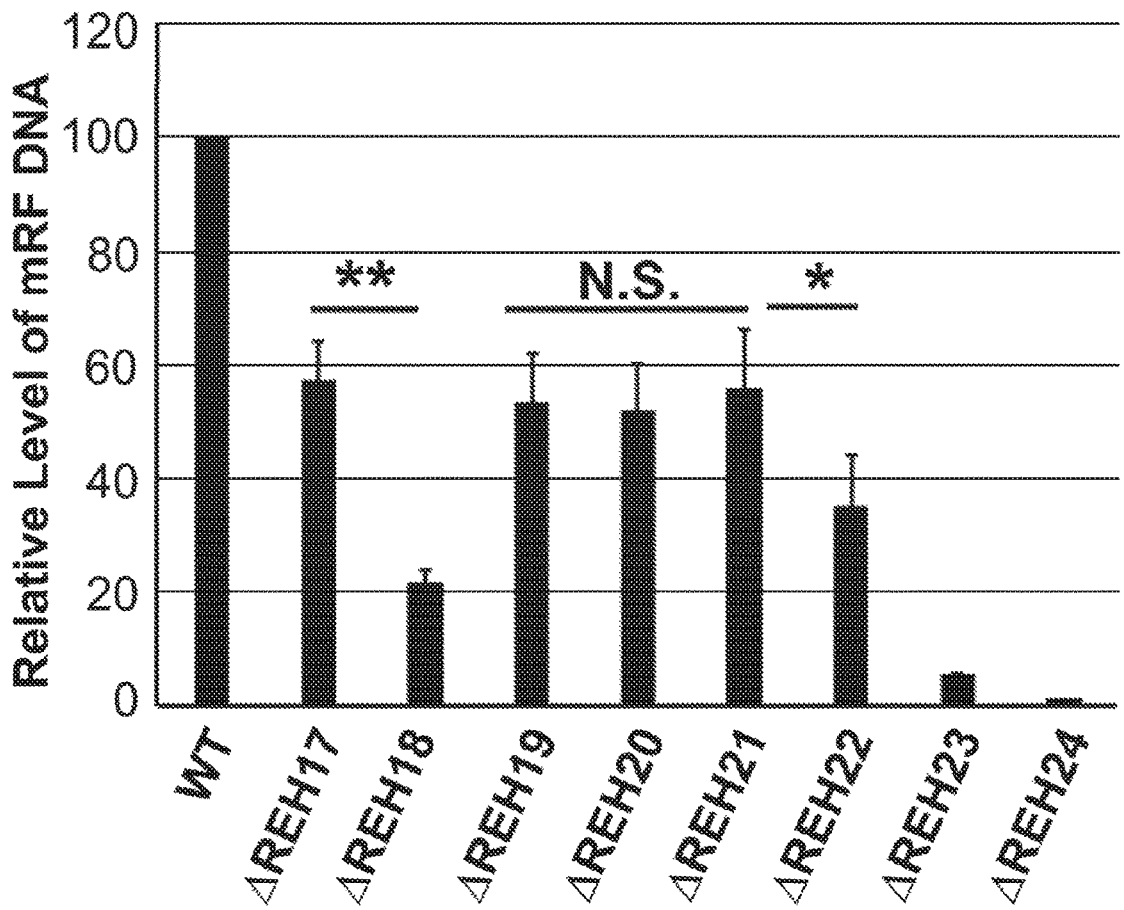

To define the 3' end of the OriR more carefully, progressive deletions from the 3' end of ΔREH10 (nt 5,357) were determined. DNA replication analysis of the mutants from ΔREH17 and ΔREH19-24 showed that further deletions of the 3' end after nt 5,402 (FIG. 2D, ΔREH21/lane 6) significantly decreased the level of RF DNA (FIG. 2E). This result defined the 3' end of the OriR at nt 5,402. In addition, ΔREH18 was created, in which three nucleotides were deleted at the 5' end in ΔREH17, to confirm the 5' end of the OriR. The result showed that replication from ΔREH17 was significantly decreased by about 3-fold (FIG. 2D, lane 3).

Figure 3A:
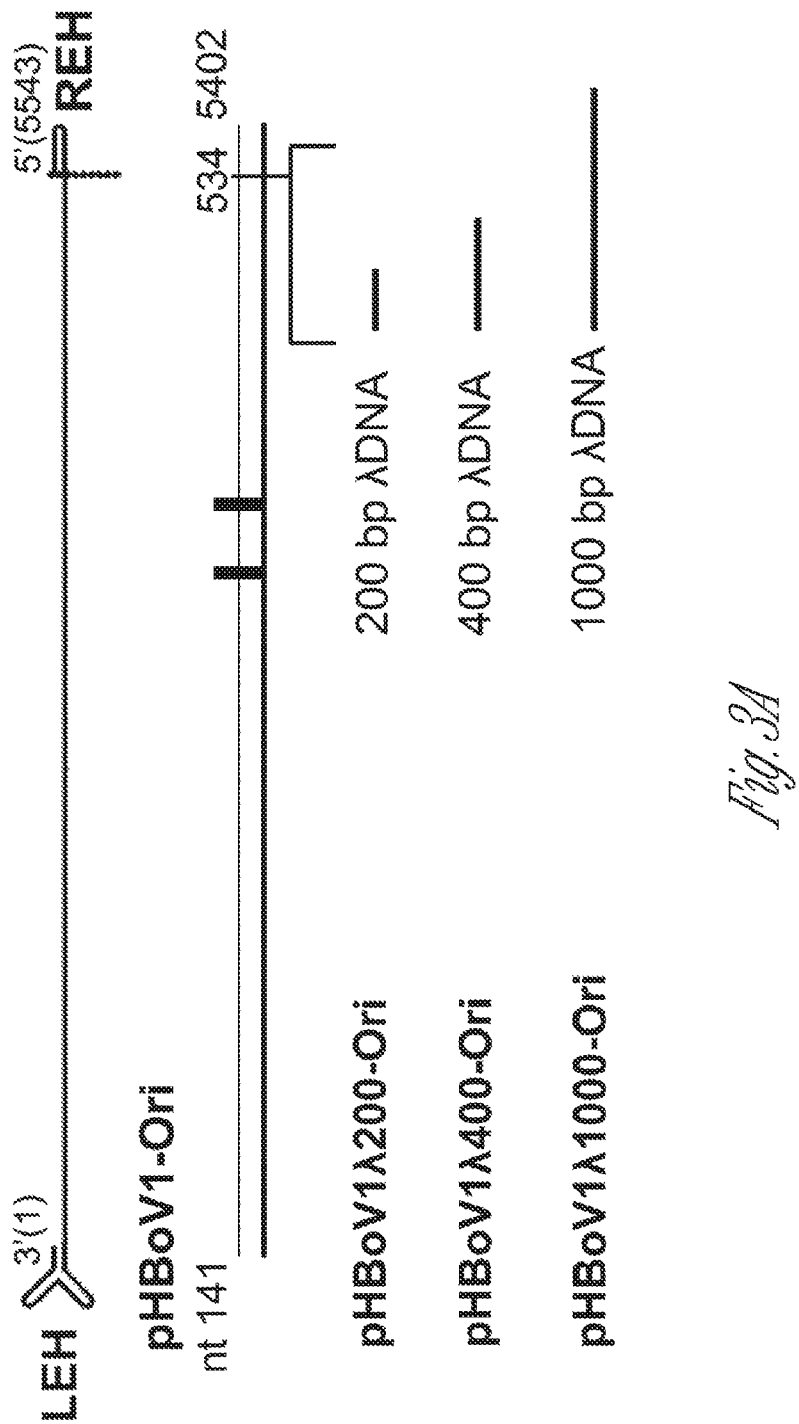
Figure 3B:
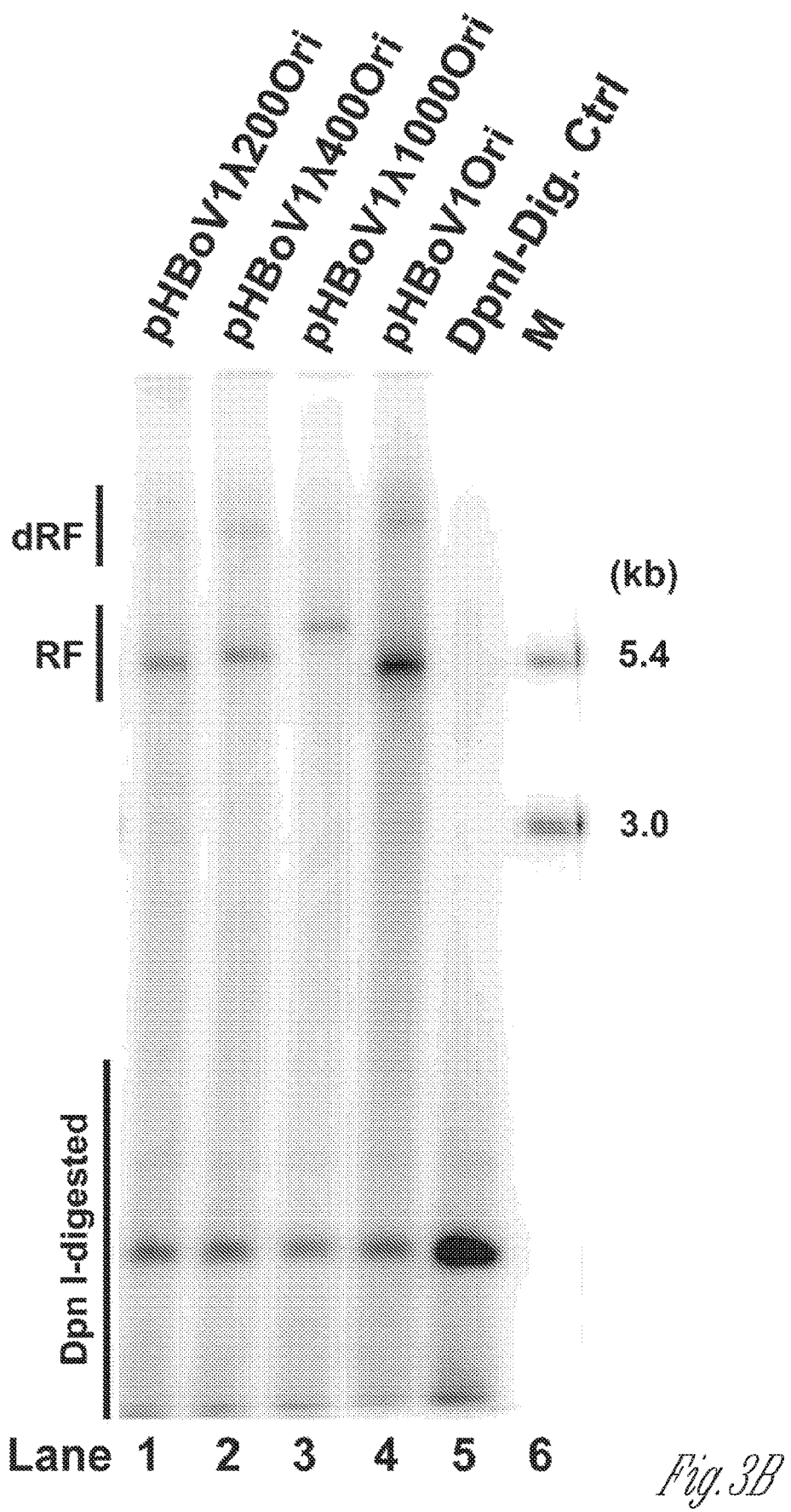

Collectively, HBoV1 OriR is defined as a 46-nt DNA of nt 5,357-5,402 (FIG. 2F). Of note, HBoV1 has a long 3' UTR signal in front of the OriR. To clarify whether the OriR replicates viral DNA independent of the 3' UTR, various λ DNA of 0.2, 0.4, and 1.0 kb were inserted between the 3' UTR and the OriR in HBoV1-Ori DNA (FIG. 3A). DNA replication analysis showed that the OriR conferred viral DNA replication regardless of the insertion sizes between the 3' UTR and OriR, supporting that the OriR functions as a template of terminal resolution independently of the adjacent 3' UTR (FIG. 3B).

Figure 4:
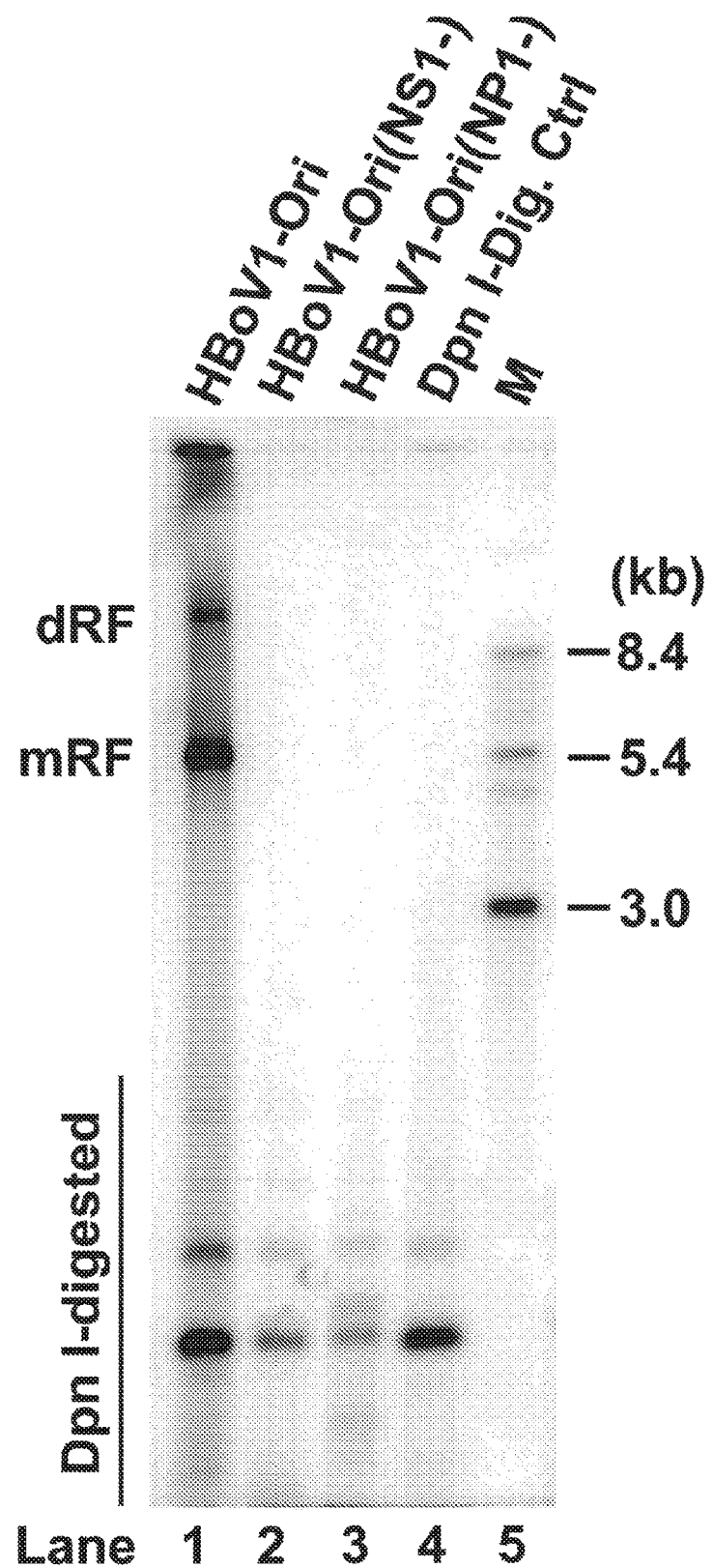

NP1 Colocalized with NS Proteins Within the APAR Bodies (Parvoviral DNA Replication Centers), and is Required for Terminal Resolution of HBoV1 DNA The trans-acting factors that facilitate terminal resolution at OriR were checked. NS1 or NP1 knockout plasmids based on pHBoV1-Ori were constructed, and viral DNA replication analysis performed. Without NS1/2 or NP1 expression, replication at the OriR was abolished (FIG. 4, lanes 2&3), reflecting that NS1 and NP1 are required for HBoV1 DNA terminal resolution, since NS2 is not required for HBoV1 DNA replication in HEK293 cells (Shen et al., 2015).

Figure 5A:
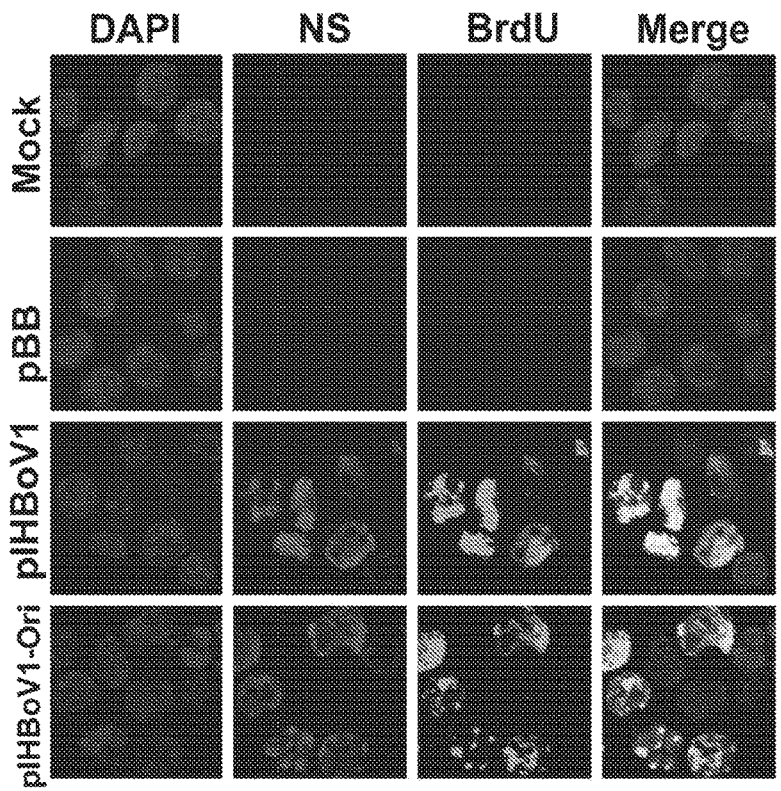
Figure 5B:
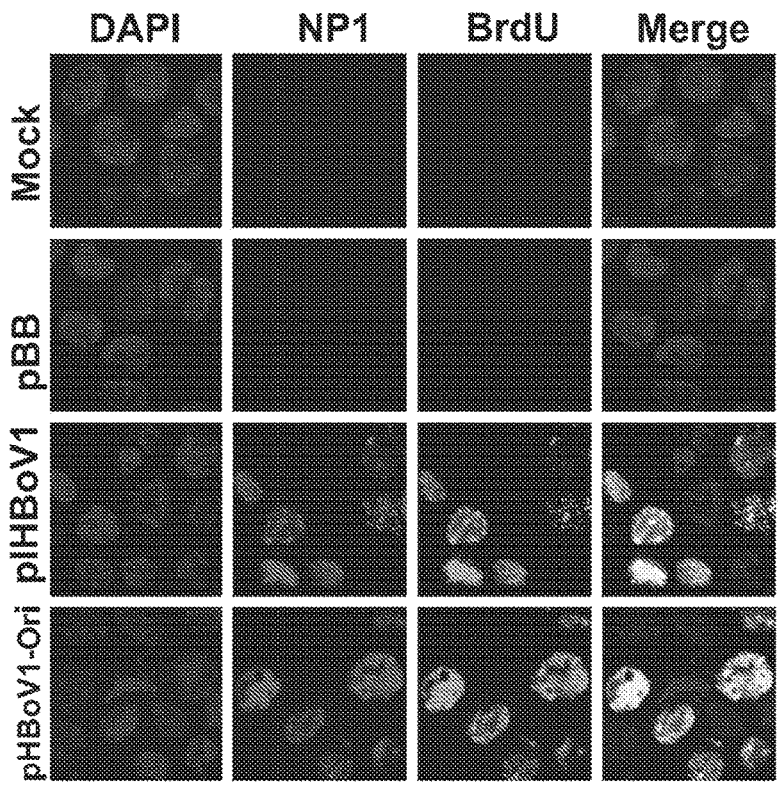
Figure 5D:
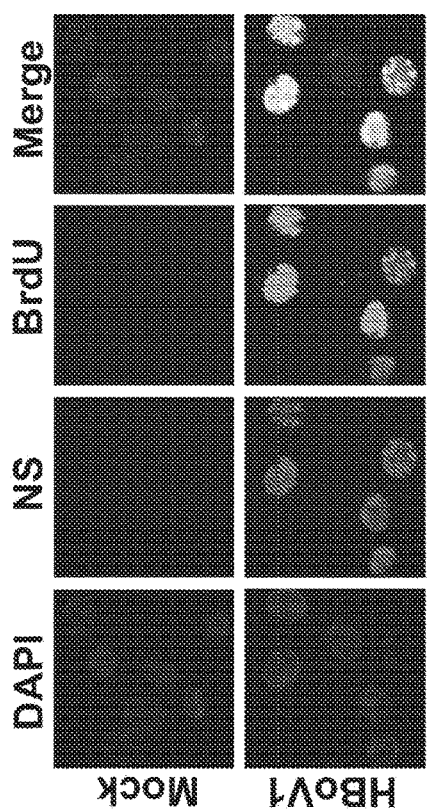
Figure 5E:
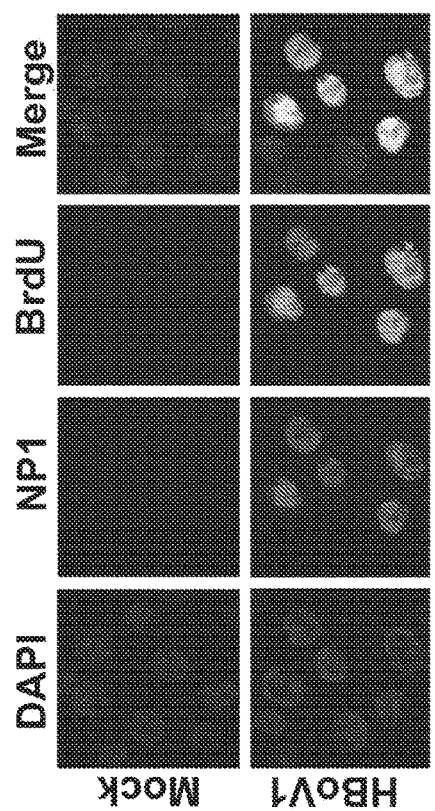
Figure 5C:
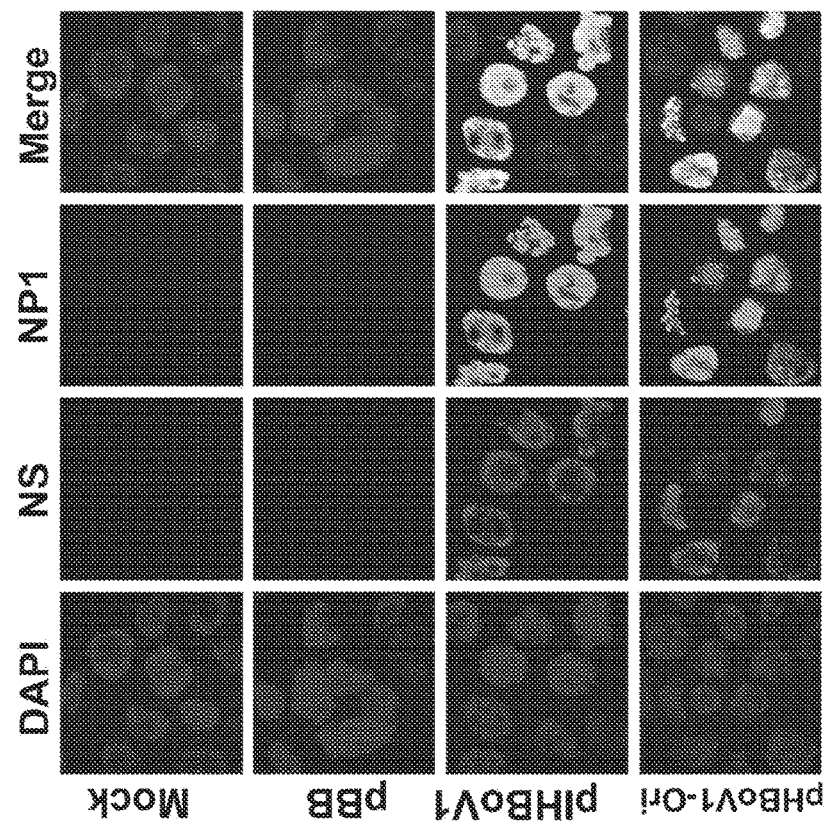
Figure 5F:
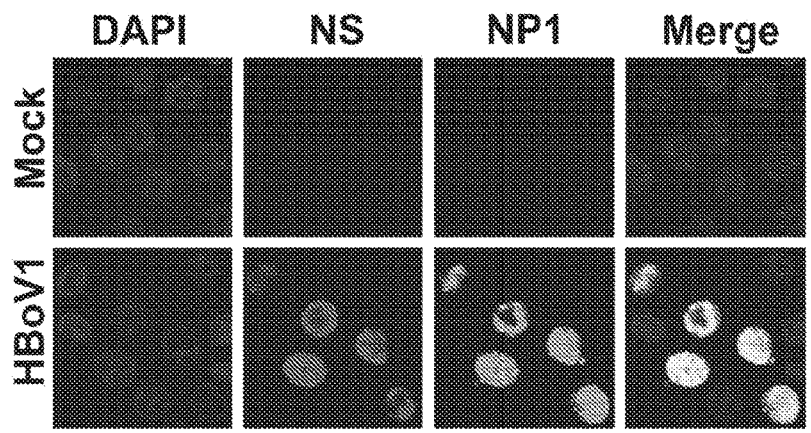
Figure 5G:
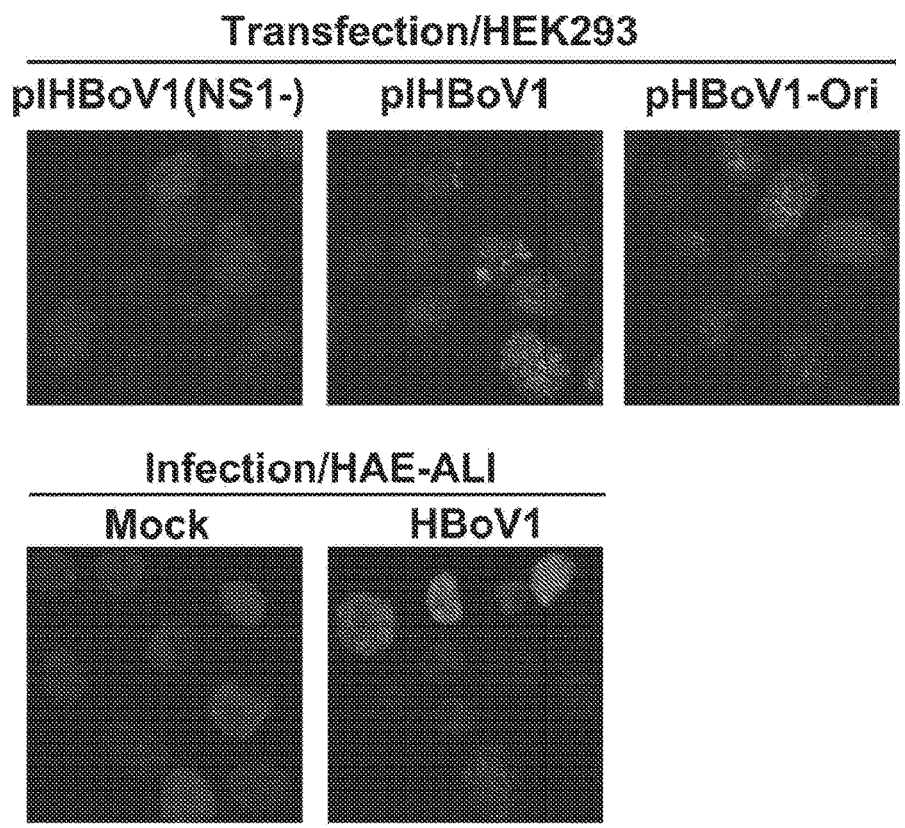

Replication of parvovirus MVM and H-1 takes place in discrete subnuclear compartments, where termed autonomous parvovirus-associated replication (APAR) bodies (Bashir et al., 2001; Cziepluch et al., 2000). APAR bodies are active sites of viral DNA replication and contain cellular DNA replication factors and parvovirus NS1 (Bashir et al., 2001). The APAR bodies were located using BrdU to pulse chase active replicating viral ssDNA (Luo et al., 2013; Luo et al., 2011). Similar to other parvoviruses (Bashir et al., 2001; Cziepluch et al., 2000), the APAR bodies of HBoV1 replication showed various patterns in different cells, from foci-like dots to broad distribution in the nucleus, and colocalized with NS proteins stained with anti-NS1C in HEK 293 cells transfected with HBoV1-Ori or pIHBoV1 (FIG. 5A, NS/BrdU). Notably, co-localization patterns of NP1 and BrdU staining were similarly observed for NS and BrdU co-staining, suggesting that both NP1 and NS localized within APAR bodies (FIG. 5B, NP1/BrdU). In support of this hypothesis, NS and NP1 proteins colocalized in the nucleus of HBoV1-Ori or pIHBoV1-transfected cells (FIG. 5C, NP1/NS). More importantly, in HBoV1-infected HAE cells, NS and NP1 co-localized well within the BrdU-chased APAR bodies (FIG. 5D-F). To confirm the localization of NP1, a proximity ligation assay (PLA) was used to visualize interactions of NP1 with BrdU-labeled viral ssDNA or dsDNA/ssDNA intermediates. Clearly positive fluorescent foci were observed in the nucleus of pHBoV1-Ori, pIHBoV1-transfected, or HBoV1-infected cells stained with anti-NP1 and anti-BrdU antibodies (FIG. 5G). PLA shows bright signals if the two molecules localize proximately at a distance of about 20 nm (Soderberg et al., 2006).

To explore a direct interaction between NS1 and NP1, immunoprecipitation assays were performed. Cells transfected with pHBoV1-Ori were lysed and pre-cleared with normal rat sera. Pre-clear lysates were immunoprecipitated with control rat IgG or anti-NP1 serum in the presence of nuclease treatment, and were then evaluated for NS1 by Western blotting. Neither NS1, NS2, NS3 nor NS4 were co-immunoprecipitated with NP1 (FIG. 6A, lanes 6 vs 4). As a control, using an anti-NS1C antibody, all NS proteins could be immunoprecipitated (FIG. 6B, lanes 3 vs 1). These results suggest that NS1-4 and NP1 proteins do not directly interact.

Taken together, these results suggest that either by transfection of pIHBoV1/pIHBoV1-Ori or during viral infection, HBoV1 NS1-4 and NP1 proteins function synergistically in the viral DNA replication centers (APAR bodies) but without a direct interaction. More importantly, these results confirm a direct involvement of the HBoV1 NP1 during viral terminal resolution at OriR.

Identification of the NS1 Binding Elements (NSBEs) and TRS within OriR

The replication origins of parvoviruses harbor multiple binding elements of Rep78/68 or NS1 and a site-specific TRS (Ryan et al., 1996; Cotmore et al., 2000; Cotmore et al., 1994; Cotmore et al., 2005). Therefore, NSBE and TRS were identified by means of mutagenesis. The NSBEs characterized in AAV and MVM by both in vivo and in vitro studies are several tetra-nucleotides repeats, which are directly recognized by the origin binding domain (OBD) of the AAV Rep68/78 or MVM NS1. Notably, there are no cognate NSBE for HBoV1 NS1 binding that can be located in both REH and LEH (Huang et al., 2012). In contrast, similar to the 4 repeats of tri-nucleotides in *Galleria mellonella densovirus* (GmDNV), there are 4 repeats of "TGT" tri-nucleotides "5'-TGT TGT TGT TGT-3' (SEQ ID NO:7)" in the OriR (FIG. 7A) (Ding et al., 2002).

Figure 7B:
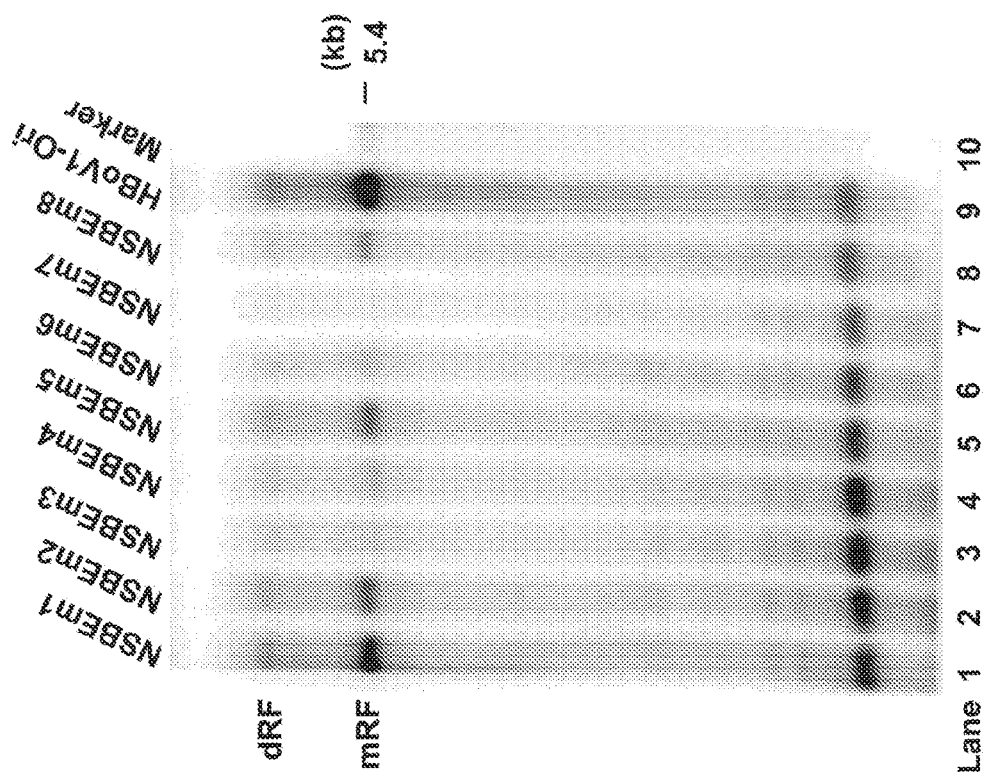

Serial mutations were made in the "TGT" repeated region in the OriR, and performed in vivo DNA replication analysis. The results showed that all these mutations of the "TGT" tri-nucleotides significantly decreased DNA replication to various levels under 40% of the activity of the wild-type (FIG. 7B&C), however, the mutation of multiple "TGT" progressively disable DNA replication to a greater extent. For example, mutating two "TGT" retained DNA replication better than mutating three "TGT" (FIG. 7B&C, lanes 1&2 vs lanes 4-7). Mutating all four "TGT" decreased DNA replication the most, at level of only 5% of the wild-type (FIGS.

7B and C, lane 3). Thus, these results suggest that this "TGT" repeating sequence is likely the HBoV1 NSBEs.

Figure 8A:
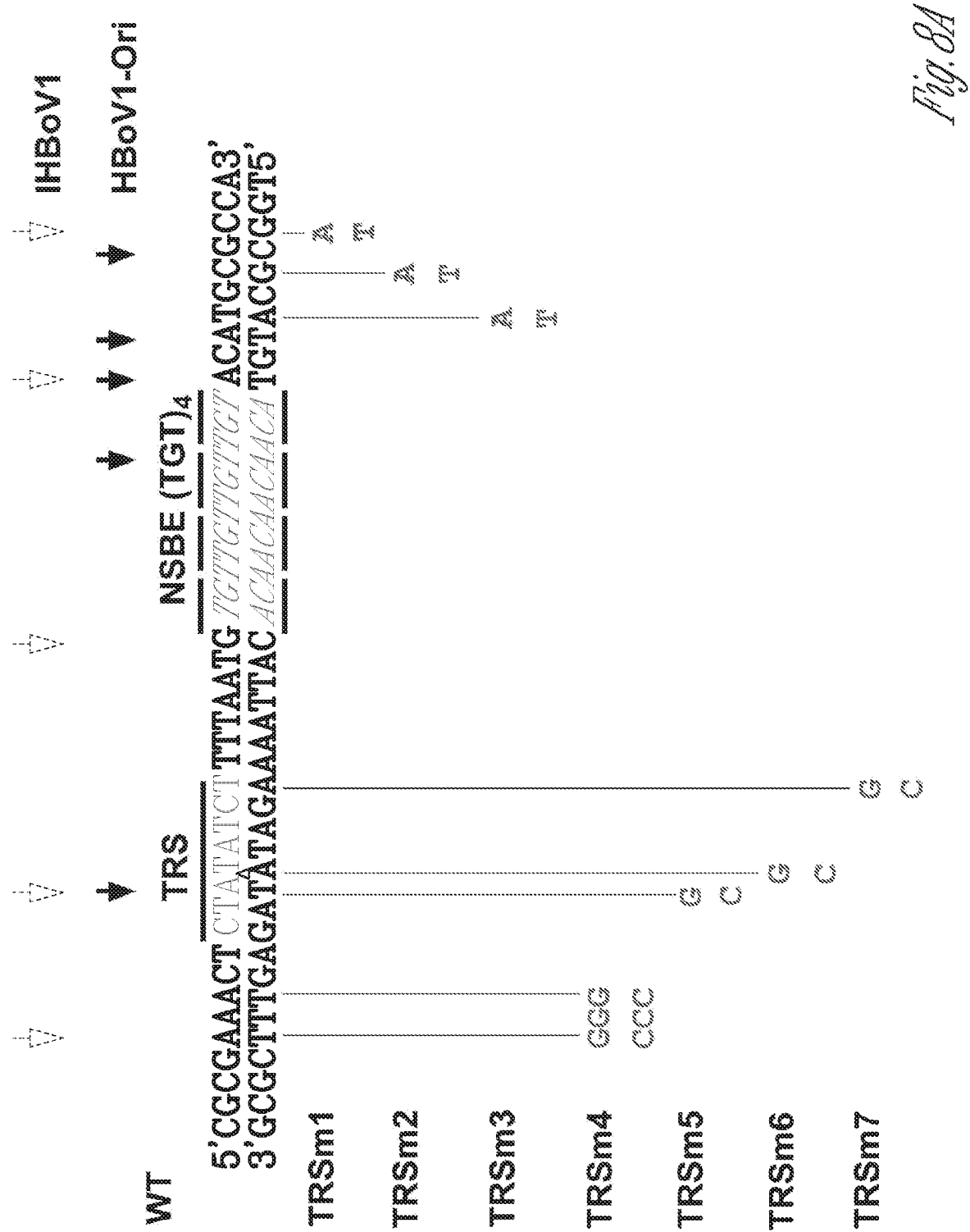
Figure 8B:
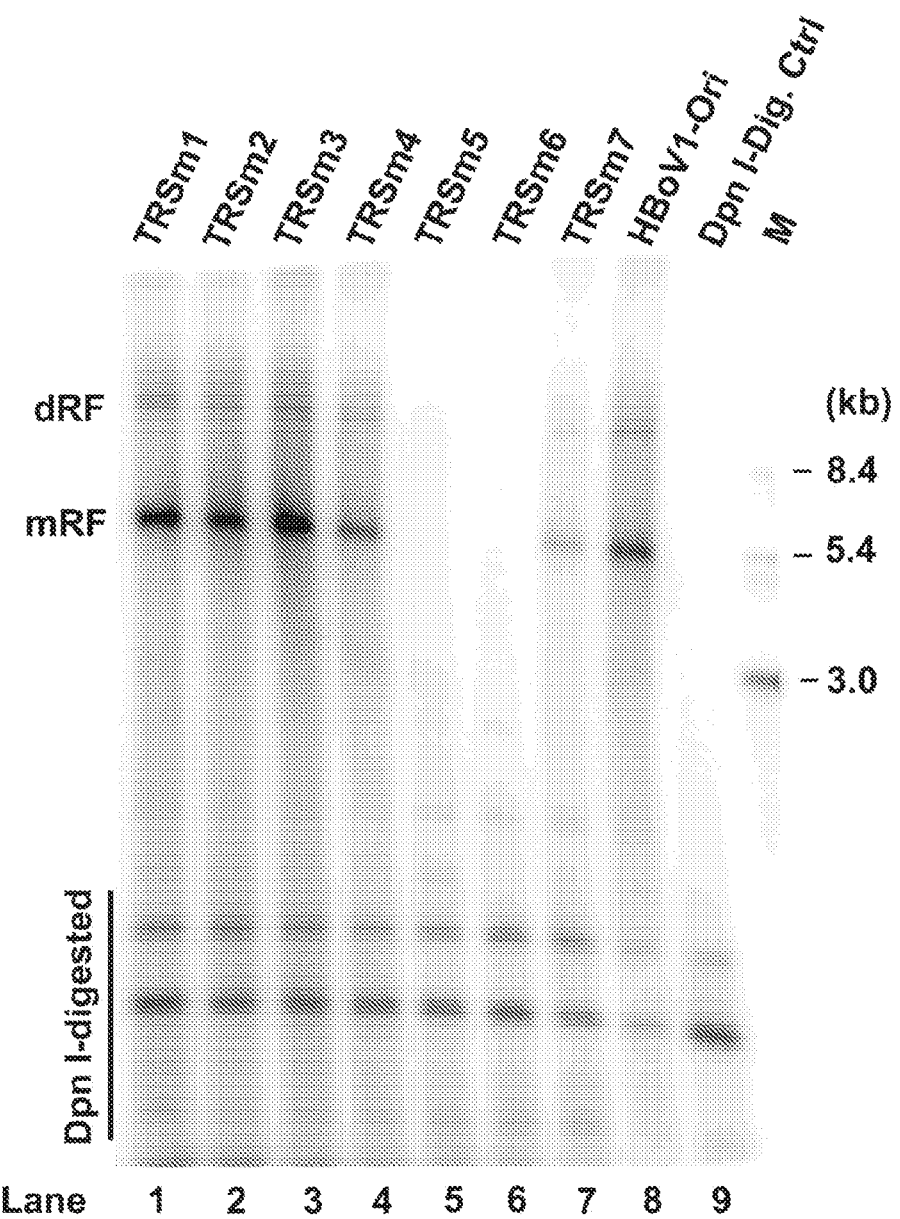

The nicking sites of parvoviruses are not conserved (Cotmore et al., 2015). In principle, after nicking, the Ori reveals transient nicked intermediate (ssDNA breaks) before the free 3'-hydroxyl (OH) extends by DNA polymerase (Cotmore et al., 2005). A strategy of rapid amplification of the nicked 3' end was used to characterize the intermediates of the resolved OriR after NS1 nicking. Using Hirt DNA extracted from pIHBoV1- or HBoV1-Ori-transfected cells, adenosines were added to extend the 3' end with polyA residues. With subsequent PCR amplification and cloning, we mapped a few transient ending sites in the OriR (FIG. 8A). To identify the nicking among these ending sites, each site located outside of the NSBEs was mutated (FIG. 8A). Analysis of in vivo DNA replication showed that mutations at either the T or A nucleotide at nt 5,368 or 5,369, but not the mutations in other locations, completely abolished viral DNA replication, (FIG. 8B, lanes 5&6 vs lanes 1-4). A mutation at nt 5,373 within the putative nicking motif (5'-CTA TAT CG-3' (SEQ ID NO:8) also reduced the level of RF DNA (FIG. 8A, TRSm7, and FIG. 8B, lane 7). This result defined the T at nt 5,368 as the nicking site (5'-CTA/TATCT-3' (SEQ ID NO:9)).

Identification of the Key OriR-binding Residues in the Origin-binding Domain (OBD) of the HBoV1 NS1

The structure of the HBoV1 OBD has been resolved, and it was predicted that NS1 utilizes two non-structured positively charged loop regions to bind Ori (Tewary et al., 2013). The binding residues of the NS1 were examined using a mutagenesis approach (FIG. 9A). To this end, mutations of either amino acids at the positively charged loops (loop K: $^{127}KR^{128}$ and loop R: $^{193}RR^{194}$) or predicted endonuclease activity motif of the NS1 ($^{115}HCH^{117}$), together with three control mutations (Mut Q, P, and E) were performed, in the context of HBoV1-Ori. Controls Mut Q and Mut P mutated putative loop K and loop L, respectively. Mut E control mutated the nearby amino acids ($^{123}EGL^{125}$) of putative loop K (FIG. 9B). Structures of the mutated NS1 OBD were predicted based on the wild-type NS1 OBD (Tewary et al., 2013). Superimposition forms of mutants with wild-type NS1 OBD showed that the mutagenesis did not significantly change the structure (FIG. 9B). In vivo DNA replication analysis showed that mutating either the basic charged loop region (Mut K and Mut R) or the endonuclease core (Mut Endo) abolished replication, whereas the three control mutations did not alter DNA replication very much (FIG. 9C). These data suggest that the two positively charged loops of the OBD, as well as the two histine residues at the predicted endonuclease motif, are required for HBoV1 DNA replication, and that the two positively charged loops likely play a significant role in the NS1 and OriR binding.

HBoV1 NS1 Did Not Specifically Bind OriR in Vitro

Figures 10A, 10B:
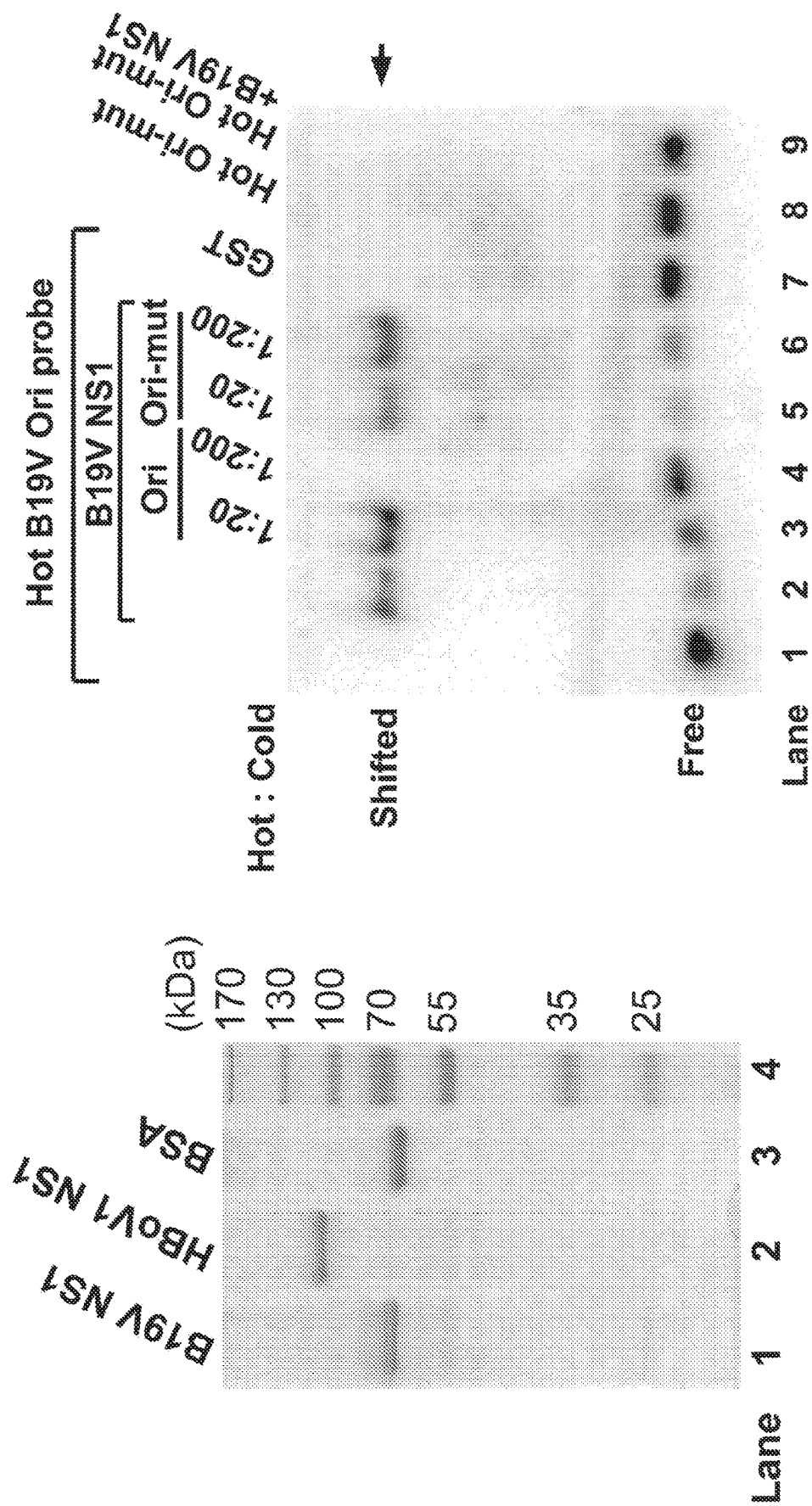
Figure 10C:
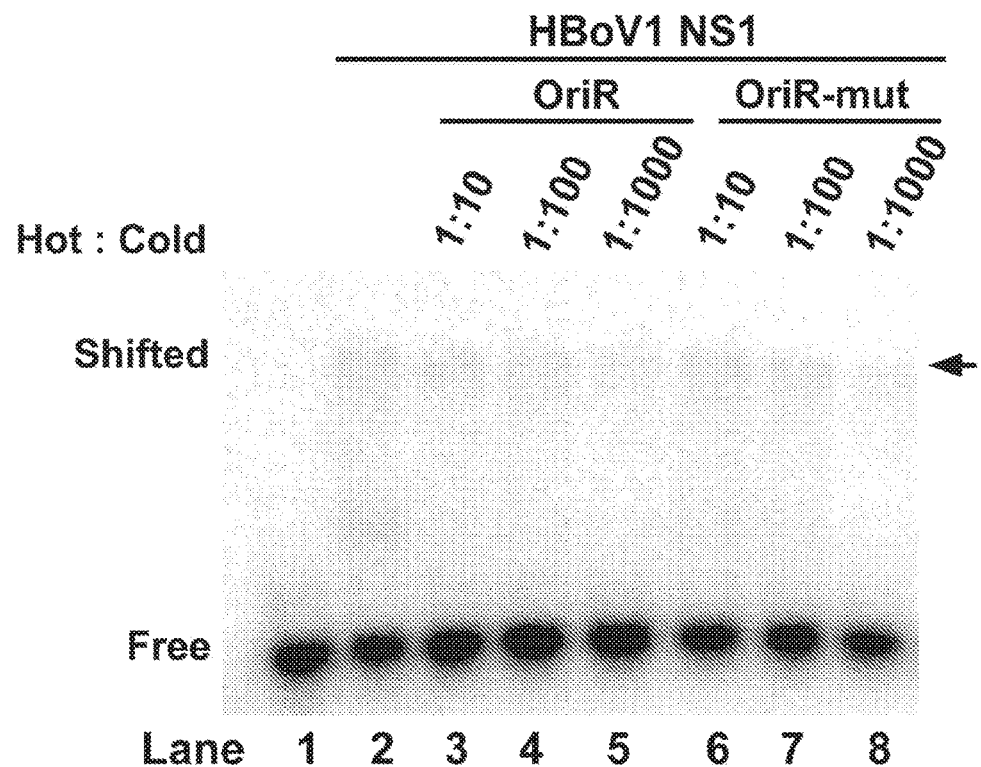
Figure 10D:
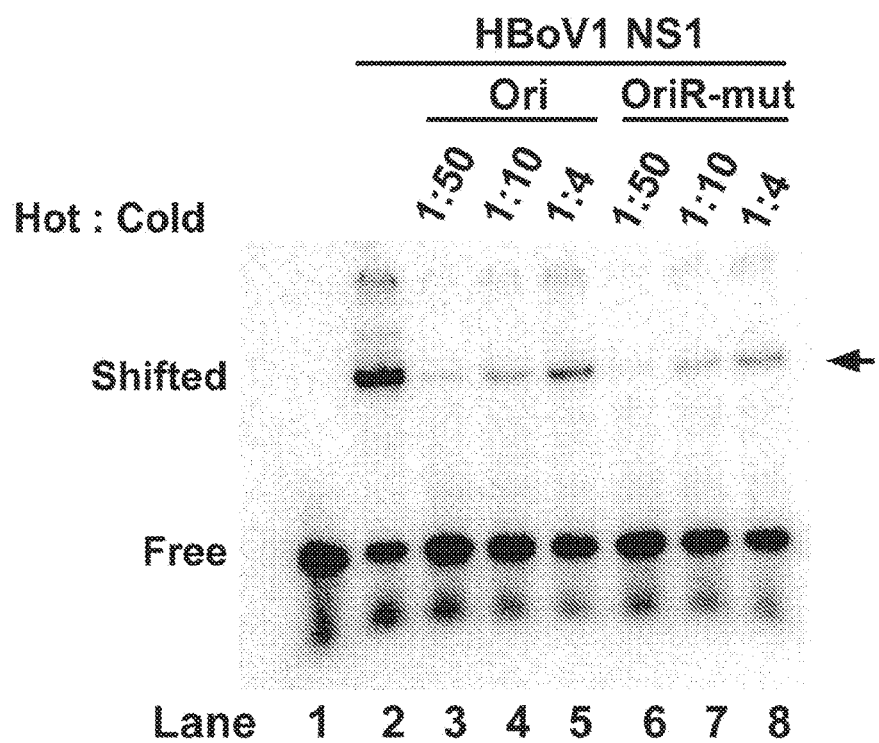

To understand the interaction between HBoV1 NS1 and OriR (FIG. 2F), HBoV1 NS1 (FIG. 10A, lane 2) was purified and studied its binding with the OriR studied in vitro. As a positive control for NS1 binding to OriR, B19V NS1 was purified (FIG. 10A, lane 1) and carried along in parallel. Electrophoresis gel shift assay showed that B19V NS1 shifted the B19V Ori (FIG. 10B, lane 2). This binding is specific because it was competed by excess cold B19V Ori but not by excessed cold mutated B19V Ori (Ori-mut) (FIG. 10B, lanes 4 vs 6). As a negative control, GST protein did not shift the B19V Ori (FIG. 10B, lane 7), and the B19V Ori-mut was not shifted by B19V NS1 (FIG. 10B, lanes 8 vs 9). In contrast, however, with the same experimental condition of the electrophoresis gel shift assay, HBoV1 NS1 did not bind its own OriR specifically (FIG. 10C, lane 2). Adding either cold OriR (FIG. 10C, lanes 3-5) or cold Ori-mut (FIG. 10C, lanes 6-8) showed similar negative signals. Of note, weak non-specific interaction were found between HBoV1 NS1 and non-specific DNA in the binding buffer without poly[d (I: C)] (FIG. 10D, lane 2). This non-specific binding was competed either by excessed cold HBoV1 OriR (FIG. 10D, lanes 3-5) or cold HBoV1 OriR-mut (FIG. 10D, lanes 6-8). Thus, the gel shift assays suggest that HBoV1 NS1 alone does not bind HBoV1 OriR specifically in vitro.

Figure 11B:
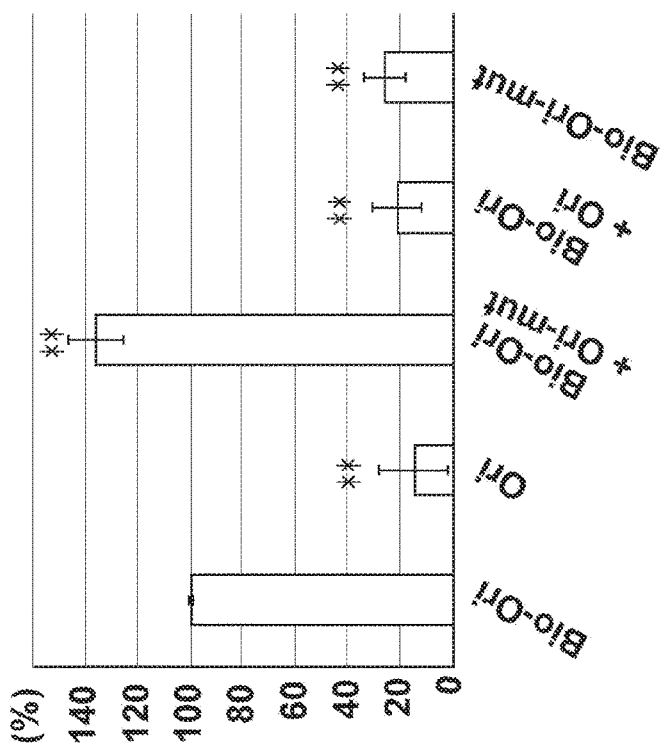
Figure 11A:
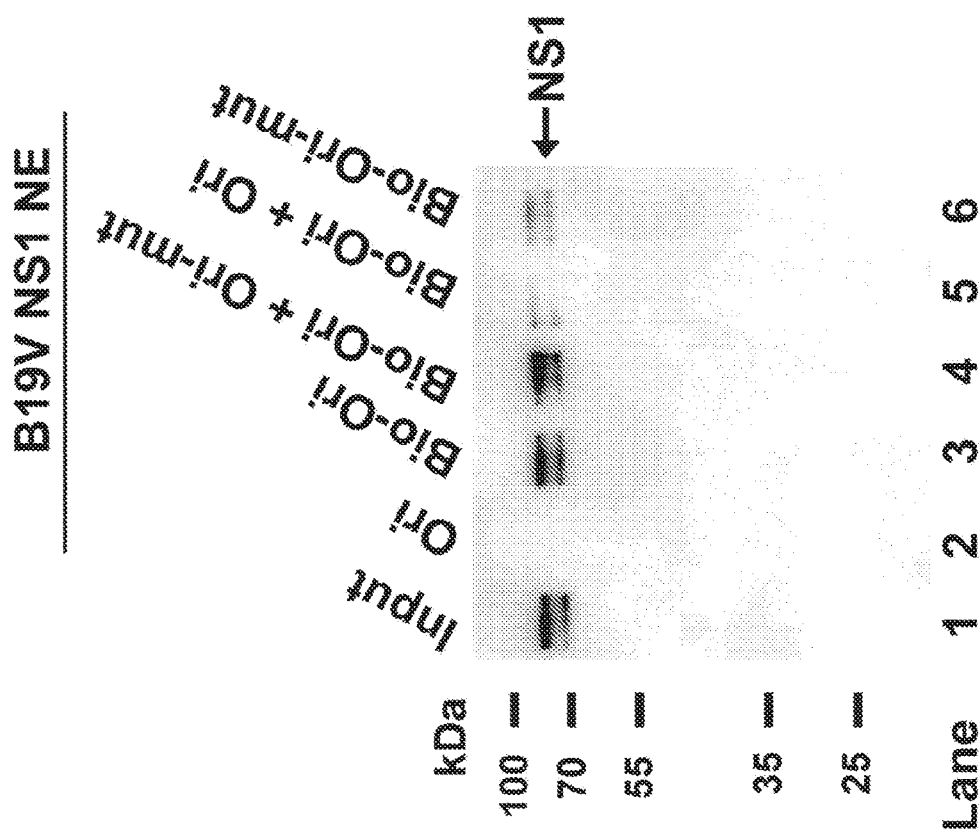
Figures 11C, 11D:
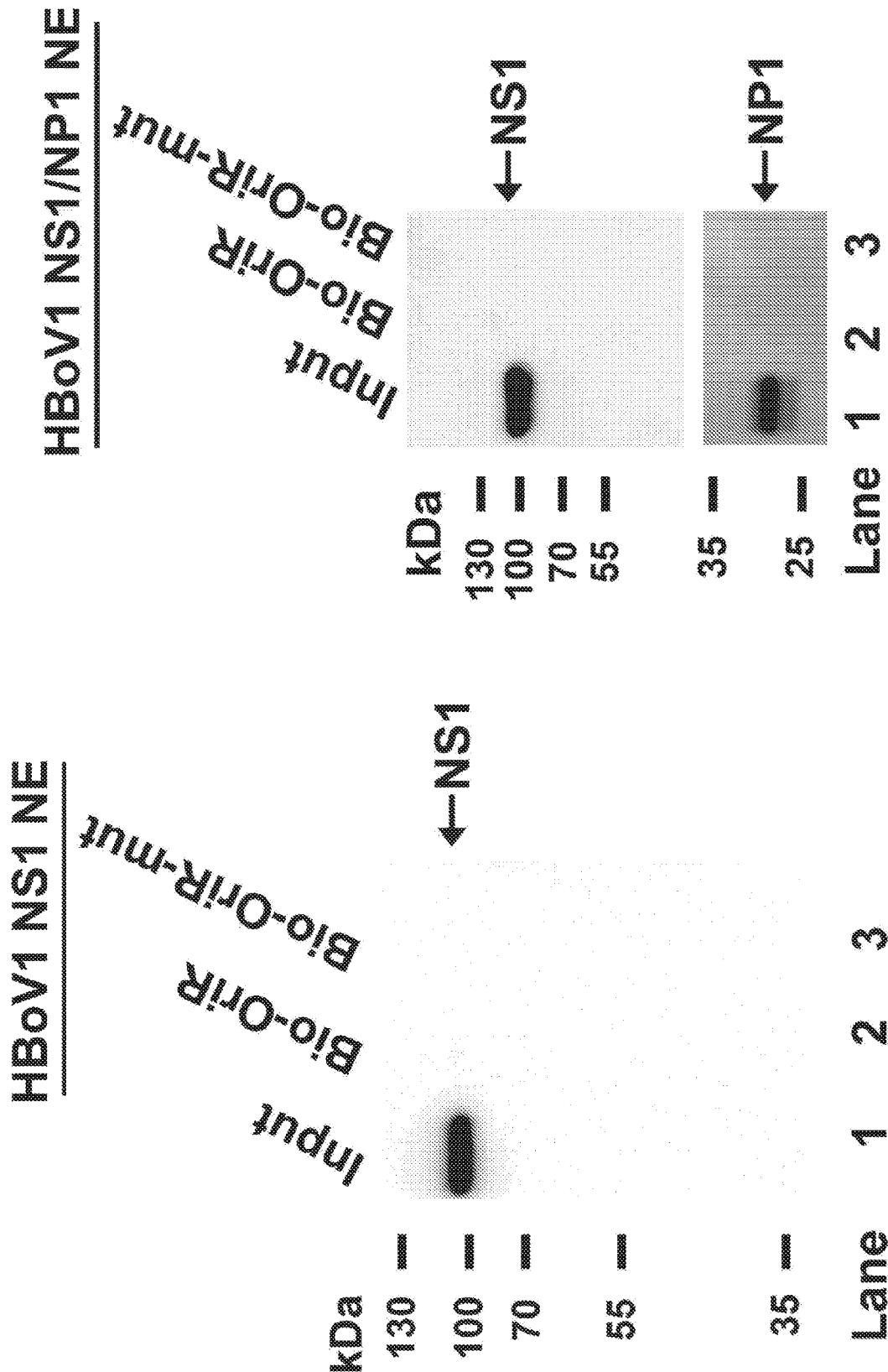

To further examine the binding property between HBoV1 NS1 and OriR in the presence of cellular proteins, a biotin pull-down assay was designed. Nuclear extract prepared from NS1-transfected HEK 293 cells was used for pull-down by biotin-labeled OriR (Bio-OriR) and streptavidin-conjugated beads, and then analyzed by Western blotting. In the experiment with B19V Ori, biotinylated B19V Ori (Bio-Ori) pulled down B19V NS1, which was competed by excess B19V Bio-Ori but not by excess biotinylated mutant Ori (Bio-Ori-mut) (FIG. 11A, lanes 4 vs 5, and FIG. 11B). As a control, non-biotin-labeled B19V Ori did not pull down any B19V NS1 (FIG. 11A, lane 2, and FIG. 11B), and Bio-Ori-mut only pulled down a few minor amount of NS1 (FIG. 11A, lane 6, and FIG. 11B). By contrast, HBoV1 NS1 was not pulled down by either biotinylated Ori or Ori-mut (FIG. 11C, lanes 2&3), despite high-level expression of NS1 (FIG. 11C, lane 1). As NP1 co-localized with BrdU labeled viral replication centers (FIG. 5), the hypothesis was tested that NP1 is important for NS1 binding with OriR. Nuclear extracts were prepared from cells co-expressing NP1 and NS1, and performed pull-down assays. The results demonstrated that biotinylated HBoV1 OriR did not pull down NS1, even in the presence of NP1 (FIG. 11D, lane 2). Collectively, the pull-down assays suggest that HBoV1 NS1 does not bind HBoV1 OriR in vitro in the presence of cellular factors and NP1.

Discussion

In this report, the viral components that are important for cis and trans HBoV1 terminal resolution at REH were studied. A 46-nt sequence at nt 5,357-5,402 was defined as the HBoV1 OriR. It contains both the NSBEs and TRS, and is used as a template for terminal resolution of HBoV1 DNA. Notably, a cis sequence in the 3' UTR was important for terminal resolution, while the large NS protein NS1 and the small NP1 played a pivotal role in trans for terminal resolution. These basic findings of HBoV1 terminal resolution at the OriR lay a foundation for further understanding the mechanism underlying NS1 binding to and nicking at the OriR, which are the key steps in HBoV1 RF DNA replication. Additionally, in this study, the specific binding of the B19V NS1 with B19V Ori was shown in vitro.

Functions of Viral Proteins in HBoV1 Terminal Resolution at OriR

NS1 function: The large non-structural protein of parvovirus, Rep78/68 or NS1, is composed of a putative DNA origin binding/endonuclease domain (OBD), helicase activity domain, and transactivation domain (TAD) at N-terminus, middle, C-terminus, respectively (Shen et al., 2015). The crystal structure of the HBoV1 OBD was resolved at 2.7-Å resolution, which is similar to the canonical histidine-hydrophobic-histidine superfamily of nucleases. The OBD structure combines two distinct functions: (i) a positively charged region formed by surface β-hairpin (aa190-198) and helix α5 (aa127-132), which is responsible for recognizing the viral DNA replication origin, and (ii) the endonuclease active site which contains signature motif HUH and per-forms strand-specific cleavage at Ori (Tewary et al., 2013). The HUH motif of HBoV1 OBD contains two histidine residues (H115/H117) separated by cysteine C116, followed by the three hydrophobic residues I118, L119, and V120 (Tewary et al., 2013). However, these active sites are only predicted from superposition of the HBoV1 OBD structure into the AAV5 OBD structure (Hickman et al., 2004). Here, it was confirmed that R193 and R194 in the surface hairpin of the OBD and K127 and R128 in the loop region are critical to terminal resolution, and, by contrast, the neighboring 123EGL125 residues are not. Mutation of the two histidine residues (H115 and H117) confirmed their nicking function. Structure study of the MVM NS1 OBD also revealed conserved residues of DNA binding and nicking activities (Tewary et al., 2015), highlighting the importance of the confirmed DNA binding and nicking residues of the HBoV1 NS1 OBD.

NP1 function: Previously it was shown that bocaparvovirus NP1 plays an important role in the replication of viral duplex DNA (Sun et al., 2009; Huang et al., 2012). HBoV1 NP1 or BPV1 NP1 can complement replication of a mutant MVC infectious clone that does not express MVC NP1 (Sun et al., 2009). Three other newly identified HBoV1 small NS proteins NS2-4 are not required for replication of HBoV1 duplex DNA genome in HEK293 cells (Sun et al., 2009). Since NS2-4 all contain the NS1C terminus, the anti-NS1C antibody reacts with all these isoforms (Sun et al., 2009). Thus, it was demonstrated that all NS1-4 proteins and NP1 colocalize within APAR bodies. Nevertheless, it is unlikely that NS2-4 recruit NP1 to the APAR bodies. Direct interactions between NS1-4 and NP1 were not confirmed (FIG. 6). NP1 contains a non-classical nuclear localization signal (ncNLS) at aa7-50 (Li et al., 2013), and is able to complement the functions of the MVM NS2 in viral DNA replication during an early phase of infection (Mihaylov et al., 2014). In fact, during MVM infection of NP1-expressing A9 cells, NP1 was progressively lost from its nucleolus-localization and began to be colocalized with MVM NS1 in APAR bodies. Moreover, NP1 expression rescues APAR body maturation in cells infected with an NS2null mutant of MVMp (Mihaylov et al., 2014). Additionally, NP1 is involved in viral pre-mRNA processing. HBoV1 NP1 is required for viral mRNA splicing at the A3 splice site and read-through of the viral mRNA through the (pA)p site. Taken together, it was hypothesize that during infection or viral DNA replication, NP1 is critical in the development of viral DNA replication centers (APAR bodies) together with NS1, in which cellular DNA replication factors are enriched; however, after the formation of the APAR bodies, NP1 could be relocated to the cellular compartment for viral RNA processing. On the other hand, NP1 could possibly be recruited by cellular DNA replication factors to the APAR bodies, in response to the efforts of NS1 in interacting with the viral Ori and cellular DNA replication factors (Cotmore et al., 1995; Nash et al., 2009; Ihalainen et al., 2007).

Identification of the HBoV1 OriR

For a homotelomeric parvovirus whose replication depends on a helper virus, a 43-nt DNA sequence, was identified as the AAV Ori, containing the Rep binding element (RBE) and TRS (Ryan et al., 1996). For homotelomeric parvoviruses that replicate autonomously, a specific 38-nt DNA sequence has been identified as the Ori of goose parvovirus (GPV) (Smith et al., 1996), and a 67-nt DNA was identified as B19V Ori that contains a TRS and four GC-rich NSBEs that are required for optimal virus replication (Guan et al., 2009). The B19V ITR resembles that of GPV in that both have an arrow-like hairpin structure (Cotmore et al., 2005; Zadori et al., 1995). For heterotelomeric parvoviruses that replicate autonomously, there are two replication origins located at the LEH and REH, respectively. The active form of MVM LEH Ori (OriL$_{TC}$) is about 50-nt in length, composed of a transcription factor PIF binding site, the (ACCA)$_2$ NSBE, and the TRS site (Cotmore et al., 2005; Cotmore et al., 1994). It functions as a template for junction resolution that generates ssDNA genome. By contrast, the MVM REH Ori (OriR) is around 125-nt in length, and contains a region composed a TRS and two closely contacted (ACCA)$_2$ NSBEs, a degenerate NSBE (CGGT) at the tip of the hairpin, and a cis sequence that is non-specifically bound by HMG1/2 family DNA binding proteins (Cotmore et al., 2000), Therefore, the MVM OriR includes almost the entire sequence of the REH (Cotmore et al., 2000; Cotmore et al., 2005).

In this study, a 46-nt sequence (OriR) at the REH of the HBoV1 genome was identified that is responsible for the replication of duplex HBoV1 genome in HEK293 cells. This OriR represents the first Ori in members of heterotelomeric parvoviruses that functions as a template of terminal resolution in a short closely contacted DNA sequence (46-nt), containing the NSBEs and TRS. That cis-acting sequences surrounding the TRS and NSBEs may be required for interacting with cellular factors, e.g., HMG1/2 with MVM OriR (Cotmore et al., 2000) and PIF with MVM OriL (Christensen et al., 1997).

Characterization of the TRS and NSBEs.

The TRS at which Rep78/68 or NS1 nicks is specific to each parvovirus (Cotmore et al., 2015). The TRS (5'-GAGT/TGG-3') is conserved only in AAV1-4 and 6, but AAV5 uses 5'-AGTG/TGGC-3' (Chiorini et al., 1999). For autonomous parvoviruses, GPV uses (5'TGAG/TCT3') (Smith et al., 1999); B19V Ori uses a unique nicking site (5'-GACA/CCA-3') (Guan et al., 2009); and MVM uses a nicking site (5'-CTWW/TCA-3', W=A/T) (Smith et al., 1999). Thus, the nicking sites of autonomous parvoviruses differ from each other. The HBoV1 TRS (5'-CTA/TATCT-3') identified in this study closely resembles the MVM TRS with an A/T-rich sequence in the center. Of note, such a similar TRS signal is not found at the LEH of the HBoV1 genome. However, one unique TRS of AAV2 Rep78/68 (5'-CTCCA/TTT-3') has been identified in the minimal replication origin present within the AAV2 P5 promoter (Francois et al., 2005; Wang et al., 1997). The nicking of the AAV2 Rep78/68 at the TRS in the P5 promoter involves the TATA box in cis and the TATA-binding protein in trans (Francois et al., 2005). HBoV1 NS1 may employ a different TRS to perform junction resolution at the OriL of the LEH, and that cellular transcriptional factors or DNA binding proteins should facilitate nicking of the NS1 at the TRS at the OriL.

Several Rep78/68 and NS1 binding elements have been characterized, and confirmed by in vitro binding assay. The AAV RBE consists of three tetramer repeats (GCTC)$_3$ plus a degenerate GCGC (Ryan et al., 1996). Similar three tetramer repeats (GTTC)$_3$ plus GAAC were found in the ITR of GPV (Smith et al., 1999). Two hexamer repeats (GCCGCCGG)$_2$ were confirmed to bind B19V NS1 OBD in an in vitro binding assay (Tewary et al., 2014). MVM NSBE in either the OriL or OriR, comprise 2-3 tandem copies of the tetranucleotide (TGGT)2-3. Densoparvovirus GmDNV NS1 binds a (GAC)$_4$ trimer repeated sequence in its ITR (Ding et al., 2002). A consensus NSBE for HBoV1 NS1 binding cannot be found in the LEH and REH of HBoV1 genome. In the HBoV1 OriR identified in this study, at about 12 nt downstream of the TRS, a tetramer tri-nucleotide [(TGT)$_4$] was proved important to viral duplex DNA replication at the OriR. However, a specific binding between HBoV1 NS1 and OriR could not be confirmed in vitro. Although in vitro binding assay is capable of revealing the specific binding. An in vitro binding assay which has been successfully used to confirm MVM NS1 binding to its NSBE (Christensen et al., 1995) is capable of revealing the specific binding and was adapted. B19V NS1 binding to the B19V Ori was demonstrated in side-by-side studies assessing HBoV1 NS1 binding of the HBoV1 OriR. Although a strong and specific binding between B19V NS1 and its Ori was observed and confirmed, no specific binding between HBoV1 NS1 and OriR was observed. Therefore, HBoV1 NS1 and OriR binding may require the involvement of cellular proteins. However, in a subsequent in vitro pull-down assay, the biotinylated HBoV1 OriR did not pull down any HBoV1 NS1 from the lysate of the cells expressing HBoV1 NS1. As a control, B19V Ori pulled down NS1 at a significantly higher level than the mutant Ori, which can be competed by the wild-type B19V Ori but not the mutant Ori. A further experiment using nuclear extract prepared from NS1- and NP1-coexpressing cells also did not show any binding between HBoV1 NS1 and OriR.

Nevertheless, based on the model of rolling circle replication in which Rep78/68 or NS1 has to bind the origin and melt the duplex viral DNA, and perform nicking of the ssDNA at the TRS of about 20-nt upstream of the NSBEs (Cotmore et al., 2005), the $(TGT)_4$ repeat in HBoV1 OriR may be the NSBEs. The $(TGT)_4$ repeat closely resembles the $(GAC)_4$ repeat of GmDNV NSBE (Ding et al., 2002). Since the $(TGT)_4$ repeat contains the $(TGTT)_2$ repeat, the HBoV1 NSBEs also resembles MVM NSBEs (TGGT)2-3 (Cotmore et al., 995). Considering no cognate binding sequence can be found in the origins at both the LEH and REH of HBoV1 genome, contrary to what has been observed, HBoV1 NS1 may bind the origins at a low affinity and require the help of other viral components and cellular proteins to do so.

Function of the 3' UTR of HBoV1

Identification of a role of the 3' UTR between VP-coding region and the REH in HBoV1 DNA replication is unexpected, In other parvoviruses, various cis-sequences that are outside of the terminal hairpins have been identified to be important for DNA replication, e.g., an additional AAV2 minimal DNA replication origin at the P5 promoter (5' UTR) (Wang and Srivastava, 1997; Tullis and Shenk, 2000; Nony et al., 2001). In MVM, it has been shown that specific elements inboard of the REH between nt 4,489-4,636 and nt 4,636-4,695 are necessary for efficient replication of MVM duplex DNA (Tam and Astell, 1993), In the development of recombinant MVMp vector (rMVMp), the rMVMp genome, a large portion of cis-element was remained at the 3' end (nt 4,631-5,149) (Hendrie et al., 2003). However, how these cis-elements outside of the hairpins facilitate viral DNA replication has not been studied.

Yan et al. (1993) developed a recombinant HBoV1 vector, in which both the rAAV2 genome and rHBoV1 genome were used, however, a large portions were retained at the 3' and 5' end in the rHBoV1 genome, in order to ensure efficient replication in the presence of a packaging plasmid. Unfortunately, the cis-sequences that remained resulted in a high rate of recombination that generated wild-type virus in the rHBoV1 preparations (Yan et al., 2013). Therefore, to define the cis minimal requirement for HBoV1 DNA replication is important to develop a better rHBoV1 vector that may hold benefits for gene targeting in human airways, since 95% of the HBoV1 genome is negative sense, while the AAV genome has equal polarity (Sun et al., 2009; Berns, 1990). We plan to further define the cis element at the left end in order to construct an rHBoV1 genome that has a minimal sequence of HBoV1 (to avoid homology recombination with the HBoV1 packaging plasmid).

REFERENCES

Allander, T., M. T. Tammi, M. Eriksson, A. Bjerkner, A. Tiveljung-Lindell, and B. Andersson. 2005. Cloning of a human Parvovirus by molecular screening of respiratory tract samples. Proc.Natl.Acad.Sci.U.S.A 102:12891-12896.

Allander, T., T. Jartti, S. Gupta, H. G. Niesters, P. Lehtinen, R. Osterback, T. Vuorinen, M. Waris, A. Bjerkner, A. Tiveljung-Lindell, B. G. van den Hoogen, T. Hyypia, and 0. Ruuskanen. 2007, Human bocavirus and acute wheezing in children. Clin.Infect.Dis. 44:904-910.

Bashir, T., J. Rommelaere, and C. Cziepluch, 2001. In vivo accumulation of cyclin A and cellular replication factors in autonomous parvovirus minute virus of mice-associated replication bodies. J.Virol. 75:4394-4398.

Berns, K. I. 1990. Parvovirus replication. Microbiol.Rev. 54:316-329.

Brodzinski, H. and R. M. Ruddy. 2009. Review of new and newly discovered respiratory tract viruses in children. Pediatr.Emerg.Care. 25:352-360.

Chen, A. Y., F. Cheng, S. Lou, Y. Luo, Z. Liu, E. Delwart, D. Pintel, and J. Qiu. 2010. Characterization of the gene expression profile of human bocavirus. Virology. 403:145-154.

Cheng, W. X., J. S. Li, C. P. Huang, D. P. Yao, N. Liu, S. X. Cui, Y. Jin, and Z. J. Duan. 2010. Identification and nearly full-length genome characterization of novel porcine bocaviruses. PLoS.ONE. 5:el 3583.

Chiorini, J. A., S. Afione, and R. M. Kotin. 1999. Adeno-associated virus (AAV) type 5 Rep protein cleaves a unique terminal resolution site compared with other AAV serotypes. J Virol. 73:4293-4298.

Christensen, J., S. F. Cotmore, and P. Tattersall. 1995. Minute virus of mice transcriptional activator protein NS1 binds directly to the transactivation region of the viral P38 promoter in a strictly ATP-dependent manner. J.Virol. 69:5422-5430.

Christensen, J., S. F. Cotmore, and P. Tattersall. 1997. Parvovirus initiation factor PIF: a novel human DNA-binding factor which coordinately recognizes two ACGT motifs. J.Virol. 71:5733-5741.

Cotmore, S. F, and P. Tattersall. 1994. An asymmetric nucleotide in the parvoviral 3' hairpin directs segregation of a single active origin of DNA replication. EMBO J. 13:4145-4152.

Cotmore, S. F, and P. Tattersall. 2005. A rolling-haipin strategy: basic mechanisms of DNA replication in the parvoviruses, p. 171-181. In: J. Kerr, S. F. Cotmore, M. E. Bloom, R. M. Linden, and C. R. Parrish (eds.), Parvoviruses. Hoddler Arond, London.

Cotmore, S. F, and P. Tattersall. 2005. Structure and Organization of the Viral Genome, p. 73-94. In: J. Kerr, S. F. Cotmore, M. E. Bloom, R. M. Linden, and C. R. Parrish (eds.), Parvoviruses. Hodder Arnold, London.

Cotmore, S. F., J. Christensen, and P. Tattersall. 2000. Two widely spaced initiator binding sites create an HMG1-dependent parvovirus rolling-hairpin replication origin. J.Virol. 74:1332-1341.

Cotmore, S. F., J. Christensen, J. P. Nuesch, and P. Tattersall. 1995. The NS1 polypeptide of the murine parvovirus minute virus of mice binds to DNA sequences containing the motif [ACCA]2-3. J.Virol. 69:1652-1660.

Cotmore, S. F., M. Agbandje-McKenna, J. A. Chiorini, D. V. Mukha, D. J. Pintel, J. Qiu, M. Soderlund-Venermo, P. Tattersall, P. Tijssen, D. Gatherer, and A. J. Davison. 2014. The family Parvoviridae. Arch.Virol. 159:1239-1247.

Cziepluch, C., S. Lampel, A. Grewenig, C. Grund, P. Lichter, and J. Rommelaere. 2000. H-1 parvovirus-associated replication bodies: a distinct virus-induced nuclear structure. J.Virol. 74:4807-4815.

Deng, X., Z. Yan, F. Cheng, J. F. Engelhardt, and J. Qiu. 2016. Replication of an Autonomous Human Parvovirus in Non-dividing Human Airway Epithelium Is Facilitated through the DNA Damage and Repair Pathways. PLoS.Pathog. 12:e1005399.

Dignam, J. D., R. M. Lebovitz, and R. G. Roeder. 1983, Accurate transcription initiation by RNA polymerase II in a soluble extract from isolated mammalian nuclei. Nucleic Acids Res. 11:1475-1489.

Ding, C., M. Urabe, M. Bergoin, and R, M. Kotin. 2002. Biochemical characterization of Junonia coenia densovirus nonstructural protein NS-1. J Virol. 76:338-345.

Don, M., M. Soderlund-Venermo, F. Valent, A. Lahtinen, L. Hedman, M. Canciani, K. Hedman, and M. Korppi. 2010. Serologically verified human bocavirus pneumonia in children. Pediatr.Pulmonol. 45:120-126.

Fasina, O. O., Y. Dong, and D. J. Pintel. 2015. NP1 Protein of the Bocaparvovirus Minute Virus of Canines Controls Access to the Viral Capsid Genes via Its Role in RNA Processing. J.Virol. 90:1718-1728.

Francois, A., M. Guilbaud, R. Awedikian, G. Chadeuf, P. Moullier, and A. Salvetti. 2005. The cellular TATA binding protein is required for rep-dependent replication of a minimal adeno-associated virus type 2 p5 element. J Virol. 79:11082-11094.

Garcia-Garcia, M. L., C. Calvo, A. Falcon, F. Pozo, P. Perez-Brena, J. M. De Cea, and I. Casas. 2010. Role of emerging respiratory viruses in children with severe acute wheezing. Pediatr.Pulmonol. 45:585-591.

Gendrel, D., R. Guedj, C. Pons-Catalano, A. Emirian, J. Raymond, F. Rozenberg, and P. Lebon. 2007. Human bocavirus in children with acute asthma. Clin.Infect.Dis. 45:404-405.

Guan, W., S Wong, N. Zhi, and J. Qiu. 2009. The genome of human parvovirus B19 virus can replicate in non-permissive cells with the help of adenovirus genes and produces infectious virus. J.Virol. 83:9541-9553.

Hendrie, P. C., R. K. Hirata, and D. W. Russell. 2003. Chromosomal integration and homologous gene targeting by replication-incompetent vectors based on the autonomous parvovirus minute virus of mice. J Virol. 77:13136-13145.

Hickman, A. B., D. R. Ronning, Z. N. Perez, R. M. Kotin, and F. Dyda. 2004. The nuclease domain of adeno-associated virus rep coordinates replication initiation using two distinct DNA recognition interfaces. Mol.Cell. 13:403-414.

Huang, Q., X. Deng, Z. Yan, F. Cheng, Y. Luo, W. Shen, D. C. Lei-Butters, A. Y. Chen, Y. Li, L. Tang, M. Soderlund-Venermo, J. F. Engelhardt, and J. Qiu. 2012. Establishment of a reverse genetics system for studying human bocavirus in human airway epithelia. PLoS.Pathog. 8:e1002899.

Ihalainen, T. O., E. A. Niskanen, J. Jylhava, T. Turpeinen, J. Rinne, J. Timonen, and M. Vihinen-Ranta. 2007. Dynamics and interactions of paroviral NS1 protein in the nucleus. Cell Microbiol. 9:1946-1959.

Jartti, T., K. Hedman, L. Jartti, O. Ruuskanen, T. Allander, and M. Soderlund-Venermo. 2011. Human bocavirus-the first 5 years. Rev.Med.Virol. 22:46-64.

Kahn, J. 2008. Human bocavirus: clinical significance and implications. Curr.Opin.Pediatr. 20:62-66.

Kapoor, A., N. Mehta, F. Esper, M. Poljsak-Prijatelj, P. L. Quan, N. Qaisar, E. Delwart, and W. I. Lipkin, 2010. Identification and characterization of a new bocavirus species in gorillas. PLoS.ONE. 5:e11948.

Li, Q., Z. Zhang, Z. Zheng, X. Ke, H. Luo, Q. Hu, and H. Wang. 2013. Identification and characterization of complex dual nuclear localization signals in human bocavirus NP1: identification and characterization of complex dual nuclear localization signals in human bocavirus NP1. J Gen.Virol. 94:1335-1342.

Luo, Y., S. Lou, X. Deng, Z. Liu, Y. Li, S. Kleiboeker, and J. Qiu, 2011. Parvovirus B19 infection of human primary erythroid progenitor cells triggers ATR-Chk1 signaling, which promotes B19 virus replication. J.Virol. 85:8046-8055.

Luo, Y., X. Deng, F. Cheng, Y. Li, and J. Qiu. 2013. SMC1-mediated intra-S phase arrest facilitates Bocavirus DNA replication. J.Virol. 87:4017-4032.

Maiti, R., G. H. Van Domselaar, H. Zhang, and D. S. Wishart. 2004. SuperPose: a simple server for sophisticated structural superposition. Nucleic Acids Res. 32:W590-W594.

Martin, E. T., J. Kuypers, J. P. McRoberts, J. A. Englund, and D. M. Zerr. 2015. Human Bocavirus-1 Primary Infection and Shedding in Infants. J.Infect.Dis. 212:516-524.

Mihaylov, I. S., S. F. Cotmore, and P. Tattersall. 2014. Complementation for an essential ancillary non-structural protein function across parvovirus genera. Virology. 468-470:226-237.

Nash, K., W. Chen, M. Salganik, and N. Muzyczka. 2009. Identification of cellular proteins that interact with the adeno-associated virus rep protein. J.Virol. 83:454-469.

Nony, P., J. Tessier, G. Chadeuf, P. Ward, A. Giraud, M. Dugast, R. M. Linden, P. Moullier, and A. Salvetti. 2001. Novel cis-acting replication element in the adeno-associated virus type 2 genome is involved in amplification of integrated rep-cap sequences. J Virol. 75:9991-9994.

Qiu, J., F. Cheng, F. B. Johnson, and D. Pintel. 2007. The transcription profile of the bocavirus bovine parvovirus is unlike those of previously characterized parvoviruses. J.Virol. 81:12080-12085.

Ryan, J. H., S. Zolotukhin, and N. Muzyczka. 1996. Sequence requirements for binding of Rep68 to the adeno-associated virus terminal repeats. J Virol. 70:1542-1553.

Schildgen, O., A. Muller, T. Allander, I. M. Mackay, S. Volz, B. Kupfer, and A. Simon. 2008. Human bocavirus: passenger or pathogen in acute respiratory tract infections? Clin.Microbiol.Rev. 21:291-304.

Shen, W., X. Deng, W. Zou, F. Cheng, J. F. Engelhardt, Z. Yan, and J. Qiu. 2015. Identification and Functional Analysis of Novel Non-structural Proteins of Human Bocavirus 1. J.Virol. 89:10097-10109.

Smith, D. H., P. Ward, and R. M. Linden. 1999. Comparative characterization of rep proteins from the helper-dependent adeno-associated virus type 2 and the autonomous goose parvovirus. J Virol. 73:2930-2937.

Soderberg, O., M. Gullberg, M. Jarvius, K. Ridderstrale, K. J. Leuchowius, J. Jarvius, K. Wester, P. Hydbring, F. Bahram, L. G. Larsson, and U. Landegren. 2006. Direct observation of individual endogenous protein complexes in situ by proximity ligation. Nat.Methods. 3:995-1000.

Sukhu, L., O. Fasina, L. Burger, A. Rai, J. Qiu, and D. J. Pintel. 2013. Characterization of the nonstructural proteins of the bocavirus minute virus of canines. J Virol. 87:1098-1104.

Sun, Y., A. Y. Chen, F. Cheng, W. Guan, F. B. Johnson, and J. Qiu. 2009. Molecular characterization of infectious clones of the minute virus of canines reveals unique features of bocaviruses. J.Virol. 83:3956-3967.

Tam, P. and C. R. Astell. 1993. Replication of minute virus of mice minigenomes: novel replication elements required for MVM DNA replication. Virology. 193:812-824.

Tewary, S. K., H. Zhao, W. Shen, J. Qiu, and L. Tang. 2013. Structure of the NS1 protein N-terminal origin-recognition/nickase domain from the emerging human bocavirus. J.Virol. 87:11487-11494.

Tewary, S. K., H. Zhao, X. Deng, J. Qiu, and L. Tang. 2014. The human parvovirus B19 non-structural protein 1 N-terminal domain specifically binds to the origin of replication in the viral DNA. Virology. 449:297-303.

Tewary, S. K., L. Liang, Z. Lin, A. Lynn, S. F. Cotmore, P. Tattersall, H. Zhao, and L. Tang. 2015. Structures of minute virus of mice replication initiator protein N-terminal domain: Insights into DNA nicking and origin binding. Virology. 476:61-71.

Tullis, G. E. and T. Shenk. 2000. Efficient replication of adeno-associated virus type 2 vectors: a cis-acting element outside of the terminal repeats and a minimal size. J Virol. 74:11511-11521.

Wang, X. S. and A. Srivastava. 1997. A novel terminal resolution-like site in the adeno-associated virus type 2 genome. J Virol. 71:1140-1146.

Ward, P. 2006. Replication of adeno-associated virus DNA, p. 189-211. In: J. Kerr, Cotmore SF, M. E. Bloom, M. E. Linden, and C. R. Parrish (eds.), The parvoviruses. Hodder Arnold, London.

Yan, Z., N. W. Keiser, Y. Song, X. Deng, F. Cheng, J. Qiu, and J. F. Engelhardt. 2013. A novel chimeric adenoassociated virus 2/human bocavirus 1 parvovirus vector efficiently transduces human airway epithelia. Mol.Ther. 21:2181-2194.

Zadori, Z., R. Stefancsik, T. Rauch, and J. Kisary. 1995. Analysis of the complete nucleotide sequences of goose and muscovy duck parvoviruses indicates common ancestral origin with adeno-associated virus 2. Virology. 212:562-573.

Zhang, Y. 2008. I-TASSER server for protein 3D structure prediction. BMC.Bioinformatics. 9:40. doi: 10.1186/1471-2105-9-40.:40-49.

Zou, W., F. Cheng, W. Shen, J. F. Engelhardt, Z. Yan, and J. Qiu. 2016. Nonstructural Protein NP1 of Human Bocavirus 1 Plays a Critical Role in the Expression of Viral Capsid Proteins, J.Virol. Feb 24. pii: JVI.02964-15. [Epub ahead of print].

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

---

What is claimed is:

1. A method of preparing helper-virus-free recombinant human bocavirus 1 (rhBoV1), comprising:
   a) providing a mutant human bocavirus (BoV1) genome comprising
      (i) a left-end hairpin (LEH), a 3' untranslated region (UTR) and a truncated right-end hairpin (REH), wherein the truncated REH consists of the contiguous nucleotide sequence of 5357 to 5402 of SEQ ID NO: 1,
      (ii) one or more mutations in each one of the human bocavirus NS2 protein, NS3 protein, NS4 protein, VP1 protein, VP2 protein, VP3 protein, NS1 protein and NP1 protein, such that human NS2, NS3, NS4, VP1, VP2, VP3, NS1 and NP1 proteins are not expressed from the genome when the genome is introduced to cells, wherein the one or more mutations include a deletion of one or more nucleotides, an insertion of one or more nucleotides, or a substitution of one or more nucleotides;
   b) providing one or more vectors encoding at least human bocavirus NP1, NS1, VP1, VP2 and VP3, which vectors do not include one or more of LEH, a 3' UTR and a REH;
   c) introducing the mutant human bocavirus genome and the one or more vectors to HEK293 cells and culturing said HEK293 cells; and
   d) collecting helper-free virus from the HEK293 cells of c).

2. The method of claim 1, wherein the mutant genome of a) comprises an expression cassette encoding a heterologous gene product or a heterologous nucleic acid sequence for homologous recombination with selected sequences in a mammalian genome.

3. The method of claim 2, wherein the heterologous gene product is a viral, bacterial, tumor, parasite, or fungal antigen.

4. The method of claim 2, wherein the heterologous nucleic acid sequence is less than about 6 kb or wherein the heterologous nucleic acid sequence comprises CFTR sequences.

5. The method of claim 2, wherein the heterologous gene product is a therapeutic gene product.

6. The method of claim 2, wherein the heterologous gene product is cystic fibrosis transmembrane conductance regulator, β-globin, γ-globin, tyrosine hydoxylase, glucocerebrosidase, aryl sulfatase A, factor VIII, dystrophin, alpha 1-antitrypsin, surfactant protein SP-D, SP-A or SP-C, erythropoietin, HBOV protein, influenza virus protein, RSV protein, a neutralizing antibody or an antigen binding fragment thereof, SARS virus protein, DNA endonuclease, zinc finger nuclease, a fusion protein including a DNA binding domain linked to a nuclease, or a cytokine.

7. The method of claim 6, wherein the cytokine is selected from the group consisting of IFN-alpha, IFN-gamma, INF, IL-1, IL-17, and IL-6.

8. A method of preparing helper-virus-free recombinant human bocavirus 1 (rhBoV1), comprising:
   a) providing a HEK293 cell that expresses human bocavirus VP1, VP2 and VP3 and bocavirus NP1 and NS1, but does not express one or more of human bocavirus NS2, NS3 or NS4;
   b) providing a mutant human BoV1 genome comprising
      (i) a left-end hairpin (LEH), a 3' untranslated region (UTR) and a truncated right-end hairpin (REH), wherein the truncated REH consists of the contiguous nucleotide sequence of 5357 to 5402 of SEQ ID NO: 1,
      (ii) one or more mutations in each one of the human bocavirus NS2 protein, NS3 protein, NS4 protein, VP1 protein, VP2 protein, VP3 protein, NS1 protein and NP1 protein, such that human NS2, NS3, NS4, VP1, VP2, VP3, NS1 and NP1 proteins are not expressed from the genome when the genome is introduced to cells, wherein the one or more mutations include a deletion of one or more nucleotides, an insertion of one or more nucleotides, or a substitution of one or more nucleotides;
   c) introducing the mutant BoV1 genome into the HEK293 cell of step (a) and culturing the HEK293 cell so as to express the mutant human BoV1 genome in the HEK293 cell; and
   d) collecting helper-free virus from the culture of c).

9. The method of claim 8, wherein the mutant genome of b) comprises an expression cassette encoding a heterologous gene product or a heterologous nucleic acid sequence for homologous recombination with selected sequences in a genome of a mammal.

10. The method of claim 9, wherein the heterologous gene product is a viral, bacterial, tumor, parasite, or fungal antigen.

11. The method of claim 9, wherein the heterologous nucleic acid sequence is less than about 6 kb or wherein the heterologous nucleic acid sequence comprises CFTR sequences.

12. The method of claim 9, wherein the heterologous gene product is a therapeutic gene product.

13. The method of claim 9, wherein the heterologous gene product is cystic fibrosis transmembrane conductance regulator, β-globin, γ-globin, tyrosine hydoxylase, glucocerebrosidase, aryl sulfatase A, factor VIII, dystrophin, alpha 1-antitrypsin, surfactant protein SP-D, SP-A or SP-C, erythropoietin, HBOV protein, influenza virus protein, RSV protein, a neutralizing antibody or an antigen binding fragment thereof, SARS virus protein, DNA endonuclease, zinc finger nuclease, a fusion protein including a DNA binding domain linked to a nuclease, or a cytokine.

14. The method of claim 13, wherein the cytokine is selected from the group consisting of IFN-alpha, IFN-gamma, INF, IL-1, IL-17, and IL-6.

15. A method of preparing helper-virus-free recombinant human bocavirus 1 (rhBoV1), comprising:
 a) providing a mutant human BoV1 genome comprising
 (i) a left-end hairpin (LEH), a heterologous nucleic acid sequence for homologous recombination with selected sequences in a genome of a mammal, a 3' untranslated region (UTR) and a truncated right-end hairpin (REH), wherein the truncated REH consists of the contiguous nucleotide sequence of 5357 to 5402 of SEQ ID NO: 1,
 (ii) one or more mutations in each one of the human bocavirus NS2 protein, NS3 protein, NS4 protein, VP1 protein, VP2 protein, VP3 protein, NS1 protein and NP1 protein, such that human NS2, NS3, NS4, VP1, VP2, VP3, NS1 and NP1 proteins are not expressed from the genome when the genome is introduced to cells, wherein the one or more mutations include a deletion of one or more nucleotides, an insertion of one or more nucleotides, or a substitution of one or more nucleotides;
 b) providing one or more vectors encoding at least human bocavirus NP1, NS1, VP1, VP2 and VP3, which vectors do not include one or more of LEH, a 3' UTR and a REH;
 c) introducing the mutant human BoV1 genome and the one or more vectors to HEK293 cells and culturing said HEK293 cells; and
 d) collecting helper-free virus from the cells of c).

16. A method of preparing helper-virus-free recombinant human bocavirus 1 (rhBoV1), comprising:
 a) providing a HEK293 cell that expresses human bocavirus VP1, VP2 and VP3 and bocavirus NP1 and NS1, but does not express one or more of human bocavirus NS2, NS3 or NS4;
 b) providing a mutant human BoV1 genome comprising
 (i) a left-end hairpin (LEH), a heterologous nucleic acid sequence for homologous recombination with selected sequences in a genome of a mammal, a 3' untranslated region (UTR) and a truncated right-end hairpin (REH), wherein the truncated REH consists of the contiguous nucleotide sequence of 5357 to 5402 of SEQ ID NO: 1,
 (ii) one or more mutations in each one of the human bocavirus NS2 protein, NS3 protein, NS4 protein, VP1 protein, VP2 protein, VP3 protein, NS1 protein and NP1 protein, such that human NS2, NS3, NS4, VP1, VP2, VP3, NS1 and NP1 proteins are not expressed from the genome when the genome is introduced to cells, wherein the one or more mutations include a deletion of one or more nucleotides, an insertion of one or more nucleotides, or a substitution of one or more nucleotides;
 c) introducing the mutant BoV1 genome into the HEK293 cell of step (a) and culturing the HEK293 cell so as to express the mutant human BoV1 genome in the host HEK293 cell; and
 d) collecting helper free virus from the culture of c).

* * * * *

SEQUENCE LISTING

<160> NUMBER OF SEQ ID NOS: 10

<210> SEQ ID NO 1
<211> LENGTH: 5543
<212> TYPE: DNA
<213> ORGANISM: Bocavirus

<400> SEQUENCE: 1

```
gtggttgtac agacgccatc ttggaatcca atatgtctgc cggctcagtc atgcctgcgc      60
tgcgcgcagc gcgctgcgcg cgcgcatgat ctaatcgccg gcagacatat tggattccaa     120
gatggcgtct gtacaaccac gtcacatata aaataataaa tattcacaag gaggagtggt     180
tatatgatgt aatccataac cactcccagg aaatgacgta tgatagccaa tcagaattga     240
gtattaaacc tatataagct gctgcacttc ctgattcaat cagactgcat ccggtctccg     300
gcgagtgaac atctctggaa aaagctccac gcttgtggtg agtctactat ggctttcaat     360
cctcctgtga ttagagcttt ttctcaacct gcttttactt atgtcttcaa atttccatat     420
ccacaatgga aagaaaaga atggctgctt catgcacttt tagctcatgg aactgaacaa     480
tctatgatac aattaagaaa ctgcgctcct catccggatg aagacataat ccgtgatgac     540
ttgcttattt ctttagaaga tcgccatttt ggggctgttc tctgcaaggc tgtttacatg     600
gcaacaacta ctctcatgtc acacaaacaa aggaatatgt ttcctcgttg tgacatcata     660
gttcagtctg agctaggaga gaaaaactta cactgccata ttatagttgg gggagaagga     720
ctaagcaaga ggaatgctaa atcatcctgt gctcagttct atggtttaat actagctgaa     780
ataattcaac gctgcaaatc tcttctggct acacgtcctt ttgaacctga agaggctgac     840
atatttcaca ctttaaaaaa ggctgagcga gaggcatggg gtggagttac tggcggcaac     900
atgcaaatcc ttcaatatag agatcgcaga ggagaccttc atgcacaaac agtggatcct     960
```

```
cttcgcttct tcaaaaacta ccttttacct aaaaatagat gtatttcatc ttacagcaaa    1020
cctgatgttt gtacttctcc tgacaactgg ttcattttag ctgaaaaaac ttactctcac    1080
actcttatta acgggctgcc gcttccagaa cattacagaa aaaactacca cgcaacccta    1140
gataacgaag tcattccagg gcctcaaaca atggcctatg gaggacgtgg tccgtgggaa    1200
catcttcctg aggtaggaga tcagcgccta gctgcgtctt ctgttagcac tacttataaa    1260
cctaacaaaa aagaaaaact tatgctaaac ttgctagaca aatgtaaaga gctaaatcta    1320
ttagtttatg aagacttagt agctaattgt cctgaactac tccttatgct gaaggtcaa     1380 ccaggagggg cacgccttat agaacaagtc ttgggcatgc accatattaa tgtttgttct    1440
aactttacag ctctcacata tcttttcat ctacatcctg ttacttcgct tgactcagac     1500
aataaagctt tacagctttt gttgattcaa ggctataatc tctagccgt tggtcacgcc     1560 ctatgctgtg tcctgaacaa acaattcggg aaacaaaaca ctgtttgctt ttacgggcct    1620
gcctcaacag gtaaaacaaa tatggccaag gcaatcgtcc aagggattag actttatggg    1680
tgtgttaatc atttgaacaa aggatttgta tttaatgact gcagacaacg cctagttgtt    1740
tggtgggagt agtgcttaat gcaccaggat tgggtggaac ctgcaaagtg tatcttgggc    1800
gggacagaat gcagaattga cgtcaagcat agagacagtg tacttttaac tcaaacacct    1860
gtaattatat ccactaacca cgatatctac gcggttgttg gtggcaattc tgtttctcat    1920
gttcacgcgg ctccattaaa agaaagagtg attcagctaa attttatgaa acaacttcct    1980
caaacatttg gagaaatcac tgctactgag attgcagctc ttctacagtg gtgtttcaat    2040
gagtacgact gtactctgac aggatttaaa caaaaatgga atttagataa aattccaaac    2100
tcatttcctc ttgggtgtcct tgtcctact cattcacagg actttacact tcacgaaaac    2160
ggatactgca ctgattgcgg tggttaccttt cctcatagtg ctgacaattc tatgtacact    2220
gatcgcgcaa gcgaaactag cacaggagac atcacaccaa gtaagtaaat acgcatgcgc    2280
aagtaattct tttactttca cttcgctatt tttaccaatt tttacttta ggtgacttgg     2340 gggattcgga cggagaagac accaagcctg agacatcgca agtggactat tgtccaccca    2400
agaaacgtcg tctaactgct ccagcaagtc ctccaaactc acctgcgagc tctgtaagta    2460
ctattacttt ctttaacact tggcacgcac agccacgtga cgaagatgag ctcagggaat    2520
atgaaagaca agcatcgctc ctacaaaaga aagggagtc cagaaagagg ggagaggaag     2580
agacactggc agacaactca tcacaggagc aggagccgca gcccgatccg acacagtggg    2640
gagagaggct cgggctcata tcatcaggaa cacccaatca gccacctatc gtcttgcact    2700
gcttcgaaga cctcagacca agtgatgaag acgagggaga gtacatcggg gaaaaaagac    2760
aatagaacaa atccatacac tgtattcagt caacacagag cttccaatcc tgaagctcca    2820
gggtggtgtg ggttctactg gcactctact cgcattgcta gagatggtac taattcaatc    2880
tttaatgaaa tgaaacaaca gtttcaacag ctacaaattg ataataaaat aggatgggat    2940
aacactagag aactattgtt taatcaaaag aaaacactag atcaaaaata cagaaatatg    3000
ttctggcact ttagaaataa ctctgattgt gaaagatgta attactggga tgatgtgtac    3060
cgtagacact tagctaatgt ttcctcacag acagaagcag acgagataac tgacgaggaa    3120
atgctttctg ctgctgaaag catggaagca gatgcctcca attaagagac agcctagagg    3180
gtgggtgctg cctggataca gatatcttgg gccatttaat ccacttgata acggtgaacc    3240
tgtaaataac gctgatcgcg ctgctcaatt acatgatcac gcctactctg aactaataaa    3300
```

```
gagtggtaaa aatccatacc tgtatttcaa taaagctgat gaaaaattca ttgatgatct    3360
aaaagacgat tggtcaattg gtggaattat tggatccagt ttttttaaaa taaagcgcgc    3420
cgtggctcct gctctgggaa ataaagagag agcccaaaaa agacactttt actttgctaa    3480
ctcaaataaa ggtgcaaaaa aaacaaaaaa aagtgaacct aaaccaggaa cctcaaaaat    3540
gtctgacact gacattcaag accaacaacc tgatactgta gacgcaccac agaacacctc    3600
aggggggagga acaggaagta ttggaggagg aaaaggatct ggtgtgggga tttccactgg    3660
agggtgggtc ggaggttctc acttttcaga caaatatgtg gttactaaaa acacaagaca    3720
atttataacc acaattcaga atggtcacct ctacaaaaca gaggccattg aaacaacaaa    3780
ccaaagtgga aaatcacagc gctgcgtcac aactccatgg acatacttta actttaatca    3840
atacagctgt cacttctcac cacaggattg gcagcgcctt acaaatgaat ataagcgctt    3900
cagacctaaa gcaatgcaag taaagattta caacttgcaa ataaaacaaa tactttcaaa    3960
tggtgctgac acaacataca acaatgacct cacagctggc gttcacatct tttgtgatgg    4020
agagcatgct tacccaaatg catctcatcc atgggatgag gacgtcatgc ctgatcttcc    4080
atacaagacc tggaaacttt ttcaatatgg atatattcct attgaaaatg aactcgcaga    4140
tcttgatgga aatgcagctg gaggcaatgc tacagaaaaa gcacttctgt atcagatgcc    4200
ttttttttcta cttgaaaaca gtgaccacca agtacttaga actggtgaga gcactgaatt    4260
tacttttaac tttgactgtg aatgggttaa caatgaaaga gcatacattc ctcctggact    4320
aatgtttaat ccaaaagttc caacaagaag agttcagtac ataagacaaa acggaagcac    4380
agcagccagc acaggcagaa ttcagccata ctcaaaacca acaagctgga tgacaggacc    4440
tggcctgctc agtgcacaga gagtaggacc acagtcatca gacactgctc cattcatggt    4500
ttgcactaac ccagaaggaa cacacataaa cacaggtgct gcaggatttg gatctggctt    4560
tgatcctcca agcggatgtc tggcaccaac taacctagaa tacaaacttc agtggtacca    4620
gacaccagaa ggaacaggaa ataatggaaa cataattgca aacccatcac tctcaatgct    4680
tagagaccaa ctcctataca aggaaaccaa gaccacatac aatctagtgg gggacatatg    4740
gatgtttcca aatcaagtct gggacagatt tcctatcacc agagaaaatc caatctggtg    4800
caaaaaacca agagctgaca acacacaat catggatcca tttgatggat caattgcaat    4860
ggatcatcct ccaggcacta tttttataaa aatggcaaaa attccagttc caactgcctc    4920
aaatgcagac tcatacctaa acatatactg tactggacaa gtcagctgtg agattgtatg    4980
ggaagtaaaa agatacgcaa caaagaactg gcgtccagaa agaagacata ctgcactcgg    5040
gatgtcactg ggaggagaaa gcaactacac gcctacatac cacgtggatc aacaggagc    5100
atacatccag cccacgtcat atgatcaatg tatgccagta aaaacaaaca tcaataaagt    5160
gttgtaatct tataagcctc ttttttgctt ctgcttacaa gttcctcctc aatggacaag    5220
cggaaagtga agggtgactg tagtcctgag ctcatgggtt caagaccaca gcccgatggt    5280
agtggtgtta ccgtctcgaa cctagccgac agcccttgta cattgtgggg ggagctgttt    5340
tgtttgctta tgcaatcgcg aaactctata tcttttaatg tgttgttgtt gtacatgcgc    5400
catcttagtt ttatatcagc tggcgcctta gttatataac atgcatgtta tataactaag    5460
gcgccagctg atataaaact aagatggcgc atgtacaaca acaacacatt aaaagatata    5520
gagtttcgcg attgcataag caa                                           5543
```

<210> SEQ ID NO 2
<211> LENGTH: 27

<212> TYPE: DNA
<213> ORGANISM: Artificial Sequence
<220> FEATURE:
<223> OTHER INFORMATION: A synthetic primer

<400> SEQUENCE: 2
ctgtctagaa tgatcaatgt atgccag                                    27

<210> SEQ ID NO 3
<211> LENGTH: 25
<212> TYPE: DNA
<213> ORGANISM: Artificial Sequence
<220> FEATURE:
<223> OTHER INFORMATION: A synthetic primer

<400> SEQUENCE: 3
cacggatcct tttttttttt ttttt                                      25

<210> SEQ ID NO 4
<211> LENGTH: 46
<212> TYPE: DNA
<213> ORGANISM: Artificial Sequence
<220> FEATURE:
<223> OTHER INFORMATION: A synthetic probe

<400> SEQUENCE: 4
cgcgaaactc tatatctttt aatggcagaa ttcagcacat gcgcca               46

<210> SEQ ID NO 5
<211> LENGTH: 38
<212> TYPE: DNA
<213> ORGANISM: Artificial Sequence
<220> FEATURE:
<223> OTHER INFORMATION: A synthetic probe

<400> SEQUENCE: 5
gccgccggtc gccgccggta ggcgggactt ccggtaca                        38

<210> SEQ ID NO 6
<211> LENGTH: 30
<212> TYPE: DNA
<213> ORGANISM: Artificial Sequence
<220> FEATURE:
<223> OTHER INFORMATION: A synthetic probe

<400> SEQUENCE: 6
agctattggt cgctattggt aggcgggact                                 30

<210> SEQ ID NO 7
<211> LENGTH: 12
<212> TYPE: DNA
<213> ORGANISM: Artificial Sequence
<220> FEATURE:
<223> OTHER INFORMATION: A synthetic oligonucleotide

<400> SEQUENCE: 7
tgttgttgtt gt                                                    12

<210> SEQ ID NO 8
<211> LENGTH: 8
<212> TYPE: DNA
<213> ORGANISM: Artificial Sequence
<220> FEATURE:
<223> OTHER INFORMATION: A synthetic oligonucleotide

<400> SEQUENCE: 8

```
<210> SEQ ID NO 9
<211> LENGTH: 8
<212> TYPE: DNA
<213> ORGANISM: Artificial Sequence
<220> FEATURE:
<223> OTHER INFORMATION: A synthetic oligonucleotide
<220> FEATURE:
<221> NAME/KEY: misc_feature
<222> LOCATION: 4
<223> OTHER INFORMATION: n = A or T

<400> SEQUENCE: 9 ctanatct                                                                    8

<210> SEQ ID NO 10
<211> LENGTH: 46
<212> TYPE: DNA
<213> ORGANISM: Artificial Sequence
<220> FEATURE:
<223> OTHER INFORMATION: A synthetic oligonucleotide

<400> SEQUENCE: 10
tggcgcatgt acaacaacaa cacattaaaa gatatagagt ttcgcg                         46
```